US009266959B2

(12) United States Patent
Stagg et al.

(10) Patent No.: US 9,266,959 B2
(45) Date of Patent: Feb. 23, 2016

(54) METHODS OF TREATING NEUROENDOCRINE TUMORS USING FRIZZLED-BINDING AGENTS

(71) Applicant: OncoMed Pharmaceuticals, Inc., Redwood City, CA (US)

(72) Inventors: Robert Joseph Stagg, Moraga, CA (US); Jakob Dupont, Hillsborough, CA (US)

(73) Assignee: ONCOMED PHARMACEUTICALS, INC., Redwood City, CA (US)

( * ) Notice: Subject to any disclaimer, the term of this patent is extended or adjusted under 35 U.S.C. 154(b) by 0 days.

(21) Appl. No.: 14/059,918

(22) Filed: Oct. 22, 2013

(65) Prior Publication Data

US 2014/0134159 A1 May 15, 2014

Related U.S. Application Data

(60) Provisional application No. 61/717,294, filed on Oct. 23, 2012, provisional application No. 61/760,529, filed on Feb. 4, 2013.

(51) Int. Cl.
| | | |
|---|---|---|
| *A61K 39/395* | (2006.01) | |
| *C07K 16/28* | (2006.01) | |
| *C07K 16/30* | (2006.01) | |
| *A61K 45/06* | (2006.01) | |
| *A61K 39/00* | (2006.01) | |

(52) U.S. Cl.
CPC ............. *C07K 16/3053* (2013.01); *A61K 45/06* (2013.01); *C07K 16/28* (2013.01); *A61K 2039/505* (2013.01); *C07K 2317/21* (2013.01)

(58) Field of Classification Search
CPC ........... A61K 39/395; A61K 39/39558; A61K 2039/505; C07K 16/28; C07K 16/3053
See application file for complete search history.

(56) References Cited

U.S. PATENT DOCUMENTS

| | | |
|---|---|---|
| 3,687,808 A | 8/1972 | Merigan et at |
| 4,109,496 A | 8/1978 | Allemann et al. |
| 4,323,546 A | 4/1982 | Crockford et al. |
| 4,411,990 A | 10/1983 | Salmon et al. |
| 4,612,282 A | 9/1986 | Schlom et al. |
| 4,670,393 A | 6/1987 | Seeburg |
| 4,873,191 A | 10/1989 | Wagner et al. |
| 4,968,103 A | 11/1990 | McNab et al. |
| 4,981,785 A | 1/1991 | Nayak |
| 5,019,497 A | 5/1991 | Olsson |
| 5,034,506 A | 7/1991 | Summerton et al. |
| 5,061,620 A | 10/1991 | Tsukamoto et al. |
| 5,087,570 A | 2/1992 | Weissman et al. |
| 5,223,409 A | 6/1993 | Ladner et al. |
| 5,225,539 A | 7/1993 | Winter |
| 5,283,317 A | 2/1994 | Saifer et al. |
| 5,358,691 A | 10/1994 | Clark et al. |
| 5,489,677 A | 2/1996 | Sanghvi et al. |
| 5,534,617 A | 7/1996 | Cunningham et al. |
| 5,538,848 A | 7/1996 | Livak et al. |
| 5,539,082 A | 7/1996 | Nielsen et al. |
| 5,565,332 A | 10/1996 | Hoogenboom et al. |
| 5,585,089 A | 12/1996 | Queen et al. |
| 5,589,376 A | 12/1996 | Anderson et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,639,606 A | 6/1997 | Willey |
| 5,643,741 A | 7/1997 | Tsukamoto et al. |
| 5,643,765 A | 7/1997 | Willey |
| 5,648,464 A | 7/1997 | Artavanis-Tsakonas et al. |
| 5,650,317 A | 7/1997 | Chang et al. |
| 5,654,183 A | 8/1997 | Anderson et al. |
| 5,672,499 A | 9/1997 | Anderson et al. |
| 5,674,739 A | 10/1997 | Shyjan |
| 5,688,666 A | 11/1997 | Bass et al. |
| 5,693,482 A | 12/1997 | Anderson et al. |
| 5,705,188 A | 1/1998 | Junichi et al. |
| 5,714,331 A | 2/1998 | Buchardt et al. |
| 5,719,262 A | 2/1998 | Buchardt et al. |
| 5,739,277 A | 4/1998 | Presta et al. |
| 5,750,373 A | 5/1998 | Garrard et al. |
| 5,750,376 A | 5/1998 | Weiss et al. |
| 5,753,229 A | 5/1998 | Mordoh et al. |
| 5,753,506 A | 5/1998 | Johe |
| 5,780,300 A | 7/1998 | Artavanis-Tsakonas et al. |

(Continued)

FOREIGN PATENT DOCUMENTS

| | | |
|---|---|---|
| EP | 1 004 669 A1 | 5/1998 |
| EP | 0 861 894 A1 | 9/1998 |

(Continued)

OTHER PUBLICATIONS

Cao et al., Mol. Cell. Biol. Oct. 2009, p. 5477-5487.*
Semba et al., Endocrine Pathology, vol. 11, No. 3, 243-250.*
International Search Report for International Application No. PCT/US2014/014443, United States Patent and Trademark Office, United States, mailed on Apr. 15, 2014.
Gaudio, A., et al., "Increased Sclerostin Serum Levels Associated with Bone Formation and Resorption Markers in Patients with Immobilization-Induced Bone Loss," *J Clin Endcrinol Metab* 95(5):2248-2253, The Endocrine Society, United States (2010).
Wheater, G., et al., "The clinical utility of bone marker measurements in osteoporosis," *Journal of Translational Medicine* 11(201): 11 pages, BioMed Central Ltd. (2013).

(Continued)

*Primary Examiner* — Daniel C Gamett
(74) *Attorney, Agent, or Firm* — Sterne, Kessler, Goldstein & Fox P.L.L.C.

(57) ABSTRACT

Novel methods of treating neuroendocrine tumors are provided. In one embodiment, the method comprises administering to a subject in need thereof a therapeutically effective dose of a Wnt antagonist. In one embodiment, the Wnt antagonist is an anti-FZD antibody. In another embodiment, the Wnt antagonist is a soluble FZD receptor polypeptide. In a further embodiment, the Wnt antagonist is an anti-Wnt antibody.

20 Claims, 5 Drawing Sheets

(56) References Cited

U.S. PATENT DOCUMENTS

Figure 1A:
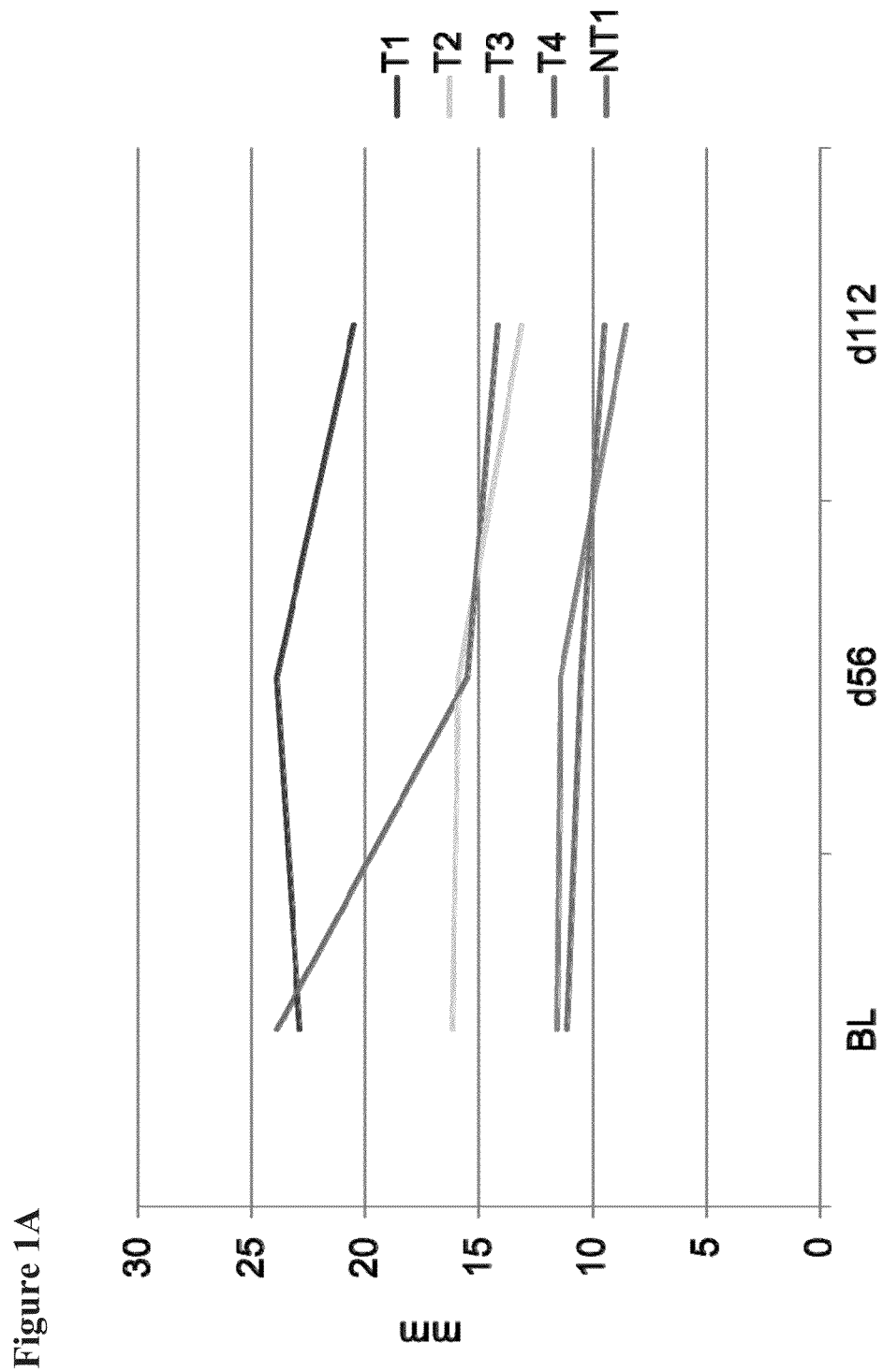
Figure 1B:
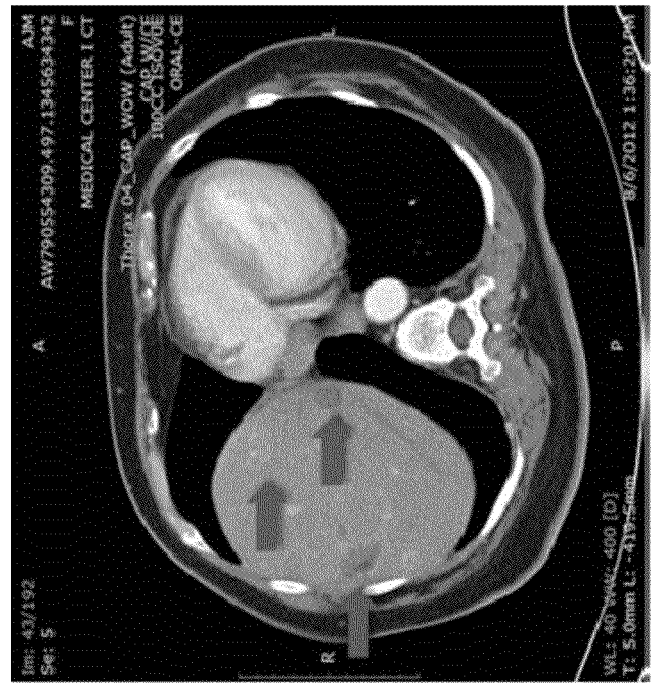
Figure 1B:
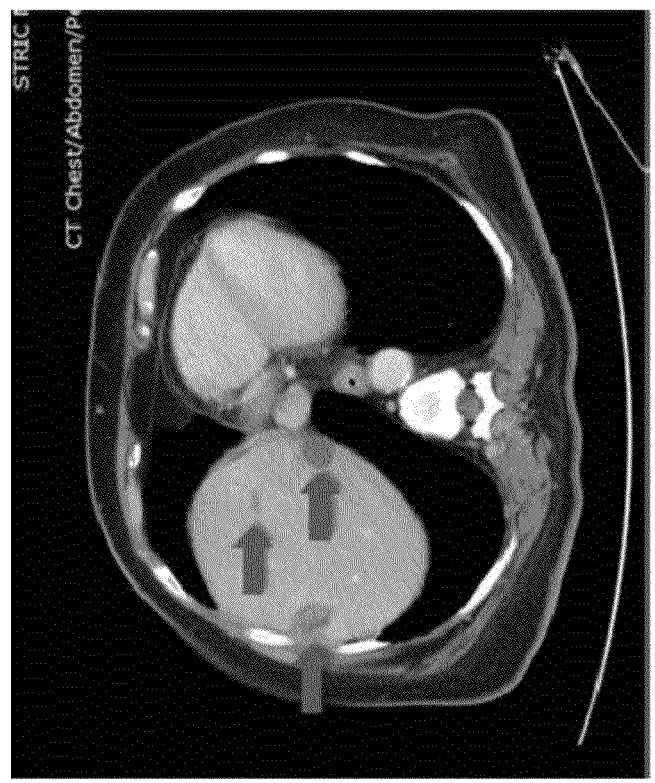
Figure 1C:
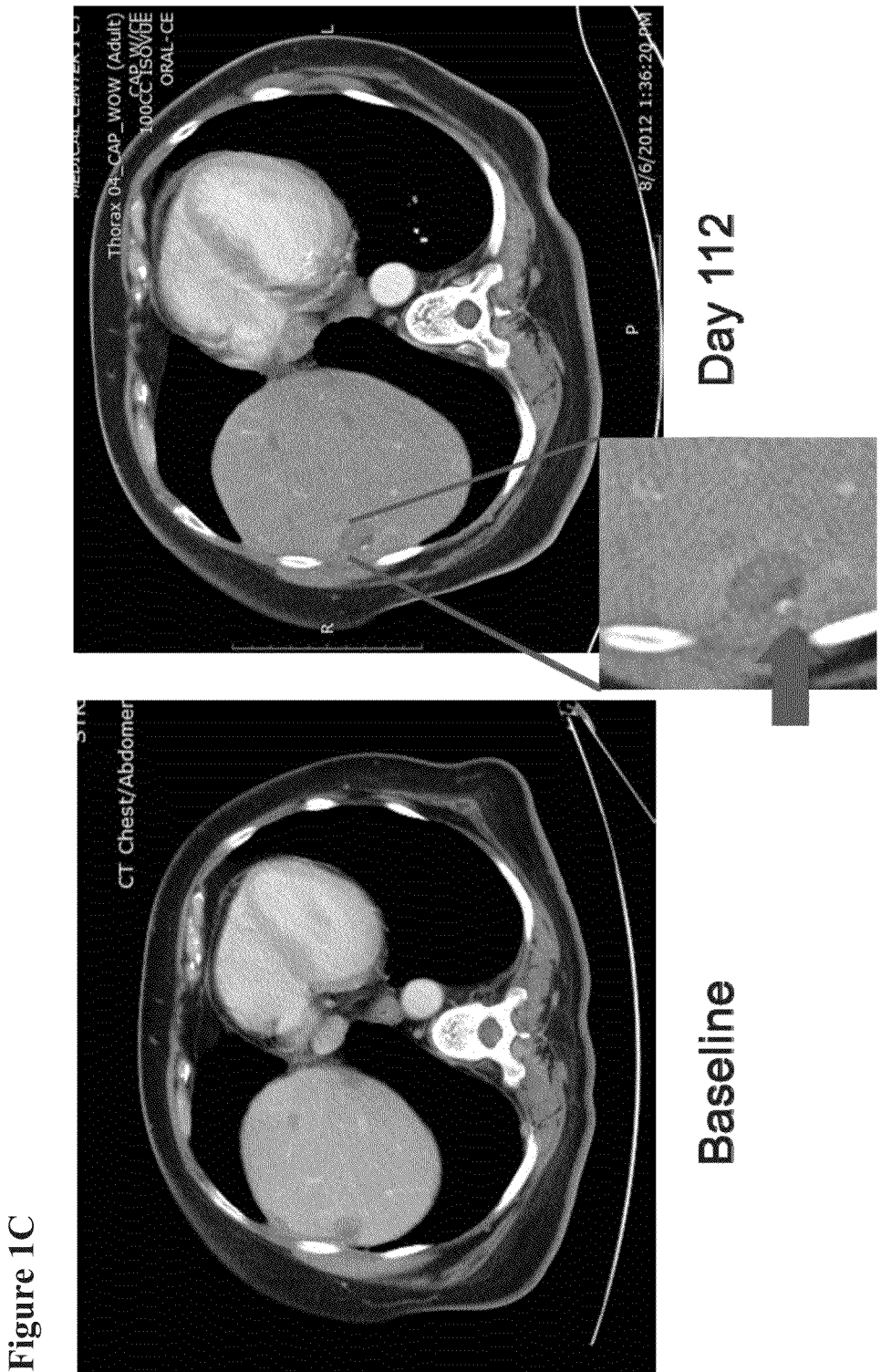

| | | |
|---|---|---|
| 5,786,158 A | 7/1998 | Artavanis-Tsakonas et al. |
| 5,789,195 A | 8/1998 | Artavanis-Tsakonas et al. |
| 5,814,511 A | 9/1998 | Chang et al. |
| 5,821,108 A | 10/1998 | Akashi et al. |
| 5,824,489 A | 10/1998 | Anderson et al. |
| 5,824,544 A | 10/1998 | Armentano et al. |
| 5,830,730 A | 11/1998 | German et al. |
| 5,834,598 A | 11/1998 | Lowman et al. |
| 5,849,535 A | 12/1998 | Cunningham et al. |
| 5,849,553 A | 12/1998 | Anderson et al. |
| 5,849,869 A | 12/1998 | Artavanis-Tsakonas et al. |
| 5,854,026 A | 12/1998 | Cunningham et al. |
| 5,856,441 A | 1/1999 | Artavanis-Tsakonas et al. |
| 5,859,535 A | 1/1999 | Liu |
| 5,861,832 A | 1/1999 | Nagaraj |
| 5,869,282 A | 2/1999 | Ish-Horowicz et al. |
| 5,872,154 A | 2/1999 | Wilson et al. |
| 5,876,978 A | 3/1999 | Willey et al. |
| 5,885,530 A | 3/1999 | Babson et al. |
| 5,885,808 A | 3/1999 | Spooner et al. |
| 5,914,108 A | 6/1999 | Tsukamoto et al. |
| 5,935,792 A | 8/1999 | Rubin et al. |
| 5,942,225 A | 8/1999 | Bruder et al. |
| 5,981,225 A | 11/1999 | Kochanek et al. |
| 5,986,170 A | 11/1999 | Subjeck |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,617 A | 11/1999 | Dick et al. |
| 6,001,557 A | 12/1999 | Wilson et al. |
| 6,004,528 A | 12/1999 | Bergstein |
| 6,004,924 A | 12/1999 | Ish-Horowicz et al. |
| 6,019,978 A | 2/2000 | Ertl et al. |
| 6,022,711 A | 2/2000 | Cunningham et al. |
| 6,033,908 A | 3/2000 | Bout et al. |
| 6,054,297 A | 4/2000 | Carter et al. |
| 6,080,912 A | 6/2000 | Bremel et al. |
| 6,083,904 A | 7/2000 | Artavanis-Tsakonas |
| 6,090,922 A | 7/2000 | Artavanis-Tsakonas et al. |
| 6,117,985 A | 9/2000 | Thomas et al. |
| 6,121,045 A | 9/2000 | McCarthy et al. |
| 6,127,526 A | 10/2000 | Blank |
| 6,135,653 A | 10/2000 | Aichi |
| 6,136,952 A | 10/2000 | Li et al. |
| 6,143,523 A | 11/2000 | Cunningham et al. |
| 6,149,902 A | 11/2000 | Artavanis-Tsakonas et al. |
| 6,156,305 A | 12/2000 | Brauker et al. |
| 6,159,750 A | 12/2000 | Edmonds |
| 6,180,370 B1 | 1/2001 | Queen et al. |
| 6,190,876 B1 | 2/2001 | Rubin et al. |
| 6,197,523 B1 | 3/2001 | Rimm et al. |
| 6,198,107 B1 | 3/2001 | Seville |
| 6,207,147 B1 | 3/2001 | Hiserodt et al. |
| 6,218,166 B1 | 4/2001 | Ravindranath et al. |
| 6,252,050 B1 | 6/2001 | Ashkenazi et al. |
| 6,262,025 B1 | 7/2001 | Ish-Horowicz et al. |
| 6,353,150 B1 | 3/2002 | Dick et al. |
| 6,379,925 B1 | 4/2002 | Kitajewski et al. |
| 6,380,362 B1 | 4/2002 | Watson et al. |
| 6,429,186 B1 | 8/2002 | Fuh et al. |
| 6,433,138 B1 | 8/2002 | Zimrin et al. |
| 6,433,155 B1 | 8/2002 | Umansky et al. |
| 6,448,229 B2 | 9/2002 | Teall et al. |
| 6,506,559 B1 | 1/2003 | Fire et al. |
| 6,537,775 B1 | 3/2003 | Tournier-Lasserve et al. |
| 6,583,115 B1 | 6/2003 | Kopchick et al. |
| 6,632,620 B1 | 10/2003 | Makarovskiy |
| 6,660,843 B1 | 12/2003 | Feige et al. |
| 6,664,098 B1 | 12/2003 | Sakano |
| 6,683,091 B2 | 1/2004 | Asberom et al. |
| 6,689,744 B2 | 2/2004 | Gao et al. |
| 6,703,221 B1 | 3/2004 | Chan et al. |
| 6,703,489 B1 | 3/2004 | Ish-Horowicz et al. |
| 6,713,206 B2 | 3/2004 | Markoski et al. |
| 6,716,974 B1 | 4/2004 | Maciag et al. |
| 6,756,511 B2 | 6/2004 | Castro Pineiro et al. |
| 6,894,522 B2 | 5/2005 | Averill et al. |
| 6,984,522 B2 | 1/2006 | Clarke et al. |
| 7,091,321 B2 | 8/2006 | Gillies et al. |
| 7,091,323 B2 | 8/2006 | Pan et al. |
| 7,115,360 B2 | 10/2006 | Clarke et al. |
| 7,115,653 B2 | 10/2006 | Baxter et al. |
| 7,118,853 B2 | 10/2006 | Botstein et al. |
| 7,138,370 B2 | 11/2006 | Oliner et al. |
| 7,211,404 B2 | 5/2007 | Lagasse et |
| 7,361,336 B1 | 4/2008 | Bergstein |
| 7,381,408 B2 | 6/2008 | Mezo et al. |
| 7,404,956 B2 | 7/2008 | Peters et al. |
| 7,413,873 B2 | 8/2008 | Waterman et al. |
| 7,442,778 B2 | 10/2008 | Gegg et al. |
| 7,507,406 B2 | 3/2009 | Gillies et al. |
| 7,608,453 B2 | 10/2009 | Cattaneo et al. |
| 7,635,530 B2 | 12/2009 | Kenis et al. |
| 7,659,116 B2 | 2/2010 | Buehring et al. |
| 7,662,931 B2 | 2/2010 | Gegg et al. |
| 7,682,607 B2 | 3/2010 | Rhee et al. |
| 7,713,526 B2 | 5/2010 | Rhee et al. |
| 7,723,477 B2 | 5/2010 | Gurney et al. |
| 7,803,370 B2 | 9/2010 | Nakamura et al. |
| 7,803,783 B2 | 9/2010 | Lee et al. |
| 7,803,913 B2 | 9/2010 | Dimitrov et al. |
| 7,867,705 B2 | 1/2011 | Wands et al. |
| 7,879,322 B2 | 2/2011 | Kneissel et al. |
| 7,947,277 B2 | 5/2011 | Ernst et al. |
| 7,982,013 B2 * | 7/2011 | Gurney et al. ............. 530/387.1 |
| 8,017,559 B2 | 9/2011 | Etzerodt et al. |
| 8,158,761 B2 | 4/2012 | Wands et al. |
| 8,410,061 B2 | 4/2013 | Williams et al. |
| 8,431,532 B2 | 4/2013 | Brennan et al. |
| 8,507,442 B2 * | 8/2013 | Gurney et al. ............. 514/19.3 |
| 8,551,789 B2 | 10/2013 | Gurney |
| 8,809,287 B2 | 8/2014 | Bafico et al. |
| 2002/0119565 A1 | 8/2002 | Clarke et al. |
| 2002/0137129 A1 | 9/2002 | Barnes et al. |
| 2002/0151487 A1 | 10/2002 | Rubin et al. |
| 2002/0169300 A1 | 11/2002 | Waterman et al. |
| 2002/0187502 A1 | 12/2002 | Waterman et al. |
| 2003/0032184 A1 | 2/2003 | Lagasse et al. |
| 2003/0044409 A1 | 3/2003 | Carson et al. |
| 2003/0064384 A1 | 4/2003 | Hung et al. |
| 2003/0086934 A1 | 5/2003 | Botstein et al. |
| 2003/0114387 A1 | 6/2003 | Castro et al. |
| 2003/0119029 A1 | 6/2003 | Glick et al. |
| 2003/0135044 A1 | 7/2003 | Asberom et al. |
| 2003/0139457 A1 | 7/2003 | Baxter et al. |
| 2003/0162709 A1 | 8/2003 | Rossi et al. |
| 2003/0165500 A1 | 9/2003 | Rhee et al. |
| 2003/0166543 A1 | 9/2003 | Williams et al. |
| 2003/0175877 A1 | 9/2003 | Baker et al. |
| 2003/0180784 A1 | 9/2003 | McCarthy et al. |
| 2003/0185829 A1 | 10/2003 | Koller et al. |
| 2003/0229023 A1 | 12/2003 | Oliner et al. |
| 2004/0023244 A1 | 2/2004 | Griffin et al. |
| 2004/0037815 A1 | 2/2004 | Clarke et al. |
| 2004/0038876 A1 | 2/2004 | Pepinsky et al. |
| 2004/0048249 A1 | 3/2004 | Tang et al. |
| 2004/0058217 A1 | 3/2004 | Ohlsen et al. |
| 2004/0058443 A1 | 3/2004 | Artavanis-Tsakonas et al. |
| 2004/0105862 A1 | 6/2004 | Pan et al. |
| 2004/0127474 A1 | 7/2004 | Dudek et al. |
| 2004/0171559 A1 | 9/2004 | Weissman et al. |
| 2004/0203003 A1 | 10/2004 | Rhee et al. |
| 2004/0214186 A1 | 10/2004 | Engelberg et al. |
| 2004/0219579 A1 | 11/2004 | Aziz et al. |
| 2004/0247593 A1 | 12/2004 | He et al. |
| 2005/0123900 A1 | 6/2005 | Dimitrov et al. |
| 2005/0130199 A1 | 6/2005 | Carson et al. |
| 2005/0272063 A1 | 12/2005 | Nakamura et al. |
| 2005/0288864 A1 | 12/2005 | Cattaneo et al. |
| 2006/0019256 A1 | 1/2006 | Clarke et al. |
| 2006/0019320 A1 | 1/2006 | Civenni et al. |
| 2006/0040883 A1 | 2/2006 | You et al. |
| 2006/0210867 A1 | 9/2006 | Kenis et al. |
| 2007/0072238 A1 | 3/2007 | Bhat |

(56) References Cited

U.S. PATENT DOCUMENTS

| | | | |
|---|---|---|---|
| 2007/0116701 A1 | 5/2007 | Gurney et al. | |
| 2007/0117751 A1 | 5/2007 | Gurney et al. | |
| 2007/0237770 A1 | 10/2007 | Lai et al. | |
| 2007/0238658 A1 | 10/2007 | Levin et al. | |
| 2008/0038272 A1 | 2/2008 | Buehring et al. | |
| 2008/0044423 A1 | 2/2008 | Cochrane et al. | |
| 2008/0075714 A1 | 3/2008 | Lee et al. | |
| 2008/0118432 A1 | 5/2008 | Bergstein et al. | |
| 2008/0194457 A1 | 8/2008 | Wands et al. | |
| 2008/0299136 A1 | 12/2008 | Ernst et al. | |
| 2009/0023905 A1 | 1/2009 | Askew et al. | |
| 2009/0074777 A1 | 3/2009 | Wands et al. | |
| 2009/0130113 A1 | 5/2009 | Kneissel et al. | |
| 2009/0163407 A1 | 6/2009 | Bafico et al. | |
| 2009/0186010 A1 | 7/2009 | Li et al. | |
| 2009/0234104 A1 | 9/2009 | Gegg et al. | |
| 2009/0263400 A1 | 10/2009 | Urdea et al. | |
| 2009/0304695 A1 | 12/2009 | He et al. | |
| 2010/0104574 A1* | 4/2010 | Gurney et al. | 424/139.1 |
| 2011/0020368 A1* | 1/2011 | Hynes | 424/172.1 |
| 2011/0224243 A1 | 9/2011 | Rethore | |
| 2011/0237514 A1 | 9/2011 | Kakitani et al. | |
| 2011/0318341 A1 | 12/2011 | Gurney et al. | |
| 2012/0003222 A1 | 1/2012 | Brennan et al. | |
| 2012/0027778 A1 | 2/2012 | Gurney | |
| 2013/0252326 A1 | 9/2013 | Gurney et al. | |
| 2013/0295105 A1 | 11/2013 | Gurney et al. | |
| 2013/0295106 A1 | 11/2013 | Gurney et al. | |
| 2014/0105917 A1 | 4/2014 | Gurney | |

FOREIGN PATENT DOCUMENTS

| | | |
|---|---|---|
| EP | 0 662 827 A1 | 4/2002 |
| EP | 1 576 119 A | 9/2005 |
| EP | 1 805 221 B1 | 4/2006 |
| EP | 1 805 519 | 7/2007 |
| EP | 1805221 A1 | 7/2007 |
| WO | WO 90/08832 A1 | 8/1990 |
| WO | WO 92/19734 A1 | 11/1992 |
| WO | WO 94/07474 A1 | 4/1994 |
| WO | WO 94/10300 A1 | 5/1994 |
| WO | WO 97/01571 A1 | 1/1997 |
| WO | WO 97/30731 A2 | 8/1997 |
| WO | WO 97/37004 A1 | 10/1997 |
| WO | WO 98/05775 A1 | 2/1998 |
| WO | WO 98/45434 A1 | 10/1998 |
| WO | WO 98/51799 A1 | 11/1998 |
| WO | WO 98/57621 A1 | 12/1998 |
| WO | WO 99/02685 A1 | 1/1999 |
| WO | WO 00/06726 A2 | 2/2000 |
| WO | WO 00/09675 A1 | 2/2000 |
| WO | WO 00/12738 A1 | 3/2000 |
| WO | WO 00/52143 A2 | 9/2000 |
| WO | WO 01/26643 A1 | 4/2001 |
| WO | WO 01/98354 A2 | 12/2001 |
| WO | WO 01/98537 A2 | 12/2001 |
| WO | WO 02/00576 A1 | 1/2002 |
| WO | WO 02/12447 A2 | 2/2002 |
| WO | WO 02/18544 A2 | 3/2002 |
| WO | WO 02/078703 A1 | 10/2002 |
| WO | WO 02/088081 A2 | 11/2002 |
| WO | WO 02/092635 A2 | 11/2002 |
| WO | WO 02/102978 A2 | 12/2002 |
| WO | WO 03/000893 A2 | 1/2003 |
| WO | WO 03/004045 A2 | 1/2003 |
| WO | WO 03/042246 A2 | 5/2003 |
| WO | WO 03/047316 A1 | 6/2003 |
| WO | WO 03/050502 A2 | 6/2003 |
| WO | WO 03/062273 A2 | 7/2003 |
| WO | WO 03/088964 A1 | 10/2003 |
| WO | WO 2004/001004 A2 | 12/2003 |
| WO | WO 2004/020668 A2 | 3/2004 |
| WO | WO 2004/032838 A2 | 4/2004 |
| WO | WO 2004/042028 A2 | 5/2004 |
| WO | WO 2004/053069 A2 | 6/2004 |
| WO | WO 2004/065545 A2 | 8/2004 |
| WO | WO 2004/073657 A2 | 9/2004 |
| WO | WO 2004/101739 A2 | 11/2004 |
| WO | WO 2005/001025 A2 | 1/2005 |
| WO | WO 2005/004912 A1 | 1/2005 |
| WO | WO 2005/005601 A2 | 1/2005 |
| WO | WO 2006/034328 A2 | 3/2006 |
| WO | WO 2006/036173 A2 | 4/2006 |
| WO | WO 2006/036175 A2 | 4/2006 |
| WO | WO 2006/040163 A1 | 4/2006 |
| WO | WO 2006/055635 A2 | 5/2006 |
| WO | WO 2006/056340 A2 | 6/2006 |
| WO | WO 2006/130076 A1 | 12/2006 |
| WO | WO 2007/053577 A2 | 5/2007 |
| WO | WO 2007/096149 A1 | 8/2007 |
| WO | WO 2007/133250 A2 | 11/2007 |
| WO | WO 2007/134876 A2 | 11/2007 |
| WO | WO 2007/142711 A2 | 12/2007 |
| WO | WO 2007/148417 A1 | 12/2007 |
| WO | WO 2008/031009 A2 | 3/2008 |
| WO | WO 2008/057459 A2 | 5/2008 |
| WO | WO 2008/061020 A2 | 5/2008 |
| WO | WO 2009/042971 A2 | 4/2009 |
| WO | WO 2009/118300 A1 | 10/2009 |
| WO | WO 2010/031979 A1 | 3/2010 |
| WO | WO 2010/037041 A2 | 4/2010 |
| WO | WO 2010/038756 A1 | 8/2010 |
| WO | WO-2011088123 A2 | 7/2011 |
| WO | WO-2011101409 A1 | 8/2011 |
| WO | WO-2011112678 A1 | 9/2011 |
| WO | WO 2011/123785 A3 | 10/2011 |
| WO | WO 2012/003189 A1 | 1/2012 |
| WO | WO 2012/006027 A1 | 1/2012 |
| WO | WO 2012/058393 A2 | 5/2012 |
| WO | WO 2014/121196 A1 | 8/2014 |

OTHER PUBLICATIONS

Austin, T.W., et al., "A role for the Wnt gene family in hematopoiesis: expansion of multilineage progenitor cells," *Blood* 89:3624-3635 (1997).

Ayyanan, A., et al., "Increased Wnt signaling triggers oncogenic conversion of human breast epithelial cells by a Notch-dependent mechanism," *PNAS* 103:3799-3804, the National Academy of Sciences, Washington, DC, U.S.A. (2006).

Bafico, A., et al., "An autocrine mechanism for constitutive Wnt pathway activation in human cancer cells," *Cancer Cell* 6:497-506 (2004).

Bafico, A., et al., "Interaction of Frizzled Related Protein (FRP) with Wnt Ligands and the Frizzled Receptor Suggests Alternative Mechanisms for FRP Inhibition of Wnt Signaling," *J. Biol. Chem.* 274:16180-16187, The American Society for Biochemistry and Molecular Biology, Inc., Bethesda, MD, U.S.A. (1999).

Barker, N. and Clevers, H., "Mining the Wnt pathway for cancer therapeutics," *Nature Reviews/Drug Discovery* 5:997-1014, Nature Publishing Group, New York, NY, U.S.A. (2006).

Battula, V.L., et al., "Prospective isolation and characterization of mesenchymal stem cells from human placenta using a frizzled-9-specific monoclonal antibody," *Differentiation* 76:326-336, International Society of Differentiation, Higgannum, CT, U.S.A. (2008).

Benhamouche, S., et al.,"Apc Tumor Suppressor Gene Is the "Zonation-Keeper" of Mouse Liver," *Developmental Cell* 10:759-770, Elsevier Inc., Amsterdam, The Netherlands (2006).

Bhanot, P., et al., "A new member of the frizzled family from *Drosophila* functions as a Wingless receptor," *Nature* 382:225-230, Nature Publishing Group, New York, NY, U.S.A. (1996).

Bienz, M., "β-Catenin: A Pivot between Cell Adhesion and Wnt Signalling," *Current Biology* 15:R64-R67, Cell Press, St. Louis, MO, U.S.A. (2004).

Booy, E.P., et al., "Monoclonal and bispecific antibodies as novel therapeutics," *Arch. Immunol. Ther. Exp.* 54:85-101, Birkhäuser publications, Basel, Switzerland (2006).

Brabletz, T., et al., "Variable β-catenin expression in colorectal cancers indicates tumor progression driven by the tumor environment," *PNAS* 98(18):10356-10361 (2001).

(56) References Cited

OTHER PUBLICATIONS

Brennan, K.R. and Brown, A.M.C., "Wnt Proteins in Mammary Development and Cancer," *J. Mammary Gland Biol. Neoplasia* 9(2):119-131, Kluwer Academic/Plenum Publishers (2004).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Bio.* 111:2129-2138, The Rockefeller University Press, New York, NY, U.S.A. (1990).

Cadigan, K.M. and Nusse, R., "Wnt signaling: a common theme in animal development," *Genes & Development* 11:3286-3305, Cold Spring Harbor Laboratory Press (1997).

Caldwell, G.M., et al., "The Wnt Antagonist sFRP1 in Colorectal Tumorigenesis," *Cancer Res* 64:883-888, American Association for Cancer Research, Philadelphia, PA, U.S.A. (2004).

Chan, E. F., et al., "A common human skin tumour is caused by activating mutations in β-catenin," *Nature Genetics* 21(4): 410-413 (1999).

Chen, Y., et al., "Selection and Analysis of an Optimized Anti-VEGF Antibody: Crystal Structure of an Affinity-matured Fab in Complex with Antigen," *Journal of Molecular Biology* 293(4): 865-881, Academic Press, England (1999).

Clevers, H., "Axin and hepatocellular carcinomas," *Nature Genetics* 24:206-208, Nature Publishing Group, New York, NY, U.S.A. (2000).

Daniel, C., et al., "Mapping of Linear Antigenic Sites on the S Glycoprotein of a Neurotropic Murine Coronavirus with Synthetic Peptides: A Combination of Nine Prediction Algorithms Fails to Identify Relevant Episodes and Peptide Immunogenicity Is Drastically Influenced by the Nature of the Protein Carrier," *Virology* 202(2):540-549, Elsevier Inc., The Netherlands (1994).

Dann, C.E., et al., "Insights into Wnt binding and signalling from the structures of two Frizzled cysteine-rich domains," *Nature* 412:86-90, Nature Publishing Group, New York, NY, U.S.A. (2001).

Datta, D.V., "Viral Hepatitis," *Jr. Asso. Phys. Ind.* 25(5):325-330, Association of Physicians of India, Mumbai, India (1977).

Davidson, G., et al., "Casein kinase 1γ couples Wnt receptor activation to cytoplasmic signal transduction," *Nature* 438:867-872, Nature Publishing Group, U.S.A. (2005).

De Lau, W, and Clevers, H., "LEF1 turns over a new leaf," *Nature Genetics* 28:3-4, Nature Publishing Group, NY, U.S.A. (2001).

De Pascalis, R., et al., "Grafting of Abbreviated Complementarity-Determining Regions Containing Specificity-Determining Residues Essential for Ligand Contact to Engineer a Less Immunogenic Humanized Monoclonal Antibody," *Journal of Immunology* 169:3076-3084 (2002).

Dealmeida, V.I., et al., "The Soluble Wnt Receptor Frizzled8CRD-hFc Inhibits the Growth of Teratocarcinomas In vivo," *Cancer Res* 67(11):5371-5379, American Association for Cancer Research (Jun. 1, 2007).

Dorvillius, Mylene et al., "Targeting of Human Brest Cancer by a Bispecific Antibody Directed against Two Tumour-Associated Antigens: ErbB-2 and Carcinoembryonic Antigen," *Tumor Biology*, Nov. 2002, pp. 337-347, vol. 23, No. 6, S. Karger Medical and Scientific Publishers, Basel.

Fillmore et al., "Human breast cancer cell lines contain stem-like cells that self-renew, give rise to phenotypically diverse progeny and survive chemotherapy" Breast Cancer Res, 2008, voi10R25: 1-13.

Finch, P.W., et al., "Purification and molecular cloning of a secreted, Frizzled-related antagonist of Wnt action," *PNAS* 94:6770-6775, the National Academy of Sciences, Washington, DC, U.S.A. (1997).

Fogel, M. et al.,"L1 expression as a predictor of progression and survival in patients with uterine and ovarian carcinomas," *The Lancet* 362:869-875, Elsevier Inc., Amsterdam, The Netherlands (2003).

Fukukawa, C., et al., "Radioimmunotherapy of human synovial sarcoma using a monoclonal antibody against FZD10," *Cancer Sci.* 99:432-440, Wiley-Blackwell, Hoboken, NJ, U.S.A. (2008).

Gavert, N. et al., "L1, a novel target of β-catenin signaling, transforms cells and is expressed at the invasive front of colon cancers," *Journal of Cell Biology* 168(4):633-642, The Rockefeller University Press (Feb. 14, 2005).

Gazit A. et al., "Human frizzles 1 interacts with transforming Wnts to transducer a TCF dependent transcriptional response," *Ocogene* 18:5959-5966, Stockton Press (1999).

Golan, T., et al., "The Human Frizzled 6 (HFz6) Acts as a Negative Regulator of the Canonical Wnt. β-Catenin Signaling Cascade," *J. Biol. Chem.* 279:14879-14888, American Society for Biochemistry and Molecular Biology (Apr. 2004).

Greenspan, N.S. and Di Cera, E., "Defining epitopes: It's not as easy as it seems," *Nature Biotechnology* 17:936-937, Nature Publishing Group, United States (1999).

Gregorieff, A., et al ., "Expression Pattern of Wnt Signaling Components in the Adult Intestine," *Gastroenterology* 129:626-638, American Gastroenterological Association (Aug. 2005).

Greiner, D.L., et al., "SCID Mouse Models of Human Stem Cell Engraftment," *Stem Cells* 16:166-177, AlphaMed Press (1998).

Guo, H.H., et al., "Protein tolerance to random amino acid change," *PNAS,* 101:9205-9210, the National Academy of Sciences, Washington, DC, U.S.A. (2004).

Harada, N., et al., "Intestinal polyposis in mice with a dominant stable mutation of the β-catenin gene," *EMBO J.* 18:5931-5942, Oxford University Press, New York, NY U.S.A. (1999).

He, X. and Axelrod, J.D., "A WNTer wonderland in Snowbird," *Development* 133:2597-2603, The Company of Biologists, Cambridge, UK, U.S.A. (2006).

Hering H et al., "Direct interaction of Frizzled-1,-2,-4 and-7 with PDZ domains of PSD-95" *FEBS Letters* 521:185-189, Elsevier, Netherlands (2002).

Hicks, et al., "Fringe differentially modulates Jagged1 and Delta1 signalling through Notch1 and Notch2" *Nat Cell Bioi.* (8):515-520 (2000).

Hill, R. P., "Identifying cancer stem cells in solid tumors: case not proven" *Cancer Research* 66:1891-1896, American Association for Cancer Research (2006).

Holcombe, R.F., et al., "Expression of Wnt ligands and Frizzled receptors in colonic mucosa and in colon carcinoma," *J. Clin. Pathol: Mol. Pathol.* 55:220-226, BMJ Publishing Group (2002).

Holmes, E.H., "PSMA specific antibodies and their diagnostic and therapeutic use," *Exp. Opin. Invest. Drugs* 10:511-519, Informa Pharmaceutical Science, London, UK (2001).

Hsieh, A.C. and Moasser, M.M., "Targeting HER proteins in cancer therapy and the role of the non-target HER3," *British J. Cancer* 97:453-457, Cancer Research UK, England (2007).

Hsieh, J-C., et al., "Biochemical characterization of Wnt-Frizzled interactions using a soluble, biologically active vertebrate Wnt protein," *Proc. Natl. Acad. Sci. U.S.A.* 96(7):3546-3551, National Academy of Sciences, United States (Mar. 1999).

Huang, H-C. and Klein, P.S., "The Frizzled family: receptors for multiple signal transduction pathways," *Genome Biol.* 5:234.1-234.7, BioMed Central Ltd. (Jun. 2004).

Ilyas, M., Wnt signalling and the mechanistic basis of tumour development, *J Pathology* 205:130-144 (2005).

International Search Report for International Patent Application No. PCT/US11/30950, ISA/US, Alexandria, Virginia 22313-1450, mailed on Oct. 18, 2011.

Ishikawa, T., et al., "Mouse Wnt receptor gene Fzd5 is essential for yolk sac and placental angiogenesis," *Development* 128:25-33, Company of Biologists Limited (2001).

Ishitani, T., et al., "The TAK1-NLK Mitogen-Activated Protein Kinase Cascade Functions in the Wnt-5a/Ca$^{2+}$ Pathway to Antagonize Wnt/β-Catenin Signaling," *Mol. Cell. Biol.* 23:131-139, American Society for Microbiology (2003).

Jamieson, C.H.M., et al., "Granulocyte-Macrophage Progenitors as Candidate Leukemic Stem Cells in Blast-Crisis CML," *N. Engl. J. Med.* 351:657-667, Massachusetts Medical Society, Waltham, MA, U.S.A. (2004).

Janssens, N., et al., "Alteration of Frizzled Expression in Renal Cell Carcinoma," *Tumor Biol.* 25:161-171, Karger (Jul. 2004).

Jiang, B., et al., "A Novel Peptide Isolated from a Phage Display Peptide Library with Trastuzumab Can Mimic Antigen Epitope of

(56) References Cited

OTHER PUBLICATIONS

HER-2," *J. Biol. Chem.* 280:4656-4662, The American Society for Biochemistry and Molecular Biology, Inc., Bethesda, MD, U.S.A. (2005).
Joesting, M.S., et al., "Identification of SFRP1 as a Candidate Mediator of Stromal-to-Epithelial Signaling in Prostate Cancer," *Cancer Res.* 65:10423-10430, the American Association for Cancer Research, Philadelphia, PA, U.S.A. (2005).
Johnson, M.L., et al., "LRP5 and Wnt Signaling: A Union Made for Bone," *J. Bone Mineral Res.* 19:1749-1757, American Society for Bone and Mineral Research, Washington DC, U.S.A. (2004).
Jones, D.T., "Critically assessing the state-of-the-art in protein structure prediction," *Pharmacogenomics Journal* 1:126-134, Nature Publishing Group, New York, NY, U.S.A. (2001).
Jonsson, M., et al., "Involvement of adenomatous polyposis coli (APC)/β-catenin signalling in human breast cancer," *Eur. J. Cancer* 36: 242-248 (2000).
Katoh, M. and Katoh, M., "WNT Signaling Pathway and Stem Cell Signaling Network," *Clin. Cancer Res.* 13:4042-4045, the American Association for Cancer Research, Philadelphia, PA, U.S.A. (2007).
Katoh, M. and Katoh, M., "STAT3-induced WNT5A signaling loop in embryonic stem cells, adult normal tissues, chronic persistent inflammation, rheumatoid arthritis and cancer (Review)," *Int. J. Mol. Med.* 19:273-278, D.A. Spandidos (Feb. 2007).
Katoh, M., "Molecular Cloning and Characterization of MFRP, a Novel Gene Encoding a Membrane-Type Frizzled-Related Protein," *Biochemical and Biophysical Research Communications* 282:116-123, Academic Press, United States (2001).
Kawakami, Y., et al., "Involvement of Frizzled-10 in Wnt-7a signaling during chick limb development," *Dev. Growth Differ.* 42:561-569, Blackwell Publishing (2000).
Kawano, Y. and Kypta, R., "Secreted antagonists of the Wnt signaling pathway," *Journal of Cell Science* 116:2627-2634, The Company of Biologists Ltd, London, UK (2003).
Kirikoshi et al., "Expression of WNT10A in human cancer," *Int J Oncology* 19:997-1001 (2001).
Kirikoshi, H., et al., "Expression profiles of 10 members of Frizzled gene family in human gastric cancer," *Int. J. Oncol.* 19:767-771, D.A. Spandidos (2001).
Kirikoshi, H., et al., "Molecular Cloning and Characterization of Human Frizzled-4 on Chromosome 11q14-q21," *Biochem. Biophys. Res. Commun.* 264:955-961, Academic Press (1999).
Kirikoshi, H., et al., "Up-regulation of Frizzled-7 (FZD7) in human gastric cancer," *Int. J. Oncol.* 19:111-115, D.A. Spandidos (2001).
Kirikoshi, H., et al., "Molecular Cloning and Genomic Structure of Human Frizzled-3 at Chromosome 8p21," *Biochemical and Biophysical Research Communications* 271:8-14, Academic Press, United States (2000).
Kirkin, A.F., et al., "Melanoma-associated antigens recognized by cytotoxic T lymphocytes," *APMIS* 106:665-679, AMPIS, Denmark (1998).
Klaus, A. and Birchmeier, W., "Wnt signaling and its impact on development and cancer," *Nature Reviews/Cancer* 8:387-398, Nature Publishing Group, New York, NY, U.S.A. (May 2008).
Kobielak, A. and Fuchs, E., "α-Catenin: at the junction of intercelullar adhesion and actin dynamics," *Nat Rev Mol Cell Bioi.* 5:614-25 (2004).
Koike, J., et al., "Molecular Cloning of Frizzled-10, a Novel Member of the Frizzled Gene Family," *Biochem. Biophys. Res. Commun.* 262:39-43, Academic Press (1999).
Korinek, V., et al., "Two Members of the Tcf Family Implicated in Wnt/β-catenin Signaling during Embryogenesis in the Mouse," *Mol Cell Bioi* 18: 1248-1256, American Society for Microbiology, United States (1998).
Kuhnert, F., et al., "Essential requirement for Wnt signaling in proliferation of adult small intestine and colon revealed by adenoviral expression of Dickkopf-1," *PNAS* 101:266-271, the National Academy of Sciences, Washington, DC, U.S.A. (2004).
Lazar, E., et al., "Transforming Growth Factor α: Mutation of Aspartic Acid 47 and Leucine 48 Results in Different Biological Activities," *Mol. Cell. Bio.* 8:1247-1252, American Society for Microbiology, Washington, DC, U.S.A. (1988).
Lee, H.X., et al., "Embryonic Dorsal-Ventral Signaling: Secreted Frizzled-related Proteins as Inhibitors of Tolloid Proteinases," *Cell* 124:147-159, Elsevier Inc., Amsterdam, The Netherlands (Jan. 13, 2006).
Li, Y., et al., "LRP6 expression promotes cancer cell proliferation and tumorigenesis by altering α-catenin subcellular distribution," *Oncogene* 23:9129-9135, Nature Publishing Group, New York, NY, U.S.A. (2004).
Li, Y., et al., "The Gene for Autosomal Dominant Familial Exudative Vitreoretinopathy (Criswick-Schepens) on the Long Arm of Chromosome 11," *Am. J. Opthamol.* 113:712-713, Elsevier Inc., Amsterdam, The Netherlands (1992).
Lin, S.Y., et al., "β-catenin, a novel prognostic marker for breast cancer: its roles in cyclin D1 expression and cancer progression," *Proc. Natl. Acad. Sci. USA* 97:4262-4266, (2000).
Liu, S., et al., "Interaction of hedgehog and notch pathways, and Bmi-1 in the regulation of human breast stem cell self-renewal" *Proc Amer Associ Cancer Res* 46: Apr. 2005.
Li, Y., et al., "Evidence that transgenes encoding components of the Wnt signaling pathway preferentially induce mammary cancers from progenitor cells." Proc. Nail. Acad. Sci. USA, 100:15853-8 (2003).
Lo, P.-K., et al., "Epigenetic Suppression of Secreted Frizzled Related Protein 1 (SFRP1) Expression in Human Breast Cancer," *Cancer Biology & Therapy* 5:e1-e6, Landes Bioscience, Austin, TX, U.S.A. (2006).
Lodygin, D., et al., "Functional Epigenomics Identifies Genes Frequently Silenced in Prostate Cancer," *Cancer Res.* 65:4218-4227, the American Association for Cancer Research, Philadelphia, PA, U.S. A. (2005).
Lu, D., et al., "Repression of β-catenin function in malignant cells by nonsteroidal antiinflammatory drugs," *PNAS* 102:18567-18571, the National Academy of Sciences, Washington, DC, U.S.A. (Dec. 20, 2005).
Lyons, J.P., et al., "Wnt-4 activates the canonical β-catenin-mediated Wnt pathway and binds Frizzled-6 CRD: functional implications of Wnt/β-catenin activity in kidney epithelial cells," *Exp. Cell Res.* 298:369-387, Elsevier Inc., United States (2004).
Mazieres, J., et al., "Wnt signaling in lung cancer," *Cancer Letters* 222:1-10, Elsevier Inc., Amsterdam, The Netherlands (2005).
Miller, J.R., et al., "Mechanism and function of signal transduction by the Wnt/β-catenin and Wnt/$Ca^{2+}$ pathways," *Oncogene* 18:7860-7872, Nature Publishing Group (1999).
Milovanovic, T., et al., "Expression of Wnt genes and frizzled 1 and 2 receptors in normal breast epithelium and infiltrating breast carcinoma," *Int. J. Oncol.* 25:1337-1342, D.A. Spandidos (Nov. 2004).
Moon, R.T., "Wnt/β-Catenin Pathway," *Sci. STKE* 271:1-3, American Association for the Advancement of Science, Washington, DC, 20005 (2005).
Morrell, N.T., et al., "Liposomal Packaging Generates Wnt protein with In Vivo Biological Activity," *PLoS One* 3:1-9, e2930, Public Library of Science (PLoS), San Francisco, CA, U.S.A. (Aug. 2008).
Murdoch, B., et al., "Wnt-5A augments repopulating capacity and primitive hemaropoietic development of human blood stem cells in vivo," *PNAS* 100:3422-3427, the National Academy of Sciences, Washington, DC, U.S.A. (2003).
Nagayama, S., et al., "Therapeutic potential of antibodies against FZD10, a cell-surface protein, for synovial sarcomas," *Oncogene* 24:6201-6212, Nature Publishing Group (Sep. 2005).
Nunnally, A.P. and Parr, B.A., "Analysis of Fz10 expression in mouse embryos," *Dev. Genes Evol.* 214:144-148, Springer-Verlag (Mar. 2004).
Nusse, R., et al., A new nomenclature for int-1 and related genes: the Wnt gene family. Cell 64, 231 (1991).
Nusse, R., "The Wnt gene family in tumorigenesis and in normal development," *Journal of Steroid Biochemistry & Molecular Biology* 43: 9-12 (1992).
Olson, D.J. and Gibo, D.M., "Antisense wnt-5a Mimics wnt-1-Mediated C57MG Mammary Epithelial Cell Transformation," *Exp. Cell Res.* 241:134-141, Elsevier Inc., Amsterdam, The Netherlands (1998).

(56) References Cited

OTHER PUBLICATIONS

Oshima, H., et al., Morphological and Molecular Processes of Polyp Formation in APC$^{\Delta716}$ Knockout Mice, *Cancer Res.* 57:1644-1649, The American Association for Cancer Research, Philadelphia, PA, U.S.A. (1997).
Patel, S., et al., "Glycogen synthase kinase-3 in insulin and Wnt signalling: a double-edged sword?" *Biochemical Society Transactions* 32:803-808, Portland Press Ltd., London, UK (2004).
Pinto, D. and Clevers, H., "Wnt control of stem cells and differentiation in the intestinal epithelium," *Experimental Cell Research* 306:357-363, Elsevier Inc., Amsterdam, The Netherlands (2005).
Polakis, P., "Wnt signaling and cancer," *Genes & Development* 14:1837-1851, Cold Spring Harbor Laboratory Press, Woodbury NY, U.S.A. (2000).
Radtke, F. and Clevers, H., "Self-Renewal and Cancer of the Gut: Two Sides of a Coin," *Science* 307:1904-1909, The Company of Biologists Ltd, London, UK (2005).
Reya, T., et al., "Wnt Signaling Regulates B Lymphocyte Proliferation through a LEF-1 Dependent Mechanism," *Immunity* 13:15-24 (2000).
Reya T., et al., "Stem cells, cancer, and cancer stem cells." *Nature* 414(6859):105-111, Nature Publishing Group, England (2001).
Reya, T. and Clevers, H., "Wnt signalling in stem cells and cancer," *Nature* 434:843-850, Nature Publishing Group, New York, NY, U.S. A. (2005).
Reya, T., et al., "A role for Wnt signalling in self-renewal of haematopoietic stem cells," *Nature* 423:409-414, Nature Publishing Group, New York, NY, U.S.A. (2003).
Rhee, C.S., et al., "Wnt and frizzled receptors as potential targets for immunotherapy in head and neck squamous cell carcinomas," *Oncogene* 21:6598-6605, Nature Publishing Group (2002).
Sagara, N., et al., "Molecular Cloning, Differential Expression, and Chromosomal Localization of Human Frizzled-1, Frizzled-2, and Frizzled-7," *Biochem. Biophys. Res. Commun.* 252:117-122, Academic Press (1998).
Saitoh, T., et al., "Frequent up-regulation of WNT5A mRNA in primary gastric cancer" *Inti J Mol Med* 9:515-519 (2002).
Saitoh, T., et al., "Molecular cloning and characterization of human Frizzled-8 gene on chromosome 10p11.2," *Int. J. Oncol.* 18:991-996, D.A. Spandidos (2001).
Saitoh, T., et al., "Up-regulation of Frizzled-10 (FZD10) by β-estradiol in MCF-7 cells and by retinoic acid in NT2 cells," *Int. J. Oncol.* 20:117-120, D.A. Spandidos (2002).
Sala, C.F., et al., "Identification, Gene Structure, and Expression of Human Frizzled-3 (FZD3)," *Biochem. Biophys. Res. Commun.* 273:27-34, Academic Press (2000).
Saldanha, J., et al., "Identification of a Frizzled-like cysteine rich domain in the extracellular region of developmental receptor tyrosine kinases," *Protein Science* 7:1632-1635, The Protein Society, United States (1998).
Saneyoshi, T., et al., "The Wnt/calcium pathway activates NF-AT and promotes ventral cell fate in Xenopus embryos," *Nature* 417:295-299, Nature Publishing Group, New York, NY, U.S.A. (2002).
Sagara, N., et al., "FZD4S, a Splicing Variant of Frizzled-4, Encodes a Soluble-Type Positive Regulator of the WNT Signaling Pathway," *Biochem. Biophys. Res. Commun.* 282:750-756, Academic Press, United States (2001).
Schweizer, L. and Varmus, H., "Wnt/Wingless signaling through β-catenin requires the function of both LRP/Arrow and frizzled classes of receptors," *BMC Cell Biology* 4, 11 pages, BioMed Central Ltd., London, UK (2003).
Seménov, M., et al., "SOST Is a Ligand for LRP5/LRP6 and a Wnt Signaling Inhibitor," *The Journal of Biological Chemistry* 280:26770-26775, American Society for Biochemistry and Molecular Biology, Bethesda, MD, U.S.A. (2005).
Sen, M., et al., "Blockade of Wnt-5A/Frizzled 5 Signaling Inhibits Rheumatoid Synoviocyte Activation," *Arthritis Rheum.* 44:772-781, Wiley-Liss, Inc. (2001).
Shalaby, M.R., et al., "Bispecific HER X CD3 Antibodies Enhance T-Cell Cytotoxicity in Vitro and Localize to HER2-Overexpressing Xenografts in Nude Mice," *Clin. Imm. and Immunopath,* 74:185-192, Elsevier Inc., Amsterdam, The Netherlands 1995.
Skolnick, J. and Fetrow, J.S., "From genes to protein structure and function: novel applications of computational approaches in the genomic era," *Trends in Biotechnology* 18:34-39, Elsevier Inc., Amsterdam, The Netherlands (2000).
Sperger, J.M., et al., "Gene expression patterns in human embryonic stem cells and human pluripotent germ cell tumors," *PNAS* 23:13350-13355, The National Academy of Sciences of the USA, United States (2003).
Suresh M.R., et al., "Advantages of bispecific hybridomas in one-step immunocytochemistry and immunoassays," *Neurobiology, Proceedings of the National Academy of Sciences of the United States of America,* Oct. 1986, pp. 7989-7993, vol. 83, USA.
Suzuki, H., et al., "A genomic screen for genes unregulated by demethylation and histone deacetylase inhibition in human colorectal cancer," *Nature Genetics* 31:141-149, Nature Publishing Group, New York, NY, U.S.A. (Jun. 2002).
Suzuki, H., et al., "Epigenetic inactivation of SFRP genes allows constitutive WNT signaling in colorectal cancer," *Nature Genetics* 36:417-422, Nature Publishing Group, New York, NY, U.S.A. (Apr. 2004).
Suzuki, H., et al., "Frequent epigenetic inactivation of Wnt antagonist genes in breast cancer," *British Journal of Cancer* 98:1147-1156, Nature Publishing Group, New York, NY, U.S.A. (2008).
Tanaka, S., et al., "A novel frizzled gene identified in human esophageal carcinoma mediates APC/β-catenin signals," *Proc. Natl. Acad. Sci. U.S.A.* 95:10164-10169, National Academy of Sciences (1998).
Terasaki, H., et al., "Frizzled-10, up-regulated in primary colorectal cancer, is a positive regulator of the WNT-β-catenin-TCF signaling pathway," *Int. J. Mol. Med.* 9:107-112, D.A. Spandidos (2002).
Tokuhara, M., et al., "Molecular Cloning of Human Frizzled-6," *Biochem. Biophys. Res. Commun.* 243:622-627, Academic Press (1998).
Topol, L., et al., "Wnt-5a inhibits the canonical Wnt pathway by promoting GSK-3-independent β-catenin degradation," *J. Cell Biol.* 162:899-908, The Rockefeller University Press, New York, NY, U.S. A. (2003).
Tosatto, S.C.E. and Toppo, S., Large-Scale Prediction of Protein Structure and Function from Sequence, *Current Pharmaceutical Design* 12:2067-2086, Bentham Science Publishers, Oak Park, IL, U.S.A. (2006).
Townsend, A. and Trowsdale, J., "The transporters associates with antigen presentation" *Seminars in Cell Biology* 4:53-61, Academic Press Limited, United States (1993).
Toyofuku, T., et al., "Wnt/frizzled-2 Signaling Induces Aggregation and Adhesion among Cardiac Myocytes by Increased Cadherin-β-Catenin Complex," *J. Cell. Biol.* 150:225-241, Rockefeller University Press (2000).
Bourhis, E., et al., "Reconstitution of a Frizzled8.Wnt3a.LRP6 Signaling Complex Reveals Multiple Wnt and Dkk1 Binding Sites on LRP6," *J. Biol. Chem.* 285(12):9172-9179, American Society for Biochemistry and Molecular Biology, United States (2010).
Umbhauer, M., et al., "The C-terminal cytoplasmic Lys-thr-X-X-X-Trp motif in frizzled receptors mediates Wnt/β-catenin signalling," *The EMBO Journal* 19:4944-4954, Oxford University Press, New York, NY, U.S.A. (2000).
Unkeless, J.C., "Characterization of a Monoclonal Antibody Directed Against Mouse Macrophage and Lymphocyte Fc Receptors," *J. Exp. Med.* 150:580-596, The Rockefeller University Press, New York, NY, U.S.A. (Sep. 1979).
Unknown Author, "Purified Rat Anti-Mouse CD16/CD32 (Mouse BD Fc BlockTM)," Technical Data Sheet 553142 Rev. 16, 2 pages, BD Biosciences, (date unknown), URL:http://www.bdbiosciences.com/external_files/pm/doc/tds/mouse/live/web_enabled/01241D_553142.pdf.
Üren, A., et al., "Secreted Frizzled-related Protein-1 Binds Directly to Wingless and Is a Biphasic Modulator of Wnt Signaling," *The Journal of Biological Chemistry* 275:4374-4382, American Society for Biochemistry and Molecular Biology, Bethesda, MD, U.S.A. (2000).

(56) References Cited

OTHER PUBLICATIONS

Uyttendaele, H., et al., "Notch4 and Wnt-1 Proteins Function to Regulate Branching Morphogeneses of Mammary Epithelial Cells in an Opposing Fashion" *Dev. Biol.* 196:204-217, Elsevier Inc., The Netherlands (1998).
Van De Vijver, M., et al., "A gene-expression signature as a predictor of survival in breast cancer" *N Eng. J Med* 347:1999-2009 (2002).
Van De Wetering, M., et al., "The β-catenin/TCF-4 complex imposes a crypt progenitor phenotype on colorectal cancer cells," *Cell* 111:241-259, Cell Press, United States (2002).
Van Den Berg, D.J., et al., "Role of Members of the Wnt Gene Family in Human Hematopoiesis," *Blood* 92:3189-3202, The American Society of Hematology, Washington, DC, U.S.A. (1998).
Van Es, J.H. and Clevers, H., "Notch and Wnt inhibitors as potential new drugs for intestinal neoplastic disease," *Trends Mol. Med.* 11:496-502, Elsevier Inc., The Netherlands (2005).
Van't Veer, L.J., et al., "Gene expression profiling predicts clinical outcome of breast cancer" *Nature* 415:530-6 (2002).
Veeman, M.T., et al., "A Second Canon: Functions and Mechanisms of β-Catenin-Independent Wnt Signaling," *Dev. Cell* 5:367-377, Elsevier Inc., Amsterdam, The Netherlands (2003).
Vincan, E., et al., "Frizzled-7 receptor ectodomain expression in a colon cancer cell line induces morphological change and attenuates tumor growth," *Differentiation* 73:142-153, Blackwell (Apr. 2005).
Voronkov, A., et al., "Molecular Model of the Wnt Protein Binding Site on the Surface of Dimeric CRD Domain of the hFzd8 Receptor," Doklady Biochemistry and Biophysics 419:75-78, Pleiades Publishing Ltd., Russia (2008).
Wang, Y., et al., "A Large Family of Putative Transmembrane Receptors Homologous to the Product of the *Drosophila* Tissue Polarity Gene frizzled," *J. Biol. Chem.* 271:4468-4476, American Society for Biochemistry and Molecular Biology (1996).
Wang, Y-K., et al., "Characterization and Expression Pattern of the frizzled Gene Fzd9, the Mouse Homolog of FZD9 which Is Deleted in Williams-Beuren Syndrome," *Genomics* 57:235-248, Academic Press (1999).
Wang, Z., et al., "Wnt7b Activates Canonical Signaling in Epithelial and Vascular Smooth Muscle Cells through Interactions with Fzd1, Fzd10, and LRP5," *Mol. Cell. Biol.* 25:5022-5030, American Society for Microbiology (2005).
Webb, T., "Work on Breast Cancer Stem Cells Raises Questions About Treatment Strategies," *Journal of the National Cancer Institute.* 95(11): 774-775, Jun. 4, 2003, printed online, pp. 1-5.
Weeraratna, A.T., et al., "Wnt5a signaling directly affects cell motility and invasion of metastatic melanoma," *Cancer Cell* 1:279-288, Cell Press (2002).
Willert, K. and Jones, K.A., "Wnt signaling: is the party in the nucleus?" *Genes & Development* 20:1394-1404, Cold Spring Harbor Laboratory Press, Cold Spring Harbor, NY, U.S.A. (2006).
Willert, K., et al., "Wnt proteins are lipid-modified and can act as stem cell growth factors," *Nature* 423:448-452, Nature Publishing Group, New York, NY, U.S.A. (2003).
Wnt-3a COPE, (Online 201 0), accessed on Oct. 1, 2010, accessed from http://www.copewithcytokines.de/cope.cgi?key=Wnt-3a.paras 2 and 5.
Wong, N.A.C.S. and Pignatelli, M., "β-catenin—A Linchpin in Colorectal Carcinogenesis?," *Am. J. Pathol.* 160:389-401, American Society for Investigative Pathology (2002).
Wong, S.C.C., et al., "Expression of frizzled-related protein and Wnt-signalling molecules in invasive human breast tumours," *J. Pathol.* 196:145-253 (2002).
Woodward, W.A., et al., "WNT/β-catenin mediates radiation resistance of mouse mammary progenitor cells," *PNAS* 104:618-623, the National Academy of Sciences, Washington, DC, U.S.A. (2007).
Wu, C-H. and Nusse, R., "Ligand Receptor Interactions in the Wnt Signaling Pathway in *Drosophila*," *J. Biol. Chem.* 277:41762-41769, American Society for Biochemistry and Molecular Biology (2002).
Yamashita, J.K., et al., Prospective identification of cardiac progenitors by a novel single cell-based cardiomyocyte induction, *The FASEB Journal,* 29 pages (Published online Jul. 20, 2005).

Yang, P., et al., "Study design considerations in clinical outcome research of lung cancer using microarray analysis" 2004 Lung Cancer 46:215-226.
Yang-Snyder, J., et al., "A frizzled homolog functions in a vertebrate Wnt signaling pathway," *Curr. Biol.* 6:1302-1306, Cell Press (1996).
Zeng, X., et al., "A dual-kinase mechanism for Wnt co-receptor phosphorylation and activation," *Nature* 438:873-877 (Dec. 8, 2005).
Zhao, Z., et al.," a Human Homologue of the *Drosophila* Polarity Gene frizzled Has Been Identified and Mapped to 17q21.1," *Genomics* 27:370-373, Academic Press (1995).
Zhu, A.J.Z., et al., "β-Catenin signaling modulates proliferative potential of human epidermal keratinocytes independently of intracellular adhesion," *Development* 126: 2285-2298, The Company of Biologists Limited, Great Britin (1999).
English language Abstract of German Patent Publication No. WO 02/00576 A1, European Patent Office, espacenet database (2002).
Lepourcelet, M., et al., "Small-molecule antagonists of the oncogenic Tcf/β-catenin protein complex," *Cancer Cell* 5:91-102, Cell Press, U.S.A. (2004).
International Search Report for International Application No. PCT/US09/58635, ISA/US, Alexandria, VA, mailed on Nov. 19, 2010.
Written Opinion for International Application No. PCT/US09/58635, ISA/US, Alexandria, VA, mailed on Nov. 19, 2010.
Lu, C., et al., "The Binding Sites for Competitive Antagonistic, Allosteric Antagonistic, and Agonistic Antibodies to the I Domain of Integrin LFA-1," *J. Immunol.* 173:3972-3978, American Society of Immunologists, Inc., United States (2004).
Wood, V., et al., "The genome sequence of *Schizosaccharomyces pombe*," *Nature* 415:871-880, Nature Publishing Group, United Kingdom (2002).
Decypher ClustalW Multiple Alignment, Stanford University (online, Sep. 2006), accessed on Sep. 30, 2010, accessed from http://web.archive.org/web/20060912071608/http://www2.stanford.edu/~rnusse/genealigns/mhfzalign.html>.
Polakis, P., "Evidence for Wnt Signaling in Cancers lacking Genetic Defects," PowerPoint NYAS Presentation and transcript, presented on Oct. 25, 2005, 71 pages.
International Search Report of the International Searching Authority for International Application No. PCT/US07/005443, mailed on Oct. 30, 2008, United States Patent and Trademark Office, United States, 4 pages.
Written Opinion for the International Searching Authority for International Application No. PC/US07/05443, mailed on Oct. 30, 2008, The International Bureau of WIPO, Switzerland, 4 pages.
Guyre, P.M., et al., "Increased potency of Fc-receptor-targeted antigens," *Cancer Immunol. Immunother.* 45:146-148, 1997.
Fredriksson, R., et al., "The G-Protein-Coupled Receptors in the Human Genome Form Five Main Families. Phylogenetic Analysis, Paralogon Groups, and Fingerprints" *Mol. Pharmacol.* 63:1256-1272, The American Society for Pharmacology and Experimental Therapeutics, United States (2003).
De Gruijl, T. and Curiel, D.T., "Cancer vaccine strategies get bigger and better," *Nat. Med.* 5(10):1124-1125, Nature Publishing Company, United States (1999).
Vajdos, F.F., et al., "Comprehensive functional maps of the antigen binding site of an anti-ErbB2 antibody obtained with shotgun scanning mutagenesis," *J. Mol. Biol.* 320:415-428, Elsevier, England (2002).
Lee, K-H., et al., "Increased vaccine specific T cell frequency after peptide based vaccination correlates with increased susceptibility to in vitro stimulation but does not lead to tumor regression," *J. Immunol.* 163(11):6292-300, Williams & Wilkins, United States (1999).
Bodey, B., et al., "Failure of cancer vaccines: the significant limitations of this approach to immunotherapy," *Anticancer Res.* 20(4):2665-2676, International Institute of Anticancer Research, Greece (2000).
MacCallum, R.M., et al., "Antibody antigen interactions: contact analysis and binding site topography," *J. Mol. Biol.* 262(5):732-745, Elsevier, England (1996).
Casset, F., et al., "A peptide mimetic of an anti-CD4 monoclonal antibody by rational design," *Biochem. Biophys. Res. Comm.* 37:198-205, Academic Press, United States (2003).

(56) References Cited

OTHER PUBLICATIONS

Holm, P., et al., "Functional mapping and single chain construction of the anti-cytokeratin 8 monoclonal antibody TS1," *Mol. Immunol.* 44:1075-1084, Pergamon Press, England (2007).
Donnelly, J., "Cancer vaccine targets leukemia," *Nat. Med.* 9(11):1354-6, Nature Publishing Company, United States (2003).
Wu, H., et al., "Humanization of a murine monoclonal antibody by simultaneous optimization of framework and CDR residues," *J. Mol. Biol.* 294:151-162, Elsevier, England (1999).
Ezzel, C., "Cancer 'Vaccines': An Idea Whose Time Has Come?" *Journal of NIH Research* 7:46-49, National Institutes of Health, United States (1995).
Forni, G., et al., "Immunoprevention of Cancer: Is the Time Ripe?" *Cancer Res* 60(10):2571-2575, American Association for Cancer Research, United States (2000).
Chatterjee, M.B., et al., "Idiotypic antibody immunotherapy of cancer," *Cancer Immunol. Immunother.* 38(2):75-82, Springer International, Germany (1994).
Rudikoff, S., et al., "Single amino acid substitution altering antigen binding specificity," *Proc. Natl. Acad. Sci.* 79(6):1979-83, National Academy of Sciences, United States (1982).
International Search Report of the International Searching Authority for International Application No. PCT/US11/20994, mailed on Aug. 15, 2011, United States Patent and Trademark Office, United States, 4 pages.
Written Opinion for the International Searching Authority for International Application No. PCT/US11/20994, mailed on Aug. 15, 2011, International Searching Authority, United States, 6 pages.
Unknown Author, "Biotinylated Anti-mouse Fzd-2 Antibody," 1 page, R&D Systems, dated Feb. 11, 2004, URL:http://www.rndsystems.com/pdf/baf1307.pdf, downloaded Sep. 27, 2012.
Schulte, G. and Bryja, V., "The Frizzled family of unconventional G-protein-coupled receptors," *Trends Pharmacol Sci.* 28(10):518-25, Elsevier in Association With the International Union of Pharmacology, England (2007).
Aruffo, A., et al.,"CD44 is the principal cell surface receptor for hyaluronate," *Cell* 61(7):1303-13, Cell Press, United States (1990).
"Frizzled 8 precursor (Frizled 8) (Fz-8) (hFz8)." [online], Sep. 2005, Accession Q9H461, Retrieved on Feb. 1, 2013 from http://www.ncbi.nlm.nih.gov/protein/17433053?sat=34&satkey=5096022.
"Frizzled 4 precursor (Frizled-4) (Fz-4) (hFz4) (FzE4)." [online], Sep. 2005, Accession Q9ULV1, Retrieved on Feb. 1, 2013 from http://www.ncbi.nlm.nih.gov/protein/62298045?sat=34&satkey=4861841.
MacLeod, R.J., et al., "Wnt5a secretion stimulated by extracellular calcium-sensing receptor inhibits defective Wnt signaling in colon cancer cells," *Am. J. Physiol. Gastrointest. Liver. Physiol.* 293(1):G403-G411, American Physiological Society, United States (2007).
Khan, N.I., et al., "Activation of Wnt/beta-catenin pathway mediates growth and survival in B-cell progenitor acute lymphoblastic leukaemia," *Br. J. Haematol.* 138(3):338-348, Wiley-Blackwell, England (2007).
You, L., et al.,"Wnt-1 signal as a potential cancer therapeutic target," *Drug News Perspect.* 19(1):27-31, Thomson Reuters, United States (2006).
Katoh, Y. and Katoh, M., "Comparative genomics on Fzd8 orthologs," *Oncol. Rep.* 13(15):993-997, D.A. Spandidos, Greece (2005).
Merle, P., et al., "Functional consequences of frizzled-7 receptor overexpression in human hepatocellular carcinoma," *Gastroenterology* 127(4):1110-1122, W.B. Saunders, United States (2004).
Gurney, A., et al., "Wnt pathway inhibition via the targeting of Frizzled receptors results in decreased growth and tumorigenicity of human tumors," *Proc. Natl. Acad. Sci. USA* 109(29):11717-22, National Academy of Sciences, United States (2012).
Luu, H.H., et al., "Wnt/β-Catenin Signaling Pathway as Novel Cancer Drug Targets," *Curr. Cancer Drug Targets* 4:653-671, Bentham Science Publishers, Netherlands (2004).

Ueno, K., et al., "Frizzled homolog proteins, microRNAs and Wnt Signaling in cancer," *Int. J. Cancer* 132:1731-1740, Wiley-Liss, United States (2013).
Accession No. UNITPROT: A6CA06, EBI database (Jul. 24, 2007).
Accession No. GSP: AVA85292, EBI database (Apr. 2, 2009).
Accession No. GSP: ARJ99386, EBI database (May 15, 2008).
International Search Report of the International Searching Authority for International Application No. PCT/US13/66087 mailed on Jan. 16, 2014, United States Patent and Trademark Office, United States, 4 pages.
Written Opinion for the International Searching Authority for International Application No. PCT/US13/66087 mailed on Jan. 16, 2014 The International Bureau of WIPO, Switzerland, 4 pages.
Al-Hajj, M., et al., "Prospective Identification of Tumorigenic Breast Cancer Cells," Proceedings of the National Academy of Sciences 100(7):3983-3988, The National Academy of Sciences, United States (2003).
Caricasole, A., et al., "Functional Characterization of WNT7A Signaling in PC12 Cells " The Journal of Biological Chemistry 278(39):37024-37031, The American Society for Biochemistry and Molecular Biology, United States (2003).
Cong, F., et al., "Wnt Signals across the Plasma Membrane to Activate the Beta-catenin Pathway by Forming Oligomers Containing its Receptors, Frizzled and LRP," Development 131(20):5103-5115, Company of Biologists, England (2004).
"frizzled Antibody (H-300): sc-9169" accessed at http://scbt.com/datasheet-9169-frizzled-h-300-antibody.html, accessed on Mar. 20, 2015, 6 pages.
Gore, L., et al., "Safety, pharmacokinetics, and pharmacodynamics results from a phase I trial of BAY 86-9766 (RDEA119), a MEK inhibitor, in patients with advanced cancer," J Clin Oncol 29:2 pages, presented at the 2011 ASCO Annual Meeting, American Society of Clinical Oncology, United States (2011) (Abstract 3007).
International Search Report for International Application No. PCT/US2012/068351, US Patent Office, Virginia, mailed on May 24, 2013.
Lin, S.Y. et al., "β-catenin, a novel prognostic marker for breast cancer: its roles in cyclin D1 expression and cancer progression," Proceedings of the National Academy of Sciences of the United States of America 97(8):4262-4266, National Academy of Sciences, United States (2000).
Lo, P.K., et al., "Epigenetic Suppression of Secreted Frizzled Related Protein 1 (SFRP1) Expression in Human Breast Cancer," Cancer Biology & Therapy 5(3):e1-e6, Landes Bioscience, Austin, United States (2006).
Miele, L. and Osborne, B., "Arbiter of Differentiation and Death: Notch Signaling Meets Apoptosis," Journal of Cellular Physiology 181(3):393-409, Wiley-Liss, Inc., United States (1999).
OncoMed Pharmaceuticals Press Release, "OncoMed Announces Abstracts Accepted at the 2014 ASCO Annual Meeting," Apr. 23, 2014, 2 pages.
OncoMed Pharmaceuticals Press Release, "OncoMed Pharmaceuticals Announces FDA Clearance to Commence Phase 1 Testing of Anti-Cancer Stem Cell Therapeutic OMP-18R5," Apr. 28, 2011, 2 pages.
OncoMed Pharmaceuticals Press Release, "OncoMed Pharmaceuticals Commences Third Phase 1 b Clinical Trial for OMP-54F28 (Fzd8-Fc) With Carboplatin and Paclitaxel in Ovarian Cancer," Feb. 20, 2014, 3 pages.
OncoMed Pharmaceuticals Press Release, "OncoMed Pharmaceuticals Initiates First Phase 1b Clinical Trial of First-in-Class WNT-Pathway-Targeting Antibody Vantictumab (OMP-18R5) With Paclitaxel in Breast Cancer," Oct. 29, 2013, 3 pages.
OncoMed Pharmaceuticals Press Release, "OncoMed Pharmaceuticals Initiates First Phase 1b Clinical Trial of OMP-54F28 (Fzd8-Fc) With Nab-Paclitaxel (Abraxane(R)) and Gemcitabine in Pancreatic Cancer," Jan. 13, 2014, 3 pages.
OncoMed Pharmaceuticals Press Release, "OncoMed Pharmaceuticals Initiates Phase I Clinical Trial of Anti-Cancer Stem Cell Therapeutic OMP-54F28 (Fzd8-Fc)," Jul. 12, 2012, 2 pages.

(56) References Cited

OTHER PUBLICATIONS

OncoMed Pharmaceuticals Press Release, "OncoMed Pharmaceuticals Initiates Second Phase 1b Clinical Trial for OMP-54F28 (Fzd8-Fc) With Sorafenib (Nexavar(R)) in Hepatocellular Cancer," Feb. 18, 2014, 3 pages.

OncoMed Pharmaceuticals Press Release, "OncoMed Pharmaceuticals Initiates Second Phase 1b Clinical Trial of First-in-Class WNT Pathway-Targeting Antibody Vantictumab (OMP-18R5) With Docetaxel in Non-Small Cell Lung Cancer (NSCLC)," Nov. 15, 2013, 3 pages.

OncoMed Pharmaceuticals Press Release, "OncoMed Pharmaceuticals Initiates Third Phase 1b Clinical Trial of First-in-Class WNT Pathway-Targeting Antibody Vantictumab (OMP-18R5) With Nab-Paclitaxel (Abraxane®) and Gemcitabine in Stage IV Pancreatic Cancer," Dec. 4, 2013, 3 pages.

OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.

OncoMed Pharmaceuticals Press Release, "OncoMed Pharmaceuticals Presents Phase 1 Data in Solid Tumor Patients for the First-in-Class Wnt Pathway Targeting Antibody Vantictumab (OMP-18R5) at ASCO," Jun. 3, 2013, 2 pages.

OncoMed Pharmaceuticals Press Release, "OncoMed Pharmaceuticals Presents Updated Phase 1a Data in Advanced Solid Tumor Patients for the First-in-Class WNT-Pathway-Targeting Antibody Vantictumab (OMP-18R5) at the European Cancer Congress 2013," Sep. 29, 2013, 3 pages.

OncoMed Pharmaceuticals Press Release, "OncoMed Pharmaceuticals Recaps New Data Presented at AACR," Apr. 3, 2012, 2 pages.

OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.

OncoMed Pharmaceuticals Press Release, "OncoMed Pharmaceuticals to Present Phase 1a Data in Advanced Solid Tumor Patients for the First-in-Class WNT-Pathway-Targeting Antibody Vantictumab (OMP-18R5) at the European Cancer Congress 2013 (ECC 2013)," Sep. 23, 2013, 2 pages.

OncoMed Pharmaceuticals Press Release, "OncoMed Presents Data on Multiple Anti-Cancer Stem Cell Programs at American Association for Cancer Research Annual Meeting," Apr. 8, 2014, 4 pages.

OncoMed Pharmaceuticals Press Release, "OncoMed Presents New Data in Six Anti-Cancer Stem Cell Programs at AACR," Apr. 9, 2013, 3 pages.

OncoMed Pharmaceuticals Press Release, "OncoMed Provides Update on FZD8-Fc (OMP-54F28) Phase I Clinical Trials," Jun. 18, 2014, 2 pages.

OncoMed Pharmaceuticals Press Release, "OncoMed to Present Data From Three Clinical Studies at the 2014 ASCO Annual Meeting," May 14, 2014, 4 pages.

OncoMed Pharmaceuticals Press Release, "OncoMed to Present New Data in Six Anti-Cancer Stem Cell Programs at AACR," Apr. 2, 2013, 2 pages.

OncoMed Pharmaceuticals Press Release, "PNAS Publishes OncoMed Data Demonstrating Potent Anti-Cancer Activity for Novel Wnt Pathway Antibody OMP-18R5," Jul. 3, 2012, 2 pages.

Uren, A., et al., "Secreted Frizzled-related Protein-1 Binds Directly to Wingless and Is a Biphasic Modulator of Wnt Signaling," The Journal of Biological Chemistry 275(6):4374-4382, American Society for Biochemistry and Molecular Biology, United States (2000).

Written Opinion for International Application No. PCT/US09/58635, ISA/US, Alexandria, VA, mailed on Nov. 19, 2010, 8 pages.

Written Opinion for the International Searching Authority for International Application No. PCT/US07/05443, mailed on Oct. 30, 2008, The International Bureau of WIPO, Switzerland, 4 pages.

Written Opinion for the International Searching Authority for International Application No. PCT/US11/20994, mailed on Aug. 15, 2011, International Searching Authority, United States, 7 pages.

Written Opinion for the International Searching Authority for International Application No. PCT/US13/66087 mailed on Jan. 16, 2014 The International Bureau of WIPO, Switzerland, 5 pages.

Jimeno, A., et al., "A first-in-human phase 1 study of anticancer stem cell agent OMP-54F28 (FZD-Fc), decoy receptor for WNT ligands, in patient with advanced solid tumors," 2014 ASCO Annual Meeting, Abstract 2505, 2 pages (2014).

Smith, D.C., et al., "A first-in-human Phase 1 study of anti-cancer stem cell (CSC) agent OMP-54F28 (FZD8-Fc) targeting the WNT pathway in patients with advanced solid tumors," AACR-NCI-EORTC International Conference on Molecular Targets and Cancer Therapeutics, Oct. 19-23, 2013, Abstract B79, 1 page (2013).

Smith, D.C., et al., "Biomarker analysis in the first-in-human Phase 1a study for vantictumab (OMP-18R5; anti-Frizzled) demonstrates pharmacodynamics (PD) modulation of the Wnt pathway in patients with advanced solid tumors," AACR-NCI-EORTC International Conference on Molecular Targets and Cancer Therapeutics in Boston, Oct. 19-23, 2013, Poster 823, 1 page (2013).

Yen, W-C., et al., "Enhanced anti-tumor effect of WNT pathway antagonists in combination with taxanes," AACR Annual Meeting 2014, Apr. 5-9, Abstract 4547, 1 page (2014).

Yeung, P. et al., "Wnt pathway antagonist OMP-54F28 (FZD8-Fc) inhibits tumor growth and reduces tumor-initiating cell frequency in patient-derived hepatocellular carcinoma and ovarian cancer xenograft models," AACR Annual Meeting 2014, Apr. 5-9, Abstract 1907, 1 page (2014).

Zhang, C., et al., "Predictive biomarker identification for response to vantictumab (OMP-18R5; anti-Frizzled) by mining gene expression data of human breast cancer xenografts," AACR Annual Meeting, Apr. 5-9, Abstract 2830, 1 page (2014).

* cited by examiner

SEQUENCE LISTING

<160> NUMBER OF SEQ ID NOS: 133

<210> SEQ ID NO 1
<211> LENGTH: 647
<212> TYPE: PRT
<213> ORGANISM: Homo sapiens

<400> SEQUENCE: 1

Met Ala Glu Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Arg Pro Pro Val Asp Pro
        35                  40                  45

Arg Arg Leu Ala Arg Gln Leu Leu Leu Leu Trp Leu Leu Glu Ala
    50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Pro Gln Gln Gln
            85                  90                  95

Gln Ser Gly Gln Gln Tyr Asn Gly Glu Arg Gly Ile Ser Val Pro Asp
        100                 105                 110

His Gly Tyr Cys Gln Pro Ile Ser Ile Pro Leu Cys Thr Asp Ile Ala
    115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
                165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
        195                 200                 205

Trp Pro Asp Thr Leu Lys Cys Glu Lys Phe Pro Val His Gly Ala Gly
    210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
                245                 250                 255

Gly His Arg Gly Gly Phe Pro Gly Ala Gly Ala Ser Glu Arg Gly
                260                 265                 270

Lys Phe Ser Cys Pro Arg Ala Leu Lys Val Pro Ser Tyr Leu Asn Tyr
            275                 280                 285

His Phe Leu Gly Glu Lys Asp Cys Gly Ala Pro Cys Glu Pro Thr Lys
290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
                325                 330                 335

Thr Val Leu Thr Tyr Leu Val Asp Met Arg Arg Phe Ser Tyr Pro Glu
            340                 345                 350

Arg Pro Ile Ile Phe Leu Ser Gly Cys Tyr Thr Ala Val Ala Val Ala
        355                 360                 365

Tyr Ile Ala Gly Phe Leu Leu Glu Asp Arg Val Val Cys Asn Asp Lys
370                 375                 380

Phe Ala Glu Asp Gly Ala Arg Thr Val Ala Gln Gly Thr Lys Lys Glu
385                 390                 395                 400

Gly Cys Thr Ile Leu Phe Met Met Leu Tyr Phe Phe Ser Met Ala Ser
                405                 410                 415

Ser Ile Trp Trp Val Ile Leu Ser Leu Thr Trp Phe Leu Ala Ala Gly
            420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
                485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
                565                 570                 575

Tyr Ala Ile Pro Cys Pro His Leu Gln Ala Gly Gly Ala Pro Pro
            580                 585                 590

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645

<210> SEQ ID NO 2
<211> LENGTH: 565

<212> TYPE: PRT
<213> ORGANISM: Homo sapiens

<400> SEQUENCE: 2

```
Met Arg Pro Arg Ser Ala Leu Pro Arg Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
    130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
        195                 200                 205

Ser Tyr Leu Ser Tyr Lys Phe Leu Gly Glu Arg Asp Cys Ala Ala Pro
    210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr Trp Ser Val Leu Cys Cys
                245                 250                 255

Ala Ser Thr Phe Phe Thr Val Thr Thr Tyr Leu Val Asp Met Gln Arg
            260                 265                 270

Phe Arg Tyr Pro Glu Arg Pro Ile Ile Phe Leu Ser Gly Cys Tyr Thr
        275                 280                 285

Met Val Ser Val Ala Tyr Ile Ala Gly Phe Val Leu Gln Glu Arg Val
    290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
                325                 330                 335

Phe Ser Met Ala Ser Ser Ile Trp Trp Val Ile Leu Ser Leu Thr Trp
            340                 345                 350

Phe Leu Ala Ala Gly Met Lys Trp Gly His Glu Ala Ile Glu Ala Asn
        355                 360                 365

Ser Gln Tyr Phe His Leu Ala Ala Trp Ala Val Pro Ala Val Lys Thr
    370                 375                 380

Ile Thr Ile Leu Ala Met Gly Gln Ile Asp Gly Asp Leu Leu Ser Gly
385                 390                 395                 400
```

-continued

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
            420                 425                 430

Ala Gly Phe Val Ser Leu Phe Arg Ile Arg Thr Ile Met Lys His Asp
        435                 440                 445

Gly Thr Lys Thr Glu Lys Leu Glu Arg Leu Met Val Arg Ile Gly Val
    450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
                485                 490                 495

Gln His Cys Lys Ser Leu Ala Ile Pro Cys Pro Ala His Tyr Thr Pro
            500                 505                 510

Arg Met Ser Pro Asp Phe Thr Val Tyr Met Ile Lys Tyr Leu Met Thr
        515                 520                 525

Leu Ile Val Gly Ile Thr Ser Gly Phe Trp Ile Trp Ser Gly Lys Thr
    530                 535                 540

Leu His Ser Trp Arg Lys Phe Tyr Thr Arg Leu Thr Asn Ser Arg His
545                 550                 555                 560

Gly Glu Thr Thr Val
                565

<210> SEQ ID NO 3
<211> LENGTH: 666
<212> TYPE: PRT
<213> ORGANISM: Homo sapiens

<400> SEQUENCE: 3

Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
            20                  25                  30

Leu Arg Met Cys Gln Asp Leu Pro Tyr Asn Thr Thr Phe Met Pro Asn
        35                  40                  45

Leu Leu Asn His Tyr Asp Gln Gln Thr Ala Ala Leu Ala Met Glu Pro
    50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95

Leu Pro Cys Arg Arg Leu Cys Gln Arg Ala Tyr Ser Glu Cys Ser Lys
            100                 105                 110

Leu Met Glu Met Phe Gly Val Pro Trp Pro Glu Asp Met Glu Cys Ser
        115                 120                 125

Arg Phe Pro Asp Cys Asp Glu Pro Tyr Pro Arg Leu Val Asp Leu Asn
    130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr Phe Ile Gly Leu

-continued

```
            195                 200                 205
Ile Ser Ile Ile Cys Leu Ser Ala Thr Leu Phe Thr Phe Leu Thr Phe
210                 215                 220

Leu Ile Asp Val Thr Arg Phe Arg Tyr Pro Glu Arg Pro Ile Ile Phe
225                 230                 235                 240

Tyr Ala Val Cys Tyr Met Met Val Ser Leu Ile Phe Phe Ile Gly Phe
                    245                 250                 255

Leu Leu Glu Asp Arg Val Ala Cys Asn Ala Ser Ile Pro Ala Gln Tyr
                260                 265                 270

Lys Ala Ser Thr Val Thr Gln Gly Ser His Asn Lys Ala Cys Thr Met
                275                 280                 285

Leu Phe Met Ile Leu Tyr Phe Phe Thr Met Ala Gly Ser Val Trp Trp
            290                 295                 300

Val Ile Leu Thr Ile Thr Trp Phe Leu Ala Ala Val Pro Lys Trp Gly
305                 310                 315                 320

Ser Glu Ala Ile Glu Lys Lys Ala Leu Leu Phe His Ala Ser Ala Trp
                325                 330                 335

Gly Ile Pro Gly Thr Leu Thr Ile Ile Leu Leu Ala Met Asn Lys Ile
                340                 345                 350

Glu Gly Asp Asn Ile Ser Gly Val Cys Phe Val Gly Leu Tyr Asp Val
                355                 360                 365

Asp Ala Leu Arg Tyr Phe Val Leu Ala Pro Leu Cys Leu Tyr Val Val
370                 375                 380

Val Gly Val Ser Leu Leu Leu Ala Gly Ile Ile Ser Leu Asn Arg Val
385                 390                 395                 400

Arg Ile Glu Ile Pro Leu Glu Lys Glu Asn Gln Asp Lys Leu Val Lys
                405                 410                 415

Phe Met Ile Arg Ile Gly Val Phe Ser Ile Leu Tyr Leu Val Pro Leu
                420                 425                 430

Leu Val Val Ile Gly Cys Tyr Phe Tyr Glu Gln Ala Tyr Arg Gly Ile
                435                 440                 445

Trp Glu Thr Thr Trp Ile Gln Glu Arg Cys Arg Glu Tyr His Ile Pro
450                 455                 460

Cys Pro Tyr Gln Val Thr Gln Met Ser Arg Pro Asp Leu Ile Leu Phe
465                 470                 475                 480

Leu Met Lys Tyr Leu Met Ala Leu Ile Val Gly Ile Pro Ser Val Phe
                485                 490                 495

Trp Val Gly Ser Lys Lys Thr Cys Phe Glu Trp Ala Ser Phe Phe His
                500                 505                 510

Gly Arg Arg Lys Lys Glu Ile Val Asn Glu Ser Arg Gln Val Leu Gln
                515                 520                 525

Glu Pro Asp Phe Ala Gln Ser Leu Leu Arg Asp Pro Asn Thr Pro Ile
                530                 535                 540

Ile Arg Lys Ser Arg Gly Thr Ser Thr Gln Gly Thr Ser Thr His Ala
545                 550                 555                 560

Ser Ser Thr Gln Leu Ala Met Val Asp Asp Gln Arg Ser Lys Ala Gly
                565                 570                 575

Ser Ile His Ser Lys Val Ser Ser Tyr His Gly Ser Leu His Arg Ser
                580                 585                 590

Arg Asp Gly Arg Tyr Thr Pro Cys Ser Tyr Arg Gly Met Glu Glu Arg
                595                 600                 605

Leu Pro His Gly Ser Met Ser Arg Leu Thr Asp His Ser Arg His Ser
                610                 615                 620
```

```
Ser Ser His Arg Leu Asn Glu Gln Ser Arg His Ser Ile Arg Asp
625                 630                 635                 640

Leu Ser Asn Asn Pro Met Thr His Ile Thr His Gly Thr Ser Met Asn
                645                 650                 655

Arg Val Ile Glu Glu Asp Gly Thr Ser Ala
            660                 665

<210> SEQ ID NO 4
<211> LENGTH: 540
<212> TYPE: PRT
<213> ORGANISM: Homo sapiens

<400> SEQUENCE: 4

Met Leu Ala Met Ala Trp Arg Gly Ala Gly Pro Ser Val Pro Gly Ala
1               5                   10                  15

Pro Gly Gly Val Gly Leu Ser Leu Gly Leu Leu Gln Leu Leu Leu
                20                  25                  30

Leu Leu Gly Pro Ala Arg Gly Phe Gly Asp Glu Glu Arg Arg Cys
            35                  40                  45

Asp Pro Ile Arg Ile Ser Met Cys Gln Asn Leu Gly Tyr Asn Val Thr
50                  55                  60

Lys Met Pro Asn Leu Val Gly His Glu Leu Gln Thr Asp Ala Glu Leu
65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
            100                 105                 110

Ile Asn Ile Pro Ile Gly Pro Cys Gly Gly Met Cys Leu Ser Val Lys
            115                 120                 125

Arg Arg Cys Glu Pro Val Leu Lys Glu Phe Gly Phe Ala Trp Pro Glu
130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175

Pro Ile Gln Pro Gly Glu Glu Cys His Ser Val Gly Thr Asn Ser Asp
            180                 185                 190

Gln Tyr Ile Trp Val Lys Arg Ser Leu Asn Cys Val Leu Lys Cys Gly
            195                 200                 205

Tyr Asp Ala Gly Leu Tyr Ser Arg Ser Ala Lys Glu Phe Thr Asp Ile
210                 215                 220

Trp Met Ala Val Trp Ala Ser Leu Cys Phe Ile Ser Thr Ala Phe Thr
225                 230                 235                 240

Val Leu Thr Phe Leu Ile Asp Ser Ser Arg Phe Ser Tyr Pro Glu Arg
                245                 250                 255

Pro Ile Ile Phe Leu Ser Met Cys Tyr Asn Ile Tyr Ser Ile Ala Tyr
            260                 265                 270

Ile Val Arg Leu Thr Val Gly Arg Glu Arg Ile Ser Cys Asp Phe Glu
            275                 280                 285

Glu Ala Ala Glu Pro Val Leu Ile Gln Glu Gly Leu Lys Asn Thr Gly
290                 295                 300

Cys Ala Ile Ile Phe Leu Leu Met Tyr Phe Phe Gly Met Ala Ser Ser
305                 310                 315                 320

Ile Trp Trp Val Ile Leu Thr Leu Thr Trp Phe Leu Ala Ala Gly Leu
```

325                 330                 335
Lys Trp Gly His Glu Ala Ile Glu Met His Ser Ser Tyr Phe His Ile
            340                 345                 350

Ala Ala Trp Ala Ile Pro Ala Val Lys Thr Ile Val Ile Leu Ile Met
        355                 360                 365

Arg Leu Val Asp Ala Asp Glu Leu Thr Gly Leu Cys Tyr Val Gly Asn
    370                 375                 380

Gln Asn Leu Asp Ala Leu Thr Gly Phe Val Val Ala Pro Leu Phe Thr
385                 390                 395                 400

Tyr Leu Val Ile Gly Thr Leu Phe Ile Ala Ala Gly Leu Val Ala Leu
            405                 410                 415

Phe Lys Ile Arg Ser Asn Leu Gln Lys Asp Gly Thr Lys Thr Asp Lys
        420                 425                 430

Leu Glu Arg Leu Met Val Lys Ile Gly Val Phe Ser Val Leu Tyr Thr
    435                 440                 445

Val Pro Ala Thr Cys Val Ile Ala Cys Tyr Phe Tyr Glu Ile Ser Asn
450                 455                 460

Trp Ala Leu Phe Arg Tyr Ser Ala Asp Asp Ser Asn Met Ala Val Glu
465                 470                 475                 480

Met Leu Lys Ile Phe Met Ser Leu Leu Val Gly Ile Thr Ser Gly Met
            485                 490                 495

Trp Ile Trp Ser Ala Lys Thr Leu His Thr Trp Gln Lys Cys Ser Asn
        500                 505                 510

Arg Leu Val Asn Ser Gly Lys Val Lys Arg Glu Lys Arg Gly Asn Gly
    515                 520                 525

Trp Val Lys Pro Gly Lys Gly Ser Glu Thr Val Val
530                 535                 540

<210> SEQ ID NO 5
<211> LENGTH: 585
<212> TYPE: PRT
<213> ORGANISM: Homo sapiens

<400> SEQUENCE: 5

Met Ala Arg Pro Asp Pro Ser Ala Pro Ser Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr Ala Pro Pro
145                 150                 155                 160

```
Arg Pro Phe Pro Ala Lys Pro Thr Leu Pro Gly Pro Gly Ala Pro
            165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
            195                 200                 205

Lys Val Arg Thr Gly Gln Val Pro Asn Cys Ala Val Pro Cys Tyr Gln
            210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Val Ala Thr
            245                 250                 255

Phe Leu Ile Asp Met Glu Arg Phe Arg Tyr Pro Glu Arg Pro Ile Ile
            260                 265                 270

Phe Leu Ser Ala Cys Tyr Leu Cys Val Ser Leu Gly Phe Leu Val Arg
            275                 280                 285

Leu Val Val Gly His Ala Ser Val Ala Cys Ser Arg Glu His Asn His
            290                 295                 300

Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
            325                 330                 335

Ser Leu Thr Trp Phe Leu Ala Ala Gly Met Lys Trp Gly Asn Glu Ala
            340                 345                 350

Ile Ala Gly Tyr Ala Gln Tyr Phe His Leu Ala Ala Trp Leu Ile Pro
            355                 360                 365

Ser Val Lys Ser Ile Thr Ala Leu Ala Leu Ser Ser Val Asp Gly Asp
            370                 375                 380

Pro Val Ala Gly Ile Cys Tyr Val Gly Asn Gln Asn Leu Asn Ser Leu
385                 390                 395                 400

Arg Gly Phe Val Leu Gly Pro Leu Val Leu Tyr Leu Leu Val Gly Thr
            405                 410                 415

Leu Phe Leu Leu Ala Gly Phe Val Ser Leu Phe Arg Ile Arg Ser Val
            420                 425                 430

Ile Lys Gln Gly Gly Thr Lys Thr Asp Lys Leu Glu Lys Leu Met Ile
            435                 440                 445

Arg Ile Gly Ile Phe Thr Leu Leu Tyr Thr Val Pro Ala Ser Ile Val
450                 455                 460

Val Ala Cys Tyr Leu Tyr Glu Gln His Tyr Arg Glu Ser Trp Glu Ala
465                 470                 475                 480

Ala Leu Thr Cys Ala Cys Pro Gly His Asp Thr Gly Gln Pro Arg Ala
            485                 490                 495

Lys Pro Glu Tyr Trp Val Leu Met Leu Lys Tyr Phe Met Cys Leu Val
            500                 505                 510

Val Gly Ile Thr Ser Gly Val Trp Ile Trp Ser Gly Lys Thr Val Glu
            515                 520                 525

Ser Trp Arg Arg Phe Thr Ser Arg Cys Cys Arg Pro Arg Arg Gly
530                 535                 540

His Lys Ser Gly Gly Ala Met Ala Ala Gly Asp Tyr Pro Glu Ala Ser
545                 550                 555                 560

Ala Ala Leu Thr Gly Arg Thr Gly Pro Pro Gly Pro Ala Ala Thr Tyr
            565                 570                 575

His Lys Gln Val Ser Leu Ser His Val
```

-continued

```
<210> SEQ ID NO 6
<211> LENGTH: 706
<212> TYPE: PRT
<213> ORGANISM: Homo sapiens

<400> SEQUENCE: 6
```

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30

Met Lys Met Ala Tyr Asn Met Thr Phe Phe Pro Asn Leu Met Gly His
        35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
        115                 120                 125

Cys Asp Glu Thr Val Pro Val Thr Phe Asp Pro His Thr Glu Phe Leu
    130                 135                 140

Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile Phe
        195                 200                 205

Cys Leu Cys Ala Thr Leu Phe Thr Phe Leu Thr Phe Leu Ile Asp Val
    210                 215                 220

Arg Arg Phe Arg Tyr Pro Glu Arg Pro Ile Ile Tyr Tyr Ser Val Cys
225                 230                 235                 240

Tyr Ser Ile Val Ser Leu Met Tyr Phe Ile Gly Phe Leu Leu Gly Asp
                245                 250                 255

Ser Thr Ala Cys Asn Lys Ala Asp Glu Lys Leu Glu Leu Gly Asp Thr
            260                 265                 270

Val Val Leu Gly Ser Gln Asn Lys Ala Cys Thr Val Leu Phe Met Leu
        275                 280                 285

Leu Tyr Phe Phe Thr Met Ala Gly Thr Val Trp Trp Val Ile Leu Thr
    290                 295                 300

Ile Thr Trp Phe Leu Ala Ala Gly Arg Lys Trp Ser Cys Glu Ala Ile
305                 310                 315                 320

Glu Gln Lys Ala Val Trp Phe His Ala Val Ala Trp Gly Thr Pro Gly
                325                 330                 335

Phe Leu Thr Val Met Leu Leu Ala Met Asn Lys Val Glu Gly Asp Asn
            340                 345                 350

Ile Ser Gly Val Cys Phe Val Gly Leu Tyr Asp Leu Asp Ala Ser Arg
        355                 360                 365

```
Tyr Phe Val Leu Leu Pro Leu Cys Leu Cys Val Phe Val Gly Leu Ser
    370                 375                 380

Leu Leu Leu Ala Gly Ile Ile Ser Leu Asn His Val Arg Gln Val Ile
385                 390                 395                 400

Gln His Asp Gly Arg Asn Gln Glu Lys Leu Lys Lys Phe Met Ile Arg
                405                 410                 415

Ile Gly Val Phe Ser Gly Leu Tyr Leu Val Pro Leu Val Thr Leu Leu
                420                 425                 430

Gly Cys Tyr Val Tyr Glu Gln Val Asn Arg Ile Thr Trp Glu Ile Thr
                435                 440                 445

Trp Val Ser Asp His Cys Arg Gln Tyr His Ile Pro Cys Pro Tyr Gln
450                 455                 460

Ala Lys Ala Lys Ala Arg Pro Glu Leu Ala Leu Phe Met Ile Lys Tyr
465                 470                 475                 480

Leu Met Thr Leu Ile Val Gly Ile Ser Ala Val Phe Trp Val Gly Ser
                485                 490                 495

Lys Lys Thr Cys Thr Glu Trp Ala Gly Phe Phe Lys Arg Asn Arg Lys
                500                 505                 510

Arg Asp Pro Ile Ser Glu Ser Arg Arg Val Leu Gln Glu Ser Cys Glu
                515                 520                 525

Phe Phe Leu Lys His Asn Ser Lys Val Lys His Lys Lys His Tyr
530                 535                 540

Lys Pro Ser Ser His Lys Leu Lys Val Ile Ser Lys Ser Met Gly Thr
545                 550                 555                 560

Ser Thr Gly Ala Thr Ala Asn His Gly Thr Ser Ala Val Ala Ile Thr
                565                 570                 575

Ser His Asp Tyr Leu Gly Gln Glu Thr Leu Thr Glu Ile Gln Thr Ser
                580                 585                 590

Pro Glu Thr Ser Met Arg Glu Val Lys Ala Asp Gly Ala Ser Thr Pro
                595                 600                 605

Arg Leu Arg Glu Gln Asp Cys Gly Glu Pro Ala Ser Pro Ala Ala Ser
                610                 615                 620

Ile Ser Arg Leu Ser Gly Glu Gln Val Asp Gly Lys Gly Gln Ala Gly
625                 630                 635                 640

Ser Val Ser Glu Ser Ala Arg Ser Glu Gly Arg Ile Ser Pro Lys Ser
                645                 650                 655

Asp Ile Thr Asp Thr Gly Leu Ala Gln Ser Asn Asn Leu Gln Val Pro
                660                 665                 670

Ser Ser Ser Glu Pro Ser Ser Leu Lys Gly Ser Thr Ser Leu Leu Val
                675                 680                 685

His Pro Val Ser Gly Val Arg Lys Glu Gln Gly Gly Gly Cys His Ser
690                 695                 700

Asp Thr
705

<210> SEQ ID NO 7
<211> LENGTH: 574
<212> TYPE: PRT
<213> ORGANISM: Homo sapiens

<400> SEQUENCE: 7

Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30
```

-continued

```
Gln Pro Tyr His Gly Glu Lys Gly Ile Ser Val Pro Asp His Gly Phe
             35                  40                  45
Cys Gln Pro Ile Ser Ile Pro Leu Cys Thr Asp Ile Ala Tyr Asn Gln
 50                  55                  60
Thr Ile Leu Pro Asn Leu Leu Gly His Thr Asn Gln Glu Asp Ala Gly
 65                  70                  75                  80
Leu Glu Val His Gln Phe Tyr Pro Leu Val Lys Val Gln Cys Ser Pro
                 85                  90                  95
Glu Leu Arg Phe Phe Leu Cys Ser Met Tyr Ala Pro Val Cys Thr Val
             100                 105                 110
Leu Asp Gln Ala Ile Pro Pro Cys Arg Ser Leu Cys Glu Arg Ala Arg
             115                 120                 125
Gln Gly Cys Glu Ala Leu Met Asn Lys Phe Gly Phe Gln Trp Pro Glu
130                 135                 140
Arg Leu Arg Cys Glu Asn Phe Pro Val His Gly Ala Gly Glu Ile Cys
145                 150                 155                 160
Val Gly Gln Asn Thr Ser Asp Gly Ser Gly Pro Gly Gly Pro
                165                 170                 175
Thr Ala Tyr Pro Thr Ala Pro Tyr Leu Pro Asp Leu Pro Phe Thr Ala
             180                 185                 190
Leu Pro Pro Gly Ala Ser Asp Gly Arg Gly Arg Pro Ala Phe Pro Phe
             195                 200                 205
Ser Cys Pro Arg Gln Leu Lys Val Pro Pro Tyr Leu Gly Tyr Arg Phe
         210                 215                 220
Leu Gly Glu Arg Asp Cys Gly Ala Pro Cys Glu Pro Gly Arg Ala Asn
225                 230                 235                 240
Gly Leu Met Tyr Phe Lys Glu Glu Arg Arg Phe Ala Arg Leu Trp
                 245                 250                 255
Val Gly Val Trp Ser Val Leu Cys Cys Ala Ser Thr Leu Phe Thr Val
             260                 265                 270
Leu Thr Tyr Leu Val Asp Met Arg Arg Phe Ser Tyr Pro Glu Arg Pro
         275                 280                 285
Ile Ile Phe Leu Ser Gly Cys Tyr Phe Met Val Ala Val Ala His Val
290                 295                 300
Ala Gly Phe Leu Leu Glu Asp Arg Ala Val Cys Val Glu Arg Phe Ser
305                 310                 315                 320
Asp Asp Gly Tyr Arg Thr Val Ala Gln Gly Thr Lys Lys Glu Gly Cys
                 325                 330                 335
Thr Ile Leu Phe Met Val Leu Tyr Phe Phe Gly Met Ala Ser Ser Ile
             340                 345                 350
Trp Trp Val Ile Leu Ser Leu Thr Trp Phe Leu Ala Ala Gly Met Lys
             355                 360                 365
Trp Gly His Glu Ala Ile Glu Ala Asn Ser Gln Tyr Phe His Leu Ala
         370                 375                 380
Ala Trp Ala Val Pro Ala Val Lys Thr Ile Thr Ile Leu Ala Met Gly
385                 390                 395                 400
Gln Val Asp Gly Asp Leu Leu Ser Gly Val Cys Tyr Val Gly Leu Ser
                 405                 410                 415
Ser Val Asp Ala Leu Arg Gly Phe Val Leu Ala Pro Leu Phe Val Tyr
             420                 425                 430
Leu Phe Ile Gly Thr Ser Phe Leu Leu Ala Gly Phe Val Ser Leu Phe
             435                 440                 445
```

```
Arg Ile Arg Thr Ile Met Lys His Asp Gly Thr Thr Glu Lys Leu
        450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Met Ser Pro Asp Phe Thr
        515                 520                 525

Val Phe Met Ile Lys Tyr Leu Met Thr Met Ile Val Gly Ile Thr Thr
530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
                565                 570

<210> SEQ ID NO 8
<211> LENGTH: 694
<212> TYPE: PRT
<213> ORGANISM: Homo sapiens

<400> SEQUENCE: 8

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
        195                 200                 205

Ala Arg Gly Gly Gly Gly Gly Lys Ala Arg Pro Pro Gly Gly Gly
    210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255
```

-continued

```
Ile Ala Asn Cys Ala Leu Pro Cys His Asn Pro Phe Ser Gln Asp
            260                 265                 270

Glu Arg Ala Phe Thr Val Phe Trp Ile Gly Leu Trp Ser Val Leu Cys
        275                 280                 285

Phe Val Ser Thr Phe Ala Thr Val Ser Thr Phe Leu Ile Asp Met Glu
    290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
            325                 330                 335

Lys Val Ala Cys Ser Gly Gly Ala Pro Gly Ala Gly Gly Ala Gly Gly
            340                 345                 350

Ala Gly Gly Ala Ala Gly Ala Gly Ala Gly Ala Gly Ala Gly
            355                 360                 365

Gly Pro Gly Gly Arg Gly Glu Tyr Glu Glu Leu Gly Ala Val Glu Gln
            370                 375                 380

His Val Arg Tyr Glu Thr Thr Gly Pro Ala Leu Cys Thr Val Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430

Ala Ile Ala Gly Tyr Ser Gln Tyr Phe His Leu Ala Ala Trp Leu Val
            435                 440                 445

Pro Ser Val Lys Ser Ile Ala Val Leu Ala Leu Ser Ser Val Asp Gly
            450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
            485                 490                 495

Thr Met Phe Leu Leu Ala Gly Phe Val Ser Leu Phe Arg Ile Arg Ser
            500                 505                 510

Val Ile Lys Gln Gln Asp Gly Pro Thr Lys Thr His Lys Leu Glu Lys
            515                 520                 525

Leu Met Ile Arg Leu Gly Leu Phe Thr Val Leu Tyr Thr Val Pro Ala
            530                 535                 540

Ala Val Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
                565                 570                 575

Gln Ala Arg Arg Pro Asp Tyr Ala Val Phe Met Leu Lys Tyr Phe Met
            580                 585                 590

Cys Leu Val Val Gly Ile Thr Ser Gly Val Trp Val Trp Ser Gly Lys
            595                 600                 605

Thr Leu Glu Ser Trp Arg Ser Leu Cys Thr Arg Cys Cys Trp Ala Ser
            610                 615                 620

Lys Gly Ala Ala Val Gly Gly Ala Gly Ala Thr Ala Ala Gly Gly
625                 630                 635                 640

Gly Gly Gly Pro Gly Gly Gly Gly Gly Pro Gly Gly Gly
            645                 650                 655

Gly Pro Gly Gly Gly Gly Ser Leu Tyr Ser Asp Val Ser Thr Gly
            660                 665                 670
```

```
Leu Thr Trp Arg Ser Gly Thr Ala Ser Ser Val Ser Tyr Pro Lys Gln
            675                 680                 685

Met Pro Leu Ser Gln Val
            690

<210> SEQ ID NO 9
<211> LENGTH: 591
<212> TYPE: PRT
<213> ORGANISM: Homo sapiens

<400> SEQUENCE: 9

Met Ala Val Ala Pro Leu Arg Gly Ala Leu Leu Trp Gln Leu Leu
1               5                   10                  15

Ala Ala Gly Gly Ala Ala Leu Glu Ile Gly Arg Phe Asp Pro Glu Arg
                20                  25                  30

Gly Arg Gly Ala Ala Pro Cys Gln Ala Val Glu Ile Pro Met Cys Arg
            35                  40                  45

Gly Ile Gly Tyr Asn Leu Thr Arg Met Pro Asn Leu Leu Gly His Thr
        50                  55                  60

Ser Gln Gly Glu Ala Ala Ala Glu Leu Ala Glu Phe Ala Pro Leu Val
65                  70                  75                  80

Gln Tyr Gly Cys His Ser His Leu Arg Phe Phe Leu Cys Ser Leu Tyr
                85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
        115                 120                 125

Phe Asn Phe Gly Trp Pro Asp Ser Leu Asp Cys Ala Arg Leu Pro Thr
130                 135                 140

Arg Asn Asp Pro His Ala Leu Cys Met Glu Ala Pro Glu Asn Ala Thr
145                 150                 155                 160

Ala Gly Pro Ala Glu Pro His Lys Gly Leu Gly Met Leu Pro Val Ala
                165                 170                 175

Pro Arg Pro Ala Arg Pro Pro Gly Asp Leu Gly Pro Gly Ala Gly Gly
            180                 185                 190

Ser Gly Thr Cys Glu Asn Pro Glu Lys Phe Gln Tyr Val Glu Lys Ser
        195                 200                 205

Arg Ser Cys Ala Pro Arg Cys Gly Pro Gly Val Glu Val Phe Trp Ser
210                 215                 220

Arg Arg Asp Lys Asp Phe Ala Leu Val Trp Met Ala Val Trp Ser Ala
225                 230                 235                 240

Leu Cys Phe Phe Ser Thr Ala Phe Thr Val Leu Thr Phe Leu Leu Glu
                245                 250                 255

Pro His Arg Phe Gln Tyr Pro Glu Arg Pro Ile Ile Phe Leu Ser Met
            260                 265                 270

Cys Tyr Asn Val Tyr Ser Leu Ala Phe Leu Ile Arg Ala Val Ala Gly
        275                 280                 285

Ala Gln Ser Val Ala Cys Asp Gln Glu Ala Gly Ala Leu Tyr Val Ile
290                 295                 300

Gln Glu Gly Leu Glu Asn Thr Gly Cys Thr Leu Val Phe Leu Leu Leu
305                 310                 315                 320

Tyr Tyr Phe Gly Met Ala Ser Ser Leu Trp Trp Val Val Leu Thr Leu
                325                 330                 335

Thr Trp Phe Leu Ala Ala Gly Lys Lys Trp Gly His Glu Ala Ile Glu
            340                 345                 350
```

```
Ala His Gly Ser Tyr Phe His Met Ala Ala Trp Gly Leu Pro Ala Leu
        355                 360                 365

Lys Thr Ile Val Ile Leu Thr Leu Arg Lys Val Ala Gly Asp Glu Leu
370                 375                 380

Thr Gly Leu Cys Tyr Val Ala Ser Thr Asp Ala Ala Leu Thr Gly
385                 390                 395                 400

Phe Val Leu Val Pro Leu Ser Gly Tyr Leu Val Leu Gly Ser Ser Phe
                405                 410                 415

Leu Leu Thr Gly Phe Val Ala Leu Phe His Ile Arg Lys Ile Met Lys
            420                 425                 430

Thr Gly Gly Thr Asn Thr Glu Lys Leu Glu Lys Leu Met Val Lys Ile
                435                 440                 445

Gly Val Phe Ser Ile Leu Tyr Thr Val Pro Ala Thr Cys Val Ile Val
            450                 455                 460

Cys Tyr Val Tyr Glu Arg Leu Asn Met Asp Phe Trp Arg Leu Arg Ala
465                 470                 475                 480

Thr Glu Gln Pro Cys Ala Ala Ala Gly Pro Gly Arg Arg Asp
                485                 490                 495

Cys Ser Leu Pro Gly Gly Ser Val Pro Thr Val Ala Val Phe Met Leu
                500                 505                 510

Lys Ile Phe Met Ser Leu Val Val Gly Ile Thr Ser Gly Val Trp Val
            515                 520                 525

Trp Ser Ser Lys Thr Phe Gln Thr Trp Gln Ser Leu Cys Tyr Arg Lys
        530                 535                 540

Ile Ala Ala Gly Arg Ala Arg Ala Lys Ala Cys Arg Ala Pro Gly Ser
545                 550                 555                 560

Tyr Gly Arg Gly Thr His Cys His Tyr Lys Ala Pro Thr Val Val Leu
                565                 570                 575

His Met Thr Lys Thr Asp Pro Ser Leu Glu Asn Pro Thr His Leu
            580                 585                 590

<210> SEQ ID NO 10
<211> LENGTH: 581
<212> TYPE: PRT
<213> ORGANISM: Homo sapiens

<400> SEQUENCE: 10

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
                20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
        50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
                100                 105                 110

Ala Arg Leu Lys Cys Ser Pro Ile Met Glu Gln Phe Asn Phe Lys Trp
            115                 120                 125

Pro Asp Ser Leu Asp Cys Arg Lys Leu Pro Asn Lys Asn Asp Pro Asn
```

-continued

```
            130                 135                 140
Tyr Leu Cys Met Glu Ala Pro Asn Asn Gly Ser Asp Glu Pro Thr Arg
145                 150                 155                 160

Gly Ser Gly Leu Phe Pro Leu Phe Arg Pro Gln Arg Pro His Ser
                165                 170                 175

Ala Gln Glu His Pro Leu Lys Asp Gly Pro Gly Arg Gly Gly Cys
                180                 185                 190

Asp Asn Pro Gly Lys Phe His His Val Glu Lys Ser Ala Ser Cys Ala
                195                 200                 205

Pro Leu Cys Thr Pro Gly Val Asp Val Tyr Trp Ser Arg Glu Asp Lys
210                 215                 220

Arg Phe Ala Val Val Trp Leu Ala Ile Trp Ala Val Leu Cys Phe Phe
225                 230                 235                 240

Ser Ser Ala Phe Thr Val Leu Thr Phe Leu Ile Asp Pro Ala Arg Phe
                245                 250                 255

Arg Tyr Pro Glu Arg Pro Ile Ile Phe Leu Ser Met Cys Tyr Cys Val
                260                 265                 270

Tyr Ser Val Gly Tyr Leu Ile Arg Leu Phe Ala Gly Ala Glu Ser Ile
                275                 280                 285

Ala Cys Asp Arg Asp Ser Gly Gln Leu Tyr Val Ile Gln Glu Gly Leu
290                 295                 300

Glu Ser Thr Gly Cys Thr Leu Val Phe Leu Val Leu Tyr Tyr Phe Gly
305                 310                 315                 320

Met Ala Ser Ser Leu Trp Trp Val Val Leu Thr Leu Thr Trp Phe Leu
                325                 330                 335

Ala Ala Gly Lys Lys Trp Gly His Glu Ala Ile Glu Ala Asn Ser Ser
                340                 345                 350

Tyr Phe His Leu Ala Ala Trp Ala Ile Pro Ala Val Lys Thr Ile Leu
                355                 360                 365

Ile Leu Val Met Arg Arg Val Ala Gly Asp Glu Leu Thr Gly Val Cys
370                 375                 380

Tyr Val Gly Ser Met Asp Val Asn Ala Leu Thr Gly Phe Val Leu Ile
385                 390                 395                 400

Pro Leu Ala Cys Tyr Leu Val Ile Gly Thr Ser Phe Ile Leu Ser Gly
                405                 410                 415

Phe Val Ala Leu Phe His Ile Arg Arg Val Met Lys Thr Gly Gly Glu
                420                 425                 430

Asn Thr Asp Lys Leu Glu Lys Leu Met Val Arg Ile Gly Leu Phe Ser
                435                 440                 445

Val Leu Tyr Thr Val Pro Ala Thr Cys Val Ile Ala Cys Tyr Phe Tyr
450                 455                 460

Glu Arg Leu Asn Met Asp Tyr Trp Lys Ile Leu Ala Ala Gln His Lys
465                 470                 475                 480

Cys Lys Met Asn Asn Gln Thr Lys Thr Leu Asp Cys Leu Met Ala Ala
                485                 490                 495

Ser Ile Pro Ala Val Glu Ile Phe Met Val Lys Ile Phe Met Leu Leu
                500                 505                 510

Val Val Gly Ile Thr Ser Gly Met Trp Ile Trp Thr Ser Lys Thr Leu
                515                 520                 525

Gln Ser Trp Gln Gln Val Cys Ser Arg Arg Leu Lys Lys Lys Ser Arg
                530                 535                 540

Arg Lys Pro Ala Ser Val Ile Thr Ser Gly Gly Ile Tyr Lys Lys Ala
545                 550                 555                 560
```

Gln His Pro Gln Lys Thr His His Gly Lys Tyr Glu Ile Pro Ala Gln
            565                 570                 575

Ser Pro Thr Cys Val
            580

<210> SEQ ID NO 11
<211> LENGTH: 321
<212> TYPE: PRT
<213> ORGANISM: Homo sapiens

<400> SEQUENCE: 11

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Pro Pro Val Asp Pro
            35                  40                  45

Arg Arg Leu Ala Arg Gln Leu Leu Leu Leu Trp Leu Leu Glu Ala
50                  55                  60

Pro Leu Leu Leu Gly Val Arg Ala Gln Ala Ala Gly Gln Gly Pro Gly
65                  70                  75                  80

Gln Gly Pro Gly Pro Gly Gln Pro Pro Pro Pro Gln Gln Gln
            85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
            115                 120                 125

Tyr Asn Gln Thr Ile Met Pro Asn Leu Leu Gly His Thr Asn Gln Glu
130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
            165                 170                 175

Cys Thr Val Leu Glu Gln Ala Leu Pro Pro Cys Arg Ser Leu Cys Glu
            180                 185                 190

Arg Ala Arg Gln Gly Cys Glu Ala Leu Met Asn Lys Phe Gly Phe Gln
            195                 200                 205

Trp Pro Asp Thr Leu Lys Cys Glu Lys Phe Pro Val His Gly Ala Gly
            210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
            245                 250                 255

Gly His Arg Gly Gly Phe Pro Gly Gly Ala Gly Ala Ser Glu Arg Gly
            260                 265                 270

Lys Phe Ser Cys Pro Arg Ala Leu Lys Val Pro Ser Tyr Leu Asn Tyr
            275                 280                 285

His Phe Leu Gly Glu Lys Asp Cys Gly Ala Pro Cys Glu Pro Thr Lys
            290                 295                 300

Val Tyr Gly Leu Met Tyr Phe Gly Pro Glu Glu Leu Arg Phe Ser Arg
305                 310                 315                 320

Thr

<210> SEQ ID NO 12

```
<211> LENGTH: 250
<212> TYPE: PRT
<213> ORGANISM: Homo sapiens

<400> SEQUENCE: 12

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
            20                  25                  30

Ile Pro Asp His Gly Phe Cys Gln Pro Ile Ser Ile Pro Leu Cys Thr
        35                  40                  45

Asp Ile Ala Tyr Asn Gln Thr Ile Met Pro Asn Leu Leu Gly His Thr
    50                  55                  60

Asn Gln Glu Asp Ala Gly Leu Glu Val His Gln Phe Tyr Pro Leu Val
65                  70                  75                  80

Lys Val Gln Cys Ser Pro Glu Leu Arg Phe Phe Leu Cys Ser Met Tyr
                85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
    130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
        195                 200                 205

Ser Tyr Leu Ser Tyr Lys Phe Leu Gly Glu Arg Asp Cys Ala Ala Pro
    210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr
                245                 250

<210> SEQ ID NO 13
<211> LENGTH: 204
<212> TYPE: PRT
<213> ORGANISM: Homo sapiens

<400> SEQUENCE: 13

Met Ala Met Thr Trp Ile Val Phe Ser Leu Trp Pro Leu Thr Val Phe
1               5                   10                  15

Met Gly His Ile Gly Gly His Ser Leu Phe Ser Cys Glu Pro Ile Thr
            20                  25                  30

Leu Arg Met Cys Gln Asp Leu Pro Tyr Asn Thr Thr Phe Met Pro Asn
        35                  40                  45

Leu Leu Asn His Tyr Asp Gln Gln Thr Ala Ala Leu Ala Met Glu Pro
    50                  55                  60

Phe His Pro Met Val Asn Leu Asp Cys Ser Arg Asp Phe Arg Pro Phe
65                  70                  75                  80

Leu Cys Ala Leu Tyr Ala Pro Ile Cys Met Glu Tyr Gly Arg Val Thr
                85                  90                  95
```

-continued

Leu Pro Cys Arg Arg Leu Cys Gln Arg Ala Tyr Ser Glu Cys Ser Lys
                100                 105                 110

Leu Met Glu Met Phe Gly Val Pro Trp Pro Glu Asp Met Glu Cys Ser
            115                 120                 125

Arg Phe Pro Asp Cys Asp Glu Pro Tyr Pro Arg Leu Val Asp Leu Asn
        130                 135                 140

Leu Ala Gly Glu Pro Thr Glu Gly Ala Pro Val Ala Val Gln Arg Asp
145                 150                 155                 160

Tyr Gly Phe Trp Cys Pro Arg Glu Leu Lys Ile Asp Pro Asp Leu Gly
                165                 170                 175

Tyr Ser Phe Leu His Val Arg Asp Cys Ser Pro Pro Cys Pro Asn Met
            180                 185                 190

Tyr Phe Arg Arg Glu Glu Leu Ser Phe Ala Arg Tyr
        195                 200

<210> SEQ ID NO 14
<211> LENGTH: 224
<212> TYPE: PRT
<213> ORGANISM: Homo sapiens

<400> SEQUENCE: 14

Met Leu Ala Met Ala Trp Arg Gly Ala Gly Pro Ser Val Pro Gly Ala
1               5                   10                  15

Pro Gly Gly Val Gly Leu Ser Leu Gly Leu Leu Leu Gln Leu Leu Leu
            20                  25                  30

Leu Leu Gly Pro Ala Arg Gly Phe Gly Asp Glu Glu Glu Arg Arg Cys
        35                  40                  45

Asp Pro Ile Arg Ile Ser Met Cys Gln Asn Leu Gly Tyr Asn Val Thr
    50                  55                  60

Lys Met Pro Asn Leu Val Gly His Glu Leu Gln Thr Asp Ala Glu Leu
65                  70                  75                  80

Gln Leu Thr Thr Phe Thr Pro Leu Ile Gln Tyr Gly Cys Ser Ser Gln
                85                  90                  95

Leu Gln Phe Phe Leu Cys Ser Val Tyr Val Pro Met Cys Thr Glu Lys
                100                 105                 110

Ile Asn Ile Pro Ile Gly Pro Cys Gly Gly Met Cys Leu Ser Val Lys
            115                 120                 125

Arg Arg Cys Glu Pro Val Leu Lys Glu Phe Gly Phe Ala Trp Pro Glu
        130                 135                 140

Ser Leu Asn Cys Ser Lys Phe Pro Pro Gln Asn Asp His Asn His Met
145                 150                 155                 160

Cys Met Glu Gly Pro Gly Asp Glu Glu Val Pro Leu Pro His Lys Thr
                165                 170                 175

Pro Ile Gln Pro Gly Glu Glu Cys His Ser Val Gly Thr Asn Ser Asp
            180                 185                 190

Gln Tyr Ile Trp Val Lys Arg Ser Leu Asn Cys Val Leu Lys Cys Gly
        195                 200                 205

Tyr Asp Ala Gly Leu Tyr Ser Arg Ser Ala Lys Glu Phe Thr Asp Ile
    210                 215                 220

<210> SEQ ID NO 15
<211> LENGTH: 233
<212> TYPE: PRT
<213> ORGANISM: Homo sapiens

<400> SEQUENCE: 15

Met Ala Arg Pro Asp Pro Ser Ala Pro Pro Ser Leu Leu Leu Leu Leu
1               5                   10                  15

Leu Ala Gln Leu Val Gly Arg Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
        130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
            195                 200                 205

Lys Val Arg Thr Gly Gln Val Pro Asn Cys Ala Val Pro Cys Tyr Gln
            210                 215                 220

Pro Ser Phe Ser Ala Asp Glu Arg Thr
225                 230

<210> SEQ ID NO 16
<211> LENGTH: 207
<212> TYPE: PRT
<213> ORGANISM: Homo sapiens

<400> SEQUENCE: 16

Met Glu Met Phe Thr Phe Leu Leu Thr Cys Ile Phe Leu Pro Leu Leu
1               5                   10                  15

Arg Gly His Ser Leu Phe Thr Cys Glu Pro Ile Thr Val Pro Arg Cys
            20                  25                  30

Met Lys Met Ala Tyr Asn Met Thr Phe Phe Pro Asn Leu Met Gly His
        35                  40                  45

Tyr Asp Gln Ser Ile Ala Ala Val Glu Met Glu His Phe Leu Pro Leu
    50                  55                  60

Ala Asn Leu Glu Cys Ser Pro Asn Ile Glu Thr Phe Leu Cys Lys Ala
65                  70                  75                  80

Phe Val Pro Thr Cys Ile Glu Gln Ile His Val Val Pro Pro Cys Arg
                85                  90                  95

Lys Leu Cys Glu Lys Val Tyr Ser Asp Cys Lys Lys Leu Ile Asp Thr
            100                 105                 110

Phe Gly Ile Arg Trp Pro Glu Glu Leu Glu Cys Asp Arg Leu Gln Tyr
            115                 120                 125

Cys Asp Glu Thr Val Pro Val Thr Phe Asp Pro His Thr Glu Phe Leu

```
            130                 135                 140
Gly Pro Gln Lys Lys Thr Glu Gln Val Gln Arg Asp Ile Gly Phe Trp
145                 150                 155                 160

Cys Pro Arg His Leu Lys Thr Ser Gly Gly Gln Gly Tyr Lys Phe Leu
                165                 170                 175

Gly Ile Asp Gln Cys Ala Pro Pro Cys Pro Asn Met Tyr Phe Lys Ser
            180                 185                 190

Asp Glu Leu Glu Phe Ala Lys Ser Phe Ile Gly Thr Val Ser Ile
        195                 200                 205
```

<210> SEQ ID NO 17
<211> LENGTH: 255
<212> TYPE: PRT
<213> ORGANISM: Homo sapiens

<400> SEQUENCE: 17

```
Met Arg Asp Pro Gly Ala Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
        50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu
                245                 250                 255
```

<210> SEQ ID NO 18
<211> LENGTH: 277
<212> TYPE: PRT
<213> ORGANISM: Homo sapiens

<400> SEQUENCE: 18

```
Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
                20                  25                  30

Leu Ala Cys Gln Glu Ile Thr Val Pro Leu Cys Lys Gly Ile Gly Tyr
            35                  40                  45
```

```
Ala Gly Leu Glu Val His Gln Phe Trp Pro Leu Val Glu Ile Gln Cys
 65                  70                  75                  80

Ser Pro Asp Leu Lys Phe Phe Leu Cys Ser Met Tyr Thr Pro Ile Cys
                 85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
        130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Pro Pro
            195                 200                 205

Ala Arg Gly Gly Gly Gly Gly Lys Ala Arg Pro Pro Gly Gly Gly
            210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr
            275

<210> SEQ ID NO 19
<211> LENGTH: 230
<212> TYPE: PRT
<213> ORGANISM: Homo sapiens

<400> SEQUENCE: 19

Met Ala Val Ala Pro Leu Arg Gly Ala Leu Leu Leu Trp Gln Leu Leu
  1               5                  10                  15

Ala Ala Gly Gly Ala Ala Leu Glu Ile Gly Arg Phe Asp Pro Glu Arg
                 20                  25                  30

Gly Arg Gly Ala Ala Pro Cys Gln Ala Val Glu Ile Pro Met Cys Arg
             35                  40                  45

Gly Ile Gly Tyr Asn Leu Thr Arg Met Pro Asn Leu Leu Gly His Thr
         50                  55                  60

Ser Gln Gly Glu Ala Ala Glu Leu Ala Glu Phe Ala Pro Leu Val
 65                  70                  75                  80

Gln Tyr Gly Cys His Ser His Leu Arg Phe Phe Leu Cys Ser Leu Tyr
                 85                  90                  95

Ala Pro Met Cys Thr Asp Gln Val Ser Thr Pro Ile Pro Ala Cys Arg
            100                 105                 110

Pro Met Cys Glu Gln Ala Arg Leu Arg Cys Ala Pro Ile Met Glu Gln
            115                 120                 125

Phe Asn Phe Gly Trp Pro Asp Ser Leu Asp Cys Ala Arg Leu Pro Thr
        130                 135                 140
```

Arg Asn Asp Pro His Ala Leu Cys Met Glu Ala Pro Glu Asn Ala Thr
145                 150                 155                 160

Ala Gly Pro Ala Glu Pro His Lys Gly Leu Gly Met Leu Pro Val Ala
            165                 170                 175

Pro Arg Pro Ala Arg Pro Pro Gly Asp Leu Gly Pro Gly Ala Gly Gly
            180                 185                 190

Ser Gly Thr Cys Glu Asn Pro Glu Lys Phe Gln Tyr Val Glu Lys Ser
            195                 200                 205

Arg Ser Cys Ala Pro Arg Cys Gly Pro Gly Val Glu Val Phe Trp Ser
            210                 215                 220

Arg Arg Asp Lys Asp Phe
225                 230

<210> SEQ ID NO 20
<211> LENGTH: 227
<212> TYPE: PRT
<213> ORGANISM: Homo sapiens

<400> SEQUENCE: 20

Met Gln Arg Pro Gly Pro Arg Leu Trp Leu Val Leu Gln Val Met Gly
1               5                   10                  15

Ser Cys Ala Ala Ile Ser Ser Met Asp Met Glu Arg Pro Gly Asp Gly
            20                  25                  30

Lys Cys Gln Pro Ile Glu Ile Pro Met Cys Lys Asp Ile Gly Tyr Asn
            35                  40                  45

Met Thr Arg Met Pro Asn Leu Met Gly His Glu Asn Gln Arg Glu Ala
        50                  55                  60

Ala Ile Gln Leu His Glu Phe Ala Pro Leu Val Glu Tyr Gly Cys His
65                  70                  75                  80

Gly His Leu Arg Phe Phe Leu Cys Ser Leu Tyr Ala Pro Met Cys Thr
                85                  90                  95

Glu Gln Val Ser Thr Pro Ile Pro Ala Cys Arg Val Met Cys Glu Gln
            100                 105                 110

Ala Arg Leu Lys Cys Ser Pro Ile Met Glu Gln Phe Asn Phe Lys Trp
        115                 120                 125

Pro Asp Ser Leu Asp Cys Arg Lys Leu Pro Asn Lys Asn Asp Pro Asn
130                 135                 140

Tyr Leu Cys Met Glu Ala Pro Asn Asn Gly Ser Asp Glu Pro Thr Arg
145                 150                 155                 160

Gly Ser Gly Leu Phe Pro Pro Leu Phe Arg Pro Gln Arg Pro His Ser
            165                 170                 175

Ala Gln Glu His Pro Leu Lys Asp Gly Gly Pro Gly Arg Gly Gly Cys
            180                 185                 190

Asp Asn Pro Gly Lys Phe His His Val Glu Lys Ser Ala Ser Cys Ala
            195                 200                 205

Pro Leu Cys Thr Pro Gly Val Asp Val Tyr Trp Ser Arg Glu Asp Lys
            210                 215                 220

Arg Phe Ala
225

<210> SEQ ID NO 21
<211> LENGTH: 151
<212> TYPE: PRT
<213> ORGANISM: Homo sapiens

<400> SEQUENCE: 21

Gln Gln Pro Pro Pro Pro Gln Gln Gln Ser Gly Gln Gln Tyr
1               5               10              15

Asn Gly Glu Arg Gly Ile Ser Val Pro Asp His Gly Tyr Cys Gln Pro
            20              25              30

Ile Ser Ile Pro Leu Cys Thr Asp Ile Ala Tyr Asn Gln Thr Ile Met
        35              40              45

Pro Asn Leu Leu Gly His Thr Asn Gln Glu Asp Ala Gly Leu Glu Val
50              55              60

His Gln Phe Tyr Pro Leu Val Lys Val Gln Cys Ser Ala Glu Leu Lys
65              70              75              80

Phe Phe Leu Cys Ser Met Tyr Ala Pro Val Cys Thr Val Leu Glu Gln
                85              90              95

Ala Leu Pro Pro Cys Arg Ser Leu Cys Glu Arg Ala Arg Gln Gly Cys
            100             105             110

Glu Ala Leu Met Asn Lys Phe Gly Phe Gln Trp Pro Asp Thr Leu Lys
        115             120             125

Cys Glu Lys Phe Pro Val His Gly Ala Gly Glu Leu Cys Val Gly Gln
    130             135             140

Asn Thr Ser Asp Lys Gly Thr
145             150

<210> SEQ ID NO 22
<211> LENGTH: 136
<212> TYPE: PRT
<213> ORGANISM: Homo sapiens

<400> SEQUENCE: 22

Gln Phe His Gly Glu Lys Gly Ile Ser Ile Pro Asp His Gly Phe Cys
1               5               10              15

Gln Pro Ile Ser Ile Pro Leu Cys Thr Asp Ile Ala Tyr Asn Gln Thr
            20              25              30

Ile Met Pro Asn Leu Leu Gly His Thr Asn Gln Glu Asp Ala Gly Leu
        35              40              45

Glu Val His Gln Phe Tyr Pro Leu Val Lys Val Gln Cys Ser Pro Glu
50              55              60

Leu Arg Phe Phe Leu Cys Ser Met Tyr Ala Pro Val Cys Thr Val Leu
65              70              75              80

Glu Gln Ala Ile Pro Pro Cys Arg Ser Ile Cys Glu Arg Ala Arg Gln
                85              90              95

Gly Cys Glu Ala Leu Met Asn Lys Phe Gly Phe Gln Trp Pro Glu Arg
            100             105             110

Leu Arg Cys Glu His Phe Pro Arg His Gly Ala Glu Gln Ile Cys Val
        115             120             125

Gly Gln Asn His Ser Glu Asp Gly
    130             135

<210> SEQ ID NO 23
<211> LENGTH: 121
<212> TYPE: PRT
<213> ORGANISM: Homo sapiens

<400> SEQUENCE: 23

His Ser Leu Phe Ser Cys Glu Pro Ile Thr Leu Arg Met Cys Gln Asp
1               5               10              15

Leu Pro Tyr Asn Thr Thr Phe Met Pro Asn Leu Leu Asn His Tyr Asp
            20              25              30

```
Gln Gln Thr Ala Ala Leu Ala Met Glu Pro Phe His Pro Met Val Asn
         35                  40                  45

Leu Asp Cys Ser Arg Asp Phe Arg Pro Phe Leu Cys Ala Leu Tyr Ala
 50                  55                  60

Pro Ile Cys Met Glu Tyr Gly Arg Val Thr Leu Pro Cys Arg Arg Leu
 65                  70                  75                  80

Cys Gln Arg Ala Tyr Ser Glu Cys Ser Lys Leu Met Glu Met Phe Gly
                 85                  90                  95

Val Pro Trp Pro Glu Asp Met Glu Cys Ser Arg Phe Pro Asp Cys Asp
                100                 105                 110

Glu Pro Tyr Pro Arg Leu Val Asp Leu
            115                 120

<210> SEQ ID NO 24
<211> LENGTH: 131
<212> TYPE: PRT
<213> ORGANISM: Homo sapiens

<400> SEQUENCE: 24

Phe Gly Asp Glu Glu Arg Arg Cys Asp Pro Ile Arg Ile Ser Met
 1               5                  10                  15

Cys Gln Asn Leu Gly Tyr Asn Val Thr Lys Met Pro Asn Leu Val Gly
                 20                  25                  30

His Glu Leu Gln Thr Asp Ala Glu Leu Gln Leu Thr Thr Phe Thr Pro
         35                  40                  45

Leu Ile Gln Tyr Gly Cys Ser Ser Gln Leu Gln Phe Phe Leu Cys Ser
 50                  55                  60

Val Tyr Val Pro Met Cys Thr Glu Lys Ile Asn Ile Pro Ile Gly Pro
 65                  70                  75                  80

Cys Gly Gly Met Cys Leu Ser Val Lys Arg Arg Cys Glu Pro Val Leu
                 85                  90                  95

Lys Glu Phe Gly Phe Ala Trp Pro Glu Ser Leu Asn Cys Ser Lys Phe
                100                 105                 110

Pro Pro Gln Asn Asp His Asn His Met Cys Met Glu Gly Pro Gly Asp
            115                 120                 125

Glu Glu Val
    130

<210> SEQ ID NO 25
<211> LENGTH: 131
<212> TYPE: PRT
<213> ORGANISM: Homo sapiens

<400> SEQUENCE: 25

Ala Ser Lys Ala Pro Val Cys Gln Glu Ile Thr Val Pro Met Cys Arg
 1               5                  10                  15

Gly Ile Gly Tyr Asn Leu Thr His Met Pro Asn Gln Phe Asn His Asp
                 20                  25                  30

Thr Gln Asp Glu Ala Gly Leu Glu Val His Gln Phe Trp Pro Leu Val
         35                  40                  45

Glu Ile Gln Cys Ser Pro Asp Leu Arg Phe Phe Leu Cys Ser Met Tyr
 50                  55                  60

Thr Pro Ile Cys Leu Pro Asp Tyr His Lys Pro Leu Pro Pro Cys Arg
 65                  70                  75                  80

Ser Val Cys Glu Arg Ala Lys Ala Gly Cys Ser Pro Leu Met Arg Gln
                 85                  90                  95
```

```
Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
            115                 120                 125

Ala Thr Thr
        130

<210> SEQ ID NO 26
<211> LENGTH: 127
<212> TYPE: PRT
<213> ORGANISM: Homo sapiens

<400> SEQUENCE: 26

His Ser Leu Phe Thr Cys Glu Pro Ile Thr Val Pro Arg Cys Met Lys
1               5                   10                  15

Met Ala Tyr Asn Met Thr Phe Phe Pro Asn Leu Met Gly His Tyr Asp
            20                  25                  30

Gln Ser Ile Ala Ala Val Glu Met Glu His Phe Leu Pro Leu Ala Asn
        35                  40                  45

Leu Glu Cys Ser Pro Asn Ile Glu Thr Phe Leu Cys Lys Ala Phe Val
50                  55                  60

Pro Thr Cys Ile Glu Gln Ile His Val Val Pro Pro Cys Arg Lys Leu
65                  70                  75                  80

Cys Glu Lys Val Tyr Ser Asp Cys Lys Lys Leu Ile Asp Thr Phe Gly
                85                  90                  95

Ile Arg Trp Pro Glu Glu Leu Glu Cys Asp Arg Leu Gln Tyr Cys Asp
            100                 105                 110

Glu Thr Val Pro Val Thr Phe Asp Pro His Thr Glu Phe Leu Gly
            115                 120                 125

<210> SEQ ID NO 27
<211> LENGTH: 138
<212> TYPE: PRT
<213> ORGANISM: Homo sapiens

<400> SEQUENCE: 27

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
            115                 120                 125

Val Gly Gln Asn Thr Ser Asp Gly Ser Gly
        130                 135

<210> SEQ ID NO 28
<211> LENGTH: 131
```

<212> TYPE: PRT
<213> ORGANISM: Homo sapiens

<400> SEQUENCE: 28

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr
    130

<210> SEQ ID NO 29
<211> LENGTH: 137
<212> TYPE: PRT
<213> ORGANISM: Homo sapiens

<400> SEQUENCE: 29

Leu Glu Ile Gly Arg Phe Asp Pro Glu Arg Gly Arg Gly Ala Ala Pro
1               5                   10                  15

Cys Gln Ala Val Glu Ile Pro Met Cys Arg Gly Ile Gly Tyr Asn Leu
            20                  25                  30

Thr Arg Met Pro Asn Leu Leu Gly His Thr Ser Gln Gly Glu Ala Ala
        35                  40                  45

Ala Glu Leu Ala Glu Phe Ala Pro Leu Val Gln Tyr Gly Cys His Ser
50                  55                  60

His Leu Arg Phe Phe Leu Cys Ser Leu Tyr Ala Pro Met Cys Thr Asp
65                  70                  75                  80

Gln Val Ser Thr Pro Ile Pro Ala Cys Arg Pro Met Cys Glu Gln Ala
                85                  90                  95

Arg Leu Arg Cys Ala Pro Ile Met Glu Gln Phe Asn Phe Gly Trp Pro
            100                 105                 110

Asp Ser Leu Asp Cys Ala Arg Leu Pro Thr Arg Asn Asp Pro His Ala
        115                 120                 125

Leu Cys Met Glu Ala Pro Glu Asn Ala
    130                 135

<210> SEQ ID NO 30
<211> LENGTH: 134
<212> TYPE: PRT
<213> ORGANISM: Homo sapiens

<400> SEQUENCE: 30

Ile Ser Ser Met Asp Met Glu Arg Pro Gly Asp Gly Lys Cys Gln Pro
1               5                   10                  15

Ile Glu Ile Pro Met Cys Lys Asp Ile Gly Tyr Asn Met Thr Arg Met

```
                20                  25                  30
Pro Asn Leu Met Gly His Glu Asn Gln Arg Glu Ala Ala Ile Gln Leu
            35                  40                  45

His Glu Phe Ala Pro Leu Val Glu Tyr Gly Cys His Gly His Leu Arg
 50                  55                  60

Phe Phe Leu Cys Ser Leu Tyr Ala Pro Met Cys Thr Glu Gln Val Ser
 65                  70                  75                  80

Thr Pro Ile Pro Ala Cys Arg Val Met Cys Glu Gln Ala Arg Leu Lys
                85                  90                  95

Cys Ser Pro Ile Met Glu Gln Phe Asn Phe Lys Trp Pro Asp Ser Leu
            100                 105                 110

Asp Cys Arg Lys Leu Pro Asn Lys Asn Asp Pro Asn Tyr Leu Cys Met
            115                 120                 125

Glu Ala Pro Asn Asn Gly
        130

<210> SEQ ID NO 31
<211> LENGTH: 10
<212> TYPE: PRT
<213> ORGANISM: Artificial Sequence
<220> FEATURE:
<223> OTHER INFORMATION: 18R5 VH CDR1

<400> SEQUENCE: 31

Gly Phe Thr Phe Ser His Tyr Thr Leu Ser
 1               5                  10

<210> SEQ ID NO 32
<211> LENGTH: 17
<212> TYPE: PRT
<213> ORGANISM: Artificial Sequence
<220> FEATURE:
<223> OTHER INFORMATION: 18R5 VH CDR2

<400> SEQUENCE: 32

Val Ile Ser Gly Asp Gly Ser Tyr Thr Tyr Tyr Ala Asp Ser Val Lys
 1               5                  10                  15

Gly

<210> SEQ ID NO 33
<211> LENGTH: 9
<212> TYPE: PRT
<213> ORGANISM: Artificial Sequence
<220> FEATURE:
<223> OTHER INFORMATION: 18R5 VH CDR3

<400> SEQUENCE: 33

Asn Phe Ile Lys Tyr Val Phe Ala Asn
 1               5

<210> SEQ ID NO 34
<211> LENGTH: 11
<212> TYPE: PRT
<213> ORGANISM: Artificial Sequence
<220> FEATURE:
<223> OTHER INFORMATION: 18R5 VL CDR1

<400> SEQUENCE: 34

Ser Gly Asp Asn Ile Gly Ser Phe Tyr Val His
 1               5                  10

<210> SEQ ID NO 35
```

```
<211> LENGTH: 8
<212> TYPE: PRT
<213> ORGANISM: Artificial Sequence
<220> FEATURE:
<223> OTHER INFORMATION: 18R5 VL CDR2

<400> SEQUENCE: 35

Asp Lys Ser Asn Arg Pro Ser Gly
1               5

<210> SEQ ID NO 36
<211> LENGTH: 9
<212> TYPE: PRT
<213> ORGANISM: Artificial Sequence
<220> FEATURE:
<223> OTHER INFORMATION: 18R5 VL CDR3

<400> SEQUENCE: 36

Gln Ser Tyr Ala Asn Thr Leu Ser Leu
1               5

<210> SEQ ID NO 37
<211> LENGTH: 118
<212> TYPE: PRT
<213> ORGANISM: Artificial Sequence
<220> FEATURE:
<223> OTHER INFORMATION: 18R5 VH

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Thr Leu Ser Trp Val Arg Gln Ala Pro Gly Lys Gly Leu Glu Trp Val
        35                  40                  45

Ser Val Ile Ser Gly Asp Gly Ser Tyr Thr Tyr Tyr Ala Asp Ser Val
    50                  55                  60

Lys Gly Arg Phe Thr Ile Ser Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Phe Ile Lys Tyr Val Phe Ala Asn Trp Gly Gln Gly Thr
            100                 105                 110

Leu Val Thr Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: 18R5 VL

<400> SEQUENCE: 38

Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Lys Ser Asn Arg Pro Ser Gly Ile Pro Glu Arg Phe Ser Gly Ser
    50                  55                  60
```

```
Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Ala Asn Thr Leu Ser Leu
                 85                  90                  95

Val Phe Gly Gly Gly Thr Lys Leu Thr Val Leu Gly
            100                 105

<210> SEQ ID NO 39
<211> LENGTH: 463
<212> TYPE: PRT
<213> ORGANISM: Artificial Sequence
<220> FEATURE:
<223> OTHER INFORMATION: 18R5 heavy chain (IgG2) amino acid sequence

<400> SEQUENCE: 39

Met Lys His Leu Trp Phe Phe Leu Leu Leu Val Ala Ala Pro Arg Trp
 1               5                  10                  15

Val Leu Ser Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Ser His Tyr Thr Leu Ser Trp Val Arg Gln Ala Pro Gly Lys Gly Leu
     50                  55                  60

Glu Trp Val Ser Val Ile Ser Gly Asp Gly Ser Tyr Thr Tyr Tyr Ala
 65                  70                  75                  80

Asp Ser Val Lys Gly Arg Phe Thr Ile Ser Ser Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asn Phe Ile Lys Tyr Val Phe Ala Asn Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320
```

```
Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
                340                 345                 350

Ser Lys Thr Lys Gly Gln Pro Arg Glu Pro Gln Val Tyr Thr Leu Pro
                355                 360                 365

Pro Ser Arg Glu Glu Met Thr Lys Asn Gln Val Ser Leu Thr Cys Leu
            370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
            435                 440                 445

His Asn His Tyr Thr Gln Lys Ser Leu Ser Leu Ser Pro Gly Lys
        450                 455                 460

<210> SEQ ID NO 40
<211> LENGTH: 232
<212> TYPE: PRT
<213> ORGANISM: Artificial Sequence
<220> FEATURE:
<223> OTHER INFORMATION: 18R5 LIGHT CHAIN light chain (lambda) amino
      acid sequence

<400> SEQUENCE: 40

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
                20                  25                  30

Pro Gly Gln Thr Ala Arg Ile Ser Cys Ser Gly Asp Asn Ile Gly Ser
            35                  40                  45

Phe Tyr Val His Trp Tyr Gln Gln Lys Pro Gly Gln Ala Pro Val Leu
        50                  55                  60

Val Ile Tyr Asp Lys Ser Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Gln Ser Tyr Ala Asn Thr
            100                 105                 110

Leu Ser Leu Val Phe Gly Gly Gly Thr Lys Leu Thr Val Leu Gly Gln
        115                 120                 125

Pro Lys Ala Ala Pro Ser Val Thr Leu Phe Pro Pro Ser Ser Glu Glu
130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
```

Thr Val Ala Pro Thr Glu Cys Ser
225             230

<210> SEQ ID NO 41
<211> LENGTH: 11
<212> TYPE: PRT
<213> ORGANISM: Artificial Sequence
<220> FEATURE:
<223> OTHER INFORMATION: 18R8 VL CDR1

<400> SEQUENCE: 41

Ser Gly Asp Lys Leu Gly Lys Lys Tyr Ala Ser
1               5                   10

<210> SEQ ID NO 42
<211> LENGTH: 8
<212> TYPE: PRT
<213> ORGANISM: Artificial Sequence
<220> FEATURE:
<223> OTHER INFORMATION: 18R8 VL CDR2

<400> SEQUENCE: 42

Glu Lys Asp Asn Arg Pro Ser Gly
1               5

<210> SEQ ID NO 43
<211> LENGTH: 9
<212> TYPE: PRT
<213> ORGANISM: Artificial Sequence
<220> FEATURE:
<223> OTHER INFORMATION: 18R8 VL CDR3

<400> SEQUENCE: 43

Ser Ser Phe Ala Gly Asn Ser Leu Glu
1               5

<210> SEQ ID NO 44
<211> LENGTH: 108
<212> TYPE: PRT
<213> ORGANISM: Artificial Sequence
<220> FEATURE:
<223> OTHER INFORMATION: 18R8 VL

<400> SEQUENCE: 44

Asp Ile Glu Leu Thr Gln Pro Pro Ser Val Ser Val Ala Pro Gly Gln
1               5                   10                  15

Thr Ala Arg Ile Ser Cys Ser Gly Asp Lys Leu Gly Lys Lys Tyr Ala
            20                  25                  30

Ser Trp Tyr Gln Gln Lys Pro Gly Gln Ala Pro Val Leu Val Ile Tyr
        35                  40                  45

Glu Lys Asp Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Phe Ala Gly Asn Ser Leu Glu
                85                  90                  95

Val Phe Gly Gly Gly Thr Lys Leu Thr Val Leu Gly
            100                 105

<210> SEQ ID NO 45
<211> LENGTH: 232
<212> TYPE: PRT

```
<213> ORGANISM: Artificial Sequence
<220> FEATURE:
<223> OTHER INFORMATION: 18R8 18R8 light chain (lambda) amino acid
      sequence

<400> SEQUENCE: 45

Met Ala Trp Ala Leu Leu Leu Thr Leu Leu Thr Gln Gly Thr Gly
1               5                   10                  15

Ser Trp Ala Asp Ile Glu Leu Thr Gln Pro Pro Ser Val Ser Val Ala
                20                  25                  30

Pro Gly Gln Thr Ala Arg Ile Ser Cys Ser Gly Asp Lys Leu Gly Lys
            35                  40                  45

Lys Tyr Ala Ser Trp Tyr Gln Gln Lys Pro Gly Gln Ala Pro Val Leu
50                  55                  60

Val Ile Tyr Glu Lys Asp Asn Arg Pro Ser Gly Ile Pro Glu Arg Phe
65                  70                  75                  80

Ser Gly Ser Asn Ser Gly Asn Thr Ala Thr Leu Thr Ile Ser Gly Thr
                85                  90                  95

Gln Ala Glu Asp Glu Ala Asp Tyr Tyr Cys Ser Ser Phe Ala Gly Asn
            100                 105                 110

Ser Leu Glu Val Phe Gly Gly Thr Lys Leu Thr Val Leu Gly Gln
        115                 120                 125

Pro Lys Ala Ala Pro Ser Val Thr Leu Phe Pro Pro Ser Ser Glu Glu
130                 135                 140

Leu Gln Ala Asn Lys Ala Thr Leu Val Cys Leu Ile Ser Asp Phe Tyr
145                 150                 155                 160

Pro Gly Ala Val Thr Val Ala Trp Lys Ala Asp Ser Ser Pro Val Lys
                165                 170                 175

Ala Gly Val Glu Thr Thr Thr Pro Ser Lys Gln Ser Asn Asn Lys Tyr
            180                 185                 190

Ala Ala Ser Ser Tyr Leu Ser Leu Thr Pro Glu Gln Trp Lys Ser His
        195                 200                 205

Arg Ser Tyr Ser Cys Gln Val Thr His Glu Gly Ser Thr Val Glu Lys
    210                 215                 220

Thr Val Ala Pro Thr Glu Cys Ser
225                 230

<210> SEQ ID NO 46
<211> LENGTH: 10
<212> TYPE: PRT
<213> ORGANISM: Artificial Sequence
<220> FEATURE:
<223> OTHER INFORMATION: 44R24 VH CDR1

<400> SEQUENCE: 46

Gly Phe Thr Phe Ser Ser Tyr Tyr Ile Thr
1               5                   10

<210> SEQ ID NO 47
<211> LENGTH: 17
<212> TYPE: PRT
<213> ORGANISM: Artificial Sequence
<220> FEATURE:
<223> OTHER INFORMATION: 44R24 VH CDR2

<400> SEQUENCE: 47

Thr Ile Ser Tyr Ser Ser Ser Asn Thr Tyr Tyr Ala Asp Ser Val Lys
1               5                   10                  15

Gly
```

```
<210> SEQ ID NO 48
<211> LENGTH: 6
<212> TYPE: PRT
<213> ORGANISM: Artificial Sequence
<220> FEATURE:
<223> OTHER INFORMATION: 44R24 VH CDR3

<400> SEQUENCE: 48

Ser Ile Val Phe Asp Tyr
1               5

<210> SEQ ID NO 49
<211> LENGTH: 11
<212> TYPE: PRT
<213> ORGANISM: Artificial Sequence
<220> FEATURE:
<223> OTHER INFORMATION: 44R24 VL CDR1

<400> SEQUENCE: 49

Ser Gly Asp Ala Leu Gly Asn Arg Tyr Val Tyr
1               5                   10

<210> SEQ ID NO 50
<211> LENGTH: 2
<212> TYPE: PRT
<213> ORGANISM: Artificial Sequence
<220> FEATURE:
<223> OTHER INFORMATION: 44R24 VL CDR2

<400> SEQUENCE: 50

Ser Gly
1

<210> SEQ ID NO 51
<211> LENGTH: 11
<212> TYPE: PRT
<213> ORGANISM: Artificial Sequence
<220> FEATURE:
<223> OTHER INFORMATION: 44R24 VL CDR3

<400> SEQUENCE: 51

Gly Ser Trp Asp Thr Arg Pro Tyr Pro Lys Tyr
1               5                   10

<210> SEQ ID NO 52
<211> LENGTH: 115
<212> TYPE: PRT
<213> ORGANISM: Artificial Sequence
<220> FEATURE:
<223> OTHER INFORMATION: 44R24 VH

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile Thr Trp Val Arg Gln Ala Pro Gly Lys Gly Leu Glu Trp Val
        35                  40                  45

Ser Thr Ile Ser Tyr Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95

Ala Arg Ser Ile Val Phe Asp Tyr Trp Gly Gln Gly Thr Leu Val Thr
                100                 105                 110

Val Ser Ser
        115

<210> SEQ ID NO 53
<211> LENGTH: 104
<212> TYPE: PRT
<213> ORGANISM: Artificial Sequence
<220> FEATURE:
<223> OTHER INFORMATION: 44R24 VL

<400> SEQUENCE: 53

Asp Ile Glu Leu Thr Gln Pro Pro Ser Val Ser Val Ala Pro Gly Gln
1               5                   10                  15

Thr Ala Arg Ile Ser Cys Ser Gly Asp Ala Leu Gly Asn Arg Tyr Val
            20                  25                  30

Tyr Trp Tyr Gln Gln Lys Pro Gly Gln Ala Pro Val Leu Val Ile Pro
        35                  40                  45

Ser Gly Ile Pro Glu Arg Phe Ser Gly Ser Asn Ser Gly Asn Thr Ala
    50                  55                  60

Thr Leu Thr Ile Ser Gly Thr Gln Ala Glu Asp Glu Ala Asp Tyr Tyr
65                  70                  75                  80

Cys Gly Ser Trp Asp Thr Arg Pro Tyr Pro Lys Tyr Val Phe Gly Gly
                85                  90                  95

Gly Thr Lys Leu Thr Val Leu Gly
            100

<210> SEQ ID NO 54
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 54

Cys Pro Leu Tyr Phe Pro Leu Tyr Cys
1               5

<210> SEQ ID NO 55
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 55

Cys Pro Leu Val Trp Pro Leu Ile Cys
1               5

<210> SEQ ID NO 56
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 56

Cys Pro Leu Ala Trp Pro Leu Ile Cys
1               5
```

```
<210> SEQ ID NO 57
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 57

Cys Pro Val Lys Tyr Pro Leu Val Cys
1               5

<210> SEQ ID NO 58
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 58

Cys Pro Leu Arg Phe Pro Leu Phe Cys
1               5

<210> SEQ ID NO 59
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 59

Cys Pro Leu Ala Trp Pro Leu Ile Cys
1               5

<210> SEQ ID NO 60
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 60

Cys Pro Val Ala Phe Pro Leu Tyr Cys
1               5

<210> SEQ ID NO 61
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 61

Cys Pro Val Asn Tyr Pro Leu Tyr Cys
1               5

<210> SEQ ID NO 62
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 62

Cys Pro Val Lys Phe Pro Leu Tyr Cys
1               5

<210> SEQ ID NO 63
```

```
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 63

Cys Pro Leu Thr Tyr Pro Leu Tyr Cys
1               5

<210> SEQ ID NO 64
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 64

Cys Pro Leu Arg Trp Pro Leu Met Cys
1               5

<210> SEQ ID NO 65
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 65

Cys Pro Leu Gln Tyr Pro Leu Met Cys
1               5

<210> SEQ ID NO 66
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 66

Cys Pro Leu Ser Phe Pro Leu Tyr Cys
1               5

<210> SEQ ID NO 67
<211> LENGTH: 9
<212> TYPE: PRT
<213> ORGANISM: Artificial Sequence
<220> FEATURE:
<223> OTHER INFORMATION: FZD-binding polypeptides

<400> SEQUENCE: 67

Cys Pro Leu Asn Trp Pro Leu Met Cys
1               5

<210> SEQ ID NO 68
<211> LENGTH: 8
<212> TYPE: PRT
<213> ORGANISM: Artificial Sequence
<220> FEATURE:
<223> OTHER INFORMATION: FZD-binding polypeptides
<220> FEATURE:
<221> NAME/KEY: MISC_FEATURE
<222> LOCATION: (3)..(3)
<223> OTHER INFORMATION: X can be L or V
<220> FEATURE:
<221> NAME/KEY: MISC_FEATURE
<222> LOCATION: (4)..(4)
<223> OTHER INFORMATION: X can be Y, F, or W
<220> FEATURE:
```

```
<221> NAME/KEY: MISC_FEATURE
<222> LOCATION: (7)..(7)
<223> OTHER INFORMATION: X can be Y, F, I, V, or M

<400> SEQUENCE: 68

Cys Pro Xaa Xaa Pro Leu Xaa Cys
1               5

<210> SEQ ID NO 69
<211> LENGTH: 12
<212> TYPE: PRT
<213> ORGANISM: Artificial Sequence
<220> FEATURE:
<223> OTHER INFORMATION: FZD-binding polypeptides

<400> SEQUENCE: 69

Asp Thr Leu Ser Ala Leu Ile Glu Arg Gly Leu Met
1               5                   10

<210> SEQ ID NO 70
<211> LENGTH: 12
<212> TYPE: PRT
<213> ORGANISM: Artificial Sequence
<220> FEATURE:
<223> OTHER INFORMATION: FZD-binding polypeptides

<400> SEQUENCE: 70

Asp Val Trp Trp Leu Gly Ser Thr Trp Leu Lys Arg
1               5                   10

<210> SEQ ID NO 71
<211> LENGTH: 12
<212> TYPE: PRT
<213> ORGANISM: Artificial Sequence
<220> FEATURE:
<223> OTHER INFORMATION: FZD-binding polypeptides

<400> SEQUENCE: 71

Phe Gly Asn Tyr Leu Asn Asp Val Arg Phe Leu Ile
1               5                   10

<210> SEQ ID NO 72
<211> LENGTH: 12
<212> TYPE: PRT
<213> ORGANISM: Artificial Sequence
<220> FEATURE:
<223> OTHER INFORMATION: FZD-binding polypeptides

<400> SEQUENCE: 72

Thr Asn Leu Ala Asp Ile Ala His Trp Ile Ser Gly
1               5                   10

<210> SEQ ID NO 73
<211> LENGTH: 112
<212> TYPE: PRT
<213> ORGANISM: Homo sapiens

<400> SEQUENCE: 73

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
```

```
Leu Glu Gln Ala Leu Pro Pro Cys Arg Ser Leu Cys Glu Arg Ala Arg
 65                  70                  75                  80

Gln Gly Cys Glu Ala Leu Met Asn Lys Phe Gly Phe Gln Trp Pro Asp
                 85                  90                  95

Thr Leu Lys Cys Glu Lys Phe Pro Val His Gly Ala Gly Glu Leu Cys
            100                 105                 110
```

<210> SEQ ID NO 74
<211> LENGTH: 112
<212> TYPE: PRT
<213> ORGANISM: Homo sapiens

<400> SEQUENCE: 74

```
Cys Gln Pro Ile Ser Ile Pro Leu Cys Thr Asp Ile Ala Tyr Asn Gln
  1               5                  10                  15

Thr Ile Met Pro Asn Leu Leu Gly His Thr Asn Gln Glu Asp Ala Gly
                 20                  25                  30

Leu Glu Val His Gln Phe Tyr Pro Leu Val Lys Val Gln Cys Ser Pro
             35                  40                  45

Glu Leu Arg Phe Phe Leu Cys Ser Met Tyr Ala Pro Val Cys Thr Val
 50                  55                  60

Leu Glu Gln Ala Ile Pro Pro Cys Arg Ser Ile Cys Glu Arg Ala Arg
 65                  70                  75                  80

Gln Gly Cys Glu Ala Leu Met Asn Lys Phe Gly Phe Gln Trp Pro Glu
                 85                  90                  95

Arg Leu Arg Cys Glu His Phe Pro Arg His Gly Ala Glu Gln Ile Cys
            100                 105                 110
```

<210> SEQ ID NO 75
<211> LENGTH: 106
<212> TYPE: PRT
<213> ORGANISM: Homo sapiens

<400> SEQUENCE: 75

```
Cys Glu Pro Ile Thr Leu Arg Met Cys Gln Asp Leu Pro Tyr Asn Thr
  1               5                  10                  15

Thr Phe Met Pro Asn Leu Leu Asn His Tyr Asp Gln Gln Thr Ala Ala
                 20                  25                  30

Leu Ala Met Glu Pro Phe His Pro Met Val Asn Leu Asp Cys Ser Arg
             35                  40                  45

Asp Phe Arg Pro Phe Leu Cys Ala Leu Tyr Ala Pro Ile Cys Met Glu
 50                  55                  60

Tyr Gly Arg Val Thr Leu Pro Cys Arg Arg Leu Cys Gln Arg Ala Tyr
 65                  70                  75                  80

Ser Glu Cys Ser Lys Leu Met Glu Met Phe Gly Val Pro Trp Pro Glu
                 85                  90                  95

Asp Met Glu Cys Ser Arg Phe Pro Asp Cys
            100                 105
```

<210> SEQ ID NO 76
<211> LENGTH: 114
<212> TYPE: PRT
<213> ORGANISM: Homo sapiens

<400> SEQUENCE: 76

```
Cys Asp Pro Ile Arg Ile Ser Met Cys Gln Asn Leu Gly Tyr Asn Val
  1               5                  10                  15
```

-continued

```
Thr Lys Met Pro Asn Leu Val Gly His Glu Leu Gln Thr Asp Ala Glu
            20                  25                  30

Leu Gln Leu Thr Thr Phe Thr Pro Leu Ile Gln Tyr Gly Cys Ser Ser
        35                  40                  45

Gln Leu Gln Phe Phe Leu Cys Ser Val Tyr Val Pro Met Cys Thr Glu
    50                  55                  60

Lys Ile Asn Ile Pro Ile Gly Pro Cys Gly Gly Met Cys Leu Ser Val
65                  70                  75                  80

Lys Arg Arg Cys Glu Pro Val Leu Lys Glu Phe Gly Phe Ala Trp Pro
                85                  90                  95

Glu Ser Leu Asn Cys Ser Lys Phe Pro Pro Gln Asn Asp His Asn His
            100                 105                 110

Met Cys

<210> SEQ ID NO 77
<211> LENGTH: 115
<212> TYPE: PRT
<213> ORGANISM: Homo sapiens

<400> SEQUENCE: 77

Cys Gln Glu Ile Thr Val Pro Met Cys Arg Gly Ile Gly Tyr Asn Leu
1               5                   10                  15

Thr His Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Arg Phe Phe Leu Cys Ser Met Tyr Thr Pro Ile Cys Leu Pro
    50                  55                  60

Asp Tyr His Lys Pro Leu Pro Pro Cys Arg Ser Val Cys Glu Arg Ala
65                  70                  75                  80

Lys Ala Gly Cys Ser Pro Leu Met Arg Gln Tyr Gly Phe Ala Trp Pro
                85                  90                  95

Glu Arg Met Ser Cys Asp Arg Leu Pro Val Leu Gly Arg Asp Ala Glu
            100                 105                 110

Val Leu Cys
        115

<210> SEQ ID NO 78
<211> LENGTH: 106
<212> TYPE: PRT
<213> ORGANISM: Homo sapiens

<400> SEQUENCE: 78

Cys Glu Pro Ile Thr Val Pro Arg Cys Met Lys Met Ala Tyr Asn Met
1               5                   10                  15

Thr Phe Phe Pro Asn Leu Met Gly His Tyr Asp Gln Ser Ile Ala Ala
            20                  25                  30

Val Glu Met Glu His Phe Leu Pro Leu Ala Asn Leu Glu Cys Ser Pro
        35                  40                  45

Asn Ile Glu Thr Phe Leu Cys Lys Ala Phe Val Pro Thr Cys Ile Glu
    50                  55                  60

Gln Ile His Val Val Pro Pro Cys Arg Lys Leu Cys Glu Lys Val Tyr
65                  70                  75                  80

Ser Asp Cys Lys Lys Leu Ile Asp Thr Phe Gly Ile Arg Trp Pro Glu
                85                  90                  95
```

```
Glu Leu Glu Cys Asp Arg Leu Gln Tyr Cys
            100                 105

<210> SEQ ID NO 79
<211> LENGTH: 112
<212> TYPE: PRT
<213> ORGANISM: Homo sapiens

<400> SEQUENCE: 79

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110

<210> SEQ ID NO 80
<211> LENGTH: 114
<212> TYPE: PRT
<213> ORGANISM: Homo sapiens

<400> SEQUENCE: 80

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Lys Phe Phe Leu Cys Ser Met Tyr Thr Pro Ile Cys Leu Glu
    50                  55                  60

Asp Tyr Lys Lys Pro Leu Pro Pro Cys Arg Ser Val Cys Glu Arg Ala
65                  70                  75                  80

Lys Ala Gly Cys Ala Pro Leu Met Arg Gln Tyr Gly Phe Ala Trp Pro
                85                  90                  95

Asp Arg Met Arg Cys Asp Arg Leu Pro Glu Gln Gly Asn Pro Asp Thr
            100                 105                 110

Leu Cys

<210> SEQ ID NO 81
<211> LENGTH: 114
<212> TYPE: PRT
<213> ORGANISM: Homo sapiens

<400> SEQUENCE: 81

Cys Gln Ala Val Glu Ile Pro Met Cys Arg Gly Ile Gly Tyr Asn Leu
1               5                   10                  15

Thr Arg Met Pro Asn Leu Leu Gly His Thr Ser Gln Gly Glu Ala Ala
            20                  25                  30

Ala Glu Leu Ala Glu Phe Ala Pro Leu Val Gln Tyr Gly Cys His Ser
        35                  40                  45
```

```
His Leu Arg Phe Phe Leu Cys Ser Leu Tyr Ala Pro Met Cys Thr Asp
        50                  55                  60

Gln Val Ser Thr Pro Ile Pro Ala Cys Arg Pro Met Cys Glu Gln Ala
65                  70                  75                  80

Arg Leu Arg Cys Ala Pro Ile Met Glu Gln Phe Asn Phe Gly Trp Pro
                85                  90                  95

Asp Ser Leu Asp Cys Ala Arg Leu Pro Thr Arg Asn Asp Pro His Ala
               100                 105                 110

Leu Cys

<210> SEQ ID NO 82
<211> LENGTH: 114
<212> TYPE: PRT
<213> ORGANISM: Homo sapiens

<400> SEQUENCE: 82

Cys Gln Pro Ile Glu Ile Pro Met Cys Lys Asp Ile Gly Tyr Asn Met
1               5                  10                  15

Thr Arg Met Pro Asn Leu Met Gly His Glu Asn Gln Arg Glu Ala Ala
                20                  25                  30

Ile Gln Leu His Glu Phe Ala Pro Leu Val Glu Tyr Gly Cys His Gly
            35                  40                  45

His Leu Arg Phe Phe Leu Cys Ser Leu Tyr Ala Pro Met Cys Thr Glu
        50                  55                  60

Gln Val Ser Thr Pro Ile Pro Ala Cys Arg Val Met Cys Glu Gln Ala
65                  70                  75                  80

Arg Leu Lys Cys Ser Pro Ile Met Glu Gln Phe Asn Phe Lys Trp Pro
                85                  90                  95

Asp Ser Leu Asp Cys Arg Lys Leu Pro Asn Lys Asn Asp Pro Asn Tyr
               100                 105                 110

Leu Cys

<210> SEQ ID NO 83
<211> LENGTH: 109
<212> TYPE: PRT
<213> ORGANISM: Homo sapiens

<400> SEQUENCE: 83

Cys Val Asp Ile Pro Ala Asp Leu Arg Leu Cys His Asn Val Gly Tyr
1               5                  10                  15

Lys Lys Met Val Leu Pro Asn Leu Leu Glu His Glu Thr Met Ala Glu
                20                  25                  30

Val Lys Gln Gln Ala Ser Ser Trp Val Pro Leu Leu Asn Lys Asn Cys
            35                  40                  45

His Ala Gly Thr Gln Val Phe Leu Cys Ser Leu Phe Ala Pro Val Cys
        50                  55                  60

Leu Asp Arg Pro Ile Tyr Pro Cys Arg Trp Leu Cys Glu Ala Val Arg
65                  70                  75                  80

Asp Ser Cys Glu Pro Val Met Gln Phe Phe Gly Phe Tyr Trp Pro Glu
                85                  90                  95

Met Leu Lys Cys Asp Lys Phe Pro Glu Gly Asp Val Cys
               100                 105

<210> SEQ ID NO 84
<211> LENGTH: 113
<212> TYPE: PRT
```

-continued

<213> ORGANISM: Homo sapiens

<400> SEQUENCE: 84

Cys Lys Pro Ile Pro Ala Asn Leu Gln Leu Cys His Gly Ile Glu Tyr
1               5                   10                  15

Gln Asn Met Arg Leu Pro Asn Leu Leu Gly His Glu Thr Met Lys Glu
            20                  25                  30

Val Leu Glu Gln Ala Gly Ala Trp Ile Pro Leu Val Met Lys Gln Cys
        35                  40                  45

His Pro Asp Thr Lys Lys Phe Leu Cys Ser Leu Phe Ala Pro Val Cys
    50                  55                  60

Leu Asp Asp Leu Asp Glu Thr Ile Gln Pro Cys His Ser Leu Cys Val
65                  70                  75                  80

Gln Val Lys Asp Arg Cys Ala Pro Val Met Ser Ala Phe Gly Phe Pro
                85                  90                  95

Trp Pro Asp Met Leu Glu Cys Asp Arg Phe Pro Gln Asp Asn Asp Leu
            100                 105                 110

Cys

<210> SEQ ID NO 85
<211> LENGTH: 113
<212> TYPE: PRT
<213> ORGANISM: Homo sapiens

<400> SEQUENCE: 85

Cys Glu Pro Val Arg Ile Pro Leu Cys Lys Ser Leu Pro Trp Asn Met
1               5                   10                  15

Thr Lys Met Pro Asn His Leu His His Ser Thr Gln Ala Asn Ala Ile
            20                  25                  30

Leu Ala Ile Glu Gln Phe Glu Gly Leu Leu Gly Thr His Cys Ser Pro
        35                  40                  45

Asp Leu Leu Phe Phe Leu Cys Ala Met Tyr Ala Pro Ile Cys Thr Ile
    50                  55                  60

Asp Phe Gln His Glu Pro Ile Lys Pro Cys Lys Ser Val Cys Glu Arg
65                  70                  75                  80

Ala Arg Gln Gly Cys Glu Pro Ile Leu Ile Lys Tyr Arg His Ser Trp
                85                  90                  95

Pro Glu Asn Leu Ala Cys Glu Leu Pro Val Tyr Asp Arg Gly Val
            100                 105                 110

Cys

<210> SEQ ID NO 86
<211> LENGTH: 113
<212> TYPE: PRT
<213> ORGANISM: Homo sapiens

<400> SEQUENCE: 86

Cys Glu Ala Val Arg Ile Pro Met Cys Arg His Met Pro Trp Asn Ile
1               5                   10                  15

Thr Arg Met Pro Asn His Leu His His Ser Thr Gln Glu Asn Ala Ile
            20                  25                  30

Leu Ala Ile Glu Gln Tyr Glu Leu Val Asp Val Asn Cys Ser Ala
        35                  40                  45

Val Leu Arg Phe Phe Cys Ala Met Tyr Ala Pro Ile Cys Thr Leu
    50                  55                  60

Glu Phe Leu His Asp Pro Ile Lys Pro Cys Lys Ser Val Cys Gln Arg

```
            65                  70                  75                  80
Ala Arg Asp Asp Cys Glu Pro Leu Met Lys Met Tyr Asn His Ser Trp
                85                  90                  95

Pro Glu Ser Leu Ala Cys Asp Glu Leu Pro Val Tyr Asp Arg Gly Val
                100                 105                 110

Cys

<210> SEQ ID NO 87
<211> LENGTH: 110
<212> TYPE: PRT
<213> ORGANISM: Homo sapiens

<400> SEQUENCE: 87

Cys Leu Asp Ile Pro Ala Asp Leu Pro Leu Cys His Thr Val Gly Tyr
1               5                   10                  15

Lys Arg Met Arg Leu Pro Asn Leu Leu Glu His Glu Ser Leu Ala Glu
                20                  25                  30

Val Lys Gln Gln Ala Ser Ser Trp Leu Pro Leu Leu Ala Lys Arg Cys
                35                  40                  45

His Ser Asp Thr Gln Val Phe Leu Cys Ser Leu Phe Ala Pro Val Cys
            50                  55                  60

Leu Asp Arg Pro Ile Tyr Pro Cys Arg Ser Leu Cys Glu Ala Val Arg
65                  70                  75                  80

Ala Gly Cys Ala Pro Leu Met Glu Ala Tyr Gly Phe Pro Trp Pro Glu
                85                  90                  95

Met Leu His Cys His Lys Phe Pro Leu Asp Asn Asp Leu Cys
                100                 105                 110

<210> SEQ ID NO 88
<211> LENGTH: 127
<212> TYPE: PRT
<213> ORGANISM: Homo sapiens

<400> SEQUENCE: 88

Cys Gln Pro Tyr Arg Gly Ile Ala Cys Ala Arg Phe Ile Gly Asn Arg
1               5                   10                  15

Thr Val Tyr Met Glu Ser Leu His Met Gln Gly Glu Ile Glu Asn Gln
                20                  25                  30

Ile Thr Ala Ala Phe Thr Met Ile Gly Thr Ser Ser His Leu Ser Asp
                35                  40                  45

Lys Cys Ser Gln Phe Ala Ile Pro Ser Leu Cys His Tyr Ala Phe Pro
            50                  55                  60

Tyr Cys Asp Glu Thr Ser Ser Val Pro Lys Pro Arg Asp Leu Cys Arg
65                  70                  75                  80

Asp Glu Cys Glu Ile Leu Glu Asn Val Leu Cys Gln Thr Glu Tyr Ile
                85                  90                  95

Phe Ala Arg Ser Asn Pro Met Ile Leu Met Arg Leu Lys Leu Pro Asn
                100                 105                 110

Cys Glu Asp Leu Pro Gln Pro Glu Ser Pro Glu Ala Ala Asn Cys
            115                 120                 125

<210> SEQ ID NO 89
<211> LENGTH: 127
<212> TYPE: PRT
<213> ORGANISM: Homo sapiens

<400> SEQUENCE: 89
```

-continued

```
Cys Gln Pro Tyr Arg Gly Ile Ala Cys Ala Arg Phe Ile Gly Asn Arg
1               5                  10                 15

Thr Ile Tyr Val Asp Ser Leu Gln Met Gln Gly Glu Ile Glu Asn Arg
              20                 25                 30

Ile Thr Ala Ala Phe Thr Met Ile Gly Thr Ser Thr His Leu Ser Asp
            35                 40                 45

Gln Cys Ser Gln Phe Ala Ile Pro Ser Phe Cys His Val Phe Pro
        50                 55                 60

Leu Cys Asp Ala Arg Ser Arg Thr Pro Lys Pro Arg Glu Leu Cys Arg
65                 70                 75                 80

Asp Glu Cys Glu Val Leu Glu Ser Asp Leu Cys Arg Gln Glu Tyr Thr
                85                 90                 95

Ile Ala Arg Ser Asn Pro Leu Ile Leu Met Arg Leu Gln Leu Pro Lys
            100                105                110

Cys Glu Ala Leu Pro Met Pro Glu Ser Pro Asp Ala Ala Asn Cys
            115                120                125
```

<210> SEQ ID NO 90
<211> LENGTH: 170
<212> TYPE: PRT
<213> ORGANISM: Homo sapiens

<400> SEQUENCE: 90

```
Met Leu Ala Met Ala Trp Arg Gly Ala Gly Pro Ser Val Pro Gly Ala
1               5                  10                 15

Pro Gly Gly Val Gly Leu Ser Leu Gly Leu Leu Gln Leu Leu Leu
              20                 25                 30

Leu Leu Gly Pro Ala Arg Gly Phe Gly Asp Glu Glu Glu Arg Arg Cys
            35                 40                 45

Asp Pro Ile Arg Ile Ser Met Cys Gln Asn Leu Gly Tyr Asn Val Thr
        50                 55                 60

Lys Met Pro Asn Leu Val Gly His Glu Leu Gln Thr Asp Ala Glu Leu
65                 70                 75                 80

Gln Leu Thr Thr Phe Thr Pro Leu Ile Gln Tyr Gly Cys Ser Ser Gln
                85                 90                 95

Leu Gln Phe Phe Leu Cys Ser Val Tyr Val Pro Met Cys Thr Glu Lys
            100                105                110

Ile Asn Ile Pro Ile Gly Pro Cys Gly Gly Met Cys Leu Ser Val Lys
            115                120                125

Arg Arg Cys Glu Pro Val Leu Lys Glu Phe Gly Phe Ala Trp Pro Glu
    130                135                140

Ser Leu Asn Cys Ser Lys Phe Pro Pro Gln Asn Asp His Asn His Met
145                150                155                160

Cys Met Glu Gly Pro Gly Asp Glu Glu Val
                165                170
```

<210> SEQ ID NO 91
<211> LENGTH: 157
<212> TYPE: PRT
<213> ORGANISM: Homo sapiens

<400> SEQUENCE: 91

```
Met Ala Arg Pro Asp Pro Ser Ala Pro Pro Ser Leu Leu Leu Leu Leu
1               5                  10                 15

Leu Ala Gln Leu Val Gly Arg Ala Ala Ala Ser Lys Ala Pro Val
              20                 25                 30
```

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
 50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
        115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr
145                 150                 155

<210> SEQ ID NO 92
<211> LENGTH: 158
<212> TYPE: PRT
<213> ORGANISM: Homo sapiens

<400> SEQUENCE: 92

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
 50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Thr
145                 150                 155

<210> SEQ ID NO 93
<211> LENGTH: 227
<212> TYPE: PRT
<213> ORGANISM: Homo sapiens

<400> SEQUENCE: 93

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

```
Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys
225

<210> SEQ ID NO 94
<211> LENGTH: 230
<212> TYPE: PRT
<213> ORGANISM: Homo sapiens

<400> SEQUENCE: 94

Lys Ser Ser Asp Lys Thr His Thr Cys Pro Pro Cys Pro Ala Pro Glu
  1               5                  10                  15

Leu Leu Gly Gly Pro Ser Val Phe Leu Phe Pro Pro Lys Pro Lys Asp
             20                  25                  30

Thr Leu Met Ile Ser Arg Thr Pro Glu Val Thr Cys Val Val Val Asp
         35                  40                  45

Val Ser His Glu Asp Pro Glu Val Lys Phe Asn Trp Tyr Val Asp Gly
 50                  55                  60

Val Glu Val His Asn Ala Lys Thr Lys Pro Arg Glu Glu Gln Tyr Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190
```

Leu Thr Val Asp Lys Ser Arg Trp Gln Gln Gly Asn Val Phe Ser Cys
          195                 200                 205

Ser Val Met His Glu Ala Leu His Asn His Tyr Thr Gln Lys Ser Leu
    210                 215                 220

Ser Leu Ser Pro Gly Lys
225             230

<210> SEQ ID NO 95
<211> LENGTH: 232
<212> TYPE: PRT
<213> ORGANISM: Homo sapiens

<400> SEQUENCE: 95

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 96
<211> LENGTH: 8
<212> TYPE: PRT
<213> ORGANISM: Artificial Sequence
<220> FEATURE:
<223> OTHER INFORMATION: Linker

<400> SEQUENCE: 96

Glu Ser Gly Gly Gly Gly Val Thr
1               5

<210> SEQ ID NO 97
<211> LENGTH: 9

```
<212> TYPE: PRT
<213> ORGANISM: Artificial Sequence
<220> FEATURE:
<223> OTHER INFORMATION: Linker

<400> SEQUENCE: 97

Leu Glu Ser Gly Gly Gly Val Thr
1               5

<210> SEQ ID NO 98
<211> LENGTH: 6
<212> TYPE: PRT
<213> ORGANISM: Artificial Sequence
<220> FEATURE:
<223> OTHER INFORMATION: Linker

<400> SEQUENCE: 98

Gly Arg Ala Gln Val Thr
1               5

<210> SEQ ID NO 99
<211> LENGTH: 6
<212> TYPE: PRT
<213> ORGANISM: Artificial Sequence
<220> FEATURE:
<223> OTHER INFORMATION: Linker

<400> SEQUENCE: 99

Trp Arg Ala Gln Val Thr
1               5

<210> SEQ ID NO 100
<211> LENGTH: 8
<212> TYPE: PRT
<213> ORGANISM: Artificial Sequence
<220> FEATURE:
<223> OTHER INFORMATION: Linker

<400> SEQUENCE: 100

Ala Arg Gly Arg Ala Gln Val Thr
1               5

<210> SEQ ID NO 101
<211> LENGTH: 27
<212> TYPE: PRT
<213> ORGANISM: Artificial Sequence
<220> FEATURE:
<223> OTHER INFORMATION: Signal Sequence

<400> SEQUENCE: 101

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala
            20                  25

<210> SEQ ID NO 102
<211> LENGTH: 27
<212> TYPE: PRT
<213> ORGANISM: Artificial Sequence
<220> FEATURE:
<223> OTHER INFORMATION: Signal Sequence

<400> SEQUENCE: 102

Met Glu Trp Gly Tyr Leu Leu Glu Val Thr Ser Leu Leu Ala Ala Leu
1               5                   10                  15

Ala Leu Leu Gln Arg Ser Ser Gly Ala Leu Ala
```

20                  25

<210> SEQ ID NO 103
<211> LENGTH: 27
<212> TYPE: PRT
<213> ORGANISM: Artificial Sequence
<220> FEATURE:
<223> OTHER INFORMATION: Signal Sequence

<400> SEQUENCE: 103

Met Glu Trp Gly Tyr Leu Leu Glu Val Thr Ser Leu Leu Ala Ala Leu
1               5                   10                  15

Ala Leu Leu Gln Arg Ser Ser Gly Val Leu Ala
            20                  25

<210> SEQ ID NO 104
<211> LENGTH: 27
<212> TYPE: PRT
<213> ORGANISM: Artificial Sequence
<220> FEATURE:
<223> OTHER INFORMATION: Signal Sequence

<400> SEQUENCE: 104

Met Glu Trp Gly Tyr Leu Leu Glu Val Thr Ser Leu Leu Ala Ala Leu
1               5                   10                  15

Leu Leu Leu Gln Arg Ser Pro Ile Val His Ala
            20                  25

<210> SEQ ID NO 105
<211> LENGTH: 27
<212> TYPE: PRT
<213> ORGANISM: Artificial Sequence
<220> FEATURE:
<223> OTHER INFORMATION: Signal Sequence

<400> SEQUENCE: 105

Met Glu Trp Gly Tyr Leu Leu Glu Val Thr Ser Leu Leu Ala Ala Leu
1               5                   10                  15

Phe Leu Leu Gln Arg Ser Pro Ile Val His Ala
            20                  25

<210> SEQ ID NO 106
<211> LENGTH: 27
<212> TYPE: PRT
<213> ORGANISM: Artificial Sequence
<220> FEATURE:
<223> OTHER INFORMATION: Signal Sequence

<400> SEQUENCE: 106

Met Glu Trp Gly Tyr Leu Leu Glu Val Thr Ser Leu Leu Ala Ala Leu
1               5                   10                  15

Leu Leu Leu Gln Arg Ser Pro Phe Val His Ala
            20                  25

<210> SEQ ID NO 107
<211> LENGTH: 27
<212> TYPE: PRT
<213> ORGANISM: Artificial Sequence
<220> FEATURE:
<223> OTHER INFORMATION: Signal Sequence

<400> SEQUENCE: 107

Met Glu Trp Gly Tyr Leu Leu Glu Val Thr Ser Leu Leu Ala Ala Leu
1               5                   10                  15

```
Leu Leu Leu Gln Arg Ser Pro Ile Ile Tyr Ala
            20                  25

<210> SEQ ID NO 108
<211> LENGTH: 27
<212> TYPE: PRT
<213> ORGANISM: Artificial Sequence
<220> FEATURE:
<223> OTHER INFORMATION: Signal Sequence

<400> SEQUENCE: 108

Met Glu Trp Gly Tyr Leu Leu Glu Val Thr Ser Leu Leu Ala Ala Leu
1               5                   10                  15

Leu Leu Leu Gln Arg Ser Pro Ile Ala His Ala
            20                  25

<210> SEQ ID NO 109
<211> LENGTH: 361
<212> TYPE: PRT
<213> ORGANISM: Artificial Sequence
<220> FEATURE:
<223> OTHER INFORMATION: FZD8-Fc amino acid sequence-variant 54F03

<400> SEQUENCE: 109

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Gly Arg Ala Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270
```

```
Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
        290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 110
<211> LENGTH: 364
<212> TYPE: PRT
<213> ORGANISM: Artificial Sequence
<220> FEATURE:
<223> OTHER INFORMATION: FZD8-Fc variant 54F03 amino acid sequence

<400> SEQUENCE: 110

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Gly Arg Ala Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270
```

Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 111
<211> LENGTH: 364
<212> TYPE: PRT
<213> ORGANISM: Artificial Sequence
<220> FEATURE:
<223> OTHER INFORMATION: FZD8-Fc variant 54F09 amino acid sequence

<400> SEQUENCE: 111

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Ala Ala Pro Ser Pro Pro Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
            325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 112
<211> LENGTH: 367
<212> TYPE: PRT
<213> ORGANISM: Artificial Sequence
<220> FEATURE:
<223> OTHER INFORMATION: FZD8-Fc variant 54F09 amino acid sequence

<400> SEQUENCE: 112

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
            85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Ala Ala Pro Ser Pro Pro Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
            165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
            245                 250                 255

Ser Lys Ala Lys Gly Gln Pro Arg Glu Pro Gln Val Tyr Thr Leu Pro
            260                 265                 270

Pro Ser Arg Asp Glu Leu Thr Lys Asn Gln Val Ser Leu Thr Cys Leu
                275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
                355                 360                 365

<210> SEQ ID NO 113
<211> LENGTH: 361
<212> TYPE: PRT
<213> ORGANISM: Artificial Sequence
<220> FEATURE:
<223> OTHER INFORMATION: FZD8-Fc variant 54F15 amino acid sequence

<400> SEQUENCE: 113

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
                20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
                100                 105                 110

Glu Gln Gly Asn Pro Asp Thr Leu Cys Met Asp Tyr Asn Arg Thr Asp
            115                 120                 125

Leu Thr Thr Ala Ala Pro Asp Lys Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
                180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
                260                 265                 270

Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
        290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
                340                 345                 350

Lys Ser Leu Ser Leu Ser Pro Gly Lys
                355                 360

<210> SEQ ID NO 114
<211> LENGTH: 364
<212> TYPE: PRT
<213> ORGANISM: Artificial Sequence
<220> FEATURE:
<223> OTHER INFORMATION: FZD8-Fc variant 54F15 amino acid sequence

<400> SEQUENCE: 114

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
                20                  25                  30

Phe Asn His Asp Thr Gln Asp Glu Ala Gly Leu Glu Val His Gln Phe
            35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Ala Ala Pro Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

```
Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
            325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
            355                 360

<210> SEQ ID NO 115
<211> LENGTH: 361
<212> TYPE: PRT
<213> ORGANISM: Artificial Sequence
<220> FEATURE:
<223> OTHER INFORMATION: FZD8-Fc variant 54F16, 54F17, 54F18, 54F23,
      54F25, 54F27, 54F29, 54F31, and 54F34 amino acid sequence

<400> SEQUENCE: 115

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Lys Ser Ser Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
```

```
                260                 265                 270
Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
        290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
        340                 345                 350

Lys Ser Leu Ser Leu Ser Pro Gly Lys
            355                 360

<210> SEQ ID NO 116
<211> LENGTH: 363
<212> TYPE: PRT
<213> ORGANISM: Artificial Sequence
<220> FEATURE:
<223> OTHER INFORMATION: FZD8-Fc variant 54F16 amino acid sequence

<400> SEQUENCE: 116

Ala Ala Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Lys Ser Ser Asp Lys Thr His Thr Cys Pro
130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
```

```
                        260                 265                 270
Asp Glu Leu Thr Lys Asn Gln Val Ser Leu Thr Cys Leu Val Lys Gly
            275                 280                 285

Phe Tyr Pro Ser Asp Ile Ala Val Glu Trp Glu Ser Asn Gly Gln Pro
        290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly
        355                 360

<210> SEQ ID NO 117
<211> LENGTH: 363
<212> TYPE: PRT
<213> ORGANISM: Artificial Sequence
<220> FEATURE:
<223> OTHER INFORMATION: FZD8-Fc variant 54F19, 54F20, 54F24, 54F26,
      54F28, 54F30, 54F32, 54F34 and 54F35 amino acid sequence

<400> SEQUENCE: 117

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
        35                  40                  45

Val Glu Ile Gln Cys Ser Pro Asp Leu Lys Phe Phe Leu Cys Ser Met
    50                  55                  60

Tyr Thr Pro Ile Cys Leu Glu Asp Tyr Lys Lys Pro Leu Pro Pro Cys
65                  70                  75                  80

Arg Ser Val Cys Glu Arg Ala Lys Ala Gly Cys Ala Pro Leu Met Arg
                85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
        115                 120                 125

Leu Thr Thr Glu Pro Lys Ser Ser Asp Lys Thr His Thr Cys Pro Pro
130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255
```

```
Gly Gln Pro Arg Glu Pro Gln Val Tyr Thr Leu Pro Pro Ser Arg Asp
                260                 265                 270

Glu Leu Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
        290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
            340                 345                 350

Thr Gln Lys Ser Leu Ser Leu Ser Pro Gly Lys
        355                 360
```

```
<210> SEQ ID NO 118
<211> LENGTH: 366
<212> TYPE: PRT
<213> ORGANISM: Artificial Sequence
<220> FEATURE:
<223> OTHER INFORMATION: FZD8-Fc variant 54F19 amino acid sequence

<400> SEQUENCE: 118

Ala Leu Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Glu Pro Lys Ser Ser Asp Lys Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255
```

-continued

```
Lys Ala Lys Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 119
<211> LENGTH: 366
<212> TYPE: PRT
<213> ORGANISM: Artificial Sequence
<220> FEATURE:
<223> OTHER INFORMATION: FZD8-Fc variant 54F20 amino acid sequence

<400> SEQUENCE: 119

Val Leu Ala Ala Ser Ala Lys Glu Leu Ala Cys Gln Glu Ile Thr Val
1               5                   10                  15

Pro Leu Cys Lys Gly Ile Gly Tyr Asn Tyr Thr Tyr Met Pro Asn Gln
            20                  25                  30

Phe Asn His Asp Thr Gln Asp Glu Ala Gly Leu Glu Val His Gln Phe
        35                  40                  45

Trp Pro Leu Val Glu Ile Gln Cys Ser Pro Asp Leu Lys Phe Phe Leu
    50                  55                  60

Cys Ser Met Tyr Thr Pro Ile Cys Leu Glu Asp Tyr Lys Lys Pro Leu
65                  70                  75                  80

Pro Pro Cys Arg Ser Val Cys Glu Arg Ala Lys Ala Gly Cys Ala Pro
                85                  90                  95

Leu Met Arg Gln Tyr Gly Phe Ala Trp Pro Asp Arg Met Arg Cys Asp
            100                 105                 110

Arg Leu Pro Glu Gln Gly Asn Pro Asp Thr Leu Cys Met Asp Tyr Asn
        115                 120                 125

Arg Thr Asp Leu Thr Thr Glu Pro Lys Ser Ser Asp Lys Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255
```

```
Lys Ala Lys Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 120
<211> LENGTH: 360
<212> TYPE: PRT
<213> ORGANISM: Artificial Sequence
<220> FEATURE:
<223> OTHER INFORMATION: FZD8-Fc variant 54F34 amino acid sequence

<400> SEQUENCE: 120

Lys Glu Leu Ala Cys Gln Glu Ile Thr Val Pro Leu Cys Lys Gly Ile
1               5                   10                  15

Gly Tyr Asn Tyr Thr Tyr Met Pro Asn Gln Phe Asn His Asp Thr Gln
            20                  25                  30

Asp Glu Ala Gly Leu Glu Val His Gln Phe Trp Pro Leu Val Glu Ile
        35                  40                  45

Gln Cys Ser Pro Asp Leu Lys Phe Phe Leu Cys Ser Met Tyr Thr Pro
    50                  55                  60

Ile Cys Leu Glu Asp Tyr Lys Lys Pro Leu Pro Pro Cys Arg Ser Val
65                  70                  75                  80

Cys Glu Arg Ala Lys Ala Gly Cys Ala Pro Leu Met Arg Gln Tyr Gly
                85                  90                  95

Phe Ala Trp Pro Asp Arg Met Arg Cys Asp Arg Leu Pro Glu Gln Gly
            100                 105                 110

Asn Pro Asp Thr Leu Cys Met Asp Tyr Asn Arg Thr Asp Leu Thr Thr
        115                 120                 125

Glu Pro Lys Ser Ser Asp Lys Thr His Thr Cys Pro Pro Cys Pro Ala
130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255
```

-continued

```
Arg Glu Pro Gln Val Tyr Thr Leu Pro Pro Ser Arg Asp Glu Leu Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 121
<211> LENGTH: 358
<212> TYPE: PRT
<213> ORGANISM: Artificial Sequence
<220> FEATURE:
<223> OTHER INFORMATION: FZD8-Fc variant 54F33 amino acid sequence

<400> SEQUENCE: 121

Lys Glu Leu Ala Cys Gln Glu Ile Thr Val Pro Leu Cys Lys Gly Ile
1               5                   10                  15

Gly Tyr Asn Tyr Thr Tyr Met Pro Asn Gln Phe Asn His Asp Thr Gln
            20                  25                  30

Asp Glu Ala Gly Leu Glu Val His Gln Phe Trp Pro Leu Val Glu Ile
        35                  40                  45

Gln Cys Ser Pro Asp Leu Lys Phe Phe Leu Cys Ser Met Tyr Thr Pro
    50                  55                  60

Ile Cys Leu Glu Asp Tyr Lys Lys Pro Leu Pro Pro Cys Arg Ser Val
65                  70                  75                  80

Cys Glu Arg Ala Lys Ala Gly Cys Ala Pro Leu Met Arg Gln Tyr Gly
                85                  90                  95

Phe Ala Trp Pro Asp Arg Met Arg Cys Asp Arg Leu Pro Glu Gln Gly
            100                 105                 110

Asn Pro Asp Thr Leu Cys Met Asp Tyr Asn Arg Thr Asp Leu Thr Thr
        115                 120                 125

Lys Ser Ser Asp Lys Thr His Thr Cys Pro Pro Cys Pro Ala Pro Glu
130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255
```

```
Pro Gln Val Tyr Thr Leu Pro Pro Ser Arg Asp Glu Leu Thr Lys Asn
                260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
        290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
            355

<210> SEQ ID NO 122
<211> LENGTH: 83
<212> TYPE: PRT
<213> ORGANISM: Homo sapiens

<400> SEQUENCE: 122

Asp Leu Val Tyr Phe Glu Lys Ser Pro Asn Phe Cys Thr Tyr Ser Gly
1               5                   10                  15

Arg Leu Gly Thr Ala Gly Thr Ala Gly Arg Ala Cys Asn Ser Ser Ser
            20                  25                  30

Pro Ala Leu Asp Gly Cys Glu Leu Leu Cys Cys Gly Arg Gly His Arg
        35                  40                  45

Thr Arg Thr Gln Arg Val Thr Glu Arg Cys Asn Cys Thr Phe His Trp
    50                  55                  60

Cys Cys His Val Ser Cys Arg Asn Cys Thr His Thr Arg Val Leu His
65                  70                  75                  80

Glu Cys Leu

<210> SEQ ID NO 123
<211> LENGTH: 94
<212> TYPE: PRT
<213> ORGANISM: Homo sapiens

<400> SEQUENCE: 123

Asp Leu Val Tyr Phe Glu Asn Ser Pro Asp Tyr Cys Ile Arg Asp Arg
1               5                   10                  15

Glu Ala Gly Ser Leu Gly Thr Ala Gly Arg Val Cys Asn Leu Thr Ser
            20                  25                  30

Arg Gly Met Asp Ser Cys Glu Val Met Cys Cys Gly Arg Gly Tyr Asp
        35                  40                  45

Thr Ser His Val Thr Arg Met Thr Lys Cys Gly Cys Lys Phe His Trp
    50                  55                  60

Cys Cys Ala Val Arg Cys Gln Asp Cys Leu Glu Ala Leu Asp Val His
65                  70                  75                  80

Thr Cys Lys Ala Pro Lys Asn Ala Asp Trp Thr Thr Ala Thr
                85                  90

<210> SEQ ID NO 124
<211> LENGTH: 94
<212> TYPE: PRT
<213> ORGANISM: Homo sapiens

<400> SEQUENCE: 124
```

Asp Leu Val Tyr Phe Asp Asn Ser Pro Asp Tyr Cys Val Leu Asp Lys
1               5                   10                  15

Ala Ala Gly Ser Leu Gly Thr Ala Gly Arg Val Cys Ser Lys Thr Ser
            20                  25                  30

Lys Gly Thr Asp Gly Cys Glu Ile Met Cys Cys Gly Arg Gly Tyr Asp
        35                  40                  45

Thr Thr Arg Val Thr Arg Val Thr Gln Cys Glu Cys Lys Phe His Trp
    50                  55                  60

Cys Cys Ala Val Arg Cys Lys Glu Cys Arg Asn Thr Val Asp Val His
65                  70                  75                  80

Thr Cys Lys Ala Pro Lys Lys Ala Glu Trp Leu Asp Gln Thr
                85                  90

<210> SEQ ID NO 125
<211> LENGTH: 83
<212> TYPE: PRT
<213> ORGANISM: Homo sapiens

<400> SEQUENCE: 125

Asp Leu Val Tyr Tyr Glu Asn Ser Pro Asn Phe Cys Glu Pro Asn Pro
1               5                   10                  15

Glu Thr Gly Ser Phe Gly Thr Arg Asp Arg Thr Cys Asn Val Thr Ser
            20                  25                  30

His Gly Ile Asp Gly Cys Asp Leu Leu Cys Cys Gly Arg Gly His Asn
        35                  40                  45

Thr Arg Thr Glu Lys Arg Lys Glu Lys Cys His Cys Ile Phe His Trp
    50                  55                  60

Cys Cys Tyr Val Ser Cys Gln Glu Cys Ile Arg Ile Tyr Asp Val His
65                  70                  75                  80

Thr Cys Lys

<210> SEQ ID NO 126
<211> LENGTH: 83
<212> TYPE: PRT
<213> ORGANISM: Homo sapiens

<400> SEQUENCE: 126

Asp Leu Val Tyr Tyr Glu Ala Ser Pro Asn Phe Cys Glu Pro Asn Pro
1               5                   10                  15

Glu Thr Gly Ser Phe Gly Thr Arg Asp Arg Thr Cys Asn Val Ser Ser
            20                  25                  30

His Gly Ile Asp Gly Cys Asp Leu Leu Cys Cys Gly Arg Gly His Asn
        35                  40                  45

Ala Arg Ala Glu Arg Arg Glu Lys Cys Arg Cys Val Phe His Trp
    50                  55                  60

Cys Cys Tyr Val Ser Cys Gln Glu Cys Thr Arg Val Tyr Asp Val His
65                  70                  75                  80

Thr Cys Lys

<210> SEQ ID NO 127
<211> LENGTH: 83
<212> TYPE: PRT
<213> ORGANISM: Homo sapiens

<400> SEQUENCE: 127

Asp Leu Val Tyr Ile Glu Lys Ser Pro Asn Tyr Cys Glu Glu Asp Pro
1               5                   10                  15

```
Val Thr Gly Ser Val Gly Thr Gln Gly Arg Ala Cys Asn Lys Thr Ala
            20                  25                  30

Pro Gln Ala Ser Gly Cys Asp Leu Met Cys Cys Gly Arg Gly Tyr Asn
        35                  40                  45

Thr His Gln Tyr Ala Arg Val Trp Gln Cys Asn Cys Lys Phe His Trp
    50                  55                  60

Cys Cys Tyr Val Lys Cys Asn Thr Cys Ser Glu Arg Thr Glu Met Tyr
65                  70                  75                  80

Thr Cys Lys

<210> SEQ ID NO 128
<211> LENGTH: 83
<212> TYPE: PRT
<213> ORGANISM: Homo sapiens

<400> SEQUENCE: 128

Asp Leu Val Tyr Ile Glu Lys Ser Pro Asn Tyr Cys Glu Glu Asp Ala
1               5                   10                  15

Ala Thr Gly Ser Val Gly Thr Gln Gly Arg Leu Cys Asn Arg Thr Ser
            20                  25                  30

Pro Gly Ala Asp Gly Cys Asp Thr Met Cys Cys Gly Arg Gly Tyr Asn
        35                  40                  45

Thr His Gln Tyr Thr Lys Val Trp Gln Cys Asn Cys Lys Phe His Trp
    50                  55                  60

Cys Cys Phe Val Lys Cys Asn Thr Cys Ser Glu Arg Thr Glu Val Phe
65                  70                  75                  80

Thr Cys Lys

<210> SEQ ID NO 129
<211> LENGTH: 108
<212> TYPE: PRT
<213> ORGANISM: Homo sapiens

<400> SEQUENCE: 129

Glu Leu Ile Phe Leu Glu Glu Ser Pro Asp Tyr Cys Thr Cys Asn Ser
1               5                   10                  15

Ser Leu Gly Ile Tyr Gly Thr Glu Gly Arg Glu Cys Leu Gln Asn Ser
            20                  25                  30

His Asn Thr Ser Arg Trp Glu Arg Arg Ser Cys Gly Arg Leu Cys Thr
        35                  40                  45

Glu Cys Gly Leu Gln Val Glu Glu Arg Lys Thr Glu Val Ile Ser Ser
    50                  55                  60

Cys Asn Cys Lys Phe Gln Trp Cys Cys Thr Val Lys Cys Asp Gln Cys
65                  70                  75                  80

Arg His Val Val Ser Lys Tyr Tyr Cys Ala Arg Ser Pro Gly Ser Ala
                85                  90                  95

Gln Ser Leu Gly Arg Val Trp Phe Gly Val Tyr Ile
            100                 105

<210> SEQ ID NO 130
<211> LENGTH: 107
<212> TYPE: PRT
<213> ORGANISM: Homo sapiens

<400> SEQUENCE: 130

Glu Leu Val His Leu Glu Asp Ser Pro Asp Tyr Cys Leu Glu Asn Lys
1               5                   10                  15
```

```
Thr Leu Gly Leu Leu Gly Thr Glu Gly Arg Glu Cys Leu Arg Arg Gly
         20                  25                  30

Arg Ala Leu Gly Arg Trp Glu Leu Arg Ser Cys Arg Leu Cys Gly
         35                  40                  45

Asp Cys Gly Leu Ala Val Glu Glu Arg Ala Glu Thr Val Ser Ser
50                   55                  60

Cys Asn Cys Lys Phe His Trp Cys Ala Val Arg Cys Glu Gln Cys
65                   70                  75                  80

Arg Arg Arg Val Thr Lys Tyr Phe Cys Ser Arg Ala Glu Pro Arg
                 85                  90                  95

Gly Gly Ala Ala His Lys Pro Gly Arg Lys Pro
         100                 105
```

<210> SEQ ID NO 131
<211> LENGTH: 83
<212> TYPE: PRT
<213> ORGANISM: Homo sapiens

<400> SEQUENCE: 131

```
Asp Leu Val Tyr Phe Glu Lys Ser Pro Asp Phe Cys Glu Arg Glu Pro
1                5                  10                  15

Arg Leu Asp Ser Ala Gly Thr Val Gly Arg Leu Cys Asn Lys Ser Ser
                 20                  25                  30

Ala Gly Ser Asp Gly Cys Gly Ser Met Cys Cys Gly Arg Gly His Asn
             35                  40                  45

Ile Leu Arg Gln Thr Arg Ser Glu Arg Cys His Cys Arg Phe His Trp
50                   55                  60

Cys Cys Phe Val Val Cys Glu Glu Cys Arg Ile Thr Glu Trp Val Ser
65                   70                  75                  80

Val Cys Lys
```

<210> SEQ ID NO 132
<211> LENGTH: 83
<212> TYPE: PRT
<213> ORGANISM: Homo sapiens

<400> SEQUENCE: 132

```
Glu Leu Val Tyr Phe Glu Lys Ser Pro Asp Phe Cys Glu Arg Asp Pro
1                5                  10                  15

Thr Met Gly Ser Pro Gly Thr Arg Gly Arg Ala Cys Asn Lys Thr Ser
                 20                  25                  30

Arg Leu Leu Asp Gly Cys Gly Ser Leu Cys Cys Gly Arg Gly His Asn
             35                  40                  45

Val Leu Arg Gln Thr Arg Val Glu Arg Cys His Cys Arg Phe His Trp
50                   55                  60

Cys Cys Tyr Val Leu Cys Asp Glu Cys Lys Val Thr Glu Trp Val Asn
65                   70                  75                  80

Val Cys Lys
```

<210> SEQ ID NO 133
<211> LENGTH: 390
<212> TYPE: PRT
<213> ORGANISM: Artificial Sequence
<220> FEATURE:
<223> OTHER INFORMATION: FZD8-Fc variant 54F28

<400> SEQUENCE: 133

```
Met Glu Trp Gly Tyr Leu Leu Glu Val Thr Ser Leu Leu Ala Ala Leu
1               5                   10                  15

Leu Leu Leu Gln Arg Ser Pro Phe Val His Ala Ala Ser Ala Lys Glu
            20                  25                  30

Leu Ala Cys Gln Glu Ile Thr Val Pro Leu Cys Lys Gly Ile Gly Tyr
            35                  40                  45

Asn Tyr Thr Tyr Met Pro Asn Gln Phe Asn His Asp Thr Gln Asp Glu
            50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
            130                 135                 140

Asp Thr Leu Cys Met Asp Tyr Asn Arg Thr Asp Leu Thr Thr Glu Pro
145                 150                 155                 160

Lys Ser Ser Asp Lys Thr His Thr Cys Pro Pro Cys Pro Ala Pro Glu
            165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
            210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
            275                 280                 285

Pro Gln Val Tyr Thr Leu Pro Pro Ser Arg Asp Glu Leu Thr Lys Asn
            290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
            370                 375                 380

Ser Leu Ser Pro Gly Lys
385                 390
```

METHODS OF TREATING NEUROENDOCRINE TUMORS USING FRIZZLED-BINDING AGENTS

CROSS-REFERENCE TO RELATED APPLICATIONS

This application claims priority benefit of U.S. Provisional Application No. 61/717,294, filed Oct. 23, 2012 and U.S. Provisional Application No. 61/760,529, filed Feb. 4, 2013, each of which is hereby incorporated by reference herein in its entirety.

FIELD OF THE INVENTION

The field of this invention generally relates to methods of treating neuroendocrine tumors. In one embodiment, the method comprises administering to a subject in need thereof a therapeutically effective dose of a Wnt antagonist.

REFERENCE TO SEQUENCE LISTING SUBMITTED ELECTRONICALLY VIA EFS-WEB

The content of the electronically submitted sequence listing (Name: 2293_0950002_SEQLISTING.ascii.txt; Size: 189 kilobytes; and Date of Creation: Jan. 9, 2014) is herein incorporated by reference in its entirety.

BACKGROUND OF THE INVENTION

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, *Cancer J. Clin.* 53:5-26).

The Wnt signaling pathway has been identified as a potential target for cancer therapy. The Wnt signaling pathway is one of several critical regulators of embryonic pattern formation, post-embryonic tissue maintenance, and stem cell biology. More specifically, Wnt signaling plays an important role in the generation of cell polarity and cell fate specification including self-renewal by stem cell populations. Unregulated activation of the Wnt pathway is associated with numerous human cancers where it can alter the developmental fate of tumor cells to maintain them in an undifferentiated and proliferative state. Thus carcinogenesis can proceed by usurping homeostatic mechanisms controlling normal development and tissue repair by stem cells (reviewed in Reya & Clevers, 2005, *Nature* 434:843; Beachy et al., 2004, *Nature* 432:324).

The Wnt signaling pathway was first elucidated in the *Drosophila* developmental mutant wingless (wg) and from the murine proto-oncogene int-1, now Wnt1 (Nusse & Varmus, 1982, *Cell* 31:99-109; Van Ooyen & Nusse, 1984, *Cell* 39:233-40; Cabrera et al., 1987, Cell 50:659-63; Rijsewijk et al., 1987, *Cell* 50:649-57). Wnt genes encode secreted lipid-modified glycoproteins of which 19 have been identified in mammals. These secreted ligands activate a receptor complex consisting of a Frizzled (Fzd) receptor family member and low-density lipoprotein (LDL) receptor-related protein 5 or 6 (LPR5/6). The Fzd receptors are seven transmembrane domain proteins of the G-protein coupled receptor (GPCR) superfamily and contain a large extracellular N-terminal ligand binding domain with 10 conserved cysteines, known as a cysteine-rich domain (CRD) or Fri domain. There are ten human FZD receptors: FZD1-10. Different Fzd CRDs have different binding affinities for specific Wnts (Wu & Nusse, 2002, *J. Biol. Chem.* 277:41762-9), and Fzd receptors have been grouped into those that activate the canonical β-catenin pathway and those that activate non-canonical pathways described below (Miller et al., 1999, *Oncogene* 18:7860-72). To form the receptor complex that binds the FZD ligands, FZD receptors interact with LRP5/6, single pass transmembrane proteins with four extracellular EGF-like domains separated by six YWTD amino acid repeats (Johnson et al., 2004, *J. Bone Mineral Res.* 19:1749).

The Wnt/beta-catenin signaling pathway has been implicated in the development of gastrointestinal carcinoid tumors. Fujimori et al., *Cancer Res.* 61(18): 6656-9 (2001). Nuclear translocation of β-catenin protein but absence of β-catenin and APC mutation in gastrointestinal carcinoid tumor has also been observed. Su et al., *Ann. Surg. Oncol.* 13(12): 1604-9 (2006). 72 cases of gastrointestinal carcinoid tumor were investigated both immunohistochemically and by direct sequencing of beta-catenin. Accumulation of beta-catenin in the cytoplasm and/or nucleus was observed in 57 cases (79.2%). Mutations were also detected in exon 3 of beta-catenin in 27 cases (37.5%), and in APC in one case (1.4%). Su et al. also reported the investigation of 91 gastrointestinal carcinoid tumors and, for comparison, 26 extragastrointestinal carcinoid tumors by immunohistochemical detection of beta-catenin protein and direct sequencing of exon 3 of the beta-catenin gene and exon 15 of the APC gene. Cytoplasmic accumulation and/or nuclear translocation of beta-catenin were found in 27 gastrointestinal carcinoid tumors (29.7%) but not in any extragastrointestinal carcinoid tumors. Neither beta-catenin nor APC gene mutation was detected in any of the cases with nuclear expression of beta-catenin.

SUMMARY OF THE INVENTION

The present invention provides methods of treating a neuroendocrine tumor. Thus in one aspect, the invention provides methods of inhibiting the growth of a neuroendocrine tumor, comprising contacting the neuroendocrine tumor with an effective amount of a Wnt antagonist. In another aspect, the invention provides methods of inhibiting the proliferation of neuroendocrine tumor cells, comprising contacting the neuroendocrine tumor cells with an effective amount of a Wnt antagonist. In another aspect, the invention provides methods of reducing the tumorigenicity of neuroendocrine tumor cells, comprising contacting the neuroendocrine tumor cells with an effective amount of a Wnt antagonist. In another aspect, the invention provides methods of inducing neuroendocrine tumor cells to differentiate, comprising contacting the neuroendocrine tumor cells with an effective amount of a Wnt antagonist. In another aspect, the invention provides methods of inhibiting the growth of a neuroendocrine tumor, comprising administering to a subject in need thereof a therapeutically effective amount of a Wnt antagonist. In another aspect, the invention provides methods of inhibiting the proliferation of neuroendocrine tumor cells, comprising administering to a subject in need thereof a therapeutically effective amount of a Wnt antagonist. In another aspect, the invention provides methods of treating neuroendocrine cancer, comprising administering to a subject in need thereof a therapeutically effective amount of a Wnt antagonist. In certain embodiments the subject is a human subject.

In certain embodiments of each of the aforementioned aspects or embodiments, as well as other aspects and/or embodiments described elsewhere herein, the neuroendocrine tumor is a low grade, medium grade, or high grade neuroendocrine tumor. In further embodiments, the neuroendocrine tumor is a functional neuroendocrine tumor or a non-functional neuroendocrine tumor. In further embodiments, the neuroendocrine tumor is selected from the group consisting of gastroenteropancreatic neuroendocrine tumor, carcinoid tumor, pheochromocytoma, paraganglioma, medullary thyroid cancer, pulmonary neuroendocrine tumor and thymic neuroendocrine tumor. In further embodiments, the neuroendocrine tumor is a carcinoid tumor or a pancreatic neuroendocrine tumor.

In certain embodiments of each of the aforementioned aspects or embodiments, as well as other aspects and/or embodiments described elsewhere herein, the Wnt antagonist is an antibody. In further embodiments, the Wnt antagonist is an antibody that specifically binds to at least one human Wnt. In further embodiments, the Wnt antagonist is an antibody that specifically binds to at least one human frizzled receptor (FZD). In further embodiments, the Wnt antagonist is a soluble FZD receptor.

In certain embodiments of each of the aforementioned aspects or embodiments, as well as other aspects and/or embodiments described elsewhere herein, the Wnt antagonist is an antibody that specifically binds to at least one human frizzled receptor (FZD). In further embodiments, the antibody specifically binds to the extracellular domain of at least one human FZD. In further embodiments, the antibody specifically binds to a human FZD selected from the group consisting of FZD1, FZD2, FZD5, FZD7, and FZD8. In further embodiments, the antibody specifically binds to FZD7. In further embodiments, the antibody specifically binds to more than one human FZD. In further embodiments, the antibody specifically binds to three or more human FZD selected from the group consisting of FZD1, FZD2, FZD5, FZD7, and FZD8. In further embodiments, the antibody specifically binds to more than one human FZD selected from the group consisting of FZD1, FZD2, FZD5, FZD7, and FZD8. In further embodiments, the antibody specifically binds to FZD1, FZD2, FZD5, FZD7, and FZD8.

In further embodiments, the antibody blocks ligand binding to FZD. In further embodiments, the antibody blocks Wnt binding to FZD. In further embodiments, the antibody blocks the activation of FZD.

In further embodiments, the antibody comprises: (1) a heavy chain CDR1 comprising GFTFSHYTLS (SEQ ID NO:31), a heavy chain CDR2 comprising VISGDGSYTYY-ADSVKG (SEQ ID NO:32), and a heavy chain CDR3 comprising NFIKYVFAN (SEQ ID NO:33); and/or (2) (a) a light chain CDR1 comprising SGDNIGSFYVH (SEQ ID NO:34), a light chain CDR2 comprising DKSNRPSG (SEQ ID NO:35), and a light chain CDR3 comprising QSYANTLSL (SEQ ID NO:36); or (b) a light chain CDR1 comprising SGDKLGKKYAS (SEQ ID NO:41), a light chain CDR2 comprising EKDNRPSG (SEQ ID NO:42), and a light chain CDR3 comprising SSFAGNSLE (SEQ ID NO:43). In further embodiments, the antibody comprises: a VH comprising the amino acid sequence of SEQ ID NO:37; and/or a VL comprising the amino acid sequence of SEQ ID NO:38 or 44. In further embodiments, the antibody comprises: a heavy chain comprising the amino acid sequence of SEQ ID NO:39; and/or a light chain comprising the amino acid sequence of SEQ ID NO:40 or 45.

In further embodiments, the antibody is a monoclonal antibody. In further embodiments, the antibody is a recombinant antibody, a chimeric antibody, a humanized antibody, a human antibody, or an antibody fragment. In further embodiments, the antibody is a monospecific antibody or a bispecific antibody. In further embodiments, the antibody is an IgA, IgD, IgE, IgG or IgM antibody. In further embodiments, the antibody is an IgG1 or IgG2 antibody.

In further embodiments, the Wnt antagonist is OMP-18R5 (also known as "vantictumab").

In certain embodiments of each of the aforementioned aspects or embodiments, as well as other aspects and/or embodiments described elsewhere herein, the Wnt antagonist is a soluble FZD receptor. In further embodiments, the soluble FZD receptor binds to Wnt. In further embodiments, the soluble receptor comprises a fragment of the extracellular domain of a human FZD receptor. In further embodiments, the fragment of the extracellular domain of the human FZD receptor comprises the Fri domain of the human FZD receptor.

In further embodiments, the human FZD receptor is selected from the group consisting of FZD4, FZD5, and FZD8. In further embodiments, the human FZD receptor is FZD8. In further embodiments, the FZD8 Fri domain comprises the amino acid sequence of SEQ ID NO:28.

In further embodiments, the soluble receptor further comprises a human Fc domain. In further embodiments, the human Fc domain comprises the amino acid sequence of SEQ ID NO:95.

In further embodiments, the Wnt antagonist is OMP-54F28.

In certain embodiments of each of the aforementioned aspects or embodiments, as well as other aspects and/or embodiments described elsewhere herein, the methods further comprise contacting the tumor or tumor cells with a second therapeutic agent, or administering a second therapeutic agent to the subject. In further embodiments, the second therapeutic agent is a chemotherapeutic agent. In further embodiments, the second therapeutic agent is a kinase inhibitor, somatostatin analog or an mTOR pathway inhibitor. In further embodiments, the second therapeutic agent is sunitinib, octreotide, or everolimus. In further embodiments, the second therapeutic agent is an antibody. In further embodiments, the second therapeutic agent is an angiogenesis inhibitor.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

BRIEF DESCRIPTIONS OF THE DRAWINGS

FIG. 1. Effect of Wnt inhibitors on neuroendocrine tumor growth. The size of tumor lesions in a pancreatic neuroendocrine tumor patient was reduced following the administration of the OMP-18R5 anti-FZD7 antibody. (A) Radiographic assessment of the size of target and non-target lesions at day 56 and day 112 of OMP-18R5 anti-FZD7 antibody treatment. BL denotes the baseline size of the lesions before the administration of OMP-18R5. (B) CT image of the tumor lesions before (Baseline) and after 112 days of OMP-18R5 administration. (C) CT image of the tumor lesions before (Baseline) and after 112 days of OMP-18R5 administration. The tumor lesion at day 112 displays radiologic signs of calcification.

Figure 2:
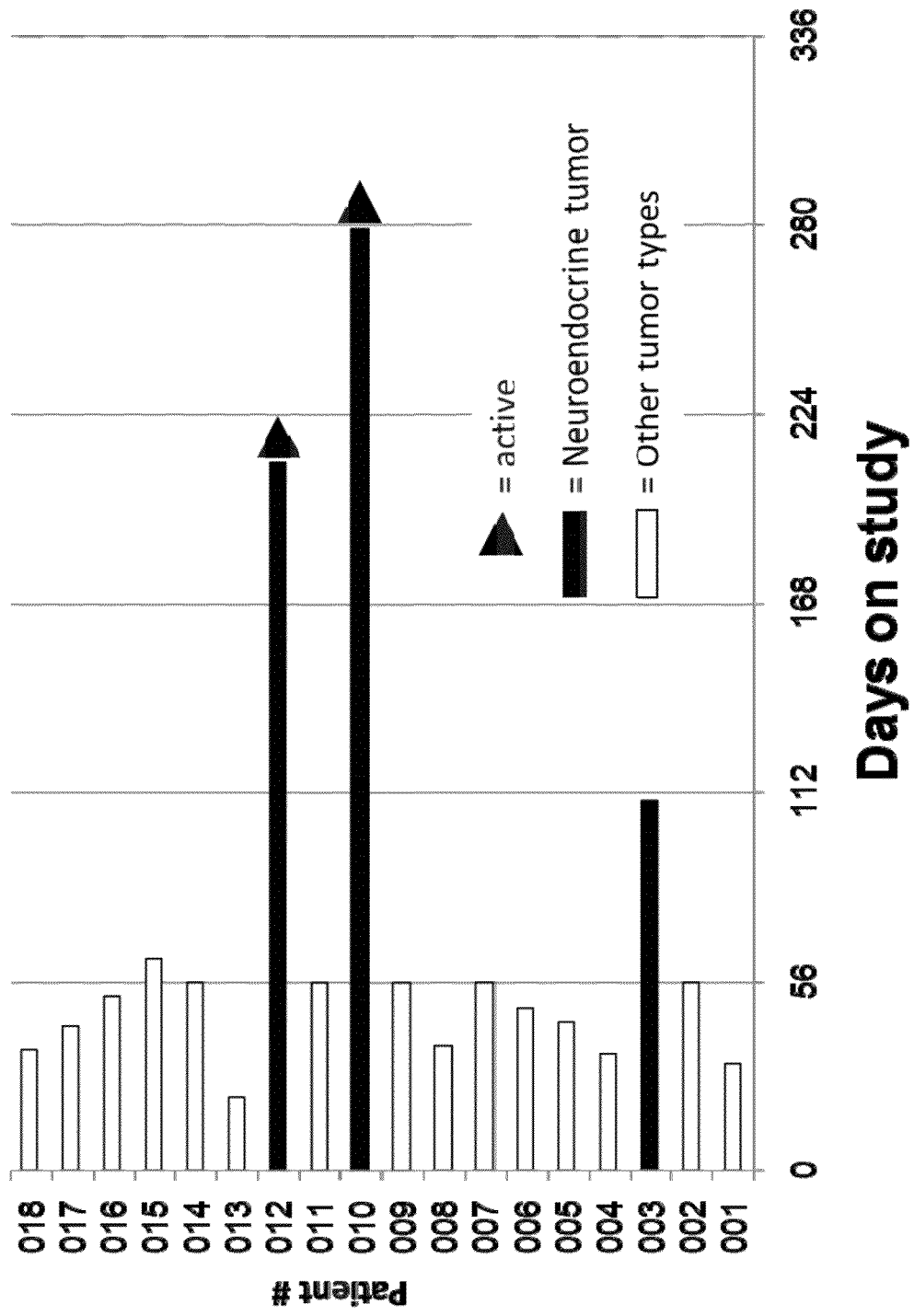

FIG. 2. Days on study for patients on OMP-18R5 Phase 1a study. The number of days each of the patients (n=18) enrolled in the OMP-18R5 Phase 1a study has stayed on the study as of Jan. 25, 2013, is shown graphically in the figure.

Arrows indicate the patients who remained on the study as of Jan. 25, 2013. The vertical lines indicate dates of tumor assessments on the study. The neuroendocrine tumor patients are patients 003 (Patient 3 in Example 1), 010 (Patient 10 in Example 1), and 012 (Patient 12 in Example 1). The other patients on the study had other types of advanced solid tumors such as colorectal cancer, breast cancer, melanoma, and pancreatic cancer.

Figure 3:
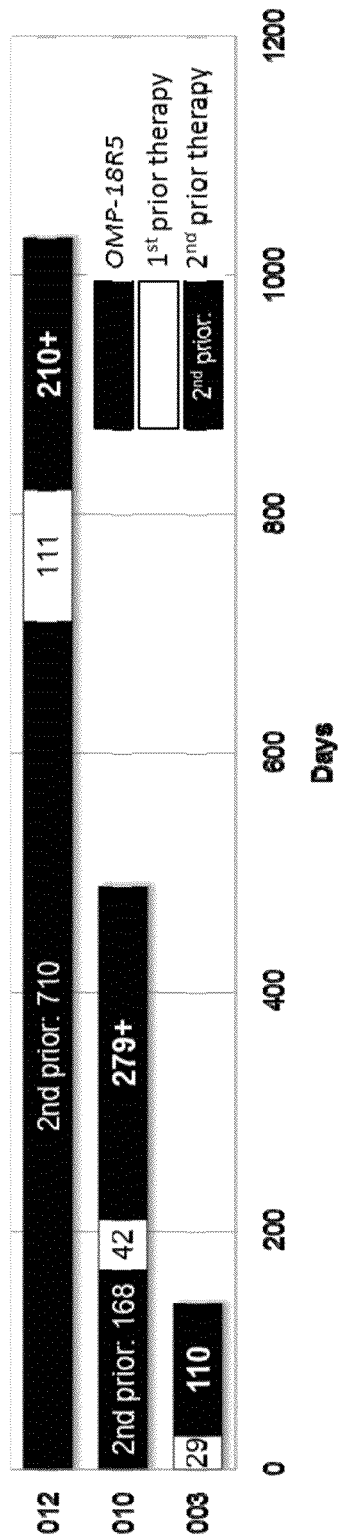

FIG. 3. Days on study for patients with neuroendocrine tumors on OMP-18R5 Phase 1a study were compared to days on treatment with prior regimens. Patient 10, a 69-year-old woman with neuroendocrine tumor of the pancreas, continues on study with stable disease for 279 days (as of Jan. 25, 2013). Patient 12, a 77-year-old woman with carcinoid, continues on study with stable disease for 210 days (as of Jan. 25, 2013).

DETAILED DESCRIPTION OF THE INVENTION

The present invention provides methods of inhibiting the growth of a neuroendocrine tumor, methods of inhibiting proliferation of neuroendocrine tumor cells, methods of treating a neuroendocrine cancer, methods of inhibiting neuroendocrine tumor metastases, methods of inducing neuroendocrine tumor cell differentiation, methods of reducing tumorgenicity of neuroendocrine tumor cells and methods of reducing the frequency of cancer stem cells or tumor initiating cells in a neuroendocrine tumor. In some embodiments, the methods provided herein comprise administering a Wnt antagonist to a subject. In some embodiments, the Wnt antagonist is a FZD-binding agent that specifically binds to one or more human FZD receptors. In further embodiments, the FZD-binding agent is an antibody that specifically binds to one or binds to one or more human FZD receptors. In some embodiments, the Wnt antagonist is a Wnt binding agent that specifically binds to one or more human Wnt polypeptide. In some embodiments, the Wnt binding agent is a soluble FZD receptor. In some embodiments, the Wnt binding agent is an anti-Wnt antibody.

Human patients with late stage neuroendocrine tumors were treated with low doses of the OMP-18R5 anti-FZD antibody in the context of a Phase 1 clinical trial for patients with late stage solid tumors. (Example 1.) Surprisingly, one of the patients (a patient having a pancreatic neuroendocrine tumor) showed a reduction in tumor lesion size after 112 days of treatment with OMP-18R5 and remained on study without evidence of any progression of disease for 279 days (as of Jan. 25, 2013). Additionally, new calcification was seen in one of the patient's lesions which may represent possible signs of tumor cell necrosis and/or differentiation. In addition, two patients with neuroendocrine tumors having carcinoid histology were also able to stay on the study for surprisingly long periods of time with stable disease during treatment with OMP-18R5. (Example 1.) Collectively, these results suggest that OMP-18R5 may be particularly useful in the treatment of a variety of neuroendocrine tumors.

1. Definitions

To facilitate an understanding of the present invention, a number of terms and phrases are defined below.

The term "antagonist" is used herein to include any molecule that partially or fully blocks, inhibits, or neutralizes the expression of or the biological activity of a protein, (e.g., a cancer stem cell marker). The blocking, inhibiting, and/or neutralizing of biological activity includes, but is not limited to, inhibition of tumor growth. The term "antagonist" also includes any molecule that partially or fully blocks, inhibits, or neutralizes a biological activity of the Wnt pathway. The term "Wnt antagonist" is used herein to include any molecule that partially or fully blocks, inhibits or neutralizes the signaling of the Wnt pathway (e.g., canonical Wnt signaling), or partially or fully blocks, inhibits or neutralizes a biological activity of a component of the Wnt pathway. Wnt antagonists do not necessarily bind Wnt. For instance, in certain embodiments Wnt antagonists bind one or more other components of the Wnt pathway such as one or more FZD receptors. Suitable Wnt antagonist molecules include, but are not limited to, fragments and/or amino acid sequence variants of native FZD receptor proteins including soluble FZD receptors, as well as derivatives of soluble Frizzled-related proteins (SFRPs), and derivatives of Ror proteins. Suitable Wnt antagonist molecules further include, but are not limited to, antibodies that specifically bind to one or more FZD receptors and antibodies that specifically bind to one or more Wnt polypeptide. Soluble SFRP and Ror receptors are described in US Pat. Appl. Pub. No. 2011/0305695, which is herein incorporated by reference.

In vivo and in vitro assays for determining whether an agent (e.g., soluble FZD receptor or anti-FZD antibody) inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro (Gazit et al., 1999, *Oncogene* 18; 5959-66). The level of Wnt signaling in the presence of one or more Wnts (e.g., Wnt(s) expressed by transfected cells or provided by Wnt-conditioned media) with the agent present is compared to the level of signaling without the agent present. In addition to the TCF/luc reporter assay, the effect of an agent (e.g., soluble FZD receptor or anti-FZD antibody) on canonical Wnt signaling can be measured in vitro or in vivo by measuring the effect of the agent on the level of expression of beta-catenin regulated genes, such as c-myc (He et al., *Science,* 281:1509-12 (1998)), cyclin D1 (Tetsu et al., *Nature,* 398:422-6 (1999)) and/or fibronectin (Gradl et al. *Mol. Cell. Biol.,* 19:5576-87 (1999)). In certain embodiments, the effect of the agent on Wnt signaling can also be assessed by measuring the effect of the agent on the phosphorylation state of Dishevelled-1, Dishevelled-2, Dishevelled-3, LRP5, LRP6, and/or beta-catenin. In still further embodiments, the effect of the agent on Wnt signaling is determined by assessing the impact of the agent on the expression level of one or more genes in a Wnt signature. Non-limiting examples of the use of such assays to assess inhibition of canonical Wnt signaling are disclosed in U.S. Pat. Appl. Pub. No. 2012/0027778, which is incorporated by reference herein in its entirety.

As used herein the term "soluble receptor" refers to an amino-terminal extracellular fragment of a receptor protein preceding the transmembrane domain that can be secreted from a cell in soluble form. In some embodiments, the receptor protein is a FZD receptor. In some embodiments, the receptor protein is the ROR1 or ROR2 receptor. In certain embodiments, the soluble receptor is linked in-frame with a polypeptide that increases the half-life of the soluble receptor. In certain embodiments, the polypeptide that increases half-life is a human Fc domain.

As used herein the term "FZD soluble receptor" refers to an amino-terminal extracellular fragment of a human FZD receptor protein preceding the transmembrane domain of the receptor that can be secreted from a cell in soluble form. FZD soluble receptors comprising the entire amino-terminal extracellular domain (ECD) (referred to herein as "FZD ECD") as well as smaller fragments of the ECD are envisioned. FZD soluble receptors comprising the Fri domain (referred herein as "FZD Fri") are also disclosed. Soluble FZD receptors are described in US Pat. Appl. Pub. No. 2011/0305695, which is herein incorporated by reference.

FZD Fri soluble receptors can demonstrate altered biological activity, (e.g., increased protein half-life) compared to soluble receptors comprising the entire FZD ECD. Protein half-life can be further increased by covalent modification with polyethylene glycol (PEG) or polyethylene oxide (PEO). FZD soluble receptors include FZD ECD or Fri domains linked in-frame to other functional and structural proteins including, but not limited to, a human Fc region (e.g., human Fc derived from immunoglobulins IgG1, IgG2, IgG3, IgG4, IgA1, IgA2, IgD, IgE, or IgM); protein tags (e.g., myc, FLAG, GST); other endogenous proteins or protein fragments; or any other useful protein sequence including any linker region between a FZD ECD or Fri domain and a linked protein. In certain embodiments, the Fri domain of a FZD receptor is directly linked to a human Fc region. In certain embodiments, the Fri domain of a FZD receptor is linked to human IgG1 Fc (referred to herein as "FZD Fri.Fc," e.g. "FZD8 Fri.Fc"). In some embodiments, the Fri domain of a FZD receptor is linked to a human Fc region with a peptide linker. FZD soluble receptors also include variant proteins comprising amino acid insertions, deletions, substitutions, and/or conservative substitutions.

As used herein, the term "linker" or "linker region" refers to a linker inserted between a first polypeptide (e.g., a FZD component) and a second polypeptide (e.g., an Fc region). In some embodiments, the linker is a peptide linker. Linkers should not adversely affect the expression, secretion, or bioactivity of the polypeptides. Preferably, linkers are not antigenic and do not elicit an immune response.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

That a polypeptide or other agent (e.g., antibody or soluble receptor) "specifically binds" to a protein means that the polypeptide or other agent reacts or associates more frequently, more rapidly, with greater duration, with greater affinity, or with some combination of the above to the protein than with alternative substances, including unrelated proteins. In certain embodiments, "specifically binds" means, for instance, that an agent (e.g., antibody or soluble receptor) binds to a protein with a $K_D$ of about 0.1 mM or less, but more usually less than about 1 µM. In certain embodiments, "specifically binds" means that an agent (e.g., antibody or soluble receptor) binds to a protein at times with a $K_D$ of at least about 0.1 µM or less, at least about 0.01 µM or less, and at other times at least about 1 nM or less. Because of the sequence identity between homologous proteins in different species, specific binding can include an agent (e.g., antibody or soluble receptor) that recognizes a particular protein such as a Wnt protein or a frizzled receptor in more than one species. Likewise, because of homology between different paralogues (e.g., the different human Wnt proteins or human frizzled proteins) in certain regions of their sequences, specific binding can include a polypeptide or an agent (e.g., antibody or soluble receptor) that recognizes more than one paralogue (e.g., more than one human Wnt protein or more than one human frizzled protein). It is understood that an agent (e.g., antibody or soluble receptor) that specifically binds to a first target may or may not specifically bind to a second target. As such, "specific binding" does not necessarily require (although it can include) exclusive binding, i.e. binding to a single target. Thus, an agent (e.g., antibody or soluble receptor) may, in certain embodiments, specifically bind to more than one target (e.g., multiple different human Wnt proteins or multiple different frizzled proteins, such as FZD1, FZD2, FZD5, FZD7, and/or FZD8). In certain embodiments, the multiple targets of an antibody may be bound by the same antigen-binding site on the antibody. For example, an antibody may, in certain instances, comprise two identical antigen-binding sites, each of which specifically binds two or more human frizzled receptors (e.g., human FZD1, FZD2, FZD5, FZD7, and/or FZD8). In certain alternative embodiments, an antibody may be bispecific and comprise at least two antigen-binding sites with differing specificities. By way of non-limiting example, a bispecific antibody may comprise one antigen-binding site that recognizes an epitope on one frizzled receptor, such as human FZD5, and further comprises a second, different antigen-binding site that recognizes a different epitope on a second frizzled receptor, such as human FZD8. Generally, but not necessarily, reference to binding means specific binding.

The terms "cancer" and "cancerous" refer to or describe the physiological condition in mammals in which a population of cells are characterized by unregulated cell growth. The term cancer is understood to encompass Wnt-dependent cancers. Examples of cancer include, but are not limited to, carcinoma, lymphoma, blastoma, sarcoma, and leukemia.

"Tumor" and "neoplasm" refer to any mass of tissue that result from excessive cell growth or proliferation, either benign (noncancerous) or malignant (cancerous) including pre-cancerous lesions.

The terms "cancer stem cell," "tumor stem cell," or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "tumor stem cells," or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised mouse compared to non-tumorigenic tumor cells, which are unable to form tumors upon serial transplantation. It has been observed that non-tumorigenic tumor cells may form a tumor upon primary transplantation into an immunocompromised mouse after obtaining the tumor cells from a solid tumor, but those non-tumorigenic tumor cells do not give rise to a tumor upon serial transplantation.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "therapeutically effective amount" refers to an amount of an agent (e.g., antibody, soluble receptor, polypeptide, polynucleotide, small organic molecule, or other drug) effective to "treat" a disease or disorder in a subject or mammal In the case of cancer, the therapeutically effective amount of the agent can reduce the number of cancer cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; decrease tumorigenicity, tumorigenic frequency, or tumorigenic capacity of a tumor; reduce the number or frequency of cancer stem cells in a tumor; differentiate tumorigenic cells to a non-tumorigenic state; or a combination of such effects. To the extent the agent prevents growth and/or kills existing cancer cells, it can be referred to as cytostatic and/or cytotoxic.

As used herein the term "inhibit tumor growth" refers to any mechanism by which tumor cell growth can be inhibited. In certain embodiments, tumor cell growth is inhibited by slowing proliferation of tumor cells. In certain embodiments, tumor cell growth is inhibited by halting proliferation of tumor cells. In certain embodiments, tumor cell growth is inhibited by killing tumor cells. In certain embodiments, tumor cell growth is inhibited by inducing apoptosis of tumor cells. In certain embodiments, tumor cell growth is inhibited by inducing differentiation of tumor cells. In certain embodiments, tumor cell growth is inhibited by depriving tumor cells of nutrients. In certain embodiments, tumor cell growth is inhibited by preventing migration of tumor cells. In certain embodiments, tumor cell growth is inhibited by preventing invasion of tumor cells.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; or some combination of effects.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The terms "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

2. Methods of Treatment

The present invention provides methods of treating neuroendocrine tumors. Neuroendocrine tumors (NETs) are tumors that arise from cells of the endocrine (hormonal) and nervous systems. Neuroendocrine tumors (NETs) include a group of tumors with a range of morphologic, functional, and behavioral characteristics. These tumors are generally slow growing and behave in an indolent fashion. However, they have the potential to spread, primarily to the liver, and when they do, they can be life threatening and difficult to treat with current modalities.

Neuroendocrine tumors are classified by the site of their origin. In certain embodiments, the NET is selected from the group consisting of pancreatic neuroendocrine tumors (pNETs) and carcinoid tumors of the lung, stomach, duodenum, jejunum, ileum, colon and rectum. In further embodiments, the NET is selected from the group consisting neuroendocrine tumors of the ovary, thymus, thyroid medulla, adrenal glands (e.g., pheocromocytoma) and paraganglia (paraganglioma). In certain embodiments, the NET treated by the methods described herein is small cell lung cancer (SCLC). In certain alternative embodiments, the NET is not small cell lung cancer. In certain embodiments, NETs are pancreatic neuroendocrine tumors (PETs) or carcinoid tumors. In certain embodiments, the NET is not small cell lung cancer, a pancreatic cancer, or a thyroid cancer.

Neuroendocrine tumors are also classified by grade and differentiation. See, e.g., Phan et al., *Pancreas*, 39(6):784-798 (2012). In certain embodiments, the neuroendocrine tumor is a well differentiated, low grade tumor. In certain embodiments, the neuroendocrine tumor is a moderately differentiated, intermediate grade tumor. In certain embodiments, the neuroendocrine tumor is a poorly differentiated, high grade tumor. In one embodiment, low grade tumors are characterized by <2 mitoses per 10 HPF (high power fields) and no necrosis. In one embodiment, intermediate grade tumors are characterized by 2-10 mitoses per 10 HPF (high power fields) or foci of necrosis. In one embodiment, high grade tumors are characterized by >10 mitoses per 10 HPF (high power fields).

Neuroendocrine tumors are also classified as functional and non-functional NETs. NETs are considered functional when a specific clinical syndrome is induced due to excessive production of hormones by the tumor cells. Examples of functional NETs include, but are not limited to, carcinoid tumors, which can result in carcinoid syndrome, and functional pNETs, for example, insulinomas, gastrinomas, vasoactive intestinal peptide (VIP)omas, glucagonomas, and somatostatinomas. Non-functional NETs are not associated with a clinical syndrome due to excessive production of hormones by the tumor cells, but can still produce symptoms related to the presence of the tumor or its metastasis (e.g., abdominal pain or bloating). In certain embodiments, the neuroendocrine tumor is a functional NET. In certain embodiments, the neuroendocrine tumor is a non-functional NET. In certain embodiments, the neuroendocrine tumor is selected from the group consisting of functional carcinoid tumor, insulinoma, gastrinoma, vaso active intestinal peptide (VIP)

oma, glucagonoma, serotoninoma, histaminoma, ACTHoma, pheocromocytoma, and somatostatinoma. In certain embodiments, the neuroendocrine tumor is not SCLC.

In certain embodiments, the neuroendocrine tumor is a primary tumor. In certain embodiments, the neuroendocrine tumor is metastatic tumor. In certain embodiments, the neuroendocrine tumor has not spread outside of the wall of the primary organ. In certain embodiments, the neuroendocrine tumor has spread through the wall of the primary organ and to nearby tissues, such as fat, muscle, or lymph nodes. In certain embodiments, the neuroendocrine tumor has spread to tissues or organs away from the primary organ, for example, to the liver, bones, or lungs.

In certain embodiments, the neuroendocrine cancer or tumor is refractory to treatment. As a non-limiting example, the cancer or tumor may be chemorefractory (i.e., resistant to one or more forms of chemotherapy). In certain embodiments, the cancer or tumor is resistant to treatment with a somatostatin analog. In certain embodiments, the cancer or tumor is resistant to treatment with a kinase inhibitor.

In certain embodiments, the neuroendocrine cancer or tumor has metastasized to the liver. By way of non-limiting example, the neuroendocrine cancer or tumor is a carcinoid or pancreatic neuroendocrine tumor that has metastasized to the liver.

In one aspect, the present invention provides the use of a Wnt antagonist (e.g., an anti-FZD antibody or soluble FZD receptor) in the treatment of neuroendocrine tumor. In certain embodiments, the Wnt antagonist is useful for inhibiting Wnt signaling (e.g., canonical Wnt signaling) in a neuroendocrine tumor cell, inhibiting neuroendocrine tumor growth, inducing neuroendocrine tumor differentiation, reducing neuroendocrine tumor volume, and/or reducing the tumorigenicity of a neuroendocrine tumor. The methods of use can be in vitro, ex vivo, or in vivo methods. In certain embodiments, the Wnt antagonist is the antibody OMP-18R5. In certain embodiments, the Wnt antagonist is the soluble receptor OMP-54F28.

The present invention provides for methods of treating neuroendocrine tumor comprising administering a therapeutically effective amount of a Wnt antagonist (e.g., an anti-FZD antibody or soluble FZD receptor) to a subject (e.g., a subject in need of treatment). In certain embodiments, the neuroendocrine tumor is a pancreatic neuroendocrine tumor. In certain embodiments, the neuroendocrine tumor is a carcinoid. In certain embodiments, the neuroendocrine tumor is neuroendocrine tumor of the lung. By way of non-limiting example, the neuroendocrine tumor in the lung may be SCLC. In certain embodiments, the neuroendocrine tumor is not SCLC. In certain embodiments, the subject is a human. In certain embodiments, the Wnt antagonist is OMP-18R5. In certain embodiments, the Wnt antagonist is OMP-54F28.

The present invention further provides methods for inhibiting neuroendocrine tumor growth using the Wnt antagonists (e.g., anti-FZD antibodies and soluble FZD receptors) described herein. In certain embodiments, the method of inhibiting the neuroendocrine tumor growth comprises contacting the tumor cell with a Wnt antagonist (e.g., an anti-FZD antibody or soluble FZD receptor) in vitro. For example, an immortalized neuroendocrine tumor cell line is cultured in medium to which is added the Wnt antagonist (e.g., an anti-FZD antibody or soluble FZD receptor) to inhibit tumor growth. In some embodiments, neuroendocrine tumor cells are isolated from a patient sample such as, for example, a tissue biopsy, pleural effusion, or blood sample and cultured in medium to which is added a Wnt antagonist (e.g., an anti-FZD antibody or soluble FZD receptor) to inhibit tumor growth. In certain embodiments, the Wnt antagonist is OMP-18R5. In certain embodiments, the Wnt antagonist is OMP-54F28.

In some embodiments, the method of inhibiting neuroendocrine tumor growth comprises contacting the neuroendocrine tumor or tumor cells with the Wnt antagonist (e.g., an anti-FZD antibody or soluble FZD receptor) in vivo. In certain embodiments, contacting a neuroendocrine tumor or tumor cell with a Wnt antagonist (e.g., an anti-FZD antibody or soluble FZD receptor) is undertaken in an animal model. For example, a Wnt antagonist (e.g., an anti-FZD antibody or soluble FZD receptor) may be administered to neuroendocrine tumor xenografts that have been grown in immunocompromised mice (e.g. NOD/SCID mice) to inhibit neuroendocrine tumor growth. In some embodiments, neuroendocrine tumor cancer stem cells are isolated from a patient sample such as, for example, a tissue biopsy, pleural effusion, or blood sample and injected into immunocompromised mice that are then administered a Wnt antagonist (e.g., an anti-FZD antibody or soluble FZD receptor) to inhibit neuroendocrine tumor cell growth. In some embodiments, the Wnt antagonist (e.g., anti-FZD antibody or soluble FZD receptor) is administered at the same time or shortly after introduction of tumorigenic cells into the animal to prevent neuroendocrine tumor growth. In some embodiments, the Wnt antagonist (e.g., anti-FZD antibody or soluble FZD receptor) is administered as a therapeutic after the tumorigenic cells have grown to a specified size. In certain embodiments, the Wnt antagonist is OMP-18R5. In certain embodiments, the Wnt antagonist is OMP-54F28.

In certain embodiments, the method of inhibiting neuroendocrine tumor growth comprises administering to a subject a therapeutically effective amount of a Wnt antagonist (e.g., an anti-FZD antibody or soluble FZD receptor). In certain embodiments, the subject is a human. In certain embodiments, the subject has a neuroendocrine tumor or has had a tumor removed.

In certain embodiments, the neuroendocrine tumor is a tumor in which Wnt signaling is active. In certain embodiment, the Wnt signaling that is active is canonical Wnt signaling. In certain embodiments, the neuroendocrine tumor is a Wnt-dependent tumor. For example, in some embodiments, the tumor is sensitive to axin over-expression. In certain embodiments, the tumor does not comprise an inactivating mutation (e.g., a truncating mutation) in the adenomatous polyposis coli (APC) tumor suppressor gene or an activating mutation in the beta-catenin gene. In certain embodiments, the tumor expresses one or more genes in a Wnt gene signature, i.e., one or more genes up-regulated or down-regulated by the Wnt signaling pathway. In certain embodiments, the neuroendocrine tumor for which a subject is being treated involves such a tumor.

In certain embodiments, the neuroendocrine tumor expresses one or more human frizzled receptors to which the Wnt antagonist FZD-binding antibody described herein binds. In certain embodiments, the neuroendocrine tumor overexpresses the human frizzled receptor(s). In certain embodiments, the Wnt antagonist is OMP-18R5.

In certain embodiments, the neuroendocrine tumor expresses one or more human Wnt polypeptides to which the Wnt antagonist soluble FZD receptor described herein binds. In certain embodiments, the neuroendocrine tumor overexpresses the human Wnt polypeptide(s). In certain embodiments, the Wnt antagonist is OMP-54F28.

In certain embodiments, the neuroendocrine tumor expresses one or more human Wnt polypeptides to which the Wnt antagonist anti-Wnt antibody described herein binds. In certain embodiments, the neuroendocrine tumor overexpresses the human Wnt polypeptide(s).

In certain embodiments, the neuroendocrine tumor is a pancreatic neuroendocrine tumor. In certain embodiments, the neuroendocrine tumor is a carcinoid. In certain embodiments, the neuroendocrine tumor is neuroendocrine tumor of the lung. In certain embodiments, the neuroendocrine tumor is not SCLC.

The invention also provides a method of inhibiting Wnt signaling in a neuroendocrine tumor cell comprising contacting the cell with an effective amount of a Wnt antagonist (e.g., an anti-FZD antibody or soluble FZD receptor). In certain embodiments, the method is an in vivo method wherein the step of contacting the cell with the Wnt antagonist (e.g., anti-FZD antibody or soluble FZD receptor) comprises administering a therapeutically effective amount of the Wnt antagonist to the subject. In some alternative embodiments, the method is an in vitro or ex vivo method. In certain embodiments, the Wnt signaling that is inhibited is canonical Wnt signaling. In certain embodiments, the Wnt signaling is signaling by Wnt1, Wnt2, Wnt3, Wnt3A, Wnt7a, Wnt7b, and/or Wnt10B. In certain embodiments, the Wnt signaling is signaling by Wnt1, Wnt3A, Wnt7b, and/or Wnt10B.

In addition, the invention provides a method of reducing the tumorigenicity of a neuroendocrine tumor in a subject, comprising administering a therapeutically effective amount of a Wnt antagonist (e.g., an anti-FZD antibody or soluble FZD receptor) to the subject. In certain embodiments, the neuroendocrine tumor comprises cancer stem cells. In certain embodiments, the frequency of cancer stem cells in the neuroendocrine tumor is reduced by administration of the agent. In certain embodiments, the Wnt antagonist is OMP-18R5. In certain embodiments, the Wnt antagonist is OMP-54F28.

Thus, the invention also provides a method of reducing the frequency of cancer stem cells in a neuroendocrine tumor, comprising contacting the tumor with an effective amount of a Wnt antagonist (e.g., an anti-FZD antibody or soluble FZD receptor).

The invention further provides methods of differentiating tumorigenic neuroendocrine tumor cells into non-tumorigenic cells comprising contacting the tumorigenic neuroendocrine tumor cells with a Wnt antagonist (e.g., an anti-FZD antibody or soluble FZD receptor) by administering the Wnt antagonist to a subject that has a neuroendocrine tumor comprising the tumorigenic cells or that has had such a neuroendocrine tumor removed.

The use of the Wnt antagonists (e.g., an anti-FZD antibodies and soluble FZD receptors) described herein to induce the differentiation of neuroendocrine tumor cells is also provided. For example, methods of inducing cells to differentiate comprising contacting the cells with an effective amount of a Wnt antagonist (e.g., an anti-FZD antibody or soluble FZD receptor) described herein are envisioned. Methods of inducing cells in a neuroendocrine tumor in a subject to differentiate comprising administering a therapeutically effective amount of a Wnt antagonist (e.g., an anti-FZD antibody or soluble FZD receptor) to the subject are also provided. In certain embodiments, the differentiation of neuroendocrine tumor cells is associated with changes in the radiographic image of the tumor lesion. In certain embodiments, the differentiation of neuroendocrine tumor cells is associated with calcification in the tumor lesion. In certain embodiments, the Wnt antagonist is OMP-18R5. In certain embodiments, the Wnt antagonist is OMP-54F28.

Methods of treating a neuroendocrine tumor in a subject, wherein the neuroendocrine tumor is associated with Wnt signaling activation and/or is characterized by an increased level of stem cells and/or progenitor cells are further provided. In some embodiments, the treatment methods comprise administering a therapeutically effective amount of a Wnt antagonist (e.g., an anti-FZD antibody or soluble FZD receptor) to the subject. In certain embodiments, the Wnt signaling is canonical Wnt signaling.

In certain embodiments, in addition to administering the Wnt antagonist (e.g., anti-FZD antibody or soluble FZD receptor) described herein, the method or treatment further comprises administering a second anti-cancer agent (prior to, concurrently with, and/or subsequently to administration of the Wnt antagonist). Pharmaceutical compositions comprising the Wnt antagonist and the second anti-cancer agent are also provided. In certain embodiments, the administration of the combination of the Wnt antagonist and a second anti-cancer agent has a synergistic effect, such as a synergistic effect on the frequency of cancer stem cells.

It will be appreciated that the combination of a Wnt antagonist (e.g., anti-FZD antibody or soluble FZD receptor) and a second anti-cancer agent may be administered in any order or concurrently. In selected embodiments, the Wnt antagonist will be administered to patients that have previously undergone treatment with the second anti-cancer agent. In certain other embodiments, the Wnt antagonist and the second anti-cancer agent will be administered substantially simultaneously or concurrently. For example, a subject may be given the Wnt antagonist while undergoing a course of treatment with the second anti-cancer agent (e.g., chemotherapy). In certain embodiments, the Wnt antagonist will be administered within 1 year of the treatment with the second anti-cancer agent. In certain alternative embodiments, the Wnt antagonist will be administered within 10, 8, 6, 4, or 2 months of any treatment with the second anti-cancer agent. In certain other embodiments, the Wnt antagonist will be administered within 4, 3, 2, or 1 week of any treatment with the second anti-cancer agent. In some embodiments, the Wnt antagonist will be administered within 5, 4, 3, 2, or 1 days of any treatment with the second anti-cancer agent. It will further be appreciated that the two agents or treatment may be administered to the subject within a matter of hours or minutes (i.e., substantially simultaneously).

Useful classes of anti-cancer agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, performing compounds, purine antimetabolites, puromycins, radiation sensitizers, steroids, taxanes, topoisomerase inhibitors, vinca alkaloids, or the like. In certain embodiments, the second anti-cancer agent is an antimetabolite, an antimitotic, a topoisomerase inhibitor, or an angiogenesis inhibitor.

Anticancer agents that may be administered in combination with the Wnt antagonists (e.g., anti-FZD antibodies or soluble FZD receptors) include chemotherapeutic agents. Thus, in some embodiments, the method or treatment involves the combined administration of a Wnt antagonist and a chemotherapeutic agent or cocktail of multiple different chemotherapeutic agents. Treatment with a Wnt antagonist can occur prior to, concurrently with, or subsequent to administration of chemotherapies. Chemotherapies contemplated by the invention include chemical substances or drugs which are known in the art and are commercially available, such as gemcitabine, irinotecan, doxorubicin, 5-fluorouracil, cytosine arabinoside ("Ara-C"), cyclophosphamide, thiotepa, busulfan, cytoxin, TAXOL, methotrexate, cisplatin, melphalan, vinblastine and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention also include, but are not limited to, alkylating agents such as thiotepa and cyclosphosphamide (CYTOXAN); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL, Bristol-Myers Squibb Oncology, Princeton, N.J.) and doxetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; especiramicins; capecitabine; and pharmaceutically acceptable salts, acids or derivatives of any of the above. Chemotherapeutic agents also include anti-hormonal agents that act to regulate or inhibit hormone action on tumors such as antiestrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a kinase inhibitor. In certain embodiments, the kinase inhibitor is a multi-targeted receptor tyrosine kinase inhibitor. Kinase inhibitors include, but are not limited to, sunitinib (marketed as Sutent by Pfizer), pazopanib, crizotinib, dasatinib. In certain embodiments, the second anticancer agent is sunitinib.

In certain embodiments, the chemotherapeutic agent is an inhibitor of mammalian target of rapamycin (mTOR). mTOR inhibitors include, but are not limited to, temsirolimus, sirolimus, deforolimus and everolimus. In certain embodiments, the second anticancer agent is everolimus.

In certain embodiments, the chemotherapeutic agent is a somatostatin analog. Somatostatin analogs act through interaction with specific, high affinity membrane receptors for somatostatin. Somatostatin analogs include, but are not limited to, octreotide, somatulin, and RC 160 (octastatin). In certain embodiments, the second anticancer agent is octreotide.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCL, actinomycin D, etoposide, Topotecan HCL, teniposide (VM-26), and irinotecan. In certain embodiments, the second anticancer agent is irinotecan.

In certain embodiments, the chemotherapeutic agent is an alkylating agent. In certain embodiments, the chemotherapeutic agent is temozolomide.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Antimetabolites include, but are not limited to, gemcitabine, fluorouracil, capecitabine, methotrexate sodium, ralitrexed, pemetrexed, tegafur, cytosine arabinoside, THIOGUANINE (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second anticancer agent is gemcitabine. In certain embodiments, the tumor to be treated is a pancreatic neuroendocrine tumor and the second anticancer agent is an anti-metabolite (e.g., gemcitabine).

In certain embodiments, the chemotherapeutic agent is an antimitotic agent, including, but not limited to, agents that bind tubulin. By way of non-limiting example, the agent comprises a taxane. In certain embodiments, the agent comprises paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (e.g., ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of Eg5 kinesin or an inhibitor of a mitotic kinase such as Aurora A or Plk1.

In certain embodiments, the treatment involves the combined administration of a Wnt antagonist (e.g., anti-FZD antibody or soluble FZD receptor) described herein and radiation therapy. Treatment with the Wnt antagonist can occur prior to, concurrently with, or subsequent to administration of radiation therapy. Any dosing schedule for such radiation therapy can be used as determined by the skilled practitioner.

In some embodiments, the second anti-cancer agent comprises an antibody. Thus, treatment can involve the combined administration of a Wnt antagonist (e.g., anti-FZD antibody or soluble FZD receptor) with antibodies against tumor-associated antigens including, but not limited to, antibodies that bind to EGFR, ErbB2, HER2, DLL4, Notch and/or VEGF. Exemplary, anti-DLL4 antibodies, are described, for example, in U.S. Patent Application Publication No. US 2008/0187532, incorporated by reference herein in its entirety. In certain embodiments, the second anti-cancer agent is an antibody that is an angiogenesis inhibitor (e.g., an anti-VEGF antibody). Additional anti-DLL4 antibodies are described in, e.g., International Patent Publication Nos. WO 2008/091222 and WO 2008/0793326, and U.S. Patent Application Publication Nos. US 2008/0014196, US 2008/0175847, US 2008/0181899, and US 2008/0107648, each of which is incorporated by reference herein in its entirety. Exemplary anti-Notch antibodies are described, for example, in U.S. Patent Application Publication No. US 2008/0131434, incorporated by reference herein in its entirety. In certain embodiments, the second anti-cancer agent is an antibody that is an angiogenesis inhibitor (e.g., an anti-VEGF antibody). In certain embodiments, the second anti-cancer agent is an inhibitor of Notch signaling. In certain embodiments, the second anti-cancer agent is AVASTIN (Bevacizumab), Herceptin (Trastuzumab), VECTIBIX (Panitumumab), or Erbitux (Cetuximab). Combined administration can include co-administration, either in a single pharmaceutical formulation or using separate formulations, or consecutive administration in either order but generally within a time period such that all active agents can exert their biological activities simultaneously.

Furthermore, treatment can include administration of one or more cytokines (e.g., lymphokines, interleukins, tumor necrosis factors, and/or growth factors) or can be accompanied by surgical removal of cancer cells or any other therapy deemed necessary by a treating physician.

For the treatment of the disease, the appropriate dosage of a Wnt antagonist (e.g., anti-FZD antibody or soluble FZD receptor) described herein depends on the type of neuroendocrine tumor to be treated, the severity and course of the neuroendocrine tumor, the responsiveness of the neuroendocrine tumor, whether the Wnt antagonist (e.g., anti-FZD antibody or soluble FZD receptor) is administered for therapeutic or preventative purposes, previous therapy, patient's clinical history, and so on all at the discretion of the treating physician. The Wnt antagonist (e.g., anti-FZD antibody or soluble FZD receptor) can be administered one time or over a series of treatments lasting from several days to several months, or until a cure is effected or a diminution of the neuroendocrine tumor is achieved (e.g. reduction in tumor size). Optimal dosing schedules can be calculated from measurements of drug accumulation in the body of the patient and will vary depending on the relative potency of an individual Wnt antagonist (e.g., anti-FZD antibody or soluble FZD receptor). The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the Wnt antagonist (e.g., anti-FZD antibody or soluble FZD receptor) is given once every two weeks or once every three weeks. In certain embodiments, the dosage of the Wnt antagonist (e.g., anti-FZD antibody or soluble FZD receptor) is from about 0.1 mg to about 20 mg per kg of body weight. The treating physician can estimate repetition rates for dosing based on measured residence times and concentrations of the drug in bodily fluids or tissues. In certain embodiments, the Wnt antagonist is OMP-18R5. In certain embodiments, the Wnt antagonist is OMP-54F28.

In certain embodiments, OMP-18R5 is administered intravenously at a dose of about 0.1 mg/kg to about 20 mg/kg or a dose of about 0.5 mg/kg to about 10 mg/kg. Such doses may, in some embodiments, be given about every week, every two weeks, every three weeks or every four weeks. In certain embodiments, OMP-18R5 is administered intravenously at a dosage of about 0.5 mg/kg to about 10 mg/kg about every two to four weeks. In certain embodiments, OMP-18R5 is administered intravenously at a dosage of about 1.0 mg/kg to about 10 mg/kg approximately about every three weeks. In certain embodiments, OMP-18R5 is administered intravenously at a dosage of (a) at least about 0.5 mg/kg about every one to two weeks or (b) at least about 1.0 mg/kg about every three weeks. In certain embodiments, the antibody is administered at a dosage of about 0.5 mg/kg to about 1.0 mg/kg about every one to two weeks. In some alternative embodiments, the antibody is administered at a dosage of about 1.0 mg/kg to about 5.0 mg/kg about every three weeks.

By way of non-limiting example, OMP-54F28 may be administered intravenously at a dose of about 0.1 mg/kg to about 20 mg/kg. This dose may, in some embodiments, be given every week, every two weeks, every three weeks or every four weeks. In certain embodiments, OMP-54F28 is administered intravenously at a dosage of about 0.5 mg/kg to about 10 mg/kg every two to four weeks. In certain embodiments, OMP-54F28 is administered intravenously at a dosage of about 0.5 mg/kg to about 10 mg/kg about every three weeks.

3. FZD-Binding Agents

Another aspect of the methods of the invention is the use of a FZD-binding agent (e.g., anti-FZD antibody) in the treatment of neuroendocrine tumors. In certain embodiments, the FZD-binding agents (e.g., anti-FZD antibodies) that are useful in the methods of the invention specifically bind one or more human frizzled receptors (FZDs). In certain embodiments, the agents specifically bind two, three, four, five, six, seven, eight, nine, or ten frizzled receptors. The human frizzled receptor or receptors bound by the agent can be selected from the group consisting of FZD1, FZD2, FZD3, FZD4, FZD5, FZD6, FZD7, FZD8, FZD9, and FZD10. In certain embodiments, the one or more human frizzled receptors comprise FZD1, FZD2, FZD5, FZD7, and/or FZD8. In certain embodiments, the one or more human frizzled receptors comprise FZD7. In certain embodiments, the one or more human frizzled receptors comprise FZD5 and/or FZD8. In certain embodiments, the agent specifically binds FZD1, FZD2, FZD5, FZD7, and FZD8. In certain embodiments, the FZD-binding agent specifically binds FZD7. In certain embodiments, the FZD-binding agent specifically binds FZD5. The full-length amino acid (aa) and nucleotide (nt) sequences for FZD1-10 are known in the art and also provided herein as SEQ ID NO:1 (FZD1 aa), SEQ ID NO:2 (FZD2 aa), SEQ ID NO:3 (FZD3 aa), SEQ ID NO:4 (FZD4 aa), SEQ ID NO:5 (FZD5 aa), SEQ ID NO:6 (FZD6 aa), SEQ ID NO:7 (FZD7 aa), SEQ ID NO:8 (FZD8 aa), SEQ ID NO:9 (FZD9 aa), SEQ ID NO: 10 (FZD 10 aa).

In certain embodiments, a FZD-binding agent (e.g., anti-FZD antibody) that is useful in the methods of the invention specifically binds to two or more human frizzled receptors. In certain embodiments, the two or more human frizzled receptors are selected from the group consisting of FZD2, FZD5, FZD7, and FZD8. In certain embodiments, the two or more frizzled receptors comprise FZD1 and a second frizzled receptor selected from the group consisting of FZD2, FZD5, FZD7, and FZD8. In certain embodiments, the two or more frizzled receptors comprise FZD2 and a second frizzled receptor selected from the group consisting of FZD1, FZD5, FZD7, and FZD8. In certain embodiments, the two or more frizzled receptors comprise FZD5 and a second frizzled receptor selected from the group consisting of FZD1, FZD2, FZD7, and FZD8. In certain embodiments, the two or more frizzled receptors comprise both FZD5 and FZD8. In certain embodiments, the two or more frizzled receptors comprise FZD7 and a second frizzled receptor selected from the group consisting of FZD1, FZD2, FZD5, and FZD8. In certain embodiments, the agent specifically binds to three or more human frizzled receptors. In certain embodiments, the three or more human frizzled receptors comprise three or more frizzled receptors selected from the group consisting of FZD1, FZD2, FZD5, FZD7, and FZD8. In certain embodiments, the agent further specifically binds to one or more additional human frizzled receptors.

In certain embodiments, a FZD-binding agent (e.g., anti-FZD antibody) that is useful in the methods of the invention specifically binds to the extracellular domain (ECD) within the one or more human frizzled receptors to which it binds. Sequences of the extracellular domain of each of the human frizzled receptors are known in the art and are also provided as SEQ ID NO:11 (FZD1 ECD), SEQ ID NO:12 (FZD2 ECD), SEQ ID NO:13 (FZD3 ECD), SEQ ID NO:14 (FZD4 ECD), SEQ ID NO:15 (FZD5 ECD), SEQ ID NO:16 (FZD6 ECD), SEQ ID NO:17 (FZD7 ECD), SEQ ID NO:18 (FZD8 ECD), SEQ ID NO:19 (FZD9 ECD), and SEQ ID NO:20 (FZD10 ECD). Particularly useful antibodies are described in U.S. Pat. No. 7,982,013 and U.S. Pat. Appl. Pub. No. 2012/0027778, which are herein incorporated by reference in their entirety.

In certain embodiments, a FZD-binding agent (e.g., anti-FZD antibody) that is useful in the methods of the invention specifically binds to the Fri domain (FR1) (also known as the cysteine-rich domain (CRD)) within the human frizzled receptor(s) to which it binds. Sequences of the Fri domain of each of the human frizzled receptors are known in the art and are also provided herein. The Fri domain of FZD 1 includes approximately amino acids 87-237 of SEQ ID NO:11. The Fri domain of FZD2 includes approximately amino acids 24-159 of SEQ ID NO:12. The Fri domain of FZD3 includes approximately amino acids 23-143 of SEQ ID NO:13. The Fri domain of FZD4 includes approximately amino acids 40-170 of SEQ ID NO:14. The Fri domain of FZD5 includes approximately amino acids 27-157 of SEQ ID NO:15. The Fri domain of FZD6 includes approximately amino acids 19-146 of SEQ ID NO:16. The Fri domain of FZD7 includes approximately amino acids 33-170 of SEQ ID NO:17. The Fri domain of FZD8 includes approximately amino acids 28-158 of SEQ ID NO:18. The Fri domain of FZD9 includes approximately amino acids 23-159 of SEQ ID NO:19. The Fri domain of FZD10 includes approximately amino acids 21-154 of SEQ ID NO:20. The corresponding, predicted Fri domains for each of the human FZD receptors are provided as SEQ ID NOs:21-30. The minimal, core Fri domain sequences for each of the human FZD receptors (FZD1-10) are provided as SEQ ID NOs:73-82. Those of skill in the art may differ in their understanding of the exact amino acids corresponding to the various Fri domains. Thus in specific embodiments, the N-terminus or C-terminus of the domains outlined above and herein can extend or be shortened by 1, 2, 3, 4, 5, 6, 7, 8, 9, or even 10 amino acids.

In certain embodiments, an individual antigen-binding site of a FZD-binding antibody is capable of binding (or binds) the one, two, three, four, or five (or more) human frizzled receptors. In certain embodiments, an individual antigen-binding site of the FZD-binding antibody is capable of specifically binding one, two, three, four, or five human frizzled receptors selected from the group consisting of FZD1, FZD2, FZD5, FZD7, and FZD8. In certain embodiments, an individual binding site of the antibody specifically binds to at least FZD5 and FZD8.

In certain embodiments, a FZD-binding agent (e.g., anti-FZD antibody) that is useful in the methods of the invention binds to one or more (for example, two or more, three or more, or four or more) human frizzled receptors with a dissociation constant ($K_D$) of about 1 μM or less, about 100 nM or less, about 40 nM or less, about 20 nM or less, or about 10 nM or less. For example, in certain embodiments, a FZD-binding agent or antibody that binds to more than one FZD, binds to those FZDs with a $K_D$ of about 100 nM or less, about 20 nM or less, or about 10 nM or less. In certain embodiments, the FZD-binding agent or antibody binds to each of one or more (e.g., 1, 2, 3, 4, or 5) of the following FZDs with a dissociation constant of about 40 nM or less: FZD1, FZD2, FZD5, FZD7, and FZD8. In certain embodiments, the FZD-binding agent or antibody binds to each of one or more of the following FZDs with a dissociation constant of about 10 nM or less: FZD1, FZD2, FZD5, FZD7, and FZD8. In certain embodiments, the FZD-binding agent or antibody binds to each of the following FZDs with a dissociation constant of about 1 nM or less: FZD1, FZD2, FZD5, FZD7, and FZD8. In certain embodiments, the dissociation constant of the agent or antibody to a particular FZD is the dissociation constant determined using an FZD-Fc fusion protein comprising the FZD extracellular domain or Fri domain immobilized on a Biacore chip.

In certain embodiments, a FZD-binding agent (e.g., anti-FZD antibody) that is useful in the methods of the invention is an antagonist of at least one human frizzled receptor (i.e., 1, 2, 3, 4, 5, 6, 7, 8, 9, or 10 FZDs) bound by the agent. In certain embodiments, the agent inhibits at least about 10%, at least about 20%, at least about 30%, at least about 50%, at least about 75%, at least about 90%, or about 100% of one or more activity of the bound human frizzled receptor.

In certain embodiments, the FZD-binding agent (e.g., anti-FZD antibody) inhibits binding of a ligand to the at least one human frizzled receptor. In certain embodiments, the ligand is a human Wnt protein. Nineteen human Wnt proteins have been identified: Wnt1, Wnt2, Wnt2B/13, Wnt3, Wnt3A, Wnt4, Wnt5A, Wnt5B, Wnt6, Wnt7A, Wnt7B, Wnt8A, Wnt8B, Wnt9A (previously Wnt14), Wnt9B (previously Wnt15), Wnt10A, Wnt10B, Wnt11, and Wnt16. In certain embodiments, the agent inhibits binding of Wnt3A to FZD8. In certain embodiments, the inhibition of binding of a particular ligand to a particular human frizzled protein provided by the FZD-binding agent is at least about 10%, at least about 25%, at least about 50%, at least about 75%, at least about 90%, or at least about 95%. In certain embodiments, an agent that inhibits binding of a ligand such as a Wnt to a FZD, further inhibits Wnt signaling (e.g., inhibits canonical Wnt signaling).

In certain embodiments, the FZD-binding agent (e.g., anti-FZD antibody) inhibits Wnt signaling. It is understood that a FZD-binding agent that inhibits Wnt signaling may, in certain embodiments, inhibit signaling by one or more Wnts, but not necessarily by all Wnts. In certain alternative embodiments, signaling by all human Wnts may be inhibited. In certain embodiments, signaling by one or more Wnts selected from the group consisting of Wnt1, Wnt2, Wnt2B/13, Wnt3, Wnt3A, Wnt4, Wnt5A, Wnt5B, Wnt6, Wnt7A, Wnt7B, Wnt8A, Wnt8B, Wnt9A (previously Wnt14), Wnt9B (previously Wnt15), Wnt10A, Wnt10B, Wnt11, and Wnt16 is inhibited. In certain embodiments, the Wnt signaling that is inhibited is signaling by Wnt1, Wnt2, Wnt3, Wnt3A, Wnt7a, Wnt7b, and/or Wnt10B. In certain embodiments, the agent inhibits signaling by (at least) Wnt1, Wnt3A, Wnt7b, and Wnt10B. In particular embodiments, the agent inhibits signaling by (at least) Wnt3A. In certain embodiments, the inhibition of signaling by a Wnt provided by the FZD-binding agent is a reduction in the level of signaling by the Wnt of at least about 10%, at least about 25%, at least about 50%, at least about 75%, at least about 90%, or at least about 95%. In certain embodiments, the Wnt signaling that is inhibited is canonical Wnt signaling.

In vivo and in vitro assays for determining whether a FZD-binding agent (or candidate FZD-binding agent) inhibits Wnt signaling are known in the art. See, e.g., U.S. Pat. Appl. Pub. No. 2012/0027778, which is incorporated by reference herein in its entirety.

In certain embodiments, the FZD-binding agents (e.g., anti-FZD antibodies) useful in the methods of the invention have one or more of the following effects: inhibit proliferation of neuroendocrine tumor cells, reduce the tumorigenicity of a neuroendocrine tumor by reducing the frequency of cancer stem cells in the neuroendocrine tumor, inhibit neuroendocrine tumor growth, increase survival, trigger cell death of neuroendocrine tumor cells, differentiate tumorigenic neuroendocrine tumor cells to a non-tumorigenic state, or prevent metastasis of tumor cells.

In certain embodiments, the FZD-binding agents useful in the methods of the invention are capable of inhibiting neuroendocrine tumor growth. In certain embodiments, the FZD-binding agents are capable of inhibiting neuroendocrine tumor growth in vivo (e.g., in a xenograft mouse model and/or in a human having cancer).

In certain embodiments, the FZD-binding agents useful in the methods of the invention are capable of reducing the tumorigenicity of a neuroendocrine tumor. In certain embodiments, the agent or antibody is capable of reducing the tumorigenicity of a neuroendocrine tumor comprising cancer stem cells in an animal model, such as a mouse xenograft model. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. An example of a limiting dilution assay used to test the efficacy of an anti-FZD antibody is provided in Example 8 of US 2012/0027778, which is incorporated by reference herein in its entirety. Additional examples and guidance regarding the use of limiting dilution assays to determine a reduction in the number or frequency of cancer stem cells in a tumor can be found, e.g., in International Publication Number WO 2008/042236, U.S. Patent Application Publication No. 2008/0064049, and U.S. Patent Application Publication No. 2008/0178305, each of which is incorporated by reference herein in its entirety.

In certain embodiments, the FZD-binding agent (e.g., antibody) useful in the methods of the invention is a polypeptide. In certain embodiments, the agent or polypeptide is an antibody. In certain embodiments, the antibody is an IgG1 antibody or an IgG2 antibody. In certain embodiments, the antibody is a monoclonal antibody. In certain embodiments, the antibody is a human antibody or a humanized antibody. In certain embodiments, the antibody is an antibody fragment.

In certain embodiments, an anti-FZD antibody for the methods of the invention comprise one, two, three, four, five and/or six of the CDRs of the 18R5, 18R8 and/or 44R24 human antibodies (see Table 1 below) with up to four (i.e., 0, 1, 2, 3, or 4) conservative amino acid substitutions per CDR. In certain embodiments, the heavy chain CDR(s) are contained within a heavy chain variable region and/or the light chain CDR(s) are contained within a light chain variable region.

TABLE 1

CDRs of 18R8, 18R5, and 44R24 human antibodies

| | Heavy Chain | | |
|---|---|---|---|
| Ab(s) | CDR1 | CDR2 | CDR3 |
| 18R8 | GFTFS<u>H</u>YTLS (SEQ ID NO: 31) | VISGDGSYTYYADSVKG (SEQ ID NO: 32) | NFIKYVFAN (SEQ ID NO: 33) |
| 18R5 | GFTFS<u>H</u>YTLS (SEQ ID NO: 31) | VISGDGSYTYYADSVKG (SEQ ID NO: 32) | NFIKYVFAN (SEQ ID NO: 33) |
| 44R24 | GFTFSSYYIT (SEQ ID NO: 46) | TISYSSSNTYYADSVKG (SEQ ID NO: 47) | SIVFDY (SEQ ID NO: 48) |

| | Light Chain | | |
|---|---|---|---|
| Ab(s) | CDR1 | CDR2 | CDR3 |
| 18R8 | SGDKLGKKYAS (SEQ ID NO: 41) | EKDNRPSG (SEQ ID NO: 42) | SSFAGNSLE (SEQ ID NO: 43) |
| 18R5 | SGDNIGSFYVH (SEQ ID NO: 34) | DKSNRPSG (SEQ ID NO: 35) | QSYANTLSL (SEQ ID NO: 36) |
| 44R24 | SGDALGNRYVY (SEQ ID NO: 49) | SG (SEQ ID NO: 50) | GSWDTRPYPKY (SEQ ID NO: 51) |

* Site directed change introduced to CDR1 to remove N-linked glycosylation site is underlined.

In one embodiment, an anti-FZD antibody that is useful in the methods of the invention comprises a heavy chain variable region comprising: (a) a heavy chain CDR1 comprising GFTFSHYTLS (SEQ ID NO:31), or a variant thereof comprising 1, 2, 3, or 4 amino acid substitutions; (b) a heavy chain CDR2 comprising VISGDGSYTYYADSVKG (SEQ ID NO:32), or a variant thereof comprising 1, 2, 3, or 4 amino acid substitutions; and/or (c) a heavy chain CDR3 comprising NFIKYVFAN (SEQ ID NO:33), or a variant thereof comprising 1, 2, 3, or 4 amino acid substitutions. In certain embodiments, the anti-FZD antibody further comprises a light chain variable region comprising: (a) a light chain CDR1 comprising SGDKLGKKYAS (SEQ ID NO:41), or a variant of thereof comprising 1, 2, 3, or 4 amino acid substitutions; (b) a light chain CDR2 comprising EKDNRPSG (SEQ ID NO:42), or a variant of thereof comprising 1, 2, 3, or 4 amino acid substitutions; and/or (c) a light chain CDR3 comprising SSFAGNSLE (SEQ ID NO:43), or a variant of thereof comprising 1, 2, 3, or 4 amino acid substitutions. In certain embodiments, the amino acid substitutions are conservative substitutions. In a further embodiment, an anti-FZD antibody that is useful in the methods of the invention comprises (a) a heavy chain variable region comprising a heavy chain CDR1 comprising GFTFSHYTLS (SEQ ID NO:31), a heavy chain CDR2 comprising VISGDGSYTYYADSVKG (SEQ ID NO:32), and a heavy chain CDR3 comprising NFIKYVFAN (SEQ ID NO:33); and/or (b) a light chain variable region comprising a light chain CDR1 comprising SGDKLGKKYAS (SEQ ID NO:41), a light chain CDR2 comprising EKDNRPSG (SEQ ID NO:42), and/or a light chain CDR3 comprising SSFAGNSLE (SEQ ID NO:43).

In one embodiment, an anti-FZD antibody that is useful in the methods of the invention comprises a heavy chain variable region comprising: (a) a heavy chain CDR1 comprising GFTFSHYTLS (SEQ ID NO:31), or a variant thereof comprising 1, 2, 3, or 4 amino acid substitutions; (b) a heavy chain CDR2 comprising VISGDGSYTYYADSVKG (SEQ ID NO:32), or a variant thereof comprising 1, 2, 3, or 4 amino acid substitutions; and/or (c) a heavy chain CDR3 comprising NFIKYVFAN (SEQ ID NO:33), or a variant thereof comprising 1, 2, 3, or 4 amino acid substitutions. In certain embodiments, the anti-FZD antibody further comprises a light chain variable region comprising: (a) a light chain CDR1 comprising SGDNIGSFYVH (SEQ ID NO:34), or a variant of thereof comprising 1, 2, 3, or 4 amino acid substitutions; (b) a light chain CDR2 comprising DKSNRPSG (SEQ ID NO:35), or a variant of thereof comprising 1, 2, 3, or 4 amino acid substitutions; and/or (c) a light chain CDR3 comprising QSYANTLSL (SEQ ID NO:36), or a variant of thereof comprising 1, 2, 3, or 4 amino acid substitutions. In certain embodiments, the amino acid substitutions are conservative substitutions. In a further embodiment, an anti-FZD antibody that is useful in the methods of the invention comprises (a) a heavy chain variable region comprising a heavy chain CDR1 comprising GFTFSHYTLS (SEQ ID NO:31), a heavy chain CDR2 comprising VISGDGSYTYYADSVKG (SEQ ID NO:32), and a heavy chain CDR3 comprising NFIKYVFAN (SEQ ID NO:33); and/or (b) light chain variable region comprising a light chain CDR1 comprising SGDNIGSFYVH (SEQ ID NO:34), a light chain CDR2 comprising DKSNRPSG (SEQ ID NO:35), and a light chain CDR3 comprising QSYANTLSL (SEQ ID NO:36).

In one embodiment, an anti-FZD antibody that is useful in the methods of the invention comprises a heavy chain variable region comprising: (a) a heavy chain CDR1 comprising GFTFSSYYIT (SEQ ID NO:46), or a variant thereof comprising 1, 2, 3, or 4 conservative amino acid substitutions; (b) a heavy chain CDR2 comprising TISYSSSNTYYADSVKG (SEQ ID NO:47), or a variant thereof comprising 1, 2, 3, or 4 conservative amino acid substitutions; and/or (c) a heavy chain CDR3 comprising SIVFDY (SEQ ID NO:48), or a variant thereof comprising 1, 2, 3, or 4 conservative amino acid substitutions. In certain embodiments, the anti-FZD antibody further comprises a light chain variable region comprising: (a) a light chain CDR1 comprising SGDALGNRYVY (SEQ ID NO:49), or a variant thereof comprising 1, 2, 3, or 4 conservative amino acid substitutions; (b) a light chain CDR2 comprising SG (SEQ ID NO:50), or a variant thereof comprising 1, 2, 3, or 4 conservative amino acid substitutions; and (c) a light chain CDR3 comprising GSWDTRPYPKY (SEQ ID NO:51), or a variant thereof comprising 1, 2, 3, or 4 conservative amino acid substitutions. In certain embodiments, the antibody comprises: (a) a heavy chain CDR1 comprising GFTFSSYYIT (SEQ ID NO:46), a heavy chain CDR2 comprising TISYSSSNTYYADSVKG (SEQ ID NO:47), and a heavy chain CDR3 comprising SIVFDY (SEQ ID NO:48); and/or (b) a light chain CDR1 comprising SGDALGNRYVY (SEQ ID NO:49), a light chain CDR2 comprising SG (SEQ ID NO:50), and a light chain CDR3 comprising GSWDTRPYPKY (SEQ ID NO:51).

In certain embodiments, an anti-FZD antibody useful for the methods of the invention comprise: (a) a heavy chain variable region having at least about 80%, at least about 85%, at least about 90%, at least about 95%, at least about 97%, or at least about 99% sequence identity to SEQ ID NO:37 or SEQ ID NO:52; and/or (b) a light chain variable region having at least about 80%, at least about 85%, at least about 90%, at least about 95%, at least about 97%, or at least about 99% sequence identity to SEQ ID NO:44, SEQ ID NO:38 or SEQ ID NO:53. In certain embodiments, an anti-FZD antibody useful for the methods of the invention comprise: (a) a heavy chain variable region having at least about 80%, at least about 85%, at least about 90%, at least about 95%, at least about 97%, or at least about 99% sequence identity to SEQ ID NO:37; and (b) a light chain variable region having at least about 80%, at least about 85%, at least about 90%, at least about 95%, at least about 97%, or at least about 99% sequence identity to SEQ ID NO:38. In certain embodiments, the anti-FZD antibody useful for the methods of the invention comprises (a) a heavy chain variable region having the amino acid sequence of SEQ ID NO:37 or SEQ ID NO:52; and/or (b) a light chain variable region having the amino acid sequence of SEQ ID NO:44, SEQ ID NO:38 or SEQ ID NO:53. In certain embodiments, the anti-FZD antibody comprises (a) a heavy chain variable region having the amino acid sequence of SEQ ID NO:37; and/or (b) a light chain variable region having the amino acid sequence of SEQ ID NO:44. In certain embodiments, the anti-FZD antibody comprises (a) a heavy chain variable region having the amino acid sequence of SEQ ID NO:37; and/or (b) a light chain variable region having the amino acid sequence of SEQ ID NO:38. In certain embodiments, the anti-FZD antibody comprises (a) a heavy chain variable region having the amino acid sequence of SEQ ID NO:52; and/or (b) a light chain variable region having the amino acid sequence of SEQ ID NO:53.

TABLE 2

VH and VL of selected human anti-FZD antibodies

| Ab(s) | Heavy Chain Variable Region (VH) amino acid sequence | Light Chain Variable Region (VL) amino acid sequence |
|---|---|---|
| 18R8 | SEQ ID NO: 37 | SEQ ID NO: 44 |
| 18R5 | SEQ ID NO: 37 | SEQ ID NO: 38 |
| 44R24 | SEQ ID NO: 52 | SEQ ID NO: 53 |

In certain embodiments, an anti-FZD antibody useful for the methods of the invention comprises (a) a heavy chain of SEQ ID NO:39 and light chain of SEQ ID NO:45; or (b) a heavy chain of SEQ ID NO:39 and light chain of SEQ ID NO:40.

TABLE 3

The heavy chain and light chain of selected human anti-FZD antibodies

| Ab(s) | Heavy Chain Variable Region (VH) amino acid sequence | Light Chain Variable Region (VL) amino acid sequence |
|---|---|---|
| 18R8 | SEQ ID NO: 39 | SEQ ID NO: 45 |
| 18R5 | SEQ ID NO: 39 | SEQ ID NO: 40 |

In certain embodiments, the FZD-binding agent useful in the methods of the invention comprises, consists essentially of, or consists of an anti-FZD antibody selected from the group consisting of 18R8, 18R5, and 44R24 IgG antibodies.

In certain embodiments, the FZD-binding agent useful in the methods of the invention comprises the heavy chains and light chains of the 18R8 IgG2 antibody (with or without the leader sequence). In certain embodiments, the FZD-binding agent is the 18R8 IgG2 antibody. DNA encoding the heavy chains and light chains of the 18R8 IgG2 antibody was deposited with the American Type Culture Collection (ATCC), 10801 University Boulevard, Manassas, Va., USA, under the conditions of the Budapest Treaty on Sep. 29, 2008, and assigned ATCC deposit designation number PTA-9540. In certain embodiments, the FZD-binding agent useful in the methods of the invention comprises the heavy chains and light chains of the 18R5 IgG2 antibody (with or without the leader sequence). In certain embodiments, the FZD-binding agent is the 18R5 IgG2 antibody. The 18R5 IgG2 antibody is also referred to herein as OMP-18R5. DNA encoding the heavy chains and light chains of the 18R5 IgG2 antibody was deposited with the ATCC, under the conditions of the Budapest Treaty on Sep. 29, 2008, and assigned ATCC deposit designation number PTA-9541. Additional information regarding the OMP-18R5 antibody can be found, for example, in U.S. Pat. No. 7,982,013, which is incorporated by reference herein in its entirety. In U.S. Pat. No. 7,982,013, the OMP-18R5 antibody is generally referred to as "18R5" or the "18R5 IgG2 antibody."

In certain embodiments, the FZD-binding agent useful in the methods of the invention is an IgG antibody encoded by the plasmid deposited with the ATCC on Aug. 26, 2009, and assigned deposit designation number PTA-10307, PTA-10309, or PTA-10311.

In certain embodiments, the FZD-binding agent useful in the methods of the invention is an agent that competes for specific binding to FZD1, FZD2, FZD5, FZD7, and/or FZD8 with an antibody encoded by the plasmid having ATCC deposit designation number PTA-9540, PTA-9541, PTA-10307, or PTA-10309 (e.g., in a competitive binding assay). In certain alternative embodiments, the FZD-binding agent is an agent that competes for specific binding to FZD5 and/or FZD8 with an antibody encoded by the plasmid having ATCC deposit designation number PTA-10311.

In certain embodiments, the FZD-binding agent (e.g., antibody) useful in the methods of the invention binds to the same epitope as or binds to an epitope that overlaps with the epitope of the 18R5, 18R8, or 44R24 antibody.

In certain embodiments, the FZD-binding agent FZD-binding agent (e.g., antibody) useful in the methods of the invention competes for specific binding to a human frizzled receptor with the 18R5, 18R8, or 44R24 antibody.

Further examples of FZD-binding agents useful in the methods of the invention are disclosed in U.S. Pat. Appl. Pub. No. 2012/0027778, which is incorporated by reference herein in its entirety.

In certain embodiments, the FZD-binding agent useful in the methods of the invention has a circulating half-life in mice, cynomolgous monkeys, or humans of at least about 10 hours, at least about 24 hours, at least about 3 days, at least about 1 week, or at least about 2 weeks. In certain embodiments, the FZD-binding agent is an IgG (e.g., IgG1 or IgG2) antibody that has a circulating half-life in mice, cynomolgous monkeys, or humans of at least about 10 hours, at least about 24 hours, at least about 3 days, at least about 1 week, or at least about 2 weeks. Methods of increasing the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Pat. Pub. Nos. 2005/0276799, 2007/0148164, and 2007/0122403). Known methods of increasing the circulating half-life of antibody fragments lacking the Fc region include such techniques as PEGylation.

In certain embodiments, an anti-FZD antibody useful for the methods of the invention is a bispecific antibody that specifically recognizes a human frizzled receptor. Bispecific antibodies are antibodies that are capable of specifically recognizing and binding at least two different epitopes. In one embodiment, the bispecific anti-FZD antibody specifically recognizes different epitopes within the same human frizzled receptor. In another embodiment, the bispecific anti-FZD antibody specifically recognizes different epitopes within a human frizzled receptor or on different human frizzled receptors.

Alternatively, in certain alternative embodiments, an anti-FZD antibody useful for the methods of the invention is not a bispecific antibody.

In certain embodiments, an anti-FZD antibody useful for the methods of the invention is monospecific. For example, in certain embodiments, each of the one or more antigen-binding sites that an antibody contains is capable of binding (or binds) the same one or more human FZD receptors (e.g., FZD1, FZD2, FZD5, FZD7, or FZD8, or a homologous epitope on some combination of the FZDs). In certain embodiments, an antigen-binding site of the monospecific anti-FZD antibody is capable of binding (or binds) one, two, three, four, or five (or more) human frizzled receptors.

In certain embodiments, the FZD-binding agent useful for the methods of the invention is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety.

In certain embodiments, the FZD-binding agent useful for the methods of the invention comprises a protein scaffold of a type selected from the group consisting of protein A, a lipocalin, a fibronectin domain, an ankyrin consensus repeat domain, and thioredoxin.

In certain embodiments, the FZD-binding agent useful for the methods of the invention has been naturally or unnaturally modified. By way of non-limiting example, the polypeptide may be labeled. In certain embodiments, the polypeptide is glycosylated, pegylated, phosphorylated, or acetylated, amidated. In certain embodiments, the modifications increase stability and/or the in vivo half-life of the polypeptide. In certain embodiments, the polypeptides are cyclic. In certain further embodiments, the polypeptides comprise one or more N-methyl amino acids.

In certain embodiments, the FZD-binding agent useful for the methods of the invention is (or comprises) a polypeptide comprising an amino acid sequence selected from the group consisting of SEQ ID NOs:54-72, or (b) an amino acid sequence having at least about 80%, at least about 85%, at least about 88%, or at least about 90% amino acid sequence identity to a sequence selected from the group consisting of SEQ ID NOs:54-67 or 69-72. In certain embodiments, the polypeptides comprise, consist essentially of, or consist of a cyclic peptide selected from the group consisting of SEQ ID NOs:54-72. In certain embodiments, the amino acid sequence is SEQ ID NO:64. In certain alternative embodiments, the amino acid sequence is SEQ ID NO:68.

In certain embodiments, the FZD-binding polypeptide useful for the methods of the invention is less than about 500 amino acids in length, less than about 200 amino acids in length, less than about 100 amino acids in length, less than about 50 amino acids in length, less than about 20 amino acids amino acids in length, or less than about 15 amino acids in length. In certain embodiments, the FZD-binding polypeptide is at least about 3, at least about 5, or at least about 7 amino acids in length. Accordingly, in certain embodiments the polypeptide is between about 5 and about 20 amino acids in length. In some embodiments, the polypeptide is between about 7 and about 15 amino acids in length.

4. Soluble Receptors

An additional aspect of the methods of the invention is the use of Wnt antagonist soluble receptors in the treatment of neuroendocrine tumors. In certain embodiments, the soluble receptor useful in the methods of the invention comprises the extracellular domain of a FZD receptor. In some embodiments, the soluble receptor useful in the methods of the invention comprises a Fri domain of a FZD receptor. In certain embodiments, the FZD receptor is a human FZD receptor. In certain embodiments, the human FZD receptor is FZD1, FZD2, FZD3, FZD4, FZD5, FZD6, FZD7, FZD8, FZD9, or FZD10. In certain embodiments, the FZD receptor is FZD8. In certain embodiments, the Wnt antagonist used in the methods described herein comprises a human FZD8 Fri domain and a human Fc region.

In some alternative embodiments, the soluble receptor useful in the methods of the invention comprises a portion of a SFRP. In some embodiments, the soluble receptor useful in the methods of the invention comprises a Fri domain of a SFRP. In certain embodiments, the SFRP is a human SFRP. In some embodiments, the human SFRP is SFRP1, SFRP2, SFRP3, SFRP4, or SFRP5. The minimal, core Fri domain sequences for each of the human SFRPs (SFRP1-5) are provided as SEQ ID NOs:83-87.

In other alternative embodiments, the soluble receptor useful in the methods of the invention comprises the extracellular domain of a Ror protein. In some embodiments, the soluble receptor useful in the methods of the invention comprises a Fri domain of a Ror protein. In certain embodiments, the Ror is a human Ror. In some embodiments, the human Ror is Ror1 or Ror2. The minimal, core Fri domain sequences of human Ror1 and Ror2 are provided as SEQ ID NO:88 and SEQ ID NO:89.

In certain embodiments, the soluble receptors (e.g., FZD8 Fri.Fc) that are useful in the methods of the invention specifically bind one, two, three, four, five, six, seven, eight, nine, ten, or more Wnt proteins. By way of non-limiting example, the Wnt-binding agent may bind Wnt1, Wnt2, Wnt2b, Wnt3, Wnt3a, Wnt7a, Wnt7b, Wnt8a, Wnt8b, Wnt10a, and/or Wnt10b. In certain embodiments, the Wnt-binding agent binds Wnt1, Wnt2, Wnt3, Wnt3a, and Wnt7b. In certain embodiments, the soluble receptor is a Wnt antagonist. In certain embodiments, the soluble receptor inhibits Wnt-signaling. In some embodiments, the soluble receptor inhibits canonical Wnt signaling.

Nonlimiting examples of soluble FZD receptors useful in the methods of the invention can be found in U.S. Pat. No. 7,723,477, which is incorporated by reference herein in its entirety. Additional soluble receptors (e.g., soluble FZD receptors) are disclosed in US 2011/0305695, which is incorporated by reference herein in its entirety.

In certain embodiments, a soluble receptor useful in the methods of the invention comprises a Fri domain of a human FZD receptor, or a fragment or variant of the Fri domain that binds one or more human Wnt proteins. In certain embodiments, the human FZD receptor is FZD4. In certain alternative embodiments, the human FZD receptor is FZD5. In certain additional alternative embodiments, the human FZD receptor is FZD8. In certain embodiments, the FZD is FZD4 and the soluble receptor comprises SEQ ID NO:76 or comprises approximately amino acids 40 to 170 of SEQ ID NO:90. In certain embodiments, the FZD is FZD5 and the soluble receptor comprises SEQ ID NO:77 or comprises approximately amino acids 27-157 of SEQ ID NO:91. In certain embodiments, the FZD is FZD8 and the soluble receptor comprises SEQ ID NO:80 or comprises approximately amino acids 28-158 of SEQ ID NO:92.

In certain embodiments, the soluble receptor useful in the methods of the invention comprises a minimal Fri domain sequence selected from the group consisting of SEQ ID NOs:73-89. In certain embodiments, the soluble receptor useful in the methods of the invention comprises a variant of any one of the aforementioned Fri domain sequences that comprises one or more (e.g., one, two, three, four, five, six, seven, eight, nine, ten, etc.) conservative substitutions and is capable of binding Wnt(s).

In certain embodiments, the soluble receptor useful in the methods of the invention, such as a soluble receptor comprising a minimum Fri domain of a human FZD receptor, further comprises a human Fc region (e.g., a human IgG1 Fc region). Soluble receptors comprising the Fri domain of a FZD receptor and human IgG1 Fc are referred to herein as "FZD Fri.Fc" (e.g. FZD8 Fri.Fc). The Fc region can be obtained from any of the classes of immunoglobulin, IgG, IgA, IgM, IgD and IgE. In some embodiments, the Fc region is a wild-type Fc region. In some embodiments, the Fc region is a mutated Fc region. In some embodiments, the Fc region is truncated at the N-terminal end by 1, 2, 3, 4, 5, 6, 7, 8, 9, or 10 amino acids, (e.g., in the hinge domain). In some embodiments, an amino acid in the hinge domain is changed to hinder undesirable disulfide bond formation. In some embodiments, a cysteine is replaced with a serine to hinder undesirable disulfide bond formation. In certain embodiments, the Fc region comprises or consists of SEQ ID NO:93, SEQ ID NO:94, or SEQ ID NO:95.

In certain embodiments, a soluble receptor useful in the methods of the invention is a fusion protein comprising at least a minimum Fri domain (e.g., a minimum Fri domain of a FZD receptor) and an Fc region. As used herein, a "fusion protein" is a hybrid protein expressed by a nucleic acid molecule comprising nucleotide sequences of at least two genes. In some embodiments, the C-terminus of the first polypeptide is linked to the N-terminus of the immunoglobulin Fc region.

In some embodiments, the first polypeptide (e.g., a FZD Fri domain) is directly linked to the Fc region (i.e. without an intervening peptide linker). In some embodiments, the first polypeptide is linked to the Fc region via a peptide linker.

As used herein, the term "linker" refers to a linker inserted between a first polypeptide (e.g., a FZD component) and a second polypeptide (e.g., an Fc region). In some embodiments, the linker is a peptide linker. Linkers should not adversely affect the expression, secretion, or bioactivity of the polypeptide. Linkers should not be antigenic and should not elicit an immune response. Suitable linkers are known to those of skill in the art and often include mixtures of glycine and serine residues and often include amino acids that are sterically unhindered. Other amino acids that can be incorporated into useful linkers include threonine and alanine residues. Linkers can range in length, for example from 1-50 amino acids in length, 1-22 amino acids in length, 1-10 amino acids in length, 1-5 amino acids in length, or 1-3 amino acids in length. Linkers may include, but are not limited to, SerGly, GGSG, GSGS, GGGS, S(GGS)$_n$ where n is 1-7, GRA, poly (Gly), poly(Ala), ESGGGGVT (SEQ ID NO:96), LESGGGGVT (SEQ ID NO:97), GRAQVT (SEQ ID NO:98), WRAQVT (SEQ ID NO:99), and ARGRAQVT (SEQ ID NO:100). As used herein, a linker is an intervening peptide sequence that does not include amino acid residues from either the C-terminus of the first polypeptide (e.g., a FZD Fri domain) or the N-terminus of the second polypeptide (e.g., the Fc region).

In certain embodiments, soluble receptors useful for the methods of the invention contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the soluble receptors useful for the methods of the invention may comprise a mixture of polypeptides with different N-termini. In some embodiments, the N-termini differ in length by 1, 2, 3, 4, or 5 amino acids. In some embodiments, the soluble receptor polypeptide is substantially homogeneous, i.e., the polypeptides have the same N-terminus. In some embodiments, the signal sequence of the polypeptide comprises amino acid substitutions and/or deletions that allow one cleavage site to be dominant, thereby resulting in a substantially homogeneous polypeptide with one N-terminus. In some embodiments, the signal sequence of the polypeptide comprises or consists of a sequence selected from the group listed in Table 3. In some embodiments, the signal sequence is SEQ ID NO:101. In some embodiments, the signal sequence is SEQ ID NO:104. In some embodiments, the signal sequence is SEQ ID NO:106.

TABLE 3

Signal sequences.

| | |
|---|---|
| MEWGYLLEVTSLLAALALLQRSSGAAA | SEQ ID NO: 101 |
| MEWGYLLEVTSLLAALALLQRSSGALA | SEQ ID NO: 102 |
| MEWGYLLEVTSLLAALALLQRSSGVLA | SEQ ID NO: 103 |
| MEWGYLLEVTSLLAALLLLQRSPIVHA | SEQ ID NO: 104 |
| MEWGYLLEVTSLLAALFLLQRSPIVHA | SEQ ID NO: 105 |
| MEWGYLLEVTSLLAALLLLQRSPFVHA | SEQ ID NO: 106 |
| MEWGYLLEVTSLLAALLLLQRSPIIYA | SEQ ID NO: 107 |
| MEWGYLLEVTSLLAALLLLQRSPIAHA | SEQ ID NO: 108 |

In certain embodiments, a soluble receptor useful in the methods of the invention comprises a first polypeptide comprising a FZD domain component and an Fc region. In some embodiments, the FZD domain component is from FZD1, FZD2, FZD3, FZD4, FZD5, FZD6, FZD7, FZD8, FZD9, or FZD10. In some embodiments, the Fc region is from an IgG1 immunoglobulin. In some embodiments, the soluble receptor comprises: (a) a first polypeptide consisting essentially of amino acids selected from the group consisting of: X1 to Y1 of SEQ ID NO:11, X2 to Y2 of SEQ ID NO:12, X3 to Y3 of SEQ ID NO:13, X4 to Y4 of SEQ ID NO:14, X5 to Y5 of SEQ ID NO:15, X6 to Y6 of SEQ ID NO:16, X7 to Y7 of SEQ ID NO:17, X8 to Y8 of SEQ ID NO:18, X9 to Y9 of SEQ ID NO:19, and X10 to Y10 of SEQ ID NO:20; and (b) a second polypeptide consisting essentially of amino acids A to B of SEQ ID NO:95; wherein X1=amino acid 69, 70, 71, 72, 73, 74, 75, or 76
Y1=amino acid 236, 237, 238, 239, 240, 241, 242, or 243
X2=amino acid 22, 23, 24, 25, 26, 27 or 28
Y2=amino acid 158, 159, 160, 161, 162, 163, 164, 165, 166, 167, 168, 169, 170, 171 or 172
X3=amino acid 18, 19, 20, 21, 22, 23, 24, or 25
Y3=amino acid 141, 142, 143, 144, 145, 146, 147, 148, or 149
X4=amino acid 38, 39, 40, 41, or 42
Y4=amino acid 168, 169, 170, 171, 172, 173, 174, 175 or 176
X5=amino acid 25, 26, 27, 28 or 29
Y5=amino acid 155, 156, 157, 158, 159, 160, 161, 162, 163, or 164
X6=amino acid 19, 20, 21, 22, 23, or 24
Y6=amino acid 144, 145, 146, 147, 148, 149, 150, 151 or 152
X7=amino acid 22, 23, 24, 25, 26, 27, 28, 29, 30, 31, 32, 33, or 34
Y7=amino acid 178, 179, 180, 181, 182, 183, 184, 185, or 186
X8=amino acid 25, 26, 27, 28, 29, 30, or 31
Y8=amino acid 156, 157, 158, 159, 160, 161, 162, 163, or 164
X9=amino acid 21, 22, 23, or 24
Y9=amino acid 137, 138, 139, 140, 141, 142, 143, 144, 145, or 146
X10=amino acid 20, 21, 22, 23, 24, or 25
Y10=amino acid 152, 153, 154, 155, 156, 157, 158, 159, or 160
A=amino acid 1, 2, 3, 4, 5, or 6
B=amino acid 231 or 232.

In some embodiments, the first polypeptide is directly linked to the second polypeptide. In some embodiments, the first polypeptide is linked to the second polypeptide via a peptide linker. In some embodiments, the first polypeptide is linked to the second polypeptide via the peptide linker GRA. A polypeptide (e.g., a first or second polypeptide) that "consists essentially of" certain amino acids or is "consisting essentially of" certain amino acids may, in some embodiments, include one or more (e.g., one, two, three, four or more) additional amino acids at one or both ends, so long as the additional amino acids do not materially affect the function of the Wnt-binding agent.

In certain embodiments, a soluble receptor useful in the methods of the invention comprises: (a) a first polypeptide consisting essentially of amino acids X to Y of SEQ ID NO:18; and (b) a second polypeptide consisting essentially of amino acids A to B of SEQ ID NO:95; wherein the first polypeptide is directly linked to the second polypeptide; and wherein X=amino acid 25, 26, 27, 28, 29, 30, or 31
Y=amino acid 156, 157, 158, 159, 160, 161, 162, 163, or 164
A=amino acid 1, 2, 3, 4, 5, or 6
B=amino acid 231 or 232.

In some embodiments, the first polypeptide consists essentially of amino acids 25-158 of SEQ ID NO:18. In other embodiments, the first polypeptide consists of amino acids 25-158 of SEQ ID NO:18. In some embodiments, the first polypeptide consists essentially of amino acids 28-158 of SEQ ID NO:18. In other embodiments, the first polypeptide consists of amino acids 28-158 of SEQ ID NO:18. In some embodiments, the first polypeptide consists of amino acids 31-158 of SEQ ID NO:18. In some embodiments, the second polypeptide consists of amino acids 1-232 of SEQ ID NO:95. In some embodiments, the second polypeptide consists of amino acids 3-232 of SEQ ID NO:95. In some embodiments, the second polypeptide consists of amino acids 6-232 of SEQ ID NO:95. In some embodiments, the first polypeptide is SEQ ID NO:28 and the second polypeptide is SEQ ID NO:95. In some embodiments, the first polypeptide is SEQ ID NO:28 and the second polypeptide is SEQ ID NO:94. In some embodiments, the first polypeptide is SEQ ID NO:28 and the second polypeptide is SEQ ID NO:93.

In some embodiments, the soluble receptor useful in the methods of the invention comprises an amino acid sequence selected from the group consisting of SEQ ID NO:109-121. In certain alternative embodiments, the soluble receptor comprises an amino acid sequence selected from the group consisting of SEQ ID NO:109-121, comprising one or more (e.g., one, two, three, four, five, six, seven, eight, nine, ten, etc.) conservative substitutions. In certain embodiments, soluble receptor comprises a sequence having at least about 90%, about 95%, or about 98% sequence identity with an amino acid sequence selected from the group consisting of SEQ ID NO:109-121. In certain embodiments, the variant soluble receptor maintains its ability to bind one or more human Wnts.

In certain embodiments, the soluble receptor useful in the methods of the invention comprises the sequence of SEQ ID NO:109. In certain embodiments, the soluble receptor comprises the sequence of SEQ ID NO:115. In some embodiments, the soluble receptor consists of a homodimer formed by polypeptides consisting of SEQ ID NO:115. In certain embodiments, the soluble receptor comprises the sequence of SEQ ID NO:117. In some embodiments, the soluble receptor consists of a homodimer formed by polypeptides consisting of SEQ ID NO:117.

In some embodiments, the soluble receptors (e.g., FZD8 Fri.Fc) useful in the methods of the invention inhibit the growth of a neuroendocrine tumor or tumor cells. In some embodiments, the soluble receptors induce neuroendocrine tumor cells to differentiate. In some embodiments, the soluble receptors induce the expression of differentiation markers on a neuroendocrine tumor or tumor cell. In certain embodiments, the soluble receptors reduce the frequency of cancer stem cells in a neuroendocrine tumor. In certain embodiments, the soluble receptors inhibit the growth of a Wnt-dependent neuroendocrine tumor. In some embodiments, a soluble receptor comprising SEQ ID NO:115 inhibits neuroendocrine tumor growth to a greater extent than a soluble receptor comprising SEQ ID NO:109. In some embodiments, a soluble receptor comprising SEQ ID NO:117 inhibits neuroendocrine tumor growth to a greater extent than a soluble receptor comprising SEQ ID NO:109. In some embodiments, a soluble receptor inhibits tumor growth to a greater extent than a soluble receptor comprising a FZD domain component, an Fc domain and a linker component connecting the FZD domain component and the Fc domain. In some embodiments, the linker component is an intervening peptide linker.

In certain embodiments, the soluble receptor useful in the methods of the invention (before signal sequence cleavage) comprises SEQ ID NO:115 and a signal sequence selected from the group consisting of SEQ ID NO: 104-108. In some embodiments, the soluble receptor (before signal sequence cleavage) comprises SEQ ID NO:117 and a signal sequence selected from the group consisting of SEQ ID NO: 104-108. In some embodiments, the soluble receptor comprises SEQ ID NO:105 and SEQ ID NO:115. In some embodiments, the soluble receptor comprises SEQ ID NO:105 and SEQ ID NO:117. In some embodiments, the soluble receptor comprises SEQ ID NO:106 and SEQ ID NO:115. In some embodiments, the soluble receptor comprises SEQ ID NO:106 and SEQ ID NO:117. In some embodiments, the soluble receptor comprises SEQ ID NO:133.

In some embodiments, the soluble receptor (e.g., FZD8 Fri.Fc) is a substantially purified polypeptide comprising an amino acid sequence selected from the group consisting of SEQ ID NO:109, SEQ ID NO:111, SEQ ID NO:113, SEQ ID NO:115, and SEQ ID NO:117. In certain embodiments, the substantially purified soluble receptor polypeptide comprises at least 80%, at least 90%, at least 95%, at least 97%, at least 98%, or at least 99% polypeptide that has an N-terminal sequence of ASA. In certain embodiments, the substantially purified soluble receptor polypeptide consists of a polypeptide that has an N-terminal sequence of ASA. In some embodiments, the nascent soluble receptor polypeptide comprises a signal sequence selected from the group consisting of SEQ ID NOs: 101-108. In some embodiments, the nascent soluble receptor polypeptide comprises a signal sequence of SEQ ID NO:106. In some embodiments, the nascent soluble receptor polypeptide comprises a signal sequence that results in a substantially homogeneous polypeptide product with one N-terminal sequence.

In certain embodiments, the soluble FZD receptor polypeptide is OMP-54F28. OMP-54F28 is a homodimer formed by two polypeptide chains that each consists of SEQ ID NO:117. Additional information regarding OMP-54F28 can be found in U.S. Pat. Appl. Pub. No. 2011/0305695, which is incorporated by reference herein in its entirety. OMP-54F28 is generally referred to as "54F28" in U.S. Pat. Appl. Pub. No. 2011/0305695.

In certain embodiments, a soluble receptor (e.g., FZD8 Fri.Fc) useful in the methods of the invention comprises an Fc region of an immunoglobulin. In certain embodiments, at least a portion of the Fc region has been deleted or otherwise altered so as to provide desired biochemical or biological characteristics, such as increased cancer cell localization, increased tumor penetration, reduced serum half-life, or increased serum half-life, reduced or no ADCC activity, reduced or no complement-dependent cytotoxicity (CDC) when compared with a soluble receptor of approximately the same immunogenicity comprising a native or unaltered Fc constant region. Modifications to the Fc region may include additions, deletions, or substitutions of one or more amino acids in one or more domains. Additional soluble receptors (e.g., soluble FZD receptors) comprising a modified Fc region are disclosed in US 2011/0305695, which is incorporated by reference herein in its entirety.

In certain embodiments, the soluble receptors (e.g., FZD8 Fri.Fc) useful in the methods of the invention bind to at least one Wnt with a dissociation constant ($K_D$) of about 1 µM or less, about 100 nM or less, about 40 nM or less, about 20 nM or less, or about 10 nM or less. The soluble receptors can be assayed for specific binding by any method known in the art. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In certain embodiments, the soluble receptor (e.g., FZD8 Fri.Fc) useful in the methods of the invention (e.g., a FZD8 Fri.Fc) is an antagonist of at least one Wnt (i.e., 1, 2, 3, 4, 5, 6, 7, 8, 9, or 10 Wnts) bound by the soluble receptor. In certain embodiments, the soluble receptor inhibits at least about 10%, at least about 20%, at least about 30%, at least about 50%, at least about 75%, at least about 90%, or about 100% of one or more activity of the bound human Wnt(s). In vivo and in vitro assays for determining whether a soluble receptor inhibits Wnt signaling are known in the art. Suitable methods are disclosed in US 2011/0305695, which is incorporated by reference herein in its entirety.

In certain embodiments, a soluble receptor (e.g., FZD8 Fri.Fc) useful in the methods of the invention is derivatized with a water soluble polymer. Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran, poly(n-vinyl pyrrolidone)-polyethylene glycol, propropylene glycol homopolymers, prolypropylene oxide/ethylene oxide co-polymers, polyoxyethylated polyols (e.g., glycerol), polyvinyl alcohol, and mixtures thereof. In certain embodiments, the water soluble polymer is polyethylene glycol (PEG).

In certain embodiments, the soluble receptor (e.g., FZD8 Fri.Fc) useful in the methods of the invention has a circulating half-life in mice, cynomolgous monkeys, or humans of at least about 5 hours, at least about 10 hours, at least about 24 hours, at least about 3 days, at least about 1 week, or at least about 2 weeks. In certain embodiments, the soluble receptors have a half-life of at least about 50 hours in a rat when administered via the tail vein at a dose ranging from about 2 mg/kg to about 10 mg/kg. In certain embodiments, the soluble receptor is a soluble FZD receptor that comprises a Fri domain of a human FZD receptor (or a fragment or variant of the Fri domain that binds one or more Wnts) and a human Fc region and has a half-life in vivo (e.g., in a mouse or rat) that is longer than a soluble FZD receptor comprising the extracellular domain of the FZD receptor and a human Fc region.

5. ANTI-Wnt Antibodies

A further aspect of the methods of the invention is the use of anti-Wnt antibodies in the treatment of neuroendocrine tumors. In certain embodiments, the anti-Wnt antibodies that are useful in the methods of the invention specifically bind one or more Wnt polypeptides. In certain embodiments, the antibodies specifically bind two, three, four, five, six, seven, eight, nine, ten or more Wnts. The human Wnt(s) bound by the antibody may be selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In certain embodiments, the one or more (or two or more, three or more, four or more, five or more, etc.) Wnts bound by the antibody or other antibody comprise Wnt1, Wnt2, Wnt2b, Wnt3, Wnt3a, Wnt7a, Wnt7b, Wnt8a, Wnt8b, Wnt10a, and Wnt10b. In certain embodiments, the one or more (or two or more, three or more, four or more, five or more, etc.) Wnts comprise Wnt1, Wnt2, Wnt2b, Wnt3, Wnt3a, Wnt8a, Wnt8b, Wnt10a, and Wnt10b.

In certain embodiments, an individual antigen-binding site of a Wnt-binding antibody useful in the methods of the invention is capable of binding (or binds) the one, two, three, four, or five (or more) human Wnts. In certain embodiments, an individual antigen-binding site of the Wnt-binding antibody is capable of specifically binding one, two, three, four, or five human Wnts selected from the group consisting of Wnt1, Wnt2, Wnt2b, Wnt3, Wnt3a, Wnt7a, Wnt7b, Wnt8a, Wnt8b, Wnt10a, and Wnt10b.

In certain embodiments, the Wnt-binding antibody useful in the methods of the invention binds to the C-terminal cysteine rich domain of a human Wnt. In certain embodiments, the antibody binds to a domain (within the one or more Wnt proteins to which the antibody binds) that is selected from the group consisting of SEQ ID NOs:122-132. In some embodiments, the Wnt-binding antibody binds within SEQ ID NO:122. In some embodiments, the Wnt-binding antibody binds within amino acids 288-370 of Wnt1.

In certain embodiments, the Wnt-binding antibody useful in the methods of the invention binds to one or more (for example, two or more, three or more, or four or more) Wnts with a dissociation constant ($K_D$) of about 1 µM or less, about 100 nM or less, about 40 nM or less, about 20 nM or less, or about 10 nM or less. For example, in certain embodiments, a Wnt-binding antibody useful in the methods of the invention that binds to more than one Wnt, binds to those Wnts with a $K_D$ of about 100 nM or less, about 20 nM or less, or about 10 nM or less. In certain embodiments, the Wnt-binding antibody binds to each of one or more (e.g., 1, 2, 3, 4, or 5) of the following Wnts with a dissociation constant of about 40 nM or less: Wnt1, Wnt2, Wnt2b, Wnt3, Wnt3a, Wnt7a, Wnt7b, Wnt8a, Wnt8b, Wnt10a, and Wnt10b.

In certain embodiments, the anti-Wnt antibody useful in the methods of the invention is an IgG1 antibody or an IgG2 antibody. In certain embodiments, the antibody is a monoclonal antibody. In certain embodiments, the antibody is a human antibody or a humanized antibody. In certain embodiments, the antibody is an antibody fragment.

The antibodies or other antibodies of the present invention can be assayed for specific binding by any method known in the art. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In certain embodiments, the Wnt-binding antibody useful in the methods of the invention is an antagonist of at least one Wnt (i.e., 1, 2, 3, 4, 5, 6, 7, 8, 9, or 10 Wnts) bound by the antibody. In certain embodiments, the antibody inhibits at least about 10%, at least about 20%, at least about 30%, at least about 50%, at least about 75%, at least about 90%, or about 100% of one or more activity of the bound human Wnt(s).

In certain embodiments, the Wnt-binding antibody useful in the methods of the invention inhibits binding of a ligand to the at least one human Wnt. In certain embodiments, the Wnt-binding antibody inhibits binding of a human Wnt protein to one or more of its ligands. Nineteen human Wnt proteins have been identified: Wnt1, Wnt2, Wnt2B/13, Wnt3, Wnt3a, Wnt4, Wnt5a, Wnt5b, Wnt6, Wnt7a, Wnt7b, Wnt8a, Wnt8b, Wnt9a (previously Wnt14), Wnt9b (previously Wnt15), Wnt10a, Wnt10b, Wnt11, and Wnt16. Ten human FZD receptors proteins have been identified (FZD1, FZD2, FZD3, FZD4, FZD5, FZD6, FZD7, FZD8, FZD9, and FZD10). In certain embodiments, the Wnt-binding antibody inhibits binding of FZD4, FZD5, and/or FZD8 to one or more Wnts (e.g., Wnt3a). In certain embodiments, the inhibition of binding of a particular ligand to a Wnt provided by the Wnt-binding antibody is at least about 10%, at least about 25%, at least about 50%, at least about 75%, at least about 90%, or at least about 95%. In certain embodiments, an antibody that inhibits binding of a Wnt to a ligand such as a FZD, further inhibits Wnt signaling (e.g., inhibits canonical Wnt signaling).

In certain embodiments, the Wnt-binding antibody useful in the methods of the invention inhibits Wnt signaling. It is understood that a Wnt-binding antibody that inhibits Wnt signaling can, in certain embodiments, inhibit signaling by one or more Wnts, but not necessarily by all Wnts. In certain alternative embodiments, signaling by all human Wnts can be inhibited. In certain embodiments, signaling by one or more Wnts selected from the group consisting of Wnt1, Wnt2, Wnt2b/13, Wnt3, Wnt3a, Wnt4, Wnt5a, Wnt5b, Wnt6, Wnt7a, Wnt7b, Wnt8a, Wnt8b, Wnt9a (previously Wnt14), Wnt9b (previously Wnt15), Wnt10a, Wnt10b, Wnt11, and Wnt16 is inhibited. In certain embodiments, the Wnt signaling that is inhibited is signaling by Wnt1, Wnt2, Wnt3, Wnt3a, Wnt7a, Wnt7b, and/or Wnt10b. In certain embodiments, the antibody inhibits signaling by (at least) Wnt1, Wnt3a, Wnt7b, and Wnt10b. In particular embodiments, the antibody inhibits signaling by (at least) Wnt3a. In certain embodiments, the inhibition of signaling by a Wnt provided by the Wnt-binding antibody is a reduction in the level of signaling by the Wnt of least about 10%, at least about 25%, at least about 50%, at least about 75%, at least about 90%, or at least about 95%. In certain embodiments, the Wnt signaling that is inhibited is canonical Wnt signaling.

In vivo and in vitro assays for determining whether a Wnt-binding antibody inhibits Wnt signaling are known in the art. For example, cell-based, luciferase reporter assays utilizing a TCF/Luc reporter vector containing multiple copies of the TCF-binding domain upstream of a firefly luciferase reporter gene may be used to measure canonical Wnt signaling levels in vitro (Gazit et al., 1999, *Oncogene*, 18; 5959-66). The level of Wnt signaling in the presence of one or more Wnts (e.g., Wnt(s) expressed by transfected cells or provided by Wnt-conditioned media) with the Wnt-binding antibody present is compared to the level of signaling without the Wnt-binding antibody present. In addition to the TCF/Luc reporter assay, the effect of a Wnt-binding antibody (or candidate antibody) on canonical Wnt signaling may be measured in vitro or in vivo by measuring the effect of the antibody on the level of expression of β-catenin regulated genes, such as c-myc (He et al., 1998, *Science*, 281:1509-12), cyclin D1 (Tetsu et al., 1999, *Nature*, 398:422-6) and/or fibronectin (Gradl et al. 1999, *Mol. Cell. Biol.*, 19:5576-87). In certain embodiments, the effect of an antibody on Wnt signaling may also be assessed by measuring the effect of the antibody on the phosphorylation state of Dishevelled-1, Dishevelled-2, Dishevelled-3, LRP5, LRP6, and/or β-catenin.

In certain embodiments, the Wnt-binding antibodies useful in the methods of the invention have one or more of the following effects: inhibit proliferation of neuroendocrine tumor cells, reduce the tumorigenicity of a neuroendocrine tumor by reducing the frequency of cancer stem cells in the tumor, inhibit neuroendocrine tumor growth, trigger cell death of neuroendocrine tumor cells, differentiate neuroendocrine tumorigenic cells to a non-tumorigenic state, prevent metastasis of neuroendocrine tumor cells or decrease survival.

In certain embodiments, the Wnt-binding antibodies useful in the methods of the invention are capable of inhibiting neuroendocrine tumor growth. In certain embodiments, the Wnt-binding antibodies are capable of inhibiting neuroendocrine tumor growth in vivo (e.g., in a xenograft mouse model, and/or in a human having cancer).

In certain embodiments, the Wnt-binding antibodies useful in the methods of the invention are capable of reducing the tumorigenicity of a neuroendocrine tumor. In certain embodiments, the antibody is capable of reducing the tumorigenicity of a neuroendocrine tumor comprising cancer stem cells in an animal model, such as a mouse xenograft model. In certain embodiments, the number or frequency of cancer stem cells in a neuroendocrine tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236, U.S. Patent Application Publication No. 2008/0064049, and U.S. Patent Application Publication No. 2008/0178305, each of which is incorporated by reference herein in its entirety.

In certain embodiments, the Wnt-binding antibody useful in the methods of the invention has a circulating half-life in mice, cynomolgous monkeys, or humans of at least about 5 hours, at least about 10 hours, at least about 24 hours, at least about 3 days, at least about 1 week, or at least about 2 weeks. In certain embodiments, the Wnt-binding antibody is an IgG (e.g., IgG1 or IgG2) antibody that has a circulating half-life in mice, cynomolgous monkeys, or humans of at least about 5 hours, at least about 10 hours, at least about 24 hours, at least about 3 days, at least about 1 week, or at least about 2 weeks.

In certain embodiments, an anti-Wnt antibody useful for the methods of the invention is a bispecific antibody that specifically recognizes a human Wnt. Bispecific antibodies are antibodies that are capable of specifically recognizing and binding at least two different epitopes. In one embodiment, the bispecific anti-Wnt antibody specifically recognizes different epitopes within the same human Wnt. In another embodiment, the bispecific anti-Wnt antibody specifically recognizes different epitopes within different human Wnts or on different Wnts.

Alternatively, in certain alternative embodiments, an anti-Wnt antibody useful for the methods of the invention is not a bispecific antibody.

In certain embodiments, an anti-Wnt antibody useful for the methods of the invention is monospecific. In certain embodiments, each of the one or more antigen-binding sites that an antibody contains is capable of binding (or binds) the same one or more human Wnts. In certain embodiments, an antigen-binding site of the monospecific antibody is capable of binding (or binds) one, two, three, four, or five (or more) human Wnts.

Anti-Wnt antibodies useful for the methods of the invention are disclosed in International Publication Number WO 2011/088127, which is incorporated by reference in its entirety.

6. Antibodies and Production Thereof

The antibodies (e.g., anti-FZD and anti-Wnt antibodies) useful in the methods of the invention can be produced by any suitable method known in the art. Polyclonal antibodies can be prepared by any known method. Polyclonal antibodies are raised by immunizing an animal (e.g. a rabbit, rat, mouse, donkey, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g. Complete or Incomplete Freund's Adjuvant) to form a stable emulsion. The polyclonal antibody is then recovered from blood, ascites and the like, of an animal so immunized Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody useful in the methods of the invention is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody useful in the methods of the invention is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and may be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments, the antibody useful in the methods of the invention is a bispecific antibody that specifically recognizes a human frizzled receptor or a human Wnt polypeptide. Bispecific antibodies are antibodies that are capable of specifically recognizing and binding at least two different epitopes. The different epitopes can either be within the same molecule (e.g. the same human frizzled receptor or same human Wnt polypeptide) or on different molecules. Bispecific antibodies can be intact antibodies or antibody fragments.

Alternatively, in certain alternative embodiments, antibodies useful for the invention are not bispecific antibodies.

In certain embodiments, the antibodies useful for the invention are monospecific. For example, in certain embodiments, each of the one or more antigen-binding sites that an antibody contains is capable of binding (or binds) the same human FZD receptor or the same human Wnt polypeptide. In certain embodiments, an antigen-binding site of a monospecific antibody is capable of binding (or binds) one, two, three, four, or five (or more) human frizzled receptors or human Wnt polypeptide.

In certain embodiments, an antibody useful for the methods of the invention is an antibody fragment. Antibody fragments can display increased tumor penetration relative to a full antibody. Various techniques are known for the production of antibody fragments. Traditionally, these fragments are derived via proteolytic digestion of intact antibodies (for example Morimoto et al., 1993, *Journal of Biochemical and Biophysical Methods* 24:107-117; Brennan et al., 1985, *Science*, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Single-chain antibodies useful in the methods of the invention can be prepared as described, for example, in U.S. Pat. No. 4,946,778. In addition, methods can be adapted for the construction of Fab expression libraries (Huse, et al., *Science* 246:1275-1281 (1989)) to allow rapid and effective identification of monoclonal Fab fragments with the desired specificity for a FZD receptor or a Wnt polypeptide. Antibody fragments may be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments. Other techniques for the production of antibody fragments will be apparent to the skilled practitioner.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

In certain embodiments, an antibody useful for the methods of the invention is a heteroconjugate antibody. Heteroconjugate antibodies are composed of two covalently joined antibodies. Such antibodies have, for example, been proposed to target immune cells to unwanted cells (U.S. Pat. No. 4,676, 980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

It is known in the art that the constant Fc region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies or soluble receptors can bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the Wnt antagonist polypeptides (antibodies and Fc comprising soluble receptors) useful for the methods of the invention provide for altered effector functions that, in turn, affect the biological profile of the administered polypeptides. For example, the deletion or inactivation (through point mutations or other means) of a constant region domain may reduce Fc receptor binding of the circulating modified antibody thereby increasing tumor localization. In other cases it may be that constant region modifications moderate complement binding and thus reduce the serum half-life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region may easily be made using well known biochemical or molecular engineering techniques well within the purview of the skilled artisan.

In certain embodiments, a Wnt antagonist polypeptide comprising an Fc region (antibodies and Fc comprising soluble receptors) useful for the methods of the invention does not have one or more effector functions. For instance, in some embodiments, the polypeptide has no antibody-dependent cellular cytotoxicity (ADCC) activity and/or no complement-dependent cytotoxicity (CDC) activity. In certain embodiments, the polypeptide does not bind to an Fc receptor and/or complement factors. In certain embodiments, the antibody has no effector function.

The invention also pertains to the use of immunoconjugates comprising a Wnt antagonist polypeptide (e.g., anti-FZD and anti-Wnt antibody) conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamycin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies including $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used.

Conjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Regardless of how useful quantities are obtained, the Wnt antagonists polypeptides (e.g., antibodies and soluble receptors) useful in the methods of the invention can be used in any one of a number of conjugated (i.e. an immunoconjugate) or unconjugated forms. Alternatively, the polypeptides can be used in a nonconjugated or "naked" form. In certain embodiments, the polypeptides are used in nonconjugated form to harness the subject's natural defense mechanisms including complement-dependent cytotoxicity (CDC) and antibody dependent cellular toxicity (ADCC) to eliminate the malignant cells. In some embodiments, the polypeptides can be conjugated to radioisotopes, such as $^{90}$Y, $^{125}$I, $^{131}$I, $^{123}$I $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well-known chelators or direct labeling. In other embodiments, the compositions can comprise Wnt antagonist polypeptides coupled to drugs, prodrugs or biological response modifiers such as methotrexate, adriamycin, and lymphokines such as interferon. Still other embodiments comprise the use of Wnt antagonist polypeptides conjugated to specific biotoxins such as ricin or diptheria toxin. In yet other embodiments, the Wnt antagonist polypeptides can be complexed with other immunologically active ligands (e.g. antibodies or fragments thereof) wherein the resulting molecule binds to both the neoplastic cell and an effector cell such as a T cell. The selection of which conjugated or unconjugated Wnt antagonist polypeptides to use will depend of the type and stage of neuroendocrine tumor, use of adjunct treatment (e.g., chemotherapy or external radiation) and patient condition. It will be appreciated that one skilled in the art could readily make such a selection in view of the teachings herein.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The chemical moieties most suitable for derivatization include water soluble polymers. A water soluble polymer is desirable because the protein to which it is attached does not precipitate in an aqueous environment, such as a physiological environment. In some embodiments, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization can be ascertained by administering the derivative, in the desired form (i.e., by osmotic pump, or by injection or infusion, or, further formulated for oral, pulmonary or other delivery routes), and determining its effectiveness. Suitable water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran, poly(n-vinyl pyrrolidone)-polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde can have advantages in manufacturing due to its stability in water.

The isolated polypeptides (e.g., antibodies and soluble receptors) useful in the methods of the invention can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci. USA* 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express Wnt antagonist polypeptides (e.g., antibodies or soluble receptors). Recombinant expression vectors are replicable DNA constructs which have synthetic or cDNA-derived DNA fragments encoding a polypeptide of interest operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts include, for example, vectors comprising expression control sequences from SV40, bovine papilloma virus, adenovims and cytomegalovirus. Useful expression vectors for bacterial hosts include known bacterial plasmids, such as plasmids from Esherichia coli, including pCR 1, pBR322, pMB9 and their derivatives, wider host range plasmids, such as M13 and filamentous single-stranded DNA phages.

Suitable host cells for expression of a Wnt antagonist polypeptide (e.g., antibody or soluble receptor) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a Wnt antagonist polypeptide (e.g., antibody or soluble receptor). Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying a Wnt antagonist polypeptide (e.g., antibody or soluble receptor) also include, for example, those described in U.S. Patent Publication No. 2008/0312425, 2008/0177048, and 2009/0187005, each of which is hereby incorporated by reference herein in its entirety.

7. Pharmaceutical Compositions

The Wnt antagonist polypeptides (e.g., antibodies and soluble receptors) can be formulated into a pharmaceutical composition by any suitable method known in the art. In certain embodiments, the pharmaceutical compositions comprise a pharmaceutically acceptable vehicle. The pharmaceutical compositions find use in inhibiting neuroendocrine tumor growth and treating neuroendocrine tumor in human patients.

In certain embodiments, formulations are prepared for storage and use by combining a purified Wnt antagonist (e.g., an anti-FZD antibody or soluble FZD receptor) with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

In certain embodiments, the pharmaceutical composition is frozen. In certain alternative embodiments, the pharmaceutical composition is lyophilized.

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc. of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

The Wnt antagonists (e.g., anti-FZD antibodies or soluble FZD receptors) can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In certain embodiments, pharmaceutical formulations include the Wnt antagonists (e.g., anti-FZD antibodies or soluble FZD receptors) complexed with liposomes (Epstein, et al., 1985, Proc. Natl. Acad. Sci. USA 82:3688; Hwang, et al., 1980, Proc. Natl. Acad. Sci. USA 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

In addition sustained-release preparations can be prepared. Suitable examples of sustained-release preparations include semipermeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(v nylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT TM (injectable microspheres composed of lactic acid-glycolic acid copolymer and leuprolide acetate), sucrose acetate isobutyrate, and poly-D-(-)-3-hydroxybutyric acid.

EXAMPLES

It is understood that the examples and embodiments described herein are for illustrative purposes only and that various modifications or changes in light thereof will be suggested to persons skilled in the art and are to be included within the spirit and purview of this application.

Example 1

Neuroendocrine Tumor Response to OMP-18R5 in a Phase 1a Clinical Study

In the context of a Phase I clinical trial for the OMP-18R5 human anti-FZD antibody in patients with advanced solid tumors, three patients with late stage neuroendocrine tumors that had previously undergone multiple other therapies were treated with low, periodic doses of OMP-18R5 as a single agent. The prolonged stable disease of all three of these neuroendocrine patients suggests that even as a single agent at low dosages OMP-18R5 may have a surprising level of efficacy against neuroendocrine tumors, including both neuroendocrine tumors having carcinoid histology and pancreatic neuroendocrine tumors.

At the time of her enrollment in the OMP-18R5 trial, Patient 3 was a 59 years old female. She was diagnosed with neuroendocrine tumor (carcinoid) in 2004. She underwent a small bowel resection and was treated with radiofrequency ablation of liver lesions. Prior to enrollment in the OMP-18R5 trial, she received prior systemic treatment with a combination of trametinib (MEK1/2 MAP kinase inhibitor) and GSK2141795 Akt inhibitor but her disease progressed after 1 month of treatment. In the OMP-18R5 trial Patient 3 received a weekly dose of 0.5 mg/kg OMP-18R5 for 112 days. Her disease remained stable during OMP-18R5 treatment, but she was removed from the trial after suffering a bone fracture on day 112. Especially in light of her rapid disease progression while on a previous therapy, this patient's extended period of disease control while being treated with OMP-18R5 suggests that the antibody may have a surprising level of clinical efficacy even as a single agent at a low dose.

At the time of her enrollment in the OMP-18R5 trial, Patient 10 was a 69 year old female with pancreatic neuroendocrine tumor. She was diagnosed in 2001 and treated with surgery comprising 80% distal pancreatectomy, splenectomy, and wedge resection of posterior wall of stomach. Prior to enrollment in the OMP-18R5 trial, she received systemic treatments with (1) regorafenib (partial response: 3 years); (2) anti-LOXL2 antibody (stable disease: 5.5 months); and (3) anti-CSFR1 antibody (progressive disease after 6 weeks on study). As of Jan. 25, 2013, Patient 10 in the OMP-18R5 trial had received 0.5 mg/kg OMP-18R5 every other week for 279 days. After 112 days of OMP-18R5 treatment, a 21% reduction in Patient 10's target tumor liver metastasis was determined by the investigator. Tumor reduction was confirmed by an independent radiographic assessment (shown in Table 4). See FIG. 1. The control non-target disease lesion showed no change during the same treatment period. Radiographic examination further revealed signs of calcification in the tumor lesion of Patient 10 following 112 days of OMP-18R5 treatment (FIG. 1). The observed calcification of the tumor lesion may indicate that OMP-18R5 induced differentiation of the tumor cells and/or tumor necrosis. Subsequent computed tomography (CT) scans on days 168, 224 and 280 indicated that the patient still did not have progressive disease.

TABLE 4

Patient 10: Independent Radiographic Assessment RECIST 1.1

| Lesion (mm) | Mar. 27, 2012 (BASELINE) | Jun. 11, 2012 | Aug. 6, 2012 |
| --- | --- | --- | --- |
| 1. Liver: Rt Lobe (Ant-Lat) (TARGET) | 13.6 × 22.9 | 17.3 × 23.9 | 13.3 × 20.5 |
| 2. Liver: IVC (TARGET) | 16.2 × 16.2 | 15.9 × 15.9 | 10.8 × 13.1 |
| 3. Liver: Rt Dome (TARGET) | 7.9 × 11.6 | 7.1 × 11.4 | 4.9 × 8.5 |
| 4. Porto-caval Node (TARGET)* | 16.6 × 23.9 | 14.1 × 15.5 | 9.1 × 14.2 |
| 5. Porto-caval Node (NON-TARGET) | 11.1 × 14.5 | 10.5 × 12.6 | 9.5 × 14.8 |
| TOTAL: Target (mm, %Δ) | 67.3 | 65.3 (−3%) | 51.2 (−24%) |
| TOTAL: Non-Target | | Non-PD | Non-PD | Normal** |

*Per RECIST 1.1: LN ≥15 mm in shortest diameter are measurable
**Per RECIST 1.1: LN <10 mm in shortest diameter considered 'normal'
Non-PD: non-progressive disease At the time of her enrollment in the OMP-18R5 trial, Patient 12 was a 77 year old female with a neuroendocrine tumor (carcinoid). She was diagnosed in 2006. Prior to enrollment in the OMP-18R5 trial, she received systemic treatments with (1) sandostatin (stable disease: 20 months); (2) inhibitor of heat shock protein 90 (stable disease: 23 months); and (3) a combination of sandostatin and anti-angiopoietin-2 antibody (stable disease: 4 months). As of Jan. 25, 2013, Patient 12 in the OMP-18R5 trial had received 1 mg/kg OMP-18R5 every third week for 210 days. This patient was assessed to have stable disease on days 56, 112 and 168. The extended period of time during which this patient has remained on the clinical trial without disease progression further supports the clinical efficacy of OMP-18R5 against neuroendocrine tumors.

FIG. 2 shows the number of days that each of the patients (n=18) enrolled in the OMP-18R5 Phase 1a study as of Jan. 25, 2013, stayed on the OMP-18R5 Phase 1a study. The patients with neuroendocrine tumors that had been treated with OMP-18R5 remained on study for surprisingly long periods of times relative to the other Phase 1a patients having other tumor types (including colorectal cancer, breast cancer, melanoma and pancreatic cancer).

Also, as of Jan. 25, 2013, the three patients with neuroendocrine tumors had had stable disease ~2 to 7-fold longer on OMP-18R5 treatment than when they were on the prior therapies on which they previously progressed. Using Growth Modulation Index as a tool to gauge the observed activity (time on current therapy divided by time on prior therapy before progressive disease; GMI≥1.33 considered excellent; *Von Hoff: Clinical Cancer Research* 4:1079-1086, 1998), all three neuroendocrine (NET) patients significantly surpassed this mark (Patient 12: 1.8; Patient 10: 6.3; Patient 3, off study: 3.8). A comparison of the time each of the three neuroendocrine tumor patients remained on the OMP-18R5 study (as of Jan. 25, 2013) versus her time on prior therapies is shown in FIG. 3.

Example 2

In Vivo Prevention of Neuroendocrine Tumor Growth Using a Wnt Antagonist

This example describes a use of a Wnt antagonist (e.g., OMP-18R5 or OMP-54F28) to prevent neuroendocrine tumor growth in a xenograft model. In certain embodiments, neuroendocrine tumor cells from a patient sample (solid tumor biopsy or pleural effusion) that have been passaged as a xenograft in mice are prepared for repassaging into experimental animals. Neuroendocrine tumor tissue is removed under sterile conditions, cut up into small pieces, minced completely using sterile blades, and single cell suspensions obtained by enzymatic digestion and mechanical disruption. Specifically, pleural effusion cells or the resulting tumor pieces are mixed with ultra-pure collagenase III in culture medium (200-250 units of collagenase per mL) and incubated at 37° C. for 3-4 hours with pipetting up and down through a 10 mL pipette every 15-20 minutes. Digested cells are filtered through a 45 μM nylon mesh, washed with RPMI/20% FBS, and washed twice with HBSS. Dissociated neuroendocrine tumor cells are then injected subcutaneously into the mammary fat pads of NOD/SCID mice to elicit tumor growth.

In certain embodiments, dissociated neuroendocrine tumor cells are first sorted into tumorigenic and non-tumorigenic cells based on cell surface markers before injection into experimental animals. Specifically, neuroendocrine tumor cells dissociated as described above are washed twice with Hepes buffered saline solution (HBSS) containing 2% heat-inactivated calf serum (HICS) and resuspended at $10^6$ cells per 100 μl. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2 Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin-tumorigenic cells are then injected subcutaneously into NOD/SCID mice to elicit tumor growth.

By way of example, Wnt antagonists (e.g., OMP-18R5 or OMP-54F28) are analyzed for their ability to reduce the growth of neuroendocrine tumor cells. Dissociated neuroendocrine tumor cells (10,000 per animal) are injected subcutaneously into the flank region of 6-8 week old NOD/SCID mice. Two days after tumor cell injection, animals are injected intraperitoneal (i.p.) with 10 mg/kg anti-FZD antibody or soluble FZD receptor two times per week. Tumor growth is monitored weekly until growth is detected, after which point tumor growth is measured twice weekly for a total of 8 weeks. FZD-binding antibodies which significantly reduce tumor growth as compared to PBS injected controls are thus identified.

Example 3

In Vivo Treatment of Neuroendocrine Tumors Using a Wnt Antagonist

This example describes the use of a Wnt antagonists (e.g., OMP-18R5 or OMP-54F28) to treat neuroendocrine cancer in a xenograft model. In certain embodiments, neuroendocrine tumor cells from a patient sample (solid tumor biopsy or pleural effusion) that have been passaged as a xenograft in mice are prepared for repassaging into experimental animals. Neuroendocrine tumor tissue is removed, cut up into small pieces, minced completely using sterile blades, and single cell suspensions obtained by enzymatic digestion and mechanical disruption. Dissociated neuroendocrine tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin-tumorigenic tumor cells are isolated as described above and injected.

Following tumor cell injection, animals are monitored for tumor growth. Once neuroendocrine tumors reach an average size of approximately 150 to 200 mm, Wnt antagonist (e.g., OMP-18R5 or OMP-54F28) treatment begins. Each animal receives 100 µg Wnt antagonist (e.g., OMP-18R5 or OMP-54F28) or control agents i.p. two to five times per week for a total of 6 weeks. Tumor size is assessed twice a week during these 6 weeks. The ability of Wnt antagonists (e.g., OMP-18R5 or OMP-54F28) to prevent further neuroendocrine tumor growth or to reduce neuroendocrine tumor size compared to control agents is thus determined.

At the end point of antibody treatment, tumors are harvested for further analysis. In some embodiments a portion of the neuroendocrine tumor is analyzed by immunofluorescence to assess Wnt antagonist (e.g., OMP-18R5 or OMP-54F28) penetration into the tumor and tumor response. A portion of each harvested neuroendocrine tumor from Wnt antagonist (e.g., OMP-18R5 or OMP-54F28) treated and control mice is fresh-frozen in liquid nitrogen, embedded in O.C.T., and cut on a cryostat as 10 µm sections onto glass slides. In some embodiments, a portion of each neuroendocrine tumor is formalin-fixed, paraffin-embedded, and cut on a microtome as 10 µm section onto glass slides. Sections are post-fixed and incubated with chromophore labeled antibodies that specifically recognize the injected Wnt antagonist (e.g., OMP-18R5 or OMP-54F28) to detect Wnt antagonists (e.g., OMP-18R5 or OMP-54F28) or control agents present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti-Ki67 antibodies to detect proliferating cells, TUNEL assays to detect dying cells, anti-β-catenin antibodies to detect Wnt signaling, and anti-intracellular domain (ICD) Notch fragment antibodies to detect Notch signaling can be used to assess the effects of Wnt antagonist (e.g., OMP-18R5 or OMP-54F28) treatment on, for example, angiogenesis, tumor growth and tumor morphology.

In certain embodiments, the effect of Wnt antagonist (e.g., OMP-18R5 or OMP-54F28) treatment on neuroendocrine tumor cell gene expression is also assessed. Total RNA is extracted from a portion of each harvested neuroendocrine tumor from Wnt antagonist (e.g., OMP-18R5 or OMP-54F28) treated and control antibody treated mice and used for quantitative RT-PCR. Expression levels of FZD receptors, components of Wnt signaling pathway including, for example, Wnt1 and β-catenin, as well as additional cancer stem cell markers previously identified (e.g. CD44) are analyzed relative to the housekeeping gene GAPDH as an internal control. Changes in neuroendocrine tumor cell gene expression upon treatment with Wnt antagonists (e.g., OMP-18R5 or OMP-54F28) are thus determined.

In addition, the effect of Wnt antagonist (e.g., OMP-18R5 or OMP-54F28) treatment on the frequency of cancer stem cells in a neuroendocrine tumor is assessed. Neuroendocrine tumor samples from Wnt antagonist (e.g., OMP-18R5 or OMP-54F28) versus control agent treated mice are cut up into small pieces, minced completely using sterile blades, and single cell suspensions obtained by enzymatic digestion and mechanical disruption. Dissociated neuroendocrine tumor cells are then analyzed by FACS analysis for the presence of tumorigenic cancer stem cells based on ESA+, CD44+, CD24−/low, Lin-surface cell marker expression as described in detail above.

The tumorigenicity of cells isolated based on ESA+, CD44+, CD24−/low, Lin-expression following Wnt antagonist (e.g., OMP-18R5 or OMP-54F28) treatment can then assessed. ESA+, CD44+, CD24−/low, Lin-cancer stem cells isolated from Wnt antagonist (e.g., OMP-18R5 or OMP-54F28) treated versus control agent treated mice are re-injected subcutaneously into the mammary fat pads of NOD/SCID mice. The tumorigenicity of cancer stem cells based on the number of injected cells required for consistent neuroendocrine tumor formation is then determined.

Example 4

Treatment of Human Neuroendocrine Tumor Using Anti-FZD Receptor Antibodies or Soluble FZD Receptors This example describes certain methods for treating neuroendocrine tumor using antibodies against a FZD receptor to target neuroendocrine tumors comprising cancer stem cells and/or tumor cells in which FZD receptor expression has been detected and/or tumor cells having a Wnt gene signature indicating that they are responsive to inhibition of Wnt signaling.

In some embodiments, the presence of cancer stem cell marker or FZD receptor or the expression of one or more genes in a Wnt gene signature can first be determined from a tumor biopsy. Tumor cells from a biopsy from a patient diagnosed with neuroendocrine tumor are removed under sterile conditions. In some embodiments the tissue biopsy is fresh-frozen in liquid nitrogen, embedded in O.C.T., and cut on a cryostat as 10 µm sections onto glass slides. In some embodiments, the tissue biopsy is formalin-fixed, paraffin-embedded, and cut on a microtome as 10 µm section onto glass slides.

Sections are incubated with antibodies against a FZD receptor to detect FZD protein expression. Alternatively, sections can be analyzed for the presence of one or more genes in the Wnt gene signature.

The presence of cancer stem cells also may be determined Tissue biopsy samples are cut up into small pieces, minced completely using sterile blades, and cells subject to enzymatic digestion and mechanical disruption to obtain a single cell suspension. Dissociated neuroendocrine tumor cells are then incubated with anti-ESA, -CD44, -CD24, -Lin, and -FZD antibodies to detect cancer stem cells, and the presence of ESA+, CD44+, CD24−/low, Lin−, FZD+ tumor stem cells is determined by flow cytometry as described in detail above.

Cancer patients whose neuroendocrine tumors are diagnosed as expressing a FZD receptor and/or one or more genes in the Wnt gene signature are treated with anti-FZD receptor antibodies or soluble FZD receptors. In certain embodiments, humanized or human monoclonal anti-FZD receptor antibodies or soluble FZD receptors are purified and formulated with a suitable pharmaceutical vehicle for injection. In some embodiments, patients are treated with the FZD antibodies or soluble FZD receptors at least once a month for at least 10 weeks. In some embodiments, patients are treated with the FZD antibodies or soluble FZD receptors at least once a week for at least about 14 weeks. Each administration of the antibody or soluble FZD receptors should be a pharmaceutically effective dose. In some embodiments, between about 2 to about 100 mg/ml of an anti-FZD antibody or soluble FZD receptors is administered. In some embodiments, between about 5 to about 40 mg/ml of an anti-FZD antibody or soluble FZD receptors is administered. The antibody or soluble FZD receptors can be administered prior to, concurrently with, or after standard radiotherapy regimens or chemotherapy regimens using one or more chemotherapeutic agent. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

All publications, patents, patent applications, internet sites, and accession numbers/database sequences (including both polynucleotide and polypeptide sequences) cited herein, as well as U.S. Ser. No. 61/717,294, filed Oct. 23, 2012, are hereby incorporated by reference in their entirety for all purposes to the same extent as if each individual publication, patent, patent application, internet site, or accession number/database sequence were specifically and individually indicated to be so incorporated by reference.

SEQUENCES

Human FZD1 full length amino acid sequence (SEQ ID NO: 1; underlining indicates ECD):
MAEEEAPKKSRAAGGGASWELCAGALSARLAEEGSGDAGGRRRPPVDPRRLARQLLLLLW
LLEAPLLLGVRAQAAGQGPGQGPGPGQQPPPPPQQQQSGQQYNGERGISVPDHGYCQPIS
IPLCTDIAYNQTIMPNLLGHTNQEDAGLEVHQFYPLVKVQCSAELKFFLCSMYAPVCTVL
EQALPPCRSLCERARQGCEALMNKFGFQWPDTLKCEKFPVHGAGELCVGQNTSDKGTPTP
SLLPEFWTSNPQHGGGGHRGGFPGGAGASERGKFSCPRALKVPSYLNYHFLGEKDCGAPC
EPTKVYGLMYFGPEELRFSRTWIGIWSVLCCASTLFTVLTYLVDMRRFSYPERPIIFLSG
CYTAVAVAYIAGFLLEDRVVCNDKFAEDGARTVAQGTKKEGCTILFMMLYFFSMASSIWW
VILSLTWFLAAGMKWGHEAIEANSQYFHLAAWAVPAIKTITILALGQVDGDVLSGVCFVG
LNNVDALRGFVLAPLFVYLFIGTSFLLAGFVSLFRIRTIMKHDGTKTEKLEKLMVRIGVF
SVLYTVPATIVIACYFYEQAFRDQWERSWVAQSCKSYAIPCPHLQAGGGAPPHPPMSPDF
TVFMIKYLMTLIVGITSGFWIWSGKTLNSWRKFYTRLTNSKQGETTV Human FZD2 full length amino acid sequence (SEQ ID NO: 2; underlining indicates ECD):
MRPRSALPRLLLLPLLLLLPAAGPAQFHGEKGISIPDHGFCQPISIPLCTDIAYNQTIMPNL
LGHTNQEDAGLEVHQFYPLVKVQCSPELRFFLCSMYAPVCTVLEQAIPPCRSICERARQG
CEALMNKFGFQWPERLRCEHFPRHGAEQICVGQNHSEDGAPALLTTAPPPGLQPGAGGTP
GGPGGGGAPPRYATLEHPFHCPRVLKVPSYLSYKFLGERDCAAPCEPARPDGSMFFSQEE
TRFARLWILTWSVLCCASTFFTVTTYLVDMQRFRYPERPIIFLSGCYTMVSVAYIAGFVL
QERVVCNERFSEDGYRTVVQGTKKEGCTILFMMLYFFSMASSIWWVILSLTWFLAAGMKW
GHEAIEANSQYFHLAAWAVPAVKTITILAMGQIDGDLLSGVCFVGLNSLDPLRGFVLAPL
FVYLFIGTSFLLAGFVSLFRIRTIMKHDGTKTEKLERLMVRIGVFSVLYTVPATIVIACY
FYEQAFREHWERSWVSQHCKSLAIPCPAHYTPRMSPDFTVYMIKYLMTLIVGITSGFWIW
SGKTLHSWRKFYTRLTNSRHGETTV Human FZD3 full length amino acid sequence (SEQ ID NO: S):
MAMTWIVFSLWPLTVFMGHIGGHSLFSCEPITLRMCQDLPYNTTFMPNLLNHYDQQTAAL
AMEPFHPMVNLDCSRDFRPFLCALYAPICMEYGRVTLPCRRLCQRAYSECSKLMEMFGVP
WPEDMECSRFPDCDEPYPRLVDLNLAGEPTEGAPVAVQRDYGFWCPRELKIDPDLGYSFL
HVRDCSPPCPNMYFRREELSFARYFIGLISIICLSATLFTFLTFLIDVTRFRYPERPIIF
YAVCYMMVSLIFFIGFLLEDRVACNASIPAQYKASTVTQGSHNKACTMLFMILYFFTMAG
SVWWVILTITWFLAAVPKWGSEAIEKKALLFHASAWGIPGTLTIILLAMNKIEGDNISGV
CFVGLYDVDALRYFVLAPLCLYVVVGVSLLLAGIISLNRVRIEIPLEKENQDKLVKFMIR
IGVFSILYLVPLLVVIGCYFYEQAYRGIWETTWIQERCREYHIPCPYQVTQMSRPDLILF
LMKYLMALIVGIPSVFWVGSKKTCFEWASFFHGRRKKEIVNESRQVLQEPDFAQSLLRDP
NTPIIRKSRGTSTQGTSTHASSTQLAMVDDQRSKAGSIHSKVSSYHGSLHRSRDGRYTPC

| SEQUENCES |
| --- |
| SYRGMEERLPHGSMSRLTDHSRHSSSHRLNEQSRHSSIRDLSNNPMTHITHGTSMNRVIE<br>EDGTSA<br><br>Human FZD4 full length amino acid sequence (SEQ ID NO: 4):<br>MLAMAWRGAGPSVPGAPGGVGLSLGLLLQLLLLLGPARGFGDEEERRCDPIRISMCQNLG<br>YNVTKMPNLVGHELQTDAELQLTTFTPLIQYGCSSQLQFFLCSVYVPMCTEKINIPIGPC<br>GGMCLSVKRRCEPVLKEFGFAWPESLNCSKFPPQNDHNHMCMEGPGDEEVPLPHKTPIQP<br>GEECHSVGTNSDQYIWVKRSLNCVLKCGYDAGLYSRSAKEFTDIWMAVWASLCFISTAFT<br>VLTFLIDSSRFSYPERPIIFLSMCYNIYSIAYIVRLTVGRERISCDFEEAAEPVLIQEGL<br>KNTGCAIIFLLMYFFGMASSIWWVILTLTWFLAAGLKWGHEAIEMHSSYFHIAAWAIPAV<br>KTIVILIMRLVDADELTGLCYVGNQNLDALTGFVVAPLFTYLVIGTLFIAAGLVALFKIR<br>SNLQKDGIKTDKLERLMVKIGVFSVLYTVPATCVIACYFYEISNWALFRYSADDSNMAVE<br>MLKIFMSLLVGITSGMWIWSAKTLHTWQKCSNRLVNSGKVKREKRGNGWVKPGKGSETVV<br><br>Human FZD5 full length amino acid sequence (SEQ ID NO: 5; underlining<br>indicates ECD):<br>MARPDPSAPPSLLLLLLAQLVGRAAAASKAPVCQEITVPMCRGIGYNLTHMPNQFNHDTQ<br>DEAGLEVHQFWPLVEIQCSPDLRFFLCSMYTPICLPDYHKPLPPCRSVCERAKAGCSPLM<br>RQYGFAWPERMSCDRLPVLGRDAEVLCMDYNRSEATTAPPRPFPAKPTLPGPPGAPASGG<br>ECPAGGPFVCKCREPFVPILKESHPLYNKVRTGQVPNCAVPCYQPSFSADERTFATFWIG<br>LWSVLCFISTSTTVATFLIDMERFRYPERPIIFLSACYLCVSLGFLVRLVVGHASVACSR<br>EHNHIHYETTGPALCTIVFLLVYFFGMASSIWWVILSLTWFLAAGMKWGNEAIAGYAQYF<br>HLAAWLIPSVKSITALALSSVDGDPVAGICYVGNQNLNSLRGFVLGPLVLYLLVGTLFLL<br>AGFVSLFRIRSVIKQGGTKTDKLEKLMIRIGIFTLLYTVPASIVVACYLYEQHYRESWEA<br>ALTCACPGHDTGQPRAKPEYWVLMLKYFMCLVVGITSGVWIWSGKTVESWRRFTSRCCCR<br>PRRGHKSGGAMAAGDYPEASAALTGRTGPPGPAATYHKQVSLSHV<br><br>Human FZD6 full length amino acid sequence (SEQ ID NO: 6; underlining<br>indicates ECD):<br>MEMFTFLLTCIFLPLLRGHSLFTCEPITVPRCMKMAYNMTFFPNLMGHYDQSIAAVEMEH<br>FLPLANLECSPNIETFLCKAFVPTCIEQIHVVPPCRKLCEKVYSDCKKLIDTFGIRWPEE<br>LECDRLQYCDETVPVTFDPHTEFLGPQKKTEQVQRDIGFWCPRHLKTSGGQGYKFLGIDQ<br>CAPPCPNMYFKSDELEFAKSFIGTVSIFCLCATLFTFLTFLIDVRRFRYPERPIIYYSVC<br>YSIVSLMYFIGFLLGDSTACNKADEKLELGDTVVLGSQNKACTVLFMLLYFFTMAGTVWW<br>VILTITWFLAAGRKWSCEAIEQKAVWFHAVAWGTPGFLTVMLLAMNKVEGDNISGVCFVG<br>LYDLDASRYFVLLPLCLCVFVGLSLLLAGIISLNHVRQVIQHDGRNQEKLKKFMIRIGVF<br>SGLYLVPLVTLLGCYVYEQVNRITWEITWVSDHCRQYHIPCPYQAKAKARPELALFMIKY<br>LMTLIVGISAVFWVGSKKTCTEWAGFFKRNRKRDPISESRRVLQESCEFFLKHNSKVKHK<br>KKHYKPSSHKLKVISKSMGTSTGATANHGTSAVAITSHDYLGQETLTEIQTSPETSMREV<br>KADGASTPRLREQDCGEPASPAASISRLSGEQVDGKGQAGSVSESARSEGRISPKSDITD<br>TGLAQSNNLQVPSSSEPSSLKGSTSLLVHPVSGVRKEQGGGCHSDT<br><br>Human FZD7 full length amino acid sequence (SEQ ID NO: 7; ECD is<br>underlined):<br>MRDPGAAAPLSSLGLCALVLALLGALSAGAGAQPYHGEKGISVPDHGFCQPISIPLCTDI<br>AYNQTILPNLLGHTNQEDAGLEVHQFYPLVKVQCSPELRFFLCSMYAPVCTVLDQAIPPC<br>RSLCERARQGCEALMNKFGFQWPERLRCENFPVHGAGEICVGQNTSDGSGGPGGGPTAYP<br>TAPYLPDLPFTALPPGASDGRGRPAFPPFSCPRQLKVPPYLGYRFLGERDCGAPCEPGRAN<br>GLMYFKEEERRFARLWVGVWSVLCCASTLFTVLTYLVDMRRFSYPERPIIFLSGCYFMVA<br>VAHVAGFLLEDRAVCVERFSDDGYRTVAQGTKKEGCTILFMVLYFFGMASSIWWVILSLT<br>WFLAAGMKWGHEATEANSQYFHLAAWAVPAVKTITILAMGQVDGDLLSGVCYVGLSSVDA<br>LRGFVLAPLFVYLFIGTSFLLAGFVSLFRIRTIMKHDGTKTEKLEKLMVRIGVFSVLYTV<br>PATIVLACYFYEQAFREHWERTWLLQTCKSYAVPCPPGHFPPMSPDFTVFMIKYLMTMIV<br>GITTGFWIWSGKTLQSWRRFYHRLSHSSKGETAV<br><br>Human FZD8 full length amino acid sequence (SEQ ID NO: 8; ECD is<br>underlined):<br>MEWGYLLEVTSLLAALALLQRSSGAAAASAKELACQEITVPLCKGIGYNYTYMPNQFNHD<br>TQDEAGLEVHQFWPLVEIQCSPDLKFFLCSMYTPICLEDYKKPLPPCRSVCERAKAGCAP<br>LMRQYGFAWPDRMRCDRLPEQGNPDTLCMDYNRTDLTTAAPSPPRRLPPPPPGEQPPSGS<br>GHGRPPGARPPHRGGGRGGGGDAAAPPARGGGGGGKARPPGGGAAPCEPGCQCRAPMVS<br>VSSERHPLYNRVKTGQIANCALPCHNPFFSQDERAFTVFWIGLWSVLCFVSTFATVSTFL<br>IDMERFKYPERPIIFLSACYLFVSVGYLVRLVAGHEKVACSGGAPGAGGAGGAGGAAAGA<br>GAAGAGAGGPGGRGEYEELGAVEQHVRYETTGPALCTVVFLLVYFFGMASSIWWVILSLT<br>WFLAAGMKWGNEATAGYSQYFHLAAWLVPSVKSIAVLALSSVDGDPVAGICYVGNQSLDN<br>LRGFVLAPLVIYLFIGTMFLLAGFVSLFRIRSVIKQQDGPTKTHKLEKLMIRLGLFTVLY<br>TVPAAVVVACLFYEQHNRPRWEATHNCPCLRDLQPDQARRPDYAVFMLKYFMCLVVGITS<br>GVWVWSGKTLESWRSLCTRCCWASKGAAVGGGAGATAAGGGGGPGGGGGGPGGGGGPGG<br>GGGSLYSDVSTGLTWRSGTASSVSYPKQMPLSQV<br><br>Human FZD9 full length amino acid sequence (SEQ ID NO: 9):<br>MAVAPLRGALLLWQLLAAGGAALEIGRFDPERGRGAAPCQAVEIPMCRGIGYNLTRMPNL<br>LGHTSQGEAAAELAEFAPLVQYGCHSHLRFFLCSLYAPMCTDQVSTPIPACRPMCEQARL<br>RCAPIMEQFNFGWPDSLDCARLPTRNDPHALCMEAPENATAGPAEPHKGLGMLPVAPRPA<br>RPPGDLGPGAGGSGTCENPEKFQYVEKSRSCAPRCGPGVEVFWSRRDKDFALVWMAVWSA<br>LCFFSTAFTVLTFLLEPHRFQYPERPIIFLSMCYNVYSLAFLIRAVAGAQSVACDQEAGA<br>LYVIQEGLENTGCTLVFLLLYYFGMASSLWWVVLTLTWFLAAGKKWGHEATEAHGSYFHM |

| SEQUENCES |
|---|
| AAWGLPALKTIVILTLRKVAGDELTGLCYVASTDAAALTGFVLVPLSGYLVLGSSFLLTG<br>FVALFHIRKIMKTGGTNTEKLEKLMVKIGVFSILYTVPATCVIVCYVYERLNMDFWRLRA<br>TEQPCAAAAGPGGRRDCSLPGGSVPTVAVFMLKIFMSLVVGITSGVWVWSSKTFQTWQSL<br>CYRKIAAGRARAKACRAPGSYGRGTHCHYKAPTVVLHMTKTDPSLENPTHL<br><br>Human FZD10 full length amino acid sequence (SEQ ID NO: 10; ECD is<br>underlined):<br><u>MQRPGPRLWLVLQVMGSCAAISSMDMERPGDGKCQPIEIPMCKDIGYNMTRMPNLMGHEN</u><br><u>QREAATQLHEFAPLVEYGCHGHLRFFLCSLYAPMCTEQVSTPIPACRVMCEQARLKCSPI</u><br><u>MEQFNFKWPDSLDCRKLPNKNDPNYLCMEAPNNGSDEPTRGSGLFPPLFRPQRPHSAQEH</u><br><u>PLKDGGPGRGGCDNPGKFHHVEKSASCCAPLCTPGVDVYWSREDKRFAVVWLAIWAVLCFF</u><br>SSAFTVLTFLIDPARFRYPERPIIFLSMCYCVYSVGYLIRLFAGAESIACDRDSGQLYVI<br>QEGLESTGCTLVFLVLYYFGMASSLWWVVLTLTWFLAAGKKWGHEATEANSSYFHLAAWA<br>IPAVKTILILVMRRVAGDELTGVCYVGSMDVNALTGFVLIPLACYLVIGTSFILSGFVAL<br>FHIRRVMKTGGENTDKLEKLMVRIGLFSVLYTVPATCVIACYFYERLNMDYWKILAAQHK<br>CKMNNQTKTLDCLMAASIPAVEIFMVKIFMLLVVGITSGMWIWTSKTLQSWQQVCSRRLK<br>KKSRRKPASVITSGGIYKKAQHPQKTHHGKYEIPAQSPTCV<br><br>Human FZD1 ECD with signal sequence (SEQ ID NO: 11):<br>MAEEEAPKKSRAAGGGASWELCAGALSARLAEEGSGDAGGRRRPPVDPRRLARQLLLLLW<br>LLEAPLLLGVRAQAAGQGPGQGPGPGQQPPPPPQQQQSGQQYNGERGISVPDHGYCQPIS<br>IPLCTDIAYNQTIMPNLLGHTNQEDAGLEVHQFYPLVKVQCSAELKFFLCSMYAPVCTVL<br>EQALPPCRSLCERARQGCEALMNKFGFQWPDTLKCEKFPVHGAGELCVGQNTSDKGTPTP<br>SLLPEFWTSNPQHGGGGHRGGFPGGAGASERGKFSCPRALKVPSYLNYHFLGEKDCGAPC<br>EPTKVYGLMYFGPEELRFSRT<br><br>Human FZD2 ECD with signal sequence (SEQ ID NO: 12):<br>MRPRSALPRLLLPLLLLPAAGPAQFHGEKGISIPDHGFCQPISIPLCTDIAYNQTIMPNL<br>LGHTNQEDAGLEVHQFYPLVKVQCSPELRFFLCSMYAPVCTVLEQAIPPCRSICERARQG<br>CEALMNKFGFQWPERLRCEHFPRHGAEQICVGQNHSEDGAPALLTTAPPPGLQPGAGGTP<br>GGPGGGGAPPRYATLEHPFHCPRVLKVPSYLSYKFLGERDCAAPCEPARPDGSMFFSQEE<br>TRFARLWILT<br><br>Human FZD3 ECD with signal sequence (SEQ ID NO: 13):<br>MAMTWIVFSLWPLTVFMGHIGGHSLFSCEPITLRMCQDLPYNTTFMPNLLNHYDQQTAAL<br>AMEPFHPMVNLDCSRDFRPFLCALYAPICMEYGRVTLPCRRLCQRAYSECSKLMEMFGVP<br>WPEDMECSRFPDCDEPYPRLVDLNLAGEPTEGAPVAVQRDYGFWCPRELKIDPDLGYSFL<br>HVRDCSPPCPNMYFRREELSFARY<br><br>Human FZD4 ECD with signal sequence (SEQ ID NO: 14):<br>MLAMAWRGAGPSVPGAPGGVGLSLGLLLQLLLLLGPARGFGDEEERRCDPIRISMCQNLG<br>YNVTKMPNLVGHELQTDAELQLTTFTPLIQYGCSSQLQFFLCSVYVPMCTEKINIPIGPC<br>GGMCLSVKRRCEPVLKEFGFAWPESLNCSKFPPQNDHNHMCMEGPGDEEVPLPHKTPIQP<br>GEECHSVGTNSDQYIWVKRSLNCVLKCGYDAGLYSRSAKEFTDI<br><br>Human FZD5 ECD with signal sequence (SEQ ID NO: 15):<br>MARPDPSAPPSLLLLLAQLVGRAAAASKAPVCQEITVPMCRGIGYNLTHMPNQFNHDTQ<br>DEAGLEVHQFWPLVEIQCSPDLRFFLCSMYTPICLPDYHKPLPPCRSVCERAKAGCSPLM<br>RQYGFAWPERMSCDRLPVLGRDAEVLCMDYNRSEATTAPPRPFPAKPTLPGPPGAPASGG<br>ECPAGGPFVCKCREPFVPILKESHPLYNKVRTGQVPNCAVPCYQPSFSADERT<br><br>Human FZD6 ECD with signal sequence (SEQ ID NO: 16):<br>MEMFTFLLTCIFLPLLRGHSLFTCEPITVPRCMKMAYNMTFFPNLMGHYDQSIAAVEMEH<br>FLPLANLECSPNIETFLCKAFVPTCIEQIHVVPPCRKLCEKVYSDCKKLIDTFGIRWPEE<br>LECDRLQYCDETVPVTFDPHTEFLGPQKKTEQVQRDIGFWCPRHLKTSGGQGYKFLGIDQ<br>CAPPCPNMYFKSDELEFAKSFIGTVSI<br><br>Human FZD7 ECD with signal sequence (SEQ ID NO: 17):<br>MRDPGAAAPLSSLGLCALVLALLGALSAGAGAQPYHGEKGISVPDHGFCQPISIPLCTDI<br>AYNQTILPNLLGHTNQEDAGLEVHQFYPLVKVQCSPELRFFLCSMYAPVCTVLDQAIPPC<br>RSLCERARQGCEALMNKFGFQWPERLRCENFPVHGAGEICVGQNTSDGSGGPGGGPTAYP<br>TAPYLPDLPFTALPPGASDGRGRPAFPFSCPRQLKVPPYLGYRFLGERDCGAPCEPGRAN<br>GLMYFKEEERRFARL<br><br>Human FZD8 ECD with signal sequence (SEQ ID NO: 18):<br>MEWGYLLEVTSLLAALALLQRSSGAAAASAKELACQEITVPLCKGIGYNYTYMPNQFNHD<br>TQDEAGLEVHQFWPLVEIQCSPDLKFFLCSMYTPICLEDYKKPLPPCRSVCERAKAGCAP<br>LMRQYGFAWPDRMRCDRLPEQGNPDTLCMDYNRTDLTTAAPSPPRRLPPPPPGEQPPSGS<br>GHGRPPGARPPHRGGRGGGGDAAAPPARGGGGGGKARPPGGGAAPCEPGCQCRAPMVS<br>VSSERHPLYNRVKTGQIANCALPCHNPFFSQDERAFT<br><br>Human FZD9 ECD with signal sequence (SEQ ID NO: 19):<br>MAVAPLRGALLLWQLLAAGGAALEIGRFDPERGRGAAPCQAVEIPMCRGIGYNLTRMPNL<br>LGHTSQGEAAAELAEFAPLVQYGCHSHLRFFLCSLYAPMCTDQVSTPIPACRPMCEQARL<br>RCAPIMEQFNFGWPDSLDCARLPTRNDPHALCMEAPENATAGPAEPHKGLGMLPVAPRPA<br>RPPGDLGPGAGGSGTCENPEKFQYVEKSRSCAPRCGPGVEVFWSRRDKDF |

SEQUENCES

Human FZD10 ECD with signal sequence (SEQ ID NO: 20):
MQRPGPRLWLVLQVMGSCAAISSMDMERPGDGKCQPIEIPMCKDIGYNMTRMPNLMGHEN
QREAAIQLHEFAPLVEYGCHGHLRFFLCSLYAPMCTEQVSTPIPACRVMCEQARLKCSPI
MEQFNFKWPDSLDCRKLPNKNDPNYLCMEAPNNGSDEPTRGSGLFPPLFRPQRPHSAQEH
PLKDGGPGRGGCDNPGKFHHVEKSASCAPLCTPGVDVYWSREDKRFA Human FZD1 Fri domain amino acid sequence (SEQ ID NO: 21; amino acids
87-237 of SEQ ID NO: 1):
QQPPPPPQQQQSGQQYNGERGISVPDHGYCQPISIPLCTDIAYNQTIMPNLLGHTNQEDA
GLEVHQFYPLVKVQCSAELKFFLCSMYAPVCTVLEQALPPCRSLCERARQGCEALMNKFG
FQWPDTLKCEKFPVHGAGELCVGQNTSDKGT Human FZD2 Fri domain amino acid sequence (SEQ ID NO: 22; amino acids
24-159 of SEQ ID NO: 2):
QFHGEKGISIPDHGFCQPISIPLCTDIAYNQTIMPNLLGHTNQEDAGLEVHQFYPLVKVQ
CSPELRFFLCSMYAPVCTVLEQAIPPCRSICERARQGCEALMNKFGFQWPERLRCEHFPR
HGAEQICVGQNHSEDG Human FZD3 Fri domain amino acid sequence (SEQ ID NO: 23; amino acids
23-143 of SEQ ID NO: 3):
HSLFSCEPITLRMCQDLPYNTTFMPNLLNHYDQQTAALAMEPFHPMVNLDCSRDF
RPFLCALYAPICMEYGRVTLPCRRLCQRAYSECSKLMEMFGVPWPEDMECSRFPDCDEPY
PRLVDL Human FZD4 Fri domain amino acid sequence (SEQ ID NO: 24; amino acids
40-170 of SEQ ID NO: 4):
FGDEEERRCDPIRISMCQNLGYNVTKMPNLVGHELQTDAELQLTTFTPLIQYGCSSQLQF
FLCSVYVPMCTEKINIPIGPCGGMCLSVKRRCEPVLKEFGFAWPESLNCSKFPPQNDHNH
MCMEGPGDEEV Human FZD5 Fri domain amino acid sequence (SEQ ID NO: 25; amino acids
27-157 of SEQ ID NO: 5):
ASKAPVCQEITVPMCRGIGYNLTHMPNQFNHDTQDEAGLEVHQFWPLVEIQCSPDLRFFL
CSMYTPICLPDYHKPLPPCRSVCERAKAGCSPLMRQYGFAWPERMSCDRLPVLGRDAEVL
CMDYNRSEATT Human FZD6 Fri domain amino acid sequence (SEQ ID NO: 26; amino acids
19-146 of SEQ ID NO: 6):
HSLFTCEPITVPRCMKMAYNMTFFPNLMGHYDQSIAAVEMEHFLPLANLECSPNIETFLC
KAFVPTCIEQIHVVPPCRKLCEKVYSDCKKLIDTFGIRWPEELECDRLQYCDETVPVTFD
PHTEFLG Human FZD7 Fri domain amino acid sequence (SEQ ID NO: 27; amino acids
33-170 of SEQ ID NO: 7):
QPYHGEKGISVPDHGFCQPISIPLCIDIAYNQTILPNLLGHTNQEDAGLEVHQFYPLVK
VQCSPELRFFLCSMYAPVCTVLDQAIPPCRSLCERARQGCEALMNKFGFQWPERLRCENF
PVHGAGEICVGQNTSDGSG Human FZD8 Fri domain amino acid sequence (SEQ ID NO: 28; amino acids
28-158 of SEQ ID NO: 8):
ASAKELACQEITVPLCKGIGYNYTYMPNQFNHDTQDEAGLEVHQFWPLVEIQCSPDLKFF
LCSMYTPICLEDYKKPLPPCRSVCERAKAGCAPLMRQYGFAWPDRMRCDRLPEQGNPDTL
CMDYNRTDLTT Human FZD9 Fri domain amino acid sequence (SEQ ID NO: 29; amino acids
23-159 of SEQ ID NO: 9):
LEIGRFDPERGRGAAPCQAVEIPMCRGIGYNLTRMPNLLGHTSQGEAAAELAEFAPLVQY
GCHSHLRFFLCSLYAPMCTDQVSTPIPACRPMCEQARLRCAPIMEQFNFGWPDSLDCARL
PTRNDPHALCMEAPENA Human FZD10 Fri domain amino acid sequence (SEQ ID NO: 30; amino
acids 21-154 of SEQ ID NO: 10):
ISSMDMERPGDGKCQPIEIPMCKDIGYNMTRMPNLMGHENQREAAIQLHEFAPLVEYGCH
GHLRFFLCSLYAPMCTEQVSTPIPACRVMCEQARLKCSPIMEQFNFKWPDSLDCRKLPNK
NDPNYLCMEAPNNG

18R5 VH CDR1 (SEQ ID NO: 31)
GFTFSHYTLS

18R5 VH CDR2 (SEQ ID NO: 32)
VISGDGSYTYYADSVKG

18R5 VH CDR3 (SEQ ID NO: 33)
NFIKYVFAN

18R5 VL CDR1 (SEQ ID NO: 34)
SGDNIGSFYVH

| SEQUENCES |
|---|

18R5 VL CDR2 (SEQ ID NO: 35)
DKSNRPSG

18R5 VL CDR3 (SEQ ID NO: 36)
QSYANTLSL

18R5 VH (SEQ ID NO: 37)
EVQLVESGGGLVQPGGSLRLSCAASGFTFSHYTLSWVRQAPGKGLEWVSVISGDGSYTYYADSVKGRF
TISSDNSKNTLYLQMNSLRAEDTAVYYCARNFIKYVFANWGQGTLVTVSS

18R5 VL (SEQ ID NO: 38)
DIELTQPPSVSVAPGQTARISCSGDNIGSFYVHWYQQKPGQAPVLVIYDKSNRPSGIPERFSGSNSGN
TATLTISGTQAEDEADYYCQSYANTLSLVFGGGTKLTVLG

18R5 heavy chain (IgG2) amino acid sequence, underlining indicates
VH (SEQ ID NO: 39)
MKHLWFFLLLVAAPRWVLSEVQLVESGGGLVQPGGSLRLSCAASGFTFSHYTLSWVRQAPGKGLEWVS
VISGDGSYTYYADSVKGRFTISSDNSKNTLYLQMNSLRAEDTAVYYCARNFIKYVFANWGQGTLVTVS
SASTKGPSVFPLAPCSRSTSESTAALGCLVKDYFPEPVTVSWNSGALTSGVHTFPAVLQSSGLYSLSS
VVTVPSSNFGTQTYTCNVDHKPSNTKVDKTVERKCCVECPPCPAPPVAGPSVFLFPPKPKDTLMISRT
PEVTCVVVDVSHEDPEVQFNWYVDGVEVHNAKTKPREEQFNSTFRVVSVLTVVHQDWLNGKEYKCKVS
NKGLPAPIEKTISKTKGQPREPQVYTLPPSREEMTKNQVSLTCLVKGFYPSDIAVEWESNGQPENNYK
TTPPMLDSDGSFFLYSKLTVDKSRWQQGNVFSCSVMHEALHNHYTQKSLSLSPGK 18R5 LIGHT CHAIN light chain (lambda) amino acid sequence,
underlining indicates VL (SEQ ID NO: 40)
MAWALLLLTLLTQGTGSWADIELTQPPSVSVAPGQTARISCSGDNIGSFYVHWYQQKPGQAPVLVIYD
KSNRPSGIPERFSGSNSGNTATLTISGTQAEDEADYYCQSYANTLSLVFGGGTKLTVLGQPKAAPSVT
LFPPSSEELQANKATLVCLISDFYPGAVTVAWKADSSPVKAGVETTTPSKQSNNKYAASSYLSLTPEQ
WKSHRSYSCQVTHEGSTVEKTVAPTECS

18R8 VL CDR1 (SEQ ID NO: 41)
SGDKLGKKYAS

18R8 VL CDR2 (SEQ ID NO: 42)
EKDNRPSG

18R8 VL CDR3 (SEQ ID NO: 43)
SSFAGNSLE

18R8 VL (SEQ ID NO: 44)
DIELTQPPSVSVAPGQTARISCSGDKLGKKYASWYQQKPGQAPVLVIYEKDNRPSGIPERFSGSNSGN
TATLTISGTQAEDEADYYCSSFAGNSLEVFGGGTKLTVLG

18R8 18R8 light chain (lambda) amino acid sequence, underlining
indicates VL (SEQ ID NO: 45)
MAWALLLLTLLTQGTGSWADIELTQPPSVSVAPGQTARISCSGDKLGKKYASWYQQKPGQAPVLVIYE
KDNRPSGIPERFSGSNSGNTATLTISGTQAEDEADYYCSSFAGNSLEVFGGGTKLTVLGQPKAAPSVT
LFPPSSEELQANKATLVCLISDFYPGAVTVAWKADSSPVKAGVETTTPSKQSNNKYAASSYLSLTPEQ
WKSHRSYSCQVTHEGSTVEKTVAPTECS

44R24 VH CDR1 (SEQ ID NO: 46)
GFTFSSYYIT

44R24 VH CDR2 (SEQ ID NO: 47)
TISYSSSNTYYADSVKG

44R24 VH CDR3 (SEQ ID NO: 48)
SIVFDY

44R24 VL CDR1 (SEQ ID NO: 49)
SGDALGNRYVY

44R24 VL CDR2 (SEQ ID NO: 50)
SG

44R24 VL CDR3 (SEQ ID NO: 51)
GSWDTRPYPKY

44R24 VH (SEQ ID NO: 52)
EVQLVESGGGLVQPGGSLRLSCAASGFTFSSYYITWVRQAPGKGLEWVSTISYSSSNTYYADSVKGRF
TISRDNSKNTLYLQMNSLRAEDTAVYYCARSIVFDYWGQGTLVTVSS

44R24 VL (SEQ ID NO: 53)
DIELTQPPSVSVAPGQTARISCSGDALGNRYVYWYQQKPGQAPVLVIPSGIPERFSGSNS
GNTATLTISGTQAEDEADYYCGSWDTRPYPKYVFGGGTKLTVLG

| SEQUENCES |
|---|

SEQ ID NO: 54
CPLYFPLYC

SEQ ID NO: 55
CPLVWPLIC

SEQ ID NO: 56
CPLAWPLIC

SEQ ID NO: 57
CPVKYPLVC

SEQ ID NO: 58
CPLRFPLFC

SEQ ID NO: 59
CPLAWPLIC

SEQ ID NO: 60
CPVAFPLYC

SEQ ID NO: 61
CPVNYPLYC

SEQ ID NO: 62
CPVKFPLYC

SEQ ID NO: 63
CPLTYPLYC

SEQ ID NO: 64
CPLRWPLMC

SEQ ID NO: 65
CPLQYPLMC

SEQ ID NO: 66
CPLSFPLYC

SEQ ID NO: 67
CPLNWPLMC

SEQ ID NO: 68
CP(L/V)X(Y/F/W)PL(Y/F/I/V/M)C

SEQ ID NO: 69
DTLSALIERGLM

SEQ ID NO: 70
DVWWLGSTWLKR

SEQ ID NO: 71
FGNYLNDVRFLI

SEQ ID NO: 72
TNLADIAHWISG

| Minimum FZD and SFRP Fri domain sequences |
|---| h-FZD1 amino acids 116-227 (SEQ ID NO: 73)
CQPISIPLCTDIAYNQTIMPNLLGHTNQEDAGLEVHQFYPLVKVQCSAELKFFLCSMYAP
VCTVLEQALPPCRSLCERARQGCEALMNKFGFQWPDTLKCEKFPVHGAGELC h-FZD2 amino acids 39-150 (SEQ ID NO: 74)
CQPISIPLCTDIAYNQTIMPNLLGHTNQEDAGLEVHQFYPLVKVQCSPELRFFLCSMYAP
VCIVLEQAIPPCRSICERARQGCEALMNKFGFQWPERLRCEHFPRHGAEQIC h-FZD3 amino acids 28-133 (SEQ ID NO: 75)
CEPITLRMCQDLPYNTTFMPNLLNHYDQQTAALAMEPFHPMVNLDCSRDFRPFLCALYAP
ICMEYGRVTLPCRRLCQRAYSECSKLMEMFGVPWPEDMECSRFPDC h-FZD4 amino acids 48-161 (SEQ ID NO: 76)
CDPIRISMCQNLGYNVTKMPNLVGHELQTDAELQLTTFTPLIQYGCSSQLQFFLCSVYVP
MCTEKINIPIGPCGGMCLSVKRRCEPVLKEFGFAWPESLNCSKFPPQNDHNHMC

SEQUENCES h-FZD5 amino acids 33-147 (SEQ ID NO: 77)
CQEITVPMCRGIGYNLTHMPNQFNHDTQDEAGLEVHQFWPLVEIQCSPDLRFFLCSMYTP
ICLPDYHKPLPPCRSVCERAKAGCSPLMRQYGFAWPERMSCDRLPVLGRDAEVLC h-FZD6 amino acids 24-129 (SEQ ID NO: 78)
CEPITVPRCMKMAYNMTFFPNLMGHYDQSIAAVEMEHFLPLANLECSPNIETFLCKAFVP
TCIEQIHVVPPCRKLCEKVYSDCKKLIDTFGIRWPEELECDRLQYC h-FZD7 amino acids 49-160 (SEQ ID NO: 79)
CQPISIPLCTDIAYNQTILPNLLGHTNQEDAGLEVHQFYPLVKVQCSPELRFFLCSMYAP
VCTVLDQAIPPCRSLCERARQGCEALMNKFGFQWPERLRCENFPVHGAGEIC h-FZD8 amino acids 35-148 (SEQ ID NO: 80)
CQEITVPLCKGIGYNYTYMPNQFNHDTQDEAGLEVHQFWPLVEIQCSPDLKFFLCSMYTP
ICLEDYKKPLPPCRSVCERAKAGCAPLMRQYGFAWPDRMRCDRLPEQGNPDTLC h-FZD9 amino acids 39-152 (SEQ ID NO: 81)
CQAVEIPMCRGIGYNLTRMPNLLGHTSQGEAAAELAEFAPLVQYGCHSHLRFFLCSLYAP
MCIDQVSTPIPACRPMCEQARLRCAPIMEQFNFGWPDSLDCARLPTRNDPHALC h-FZD10 amino acids 34-147 (SEQ ID NO: 82)
CQPIEIPMCKDIGYNMTRMPNLMGHENQREAAIQLHEFAPLVEYGCHGHLRFFLCSLYAP
MCTEQVSTPIPACRVMCEQARLKCSPIMEQFNFKWPDSLDCRKLPNKNDPNYLC h-SFRP1 amino acids 57-165 (SEQ ID NO: 83)
CVDIPADLRLCHNVGYKKMVLPNLLEHETMAEVKQQASSWVPLLNKNCHAGTQVFLCSLF
APVCLDRPIYPCRWLCEAVRDSCEPVMQFFGFYWPEMLKCDKFPEGDVC h-SFRP2 amino acids 40-152 (SEQ ID NO: 84)
CKPIPANLQLCHGIEYQNMRLPNLLGHETMKEVLEQAGAWIPLVMKQCHPDTKKFLCSLF
APVCLDDLDETIQPCHSLCVQVKDRCAPVMSAFGFPWPDMLECDRFPQDNDLC h-SFRP3 amino acids 35-147 (SEQ ID NO: 85)
CEPVRIPLCKSLPWNMTKMPNHLHHSTQANAILAIEQFEGLLGTHCSPDLLFFLCAMYAP
ICTIDFQHEPIKPCKSVCERARQGCEPILIKYRHSWPENLACEELPVYDRGVC h-SFRP4 amino acids 24-136 (SEQ ID NO: 86)
CEAVRIPMCRHMPWNITRMPNHLHHSTQENAILAIEQYEELVDVNCSAVLRFFFCAMYAP
ICTLEFLHDPIKPCKSVCQRARDDCEPLMKMYNHSWPESLACDELPVYDRGVC h-SFRP5 amino acids 53-162 (SEQ ID NO: 87)
CLDIPADLPLCHTVGYKRMRLPNLLEHESLAEVKQQASSWLPLLAKRCHSDTQVFLCSLF
APVCLDRPTYPCRSLCEAVRAGCAPLMEAYGFPWPEMLHCHKFPLDNDLC h-ROR1 minimal Fri domain (SEQ ID NO: 88)
CQPYRGIACARFIGNRTVYMESLHMQGEIENQITAAFTMIGTSSHLSDKCSQFAIPSLCH
YAFPYCDETSSVPKPRDLCRDECEILENVLCQTEYIFARSNPMILMRLKLPNCEDLPQPE
SPEAANC h-ROR2 minimal Fri domain (SEQ ID NO: 89)
CQPYRGIACARFIGNRTIYVDSLQMQGEIENRITAAFTMIGTSTHLSDQCSQFAIPSFCH
FVFPLCDARSRTPKPRELCRDECEVLESDLCRQEYTIARSNPLILMRLQLPKCEALPMPE
SPDAANC Human FZD4 Fri domain (predicted signal sequence underlined)(SEQ ID NO: 90)
<u>MLAMAWRGAGPSVPGAPGGVGLSLGLLLQLLLLLGPARG</u>FGDEEERRCDPIRISMCQNLG
YNVTKMPNLVGHELQTDAELQTTFTPLIQYGCSSQLQFFLCSVYVPMCTEKINIPIGPC
GGMCLSVKRRCEPVLKEFGFAWPESLNCSKFPPQNDHNHMCMEGPGDEEV Human FZD5 Fri domain (predicted signal sequence underlined)(SEQ ID NO: 91)
<u>MARPDPSAPPSLLLLLLAQLVGRAAAA</u>SKAPVCQEITVPMCRGIGYNLTHMPNQFNHDTQ
DEAGLEVHQFWPLVEIQCSPDLRFFLCSMYTPICLPDYHKPLPPCRSVCERAKAGCSPLM
RQYGFAWPERMSCDRLPVLGRDAEVLCMDYNRSEATT Human FZD8 Fri domain (predicted signal sequence underlined)(SEQ ID NO: 92)
<u>MEWGYLLEVTSLLAALALLQRSSGAAAAS</u>AKELACQEITVPLCKGIGYNYTYMPNQFNHD
TQDEAGLEVHQFWPLVEIQCSPDLKFFLCSMYTPICLEDYKKPLPPCRSVCERAKAGCAP
LMRQYGFAWPDRMRCDRLPEQGNPDTLCMDYNRTDLTT Human IgG1 Fc region (SEQ ID NO: 93)
DKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAK

SEQUENCES

GQPREPQVYTLPPSRDELTKNQVSLTCLVKGFYPSDIAVEWESNGQPENNYKTTPPVLDS
DGS FFLYSKLTVDKSRWQQGNVFSCSVMHEALHNHYTQKSLSLSPGK

Human IgG1 Fc region (SEQ ID NO: 94)
KSSDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTIS
KAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK Human IgG1 Fc region (SEQ ID NO: 95)
EPKSSDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKT
ISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK Linker (SEQ ID NO: 96)
ESGGGGVT Linker (SEQ ID NO: 97)
LESGGGGVT Linker (SEQ ID NO: 98)
GRAQVT Linker (SEQ ID NO: 99)
WRAQVT Linker (SEQ ID NO: 100)
ARGRAQVT Signal Sequence (SEQ ID NO: 101)
MEWGYLLEVTSLLAALALLQRSSGAAA Signal Sequence (SEQ ID NO: 102)
MEWGYLLEVTSLLAALALLQRSSGALA Signal Sequence (SEQ ID NO: 103)
MEWGYLLEVTSLLAALALLQRSSGVLA Signal Sequence (SEQ ID NO: 104)
MEWGYLLEVTSLLAALLLLQRSPIVHA Signal Sequence (SEQ ID NO: 105)
MEWGYLLEVTSLLAALFLLQRSPIVHA Signal Sequence (SEQ ID NO: 106)
MEWGYLLEVTSLLAALLLLQRSPFVHA Signal Sequence (SEQ ID NO: 107)
MEWGYLLEVTSLLAALLLLQRSPIIYA Signal Sequence (SEQ ID NO: 108)
MEWGYLLEVTSLLAALLLLQRSPIAHA FZD8-Fc amino acid sequence-variant 54F03 (without predicted signal
sequence; the "GRA" linker sequence between the FZD8 sequence and
the Fc sequence of the fusion protein is underlined) (SEQ ID NO: 109)
ASAKELACQEITVPLCKGIGYNYTYMPNQFNHDTQDEAGLEVHQFWPLVEIQCSPDLKFFLCSMYTPI
CLEDYKKPLPPCRSVCERAKAGCAPLMRQYGFAWPDRMRCDRLPEQGNPDTLCMDYNRTDLTT<u>GRA</u>DK
THTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCS
VMHEALHNHYTQKSLSLSPGK FZD8-Fc variants
FZD8-Fc variant 54F03 amino acid sequence (without predicted signal
sequence; alternative cleavage) (SEQ ID NO: 110)
AAAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTGR
ADKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVF
SCSVMHEALHNHYTQKSLSLSPGK

SEQUENCES

FZD8-Fc variant 54F09 amino acid sequence (without predicted signal
sequence) (SEQ ID NO: 111)
ASAKELACQEITVPLCKGIGYNYTYMPNQFNHDTQDEAGLEVHQFWPLVEIQCSPDLKFFLCSMYTPI
CLEDYKKPLPPCRSVCERAKAGCAPLMRQYGFAWPDRMRCDRLPEQGNPDTLCMDYNRTDLTTAAPSP
PDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVF
SCSVMHEALHNHYTQKSLSLSPGK FZD8-Fc variant 54F09 amino acid sequence (without predicted signal
sequence; alternative cleavage) (SEQ ID NO: 112)
AAAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTAA
PSPPDKTHTCPPCPAPELLGGPSVFLFPPKPKDTLMISRTPEVTCVVVDVSHEDPEVKFNWYVDGVEV
HNAKTKPREEQYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQG
NVFSCSVMHEALHNHYTQKSLSLSPGK FZD8-Fc variant 54F15 amino acid sequence (without predicted signal
sequence) (SEQ ID NO: 113)
ASAKELACQEITVPLCKGIGYNYTYMPNQFNHDTQDEAGLEVHQFWPLVEIQCSPDLKFFLCSMYTPI
CLEDYKKPLPPCRSVCERAKAGCAPLMRQYGFAWPDRMRCDRLPEQGNPDTLCMDYNRTDLTTAAPDK
THTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCS
VMHEALHNHYTQKSLSLSPGK FZD8-Fc variant 54F15 amino acid sequence (without predicted signal
sequence; alternative cleavage) (SEQ ID NO: 114)
AAAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTAA
PDKTHTCPPCPAPELLGGPSVFLFPPKPKDTLMISRTPEVTCVVVDVSHEDPEVKFNWYVDGVEHNA
KTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVF
SCSVMHEALHNHYTQKSLSLSPGK FZD8-Fc variant 54F16, 54F17, 54F18, 54F23, 54F25, 54F27, 54F29,
54F31, and 54F34 amino acid sequence (without predicted signal
sequence) (SEQ ID NO: 115)
ASAKELACQEITVPLCKGIGYNYTYMPNQFNHDTQDEAGLEVHQFWPLVEIQCSPDLKFFLCSMYTPI
CLEDYKKPLPPCRSVCERAKAGCAPLMRQYGFAWPDRMRCDRLPEQGNPDTLCMDYNRTDLTTKSSDK
THTCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQGNVFSCS
VMHEALHNHYTQKSLSLSPGK FZD8-Fc variant 54F16 amino acid sequence (without predicted signal
sequence; alternative cleavage)
(SEQ ID NO: 116)
AAAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTKS
SDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSR
DELTKNQVSLTCLVKGFYPSDIAVEWESNGQPENNYKTTPPVLDSDGSFFLYSKLTVDKSRWQQGNVF
SCSVMHEALHNHYTQKSLSLSPG FZD8-Fc variant 54F19, 54F20, 54F24, 54F26, 54F28, 54F30, 54F32,
54F34 and 54F35 amino acid sequence (without predicted signal
sequence) (SEQ ID NO: 117)
ASAKELACQEITVPLCKGIGYNYTYMPNQFNHDTQDEAGLEVHQFWPLVEIQCSPDLKFFLCSMYTPI
CLEDYKKPLPPCRSVCERAKAGCAPLMRQYGFAWPDRMRCDRLPEQGNPDTLCMDYNRTDLTTEPKSS
DKTHTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFS
CSVMHEALHNHYTQKSLSLSPGK FZD8-Fc variant 54F19 amino acid sequence (without predicted signal
sequence; alternative cleavage) (SEQ ID NO: 118)
ALAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTEP
KSSDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTVDKSRWQQGN
VFSCSVMHEALHNHYTQKSLSLSPGK

| SEQUENCES |
| --- |

FZD8-Fc variant 54F20 amino acid sequence (without predicted signal
sequence; alternative cleavage) (SEQ ID NO: 119)
VLAASAKELACQEITVPLCKGIGYNYTYMPNQFNHDTQDEAGLEVHQFWPLVEIQCSPDLKFFLCSMY
TPICLEDYKKPLPPCRSVCERAKAGCAPLMRQYGFAWPDRMRCDRLPEQGNPDTLCMDYNRTDLTTEP
KSSDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTVDKSRWQQGN
VFSCSVMHEALHNHYTQKSLSLSPGK FZD8-Fc variant 54F34 amino acid sequence (without predicted signal
sequence) (SEQ ID NO: 120)
KELACQEITVPLCKGIGYNYTYMPNQFNHDTQDEAGLEVHQFWPLVEIQCSPDLKFFLCSMYTPICLE
DYKKPLPPCRSVCERAKAGCAPLMRQYGFAWPDRMRCDRLPEQGNPDTLCMDYNRTDLTTEPKSSDKT
HTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGNVFSCSV
MHEALHNHYTQKSLSLSPGK FZD8-Fc variant 54F33 amino acid sequence (without predicted signal
sequence) (SEQ ID NO: 121)
KELACQEITVPLCKGIGYNYTYMPNQFNHDTQDEAGLEVHQFWPLVEIQCSPDLKFFLCSMYTPICLE
DYKKPLPPCRSVCERAKAGCAPLMRQYGFAWPDRMRCDRLPEQGNPDTLCMDYNRTDLTTKSSDKTHT
CPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKN
QVSLTCLVKGFYPSDIAVEWESNGQPENNYKTTPPVLDSDGSFFLYSKLTVDKSRWQQGNVFSCSVMH
EALHNHYTQKSLSLSPGK h-Wnt1 C-terminal cysteine rich domain (aa 288-370) (SEQ ID NO: 122):
DLVYFEKSPNFCTYSGRLGTAGTAGRACNSSSPALDGCELLCCGRGHRTRTQRVTERCNCTFHWCCHV
SCRNCTHTRVLHECL h-Wnt2 C-terminal cysteine rich domain (aa 267-360) (SEQ ID NO: 123):
DLVYFENSPDYCIRDREAGSLGTAGRVCNLTSRGMDSCEVMCCGRGYDTSHVTRMTKCGCKFHWCCAV
RCQDCLEALDVHTCKAPKNADWTTAT h-Wnt2b C-terminal cysteine rich domain (aa 298-391) (SEQ ID
NO: 124):
DLVYFDNSPDYCVLDKAAGSLGTAGRVCSKTSKGTDGCEIMCCGRGYDTTRVTRVTQCECKFHWCCAV
RCKECRNTVDVHTCKAPKKAEWLDQT h-Wnt3 C-terminal cysteine rich domain (aa 273-355) (SEQ ID NO: 125):
DLVYYENSPNFCEPNPETGSFGTRDRTCNVTSHGIDGCDLLCCGRGHNTRTEKRKEKCHCIFHWCCYV
SCQECIRIYDVHTCK h-Wnt3a C-terminal cysteine rich domain (aa 270-352) (SEQ ID
NO: 126):
DLVYYEASPNFCEPNPETGSFGTRDRTCNVSSHGIDGCDLLCCGRGHNARAERRREKCRCVFHWCCYV
SCQECIRIYDVHTCK h-Wnt7a C-terminal cysteine rich domain (aa 267-359) (SEQ ID
NO: 127):
DLVYIEKSPNYCEEDPVTGSVGTQGRACNKTAPQASGCDLMCCGRGYNTHQYARVWQCNCKFHWCCYV
KCNTCSERTEMYTCK h-Wnt7b C-terminal cysteine rich domain (aa 267-349) (SEQ ID
NO: 128):
DLVYIEKSPNYCEEDAATGSVGTQGRLCNRTSPGADGCDTMCCGRGYNTHQYTKVWQCNCKFHWCCFV
KCNTCSERTEVFTCK h-Wnt8a C-terminal cysteine rich domain (aa 248-355) (SEQ ID
NO: 129):
ELIFLEESPDYCTCNSSLGIYGTEGRECLQNSHNTSRWERRSCGRLCTECGLQVEERKTEVISSCNCK
FQWCCTVKCDQCRHVVSKYYCARSPGSAQSLGRVWFGVYI h-Wnt8b C-terminal cysteine rich domain (aa 245-351) (SEQ ID
NO: 130):
ELVHLEDSPDYCLENKTLGLLGTEGRECLRRGRALGRWELRSCRRLCGDCGLAVEERRAETVSSCNCK
FHWCCAVRCEQCRRRVTKYFCSRAERPRGGAAHKPGRKP h-Wnt10a C-terminal cysteine rich domain (aa 335-417) (SEQ ID
NO: 131):
DLVYFEKSPDFCEREPRLDSAGTVGRLCNKSSAGSDGCGSMCCGRGHNILRQTRSERCHCRFHWCCFV
VCEECRITEWVSVCK

SEQUENCES h-Wnt10b C-terminal cysteine rich domain (aa 307-389) (SEQ ID NO: 132):
ELVYFEKSPDFCERDPTMGSPGTRGRACNKTSRLLDGCGSLCCGRGHNVLRQTRVERCHCRFHWCCYV
LCDECKVTEWVNVCK FZD8-Fc variant 54F28 with predicted signal sequence underlined (SEQ ID NO: 133)
<u>MEWGYLLEVTSLLAALLLLQRSPFVHAA</u>SAKELACQEITVPLCKGIGYNYTYMPNQFNHDTQDEAGLE
VHQFWPLVEIQCSPDLKFFLCSMYTPICLEDYKKPLPPCRSVCERAKAGCAPLMRQYGFAWPDRMRCD
RLPEQGNPDTLCMDYNRTDLTTEPKSSDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

What we claim is:

1. A method of treating neuroendocrine cancer, wherein the method comprises administering to a subject in need thereof a therapeutically effective amount of an anti-frizzled (FZD) receptor antibody that specifically binds two or more human FZD receptors selected from the group consisting of: FZD1, FZD2, FZD5, FZD7, and FZD8, wherein the neuroendocrine cancer is resistant to treatment with one or more of a chemotherapeutic, a somatostatin analog and a kinase inhibitor.

2. The method of claim 1, wherein the antibody comprises:
   (a) a heavy chain CDR1 comprising GFTFSHYTLS (SEQ ID NO:31), a heavy chain CDR2 comprising VISGDGSYTYYADSVKG (SEQ ID NO:32), and a heavy chain CDR3 comprising NFIKYVFAN (SEQ ID NO:33); and
   (b) a light chain CDR1 comprising SGDNIGSFYVH (SEQ ID NO:34), a light chain CDR2 comprising DKSNRPSG (SEQ ID NO:35), and a light chain CDR3 comprising QSYANTLSL (SEQ ID NO:36); or
   a light chain CDR1 comprising SGDKLGKKYAS (SEQ ID NO:41), a light chain CDR2 comprising EKDNRPSG (SEQ ID NO:42), and a light chain CDR3 comprising SSFAGNSLE (SEQ ID NO:43).

3. The method of claim 1, wherein the antibody comprises:
   (a) a heavy chain variable region comprising the amino acid sequence of SEQ ID NO:37; and/or
   (b) a light chain variable region comprising the amino acid sequence of SEQ ID NO:38 or SEQ ID NO:44.

4. The method of claim 1, wherein the antibody comprises:
   (a) a heavy chain comprising the amino acid sequence of SEQ ID NO:39; and/or
   (b) a light chain comprising the amino acid sequence of SEQ ID NO:40 or SEQ ID NO:45.

5. The method of claim 1, wherein the antibody is a monoclonal antibody, is a recombinant antibody, is a chimeric antibody, is a humanized antibody, is a human antibody, is an IgG1 or IgG2 antibody, or is an antibody fragment.

6. The method of claim 1, wherein the antibody is OMP-18R5.

7. The method of claim 1, which further comprises administering at least one additional therapeutic agent to the subject.

8. The method of claim 7, wherein the additional therapeutic agent is a chemotherapeutic agent.

9. The method of claim 7, wherein the additional therapeutic agent is:
   (a) albumin-bound paclitaxel;
   (b) gemcitabine; or
   (c) albumin-bound paclitaxel and gemcitabine.

10. The method of claim 1, wherein the neuroendocrine cancer is a carcinoid cancer or a pancreatic neuroendocrine cancer.

11. A method of inhibiting the growth of a neuroendocrine tumor, comprising contacting the neuroendocrine tumor with an effective amount of an anti-frizzled (FZD) receptor antibody that specifically binds two or more human FZD receptors selected from the group consisting of: FZD1, FZD2, FZD5, FZD7, and FZD8, wherein the neuroendocrine tumor is resistant to treatment with one or more of a chemotherapeutic, a somatostatin analog and a kinase inhibitor.

12. The method of claim 11, wherein the antibody comprises:
   (a) a heavy chain CDR1 comprising GFTFSHYTLS (SEQ ID NO:31), a heavy chain CDR2 comprising VISGDGSYTYYADSVKG (SEQ ID NO:32), and a heavy chain CDR3 comprising NFIKYVFAN (SEQ ID NO:33); and
   (b) a light chain CDR1 comprising SGDNIGSFYVH (SEQ ID NO:34), a light chain CDR2 comprising DKSNRPSG (SEQ ID NO:35), and a light chain CDR3 comprising QSYANTLSL (SEQ ID NO:36); or
   a light chain CDR1 comprising SGDKLGKKYAS (SEQ ID NO:41), a light chain CDR2 comprising EKDNRPSG (SEQ ID NO:42), and a light chain CDR3 comprising SSFAGNSLE (SEQ ID NO:43).

13. The method of claim 11, wherein the antibody comprises:
   (a) a heavy chain variable region comprising the amino acid sequence of SEQ ID NO:37; and/or
   (b) a light chain variable region comprising the amino acid sequence of SEQ ID NO:38 or SEQ ID NO:44.

14. The method of claim 11, wherein the antibody comprises:
   (a) a heavy chain comprising the amino acid sequence of SEQ ID NO:39; and/or
   (b) a light chain comprising the amino acid sequence of SEQ ID NO:40 or SEQ ID NO:45.

15. The method of claim 11, wherein the antibody is a monoclonal antibody, is a recombinant antibody, is a chimeric antibody, is a humanized antibody, is a human antibody, is an IgG1 or IgG2 antibody, or is an antibody fragment.

16. The method of claim 11, wherein the antibody is OMP-18R5.

17. The method of claim 11, which further comprises administering at least one additional therapeutic agent to the subject.

18. The method of claim 17, wherein the additional therapeutic agent is a chemotherapeutic agent.

19. The method of claim 17, wherein the additional therapeutic agent is:
   (a) albumin-bound paclitaxel;
   (b) gemcitabine; or
   (c) albumin-bound paclitaxel and gemcitabine.

20. The method of claim 11, wherein the neuroendocrine tumor is a carcinoid tumor or a pancreatic neuroendocrine tumor.

* * * * *